United States Patent
Yoshikawa et al.

(10) Patent No.: US 12,109,019 B2
(45) Date of Patent: Oct. 8, 2024

(54) SYSTEMS AND METHODS FOR ANALYTE DETECTION

(71) Applicant: Adaptyx Biosciences, Inc., Redwood City, CA (US)

(72) Inventors: Alexander Yoshikawa, Redwood City, CA (US); Vijit Sabnis, Cupertino, CA (US); Pawan Kapur, San Mateo, CA (US); Vladimir Kesler, Palo Alto, CA (US); Donald A. Ice, Milpitas, CA (US); George M. Mihalakis, San Jose, CA (US)

(73) Assignee: Adaptyx Biosciences, Inc., Redwood City, CA (US)

( * ) Notice: Subject to any disclaimer, the term of this patent is extended or adjusted under 35 U.S.C. 154(b) by 0 days.

(21) Appl. No.: 18/542,386

(22) Filed: Dec. 15, 2023

(65) Prior Publication Data

US 2024/0197213 A1    Jun. 20, 2024

Related U.S. Application Data

(60) Provisional application No. 63/523,500, filed on Jun. 27, 2023, provisional application No. 63/453,746, filed on Mar. 21, 2023, provisional application No. 63/443,425, filed on Feb. 5, 2023, provisional application No. 63/443,039, filed on Feb. 2, 2023,
(Continued)

(51) Int. Cl.
*A61B 5/145*    (2006.01)
*A61B 5/00*    (2006.01)
*A61B 5/1459*    (2006.01)

(52) U.S. Cl.
CPC ........ *A61B 5/14546* (2013.01); *A61B 5/1459* (2013.01); *A61B 5/685* (2013.01); *A61B 5/725* (2013.01)

(58) Field of Classification Search
CPC . A61B 5/1455; A61B 5/14546; A61B 5/1459; A61B 5/685; A61B 5/725
See application file for complete search history.

(56) References Cited

U.S. PATENT DOCUMENTS

| | | |
|---|---|---|
| 833,145 A | 10/1906 | Agnor |
| 5,820,622 A | 10/1998 | Gross et al. |
| 5,879,310 A | 3/1999 | Sopp et al. |

(Continued)

FOREIGN PATENT DOCUMENTS

| | | |
|---|---|---|
| CN | 112033528 A | 12/2020 |
| EP | 1968648 A2 | 9/2008 |

(Continued)

OTHER PUBLICATIONS

PCT/US2023/084285 International Search Report and Written Opinion dated May 9, 2024.

*Primary Examiner* — Eric F Winakur
(74) *Attorney, Agent, or Firm* — Wilson Sonsini Goodrich & Rosati

(57) ABSTRACT

The present disclosure provides systems and methods to monitor analytes present in a biological sample of a subject using a piercing element coupled to a support configured to pierce a body surface of the subject, an analyte binding probe on or within the piercing to provide a change in an optical signal when contacting an analyte in the biological sample of the subject, and a detector configured to detect the optical signal.

19 Claims, 64 Drawing Sheets

Related U.S. Application Data provisional application No. 63/432,983, filed on Dec. 15, 2022.

(56) References Cited

U.S. PATENT DOCUMENTS

| | | | |
|---|---|---|---|
| 6,153,971 | A | 11/2000 | Shimizu et al. |
| 6,882,415 | B1 | 4/2005 | Watkins et al. |
| 7,469,076 | B2 | 12/2008 | Carlson |
| 7,708,944 | B1 | 5/2010 | Sadik et al. |
| 7,741,031 | B2 | 6/2010 | Kramer et al. |
| 7,834,329 | B2 | 11/2010 | Lundquist et al. |
| 7,838,847 | B2 | 11/2010 | Lundquist et al. |
| 7,944,563 | B2 | 5/2011 | Horii et al. |
| 7,951,583 | B2 | 5/2011 | Duer |
| 7,955,837 | B2 | 6/2011 | Pawlak et al. |
| 7,957,617 | B2 | 6/2011 | Vollmer et al. |
| 8,053,742 | B2 | 11/2011 | Lundquist et al. |
| 8,101,402 | B2 | 1/2012 | Holmes |
| 8,187,866 | B2 | 5/2012 | Duer |
| 8,207,509 | B2 | 6/2012 | Lundquist et al. |
| 8,288,157 | B2 | 10/2012 | Duer |
| 8,414,844 | B2 | 4/2013 | Sadik et al. |
| 8,452,356 | B2 | 5/2013 | Vestel et al. |
| 8,471,219 | B2 | 6/2013 | Lundquist et al. |
| 8,563,328 | B2 | 10/2013 | Kang et al. |
| 8,586,347 | B2 | 11/2013 | Lochhead et al. |
| 8,615,281 | B2 * | 12/2013 | Yodfat .................. A61B 5/1459 600/340 |
| 8,618,507 | B1 | 12/2013 | Lundquist et al. |
| 8,642,009 | B2 | 2/2014 | Shachaf et al. |
| 8,747,751 | B2 | 6/2014 | Duer et al. |
| 8,785,132 | B2 | 7/2014 | Chae et al. |
| 8,906,670 | B2 | 12/2014 | Gray et al. |
| 9,029,802 | B2 | 5/2015 | Lundquist et al. |
| 9,151,713 | B2 | 10/2015 | Fan et al. |
| 9,155,497 | B1 | 10/2015 | Plumley et al. |
| 9,157,864 | B2 | 10/2015 | Fehr et al. |
| 9,212,995 | B2 | 12/2015 | Moll et al. |
| 9,222,123 | B2 | 12/2015 | Zhong et al. |
| 9,222,133 | B2 | 12/2015 | Lundquist et al. |
| 9,354,226 | B2 | 5/2016 | Chinnayelka et al. |
| 9,410,891 | B2 | 8/2016 | Fehr et al. |
| 9,481,903 | B2 | 11/2016 | Rey et al. |
| 9,528,939 | B2 | 12/2016 | Duer |
| 9,551,667 | B2 | 1/2017 | Schmidt et al. |
| 9,587,276 | B2 | 3/2017 | Lundquist et al. |
| 9,655,553 | B2 | 5/2017 | Plumley et al. |
| 9,658,161 | B2 | 5/2017 | Saxena et al. |
| 9,719,138 | B2 | 8/2017 | Zhong et al. |
| 9,835,618 | B1 | 12/2017 | Swanson et al. |
| 9,946,017 | B2 | 4/2018 | Saxena et al. |
| 10,106,839 | B2 | 10/2018 | Hassibi |
| 10,136,846 | B2 | 11/2018 | Wang et al. |
| 10,222,339 | B2 | 3/2019 | Van Veen et al. |
| 10,310,178 | B2 | 6/2019 | Saxena et al. |
| 10,330,598 | B2 | 6/2019 | Schleipen et al. |
| 10,365,288 | B2 | 7/2019 | Van Eyk et al. |
| 10,383,558 | B2 | 8/2019 | Cho et al. |
| 10,451,615 | B2 | 10/2019 | Husar et al. |
| 10,529,003 | B2 | 1/2020 | Mazed |
| 10,551,318 | B2 | 2/2020 | Duer |
| 10,590,493 | B2 | 3/2020 | Duer et al. |
| 10,631,766 | B2 | 4/2020 | Sia et al. |
| 10,768,362 | B2 | 9/2020 | Saxena et al. |
| 10,901,145 | B2 | 1/2021 | Gray et al. |
| 11,001,881 | B2 | 5/2021 | Hassibi et al. |
| 11,064,946 | B2 | 7/2021 | Rogers et al. |
| 11,098,345 | B2 | 8/2021 | Hassibi et al. |
| 11,484,695 | B2 | 11/2022 | Quan et al. |
| 11,525,156 | B2 | 12/2022 | Hassibi et al. |
| 11,560,588 | B2 | 1/2023 | Hassibi et al. |
| 11,560,591 | B2 | 1/2023 | Zhong et al. |
| 2004/0096959 | A1 | 5/2004 | Stiene et al. |
| 2005/0113658 | A1 * | 5/2005 | Jacobson .............. A61B 5/1459 600/316 |
| 2005/0148003 | A1 | 7/2005 | Keith et al. |
| 2006/0029941 | A1 | 2/2006 | Koo et al. |
| 2006/0216696 | A1 | 9/2006 | Goguen |
| 2007/0030578 | A1 | 2/2007 | Vinogradov et al. |
| 2007/0276211 | A1 * | 11/2007 | Mir .................... A61B 5/14546 600/345 |
| 2008/0312518 | A1 | 12/2008 | Jina et al. |
| 2009/0259118 | A1 | 10/2009 | Feldman et al. |
| 2011/0287407 | A1 | 11/2011 | Zenhausern |
| 2013/0260479 | A1 | 10/2013 | Chou et al. |
| 2014/0056815 | A1 | 2/2014 | Peyman |
| 2015/0141267 | A1 | 5/2015 | Rothberg et al. |
| 2015/0268237 | A1 | 9/2015 | Kerimo et al. |
| 2016/0084761 | A1 | 3/2016 | Rothberg et al. |
| 2017/0023569 | A1 | 1/2017 | Daiss et al. |
| 2017/0370836 | A1 | 12/2017 | Gerion et al. |
| 2019/0361015 | A1 | 11/2019 | Mendes et al. |
| 2021/0364703 | A1 | 11/2021 | Fondeur et al. |
| 2021/0372929 | A1 | 12/2021 | Hariri et al. |
| 2022/0088596 | A1 | 3/2022 | Heikenfeld |
| 2023/0001414 | A1 | 1/2023 | Florescu |

FOREIGN PATENT DOCUMENTS

| | | |
|---|---|---|
| EP | 2064488 A2 | 6/2009 |
| EP | 2362947 A2 | 9/2011 |
| EP | 2604168 A2 | 6/2013 |
| EP | 2977347 A1 | 1/2016 |
| EP | 3068901 A1 | 9/2016 |
| EP | 3123172 A1 | 2/2017 |
| EP | 3180464 A1 | 6/2017 |
| EP | 3194934 A1 | 7/2017 |
| EP | 3472355 A1 | 4/2019 |
| EP | 4123294 A1 | 1/2023 |
| WO | WO-2010011884 A2 | 1/2010 |
| WO | WO-2013052318 A1 | 4/2013 |
| WO | WO-2020086764 A1 | 4/2020 |
| WO | WO-2022081541 A1 | 4/2022 |
| WO | WO-2022087438 A1 | 4/2022 |
| WO | WO-2022221419 A1 | 10/2022 |
| WO | WO-2022226357 A1 | 10/2022 |
| WO | WO-2023003983 A1 | 1/2023 |
| WO | WO-2023004014 A1 | 1/2023 |

* cited by examiner

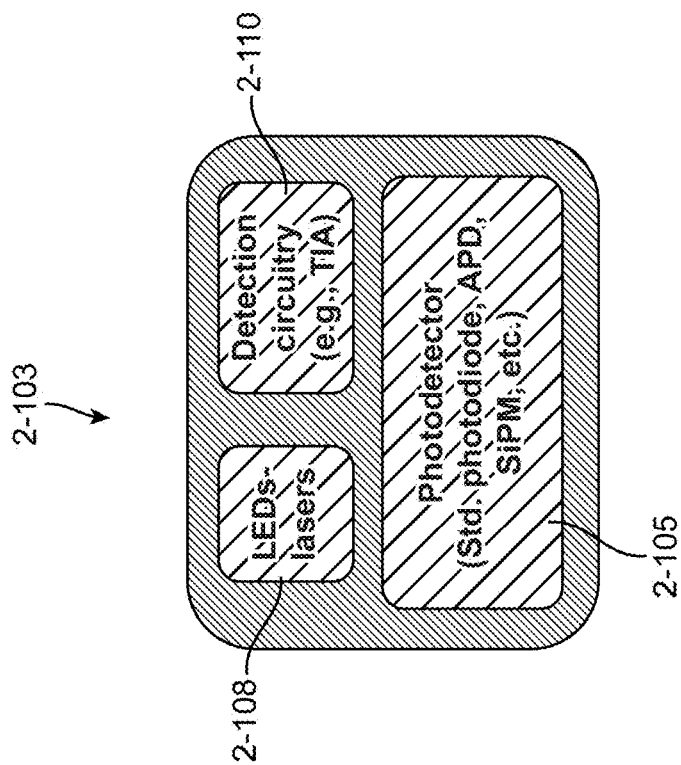
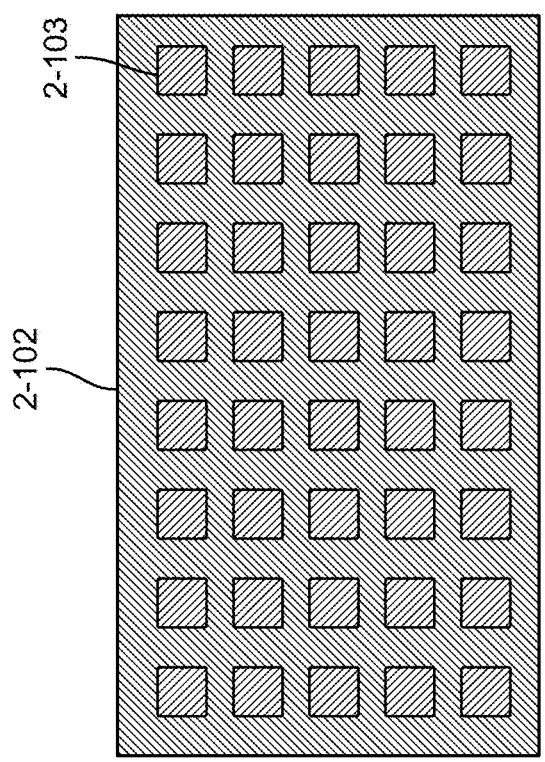
FIG. 2B
FIG. 2A

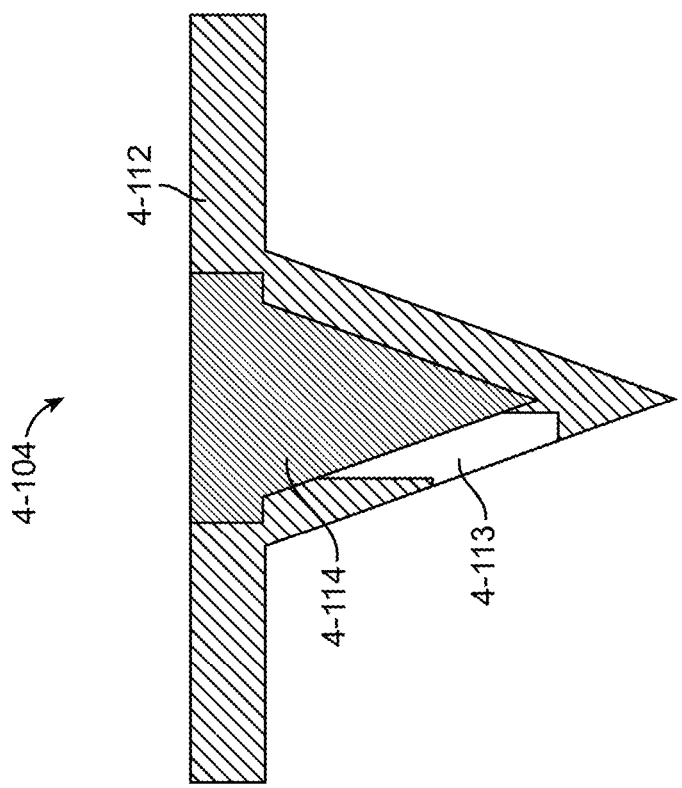
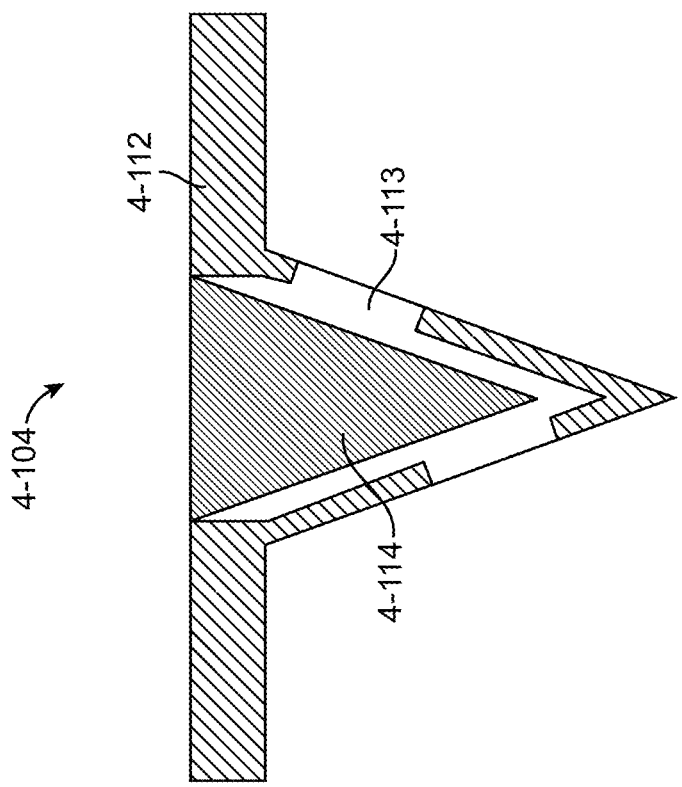

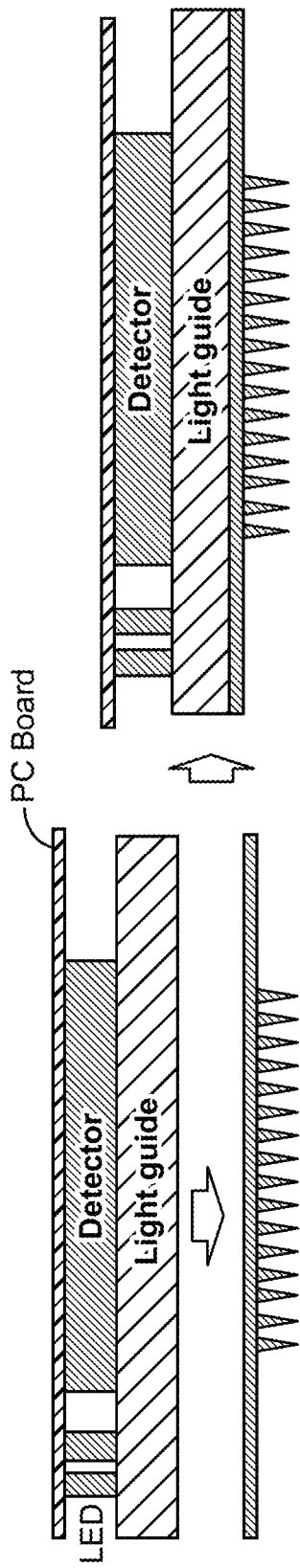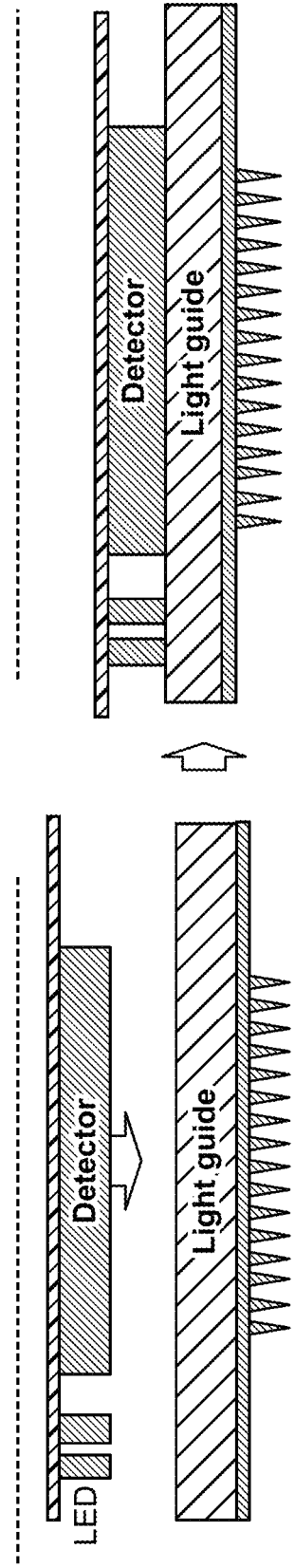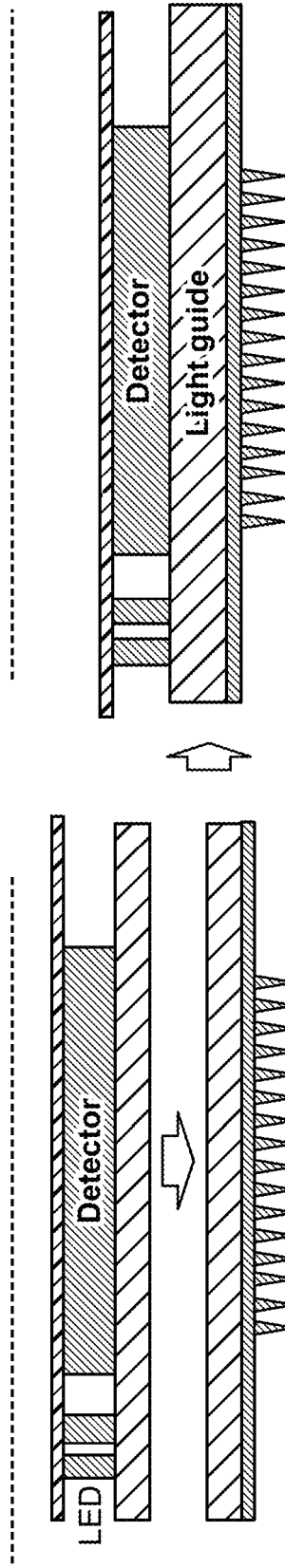

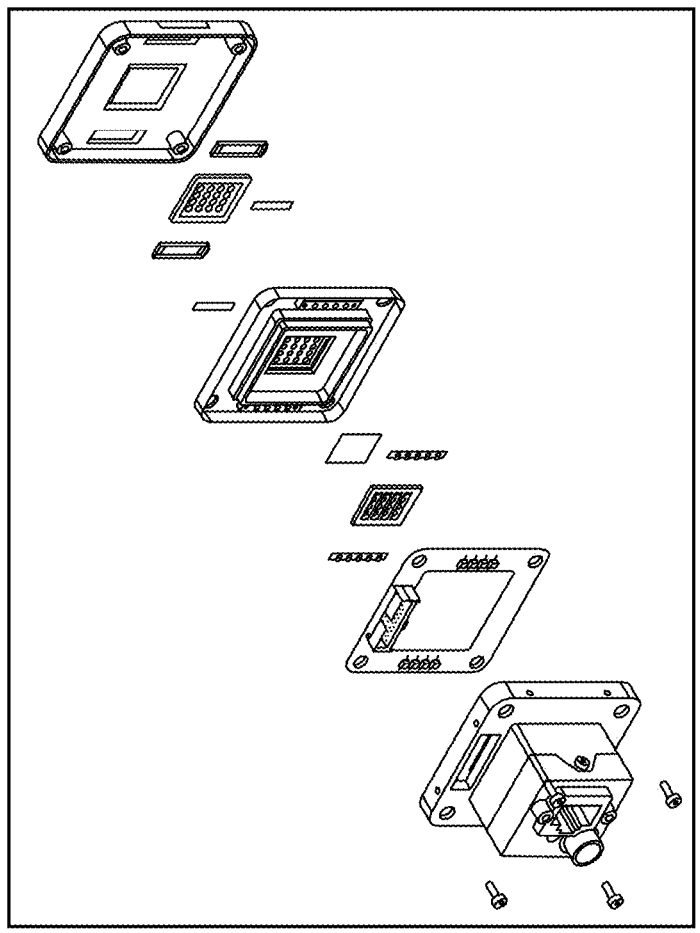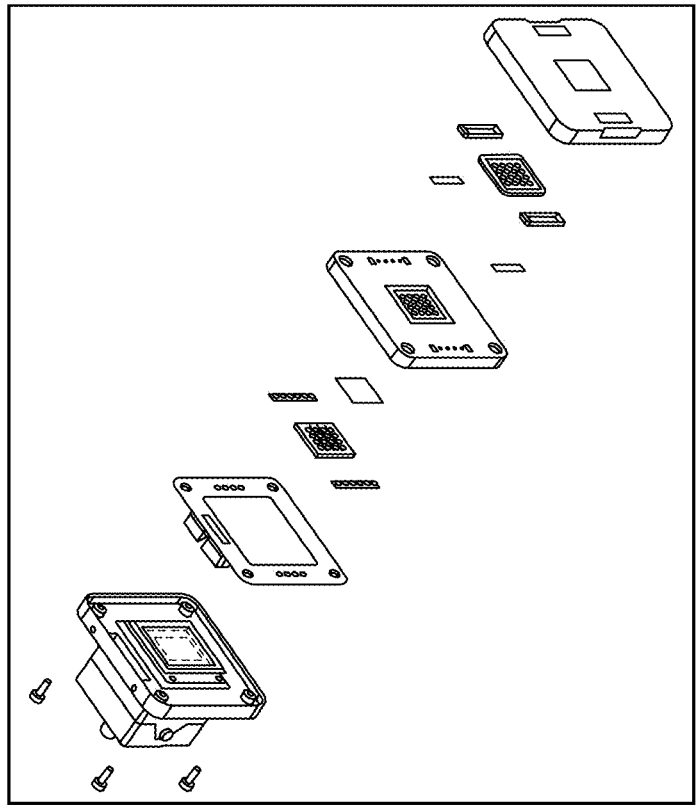
FIG. 48

SYSTEMS AND METHODS FOR ANALYTE DETECTION

CROSS REFERENCE

This application claims the benefit of U.S. Provisional Patent Application No. 63/432,983 filed Dec. 15, 2022, U.S. Provisional Patent Application No. 63/443,039 filed Feb. 2, 2023, U.S. Provisional Patent Application No. 63/443,425 filed Feb. 5, 2023, U.S. Provisional Patent Application No. 63/453,746 filed Mar. 21, 2023, and U.S. Provisional Patent Application No. 63/523,500 filed Jun. 27, 2023, each of which is hereby incorporated by reference in their entirety.

BACKGROUND

Analytes, such as ribonucleic acid (RNA), deoxyribonucleic acid (DNA), proteins, small molecules, or peptides, may be detected in a body of a subject and may be correlated with a health or physiological condition of the subject. Such analytes may be detected with a variety of approaches, such as sequencing or polymerase chain reaction (PCR). However, most assays to detect such analytes are generally performed at a laboratory facility following sample collection, and involve significant delays between the time a sample is collected and the time a result is eventually provided to the patient.

SUMMARY

A variety of minimally invasive, transdermal biosensors are available for analyte detection, but these biosensors face multiple limitations, as recognized herein, including prolonged response time, lack of precise specificity, high background noise, and lack of multiplexed detection capability. Such biosensors may not have the appropriate response functionality or ligand specificity for detection of an analyte in interstitial fluid, such as skin interstitial fluid. Recognized herein is an unmet need for improved biosensors which can perform an assay for analyte detection at the point of care which can deliver a result to a subject shortly following sample collection, and improved biosensors which can perform multiplexed or continuous assays for ongoing monitoring of an analyte, including the concentration of an analyte. Disclosed herein are biosensors for minimally invasive, continuous, real-time measurement of one or more target analytes in the body of a subject from a biological sample. In some cases, the biological sample is interstitial fluid (e.g., skin interstitial fluid).

Provided herein is a device for sensing an analyte in a biological sample of a subject, comprising: a support; a piercing element coupled to the support, wherein the piercing element is configured to pierce a body surface of the subject when the device is coupled to the body surface, to thereby bring the piercing element in contact with the biological sample; an analyte binding probe on or within the piercing element, wherein the analyte binding probe is configured to provide a change in an optical signal when the analyte binding probe comes in contact with the analyte in the biological sample of the subject; a detector operatively coupled to the support, wherein the detector is configured to detect the optical signal; a waveguide; an optical excitation path comprising the waveguide; an optical emission path comprising the waveguide, wherein the waveguide transmits light from a light source to the analyte binding probe, and wherein the waveguide is configured to permit light to be transmitted through the waveguide from the analyte binding probe to the detector. In some embodiments, the light coupler is configured to couple light from the light source into the waveguide. In some embodiments, the waveguide comprises a dielectric core, wherein the reflective cladding surrounds the dielectric core. In some embodiments, the reflective cladding comprises an aperture between the light source and the light coupler and the aperture is defined by the absence of the reflective cladding. In some embodiments, the piercing element comprises a reflective material about a base of the piercing element, wherein the optical excitation path guides light from a light source through the protruding portion of waveguide and to the reflective material about the base of the piercing element, wherein the reflective material about the base of the piercing element reflects the light to the analyte binding probe. In some embodiments, the optical emission path further comprises apertures in a reflective cladding layer surrounding the waveguide configured to transmit an emission light from the analyte probe towards the detector. In some embodiments, the optical emission path further comprises one or more focusing elements configured to focus emission light from the analyte binding probe towards the detector. In some embodiments, one or more focusing elements comprises a first focusing element configured to focus at least part of the emission light from the analyte binding probe into a first beam, and a second focusing element configured to focus the first beam towards the detector. In some embodiments, a diameter of the second beam coming from the second focusing element is configured to be a smaller size diameter than the first beam when the second beam crosses the plane of the detector and is incident on one or more pixels of the detector, thereby improving the signal to noise ratio of the detector. In some embodiments, the portion of the light blocked from transmission by filter has a wavelength which is a same wavelength as the light source. In some embodiments, the first focusing element transmits light to the optical filter at an angle within approximately +/−25 degrees with respect to a surface normal vector of the filter. In some embodiments, the optical emission path is configured to reject emission light from the analyte binding probe which does not enter the waveguide at a critical angle between ±20 degrees as measured from a vector normal to a base of the piercing element. In some embodiments, the analyte binding probe is comprised in a sensing domain comprising a hydrogel matrix comprising one or more particles comprising the analyte binding probe. In some embodiments, the analyte binding probe comprises a fluorophore conjugated to an aptamer configured to bind to the analyte, wherein the aptamer is configured to undergo a conformation change resulting in a shift in optical signal upon contacting the analyte. In some embodiments, the analyte binding probe is comprised in a sensing domain comprising a hydrogel matrix comprising one or more particles comprising the analyte binding probe. In some embodiments, the particles comprise a diameter of about 1 micron to about 50 microns. In some embodiments, the piercing element comprises a plurality of microneedles, wherein a number of particles in any one of the plurality of microneedle is at least $10^3$ particles. In some embodiments, the concentration of analyte binding probes on a surface of the one or more particles is about at least $10^6$ analyte binding probes per $cm^2$.

Provided herein is a device for sensing an analyte in a biological sample of a subject, comprising: a support; a piercing element coupled to the support, wherein the piercing element is configured to pierce a body surface of the subject when the device is coupled to the body surface, to thereby bring the piercing element in contact with the biological sample; an analyte binding probe on or within the piercing element, wherein the analyte binding probe is configured to provide a change in an optical signal when the analyte binding probe comes in contact with the analyte in the biological sample of the subject; a detector operatively coupled to the support, wherein the detector is configured to detect the optical signal; and at least one of: an optical excitation path comprising a waveguide and a light coupler and: i) comprising one or more focusing elements configured to focus light from a light source towards the light coupler, ii) a reflective cladding layer surrounding the waveguide configured to reflect the light back inside the waveguide and guide the light toward the piercing element; or iii) the light coupler being configured to couple light from a light source into the waveguide; or an optical emission path comprising: i) apertures in a reflective cladding layer surrounding a waveguide configured to transmit an emission light from the analyte probe towards the detector, or ii) one or more focusing elements configured to focus emission light from the analyte binding probe towards the detector; or comprising a waveguide, an optical excitation path comprising the waveguide, and an optical emission path comprising the waveguide, wherein the waveguide transmits light from a light source to the analyte binding probe, and wherein the waveguide is configured to permit light to be transmitted through the waveguide from the analyte binding probe to the detector; or wherein the analyte binding probe is comprised in a hydrogel matrix in the sensing domain, wherein the analyte binding probe is comprised on one or more beads comprised by the hydrogel matrix, or wherein the analyte binding probe has a dissociation constant of at least 1 pM with respect to the analyte. In some embodiments, including a light source, wherein the light source emits light at wavelengths of 600 nm to 750 nm. In some embodiments, including a light source, wherein the light source emits light at wavelengths of 350 nm to 1500 nm. In some embodiments, the light source emits light within a 50 nm band within the wavelengths of 600 nm to 750 nm. In some embodiments, the light source emits light within a 50 nm band within the wavelengths of 350 nm to 1500 nm. In some embodiments, the optical waveguide is configured to transmit light at wavelengths of 350 nm to 1500 nm. In some embodiments, the optical emission path is configured to reject light from the optical excitation path. In some embodiments, the optical emission path is configured to reject at least 75% of light from the optical excitation path. In some embodiments, the optical emission path is configured to reject light that is a which is a same wavelength as light emitted by the light source. In some embodiments, the optical emission path is configured to reject light which is a same wavelength through the optical waveguide from the light source In some embodiments, the optical excitation path and the optical emission path are configured to minimize interference with each other. In some embodiments, the optical excitation path and the optical emission path are partially co-located within the optical waveguide. In some embodiments, the excitation path is configured to transmit light in a vertical direction and a horizontal direction. In some embodiments, the emission path is configured to transmit light in a vertical direction. In some embodiments, the emission path is configured to transmit light only in a vertical direction. In some embodiments, the reflective cladding layer comprises an air gap. In some embodiments, at least a portion of the air gap is positioned between a base of the piercing element and the optical waveguide. In some embodiments, the air gap is configured to reflect light towards the piercing element. In some embodiments, the air gap has a lower refractive index than the waveguide. In some embodiments, the waveguide comprises a refractive index of greater than 1. In some embodiments, the waveguide comprises a geometrical core that is made of a dielectric material, wherein the reflective cladding surrounding the dielectric core is a reflective metal or a dielectric material of lower refractive index that the dielectric core, optionally, wherein the reflective metal comprises Al or Ag. In some embodiments, the waveguide comprises a geometrical cross section that is a rectangle. In some embodiments, the two dimensions of the rectangle range from 100 microns to 5 mm. In some embodiments, the optical waveguide is configured to only transmit the excitation light to the piercing element, and wherein the optical waveguide is a dielectric waveguide comprising the reflective cladding, wherein light is configured to enter the optical waveguide within a narrow range of angles around the surface normal of the top, light-source facing side of the waveguide. In some embodiments, the range of the angles is 40-50 degrees as measured from the surface normal of the bottom coupling surface of the waveguide. In some embodiments, including a light coupler. In some embodiments, the light coupler is configured to transmit light from the light source to a waveguide. In some embodiments, the waveguide comprises a dielectric core, wherein the reflective cladding surrounds the dielectric core. In some embodiments, the reflective cladding comprises a metal, Al, or Ag. In some embodiments, the reflective cladding comprises an aperture between the light source and the light coupler and the aperture is defined by the absence of the reflective cladding. In some embodiments, the dielectric core surrounded by the reflective cladding is configured to confine light within the waveguide. In some embodiments, the waveguide comprises a protruding portion which extends into a base of the piercing element. In some embodiments, the waveguide comprises a connecting portion which extends into a base of the piercing element. In some embodiments, the excitation path comprises connecting materials between the waveguide and the location of the analyte probe that optically extracts light from the waveguide towards the piercing element and the analyte probe. In some embodiments, the connecting material is an extension of the dielectric core material of the waveguide. In some embodiments, the connecting material is different than the core of the waveguide and comprises a substantially similar refractive index as the core of the wave guide, and, optionally, comprises multiple layers. In some embodiments, the piercing element comprises a reflective material about a base of the piercing element. In some embodiments, the optical excitation path guides light from a light source through the protruding portion of waveguide and to the reflective material about the base of the piercing element, wherein the reflective material about the base of the piercing element reflects the light to the analyte binding probe on or within the piercing element. In some embodiments, the optical excitation path is configured to reject light which does not enter the waveguide at a critical angle. In some embodiments, the critical angle is between ±20 degrees as measured from a vector normal to a base of the piercing element. In some embodiments, the critical angle is an angle which is approximately 0 degrees from the vector normal to the base of the piercing element. In some embodiments, including an opaque layer comprising apertures, wherein light must enter the optical excitation path at the critical angle to pass through the apertures. In some embodiments, the optical emission path comprises a first focusing element configured to focus at least part of the emission light from the analyte binding probe into a first beam. In some embodiments, the first beam comprises light rays that are substantially parallel to each other and substantially perpendicular to the surface of the detector. In some embodiments, the first beam is configured to be incident on one or more pixels of the detector. In some embodiments, including a second focusing element configured to focus the first beam towards the detector. In some embodiments, a diameter of the second beam coming from the second focusing element is configured to be a smaller size diameter than the first beam when the second beam crosses the plane of the detector and is incident on one or more pixels of the detector, thereby improving the signal to noise ratio of the detector. In some embodiments, an optical path of the first beam is isolated from an optical path of the excitation light. In some embodiments, including an optical filter between the first beam and the detector which does not transmit a portion of light that falls on the filter. In some embodiments, the portion of the light blocked from transmission by filter has a wavelength which is a same wavelength as the light source. In some embodiments, the optical filter is a dichroic filter, an absorptive filter, or a combination thereof. In some embodiments, the first focusing element transmits light to the filter at an angle within approximately +/−25 degrees with respect to a surface normal vector of the filter. In some embodiments, the first focusing element transmits light to the filter at an angle of approximately 0 degrees with respect to the surface normal vector of the filter. In some embodiments, the portion of light not transmitted through the filter comprises wavelengths of light less than 700 nm in wavelength. In some embodiments, the optical filter substantially transmits emission light wavelengths coming from the analyte probe, while substantially blocking light which is a similar wavelength as excitation light. In some embodiments, the optical filter is configured to block at least 99, 99.9, 99.99, 99.999, 99.9999, 99.99999, 99.999999% of light having a same wavelength as light from the light source transmitted through the excitation path. In some embodiments, having a same wavelength as light from the light source transmitted through the emission path. In some embodiments, including a second optical filter, wherein the second optical filter is a dichroic filter, an absorptive filter, or a combination thereof. In some embodiments, the first optical filter and the second optical filter in combination transmit emission light while substantially blocking light which is a similar wavelength as excitation light. In some embodiments, including a light source. In some embodiments, the light source is a downward firing light source positioned above the pierceable member. In some embodiments, including an opaque layer comprising apertures, wherein light must enter the optical excitation path at the critical angle to pass through the apertures. In some embodiments, the light source is positioned on a first side of the opaque layer, and wherein the detector is positioned on a opposite side of the opaque layer. In some embodiments, including an opaque material with an aperture in the emission path that is configured to block transmission of excitation light that does not strike the optical filter within approximately +/−25 degrees with respect to a vector normal to the surface of the optical filter. In some embodiments, the optical excitation path further comprises an optical filter between the light source and the light coupler. In some embodiments, the optical filter is a dichroic filter, an absorptive filter, or a combination thereof. In some embodiments, the analyte binding probe is an aptamer switch, or an antibody switch. In some embodiments, the light coupler comprises a faceted mirror. In some embodiments, the faceted mirror is configured to direct light towards the waveguide. In some embodiments, the faceted mirror is configured to direct light from a section of free space optics towards the waveguide. In some embodiments, the faceted mirror is partially metalized. In some embodiments, the faceted mirror is fully metalized. In some embodiments, the faceted mirror is non-metalized. In some embodiments, including an optoelectronics system, the optoelectronics system comprising the detector, wherein the optoelectronics system is operatively coupled to the support, and wherein the optoelectronic system is configured to detect the change in the optical signal using the detector. In some embodiments, including an excitation light source. In some embodiments, the excitation light source comprises a laser, or an LED. In some embodiments, including an electrical system coupled to the detector that processes the change and generates an electrical signal related to the concentration of the analyte. In some embodiments, the optical excitation path comprises a section of free space optics between a light source and a waveguide. In some embodiments, the optical emission path comprises a section of free space optics between where the emission light starts from the analyte probe area and a detector. In some embodiments, the device further comprises a battery. In some embodiments, the light source is configured to increase a single battery cycle life of the device. In some embodiments, the detector is configured to increase a single battery cycle life of the device. In some embodiments, the optical excitation path is configured to increase light coupling efficiency from the excitation light source to the analyte probe, and is configured to increase a single battery cycle life of the device. In some embodiments, the optical emission path is configured to increase light coupling efficiency from the analyte probe to a detector, and is configured to increase a single battery cycle life of the device. In some embodiments, the piercing element comprises a structural domain, a barrier domain, and a sensing domain. In some embodiments, the hydrogel matrix is based on PEG or PVA. In some embodiments, the PEG-based hydrogel is comprised of PEGDMA monomer subunits with a weight of about 750 daltons to 20 kilodaltons at weight percentages of about 5% to about 30%. In some embodiments, the PEGDMA monomer subunits are photo-crosslinked or chemically crosslinked. In some embodiments, the analyte binding probe is comprised in a sensing domain comprising a hydrogel matrix comprising one or more particles comprising the analyte binding probe. In some embodiments, the particles comprise a polymer, optionally, wherein the polymer is polystyrene. In some embodiments, the particles are magnetic. In some embodiments, the particles comprise a diameter of about 100 nm to about 1000 microns. In some embodiments, the particles comprise a diameter of at least 100 nm. In some embodiments, the particles comprise a diameter of up to about 100 microns. In some embodiments, the particles comprise a diameter of about 1 micron to about 50 microns. In some embodiments, the number of particles in a single sensor is about 1 particle to about $10^9$ particles. In some embodiments, the number of particles in a single sensor is at least $10^3$ particles. In some embodiments, the number of particles in a single sensor is at least $10^5$ particles. In some embodiments, the number of particles in a single sensor is about $10^5$ particles to about $10^8$ particles. In some embodiments, the single sensor is an individual member of the piercing element. In some embodiments, the single sensor is located in a well separate from the piercing element, and is fluidically connected to the piercing element. In some embodiments, a concentration of particles in the sensing domain ranges from $10^3$ particles to $10^9$ particles/mL. In some embodiments, a concentration of particles in the sensing domain ranges from $10^5$ particles to 10^8 particles/mL. In some embodiments, the concentration of analyte binding probes on a surface of the one or more particles is about 10^6 to about 5*10^3 analyte binding probes per cm^2. In some embodiments, the concentration of analyte binding probes on a surface of the one or more particles is about 10^10 to about 10^13 analyte binding probes per cm^2. In some embodiments, the analyte binding probe is an aptamer, wherein the concentration of analyte binding probes on a surface of the one or more particles is about 10^6 to about 5*10^13 DNA strands per cm^2. In some embodiments, the analyte binding probe is an aptamer, wherein the concentration of analyte binding probes on a surface of the one or more particles is about 10^10 DNA strands/cm$^2$ to about 10^13 DNA strands/cm$^2$. In some embodiments, the analyte binding probe is an aptamer, wherein an average spacing of the analyte binding probes ranges from about 1.4 nm to about 10 micrometers between DNA strands. In some embodiments, the analyte binding probe is an aptamer, wherein an average spacing of the analyte binding probes ranges from about 3 nm to about 100 nm between DNA strands. In some embodiments, including a light source. In some embodiments, the device is configured to be placed in optical communication with an external light source. In some embodiments, including two or more analyte binding probes on or within the piercing element, each of the two or more analyte binding probes configured to provide a change in an optical signal when the two or more analyte binding probes contact a second analyte in the biological sample of the subject. In some embodiments, including two or more analyte binding probes on or within the piercing element, each of the two or more analyte binding probes configured to provide a change in an optical signal when the two or more analyte binding probes contact a second analyte in the biological sample of the subject. In some embodiments, the analyte binding probe comprises a fluorophore conjugated to an aptamer configured to bind to the analyte, wherein the analyte binding probe is configured to contact the biological sample of the subject and provide the change in an optical signal when the piercing element is inserted into a skin of a subject. In some embodiments, including a multiplexed array of analyte binding probes on or within the piercing element, each of the multiplexed array of analyte binding probes configured to provide a change in an optical signal when the multiplexed array of analyte binding probe contacts a subsequent analyte in the biological sample of the subject. In some embodiments, the subsequent analyte is a different analyte, the multiplexed array of analyte binding probes is configured to detect a plurality of analytes in the biological sample of the subject. In some embodiments, the piercing element comprises a plurality of piercing elements. In some embodiments, the plurality of piercing elements defines subsets of piercing elements, wherein each subset of piercing elements comprises a different analyte binding probe configured to detect a different analyte in the biological sample of the subject. In some embodiments, the subsets of piercing elements comprising the different analyte binding probes comprises the multiplexed array of analyte binding probes. In some embodiments, the waveguide comprises a polymer glassy matrix comprising dispersed photoluminescent particles. In some embodiments, the polymer comprises silicones, polysiloxanes, silsequioxanes, or combinations thereof. In some embodiments, the polymer comprises: polymethylmethacrylate (PMMA), polystyrene (PS), polycarbonate (PC), polyurethane (PU), epoxy resin, deuterated and halogenated polyacrylates, fluorinated polyimides, perfluorocyclobutyl (PFCB) aryl ether polymers, nonlinear optical polymers, benzocylcobutene (BCB), perfluorovinyl ether cyclopolymer (CYTOP), tetrafluoroethylene and perfluorovinyl ether copolymer (Teflon AF), silicone, fluorinated poly(arylene ether sulfide), poly(pentafluorostyrene), fluorinated dendrimers, fluorinated hyperbranched polymers, or combinations thereof. In some embodiments, the piercing element is coupled to the support using a lock and key attachment. In some embodiments, the piercing element is coupled to the support using a mortise and tenon attachment. In some embodiments, the piercing element is coupled to the support using a dovetail attachment. In some embodiments, the piercing element is coupled to the support using a magnetic attachment. In some embodiments, the piercing element is coupled to the support using an adhesive. In some embodiments, the piercing element is coupled to the support using one or more elastically deformable attachment elements. In some embodiments, the piercing element is coupled to the support using one or more elastically deformable attachment elements configured to rebound once inserted into the support. In some embodiments, the piercing element is removably coupled to the support. In some embodiments, the piercing element comprises a microneedle array which is removably coupled to the support. In some embodiments, the optical light guide is removably coupled to the support. In some embodiments, the analyte binding probe coupled to the optical reporter is an oligonucleotide probe. In some embodiments, the oligonucleotide probe is an aptamer. In some embodiments, the aptamer is coupled to a displacement strand, wherein the displacement strand is partially complementary to the aptamer. In some embodiments, the displacement strand is coupled to a second optical reporter. In some embodiments, the second optical reporter is a fluorophore or a quencher. In some embodiments, the aptamer is coupled to a linker moiety placed between the aptamer and the displacement strand. In some embodiments, the linker moiety is a nucleotide acid moiety, a peptide nucleic acid (PNA) moiety, a peptide moiety, a disulfide bond, a phosphodiester linkage, or a polymer. In some embodiments, one or more sidewalls of the piercing element are reflective. In some embodiments, one or more sidewalls of each microneedle of the microneedle array are reflective. In some embodiments, the piercing element comprises a structural domain, a barrier domain, and a sensing domain. In some embodiments, the structural domain is positioned on a surface of the support and extends outward from the surface to define a needle, and defines an interior space, wherein the sensing domain is contained within the interior space. In some embodiments, the structural domain encapsulates the barrier domain. In some embodiments, the structural domain encloses the sensing domain. In some embodiments, the sensing domain encapsulates the analyte binding probe within a matrix of the sensing domain, wherein the barrier domain comprises a hydrogel, a polymer, or combinations thereof. In some embodiments, the sensing domain comprises the analyte binding probe. In some embodiments, the sensing domain comprises the analyte binding probe in a hydrogel matrix. In some embodiments, the analyte binding probe is bound to one or more beads in the hydrogel matrix. In some embodiments, the barrier domain comprises a hydrogel, a polymer, or combinations thereof. In some embodiments, the structural domain encapsulates the sensing domain, wherein the sensing domain is configured to control transfer of the analyte to the analyte binding probe. In some embodiments, the barrier domain is configured to control transfer of the analyte to sensing domain via diffusion. In some embodiments, the sensing domain and/or the barrier domain comprise a plurality of pores. In some embodiments, the analyte binding probe is contained within the sensing domain at a concentration of about 10 pM to about 1 mM. In some embodiments, the analyte binding probe is contained within the sensing domain at a concentration of about 1 nM to about 1 uM. In some embodiments, the detector comprises a semiconductor material. In some embodiments, the detector comprises a semiconductor photodetector. In some embodiments, the detector comprises a semiconductor photodetector comprising a silicon photomultiplier chip, an avalanche photodiode, a metal-semiconductor-metal photodiode, a CMOS sensor array, a CCD (charge coupled device), a lateral semiconductor photodiode, an array of photodetectors, an ambient light sensor, an array of ambient light sensors, or combinations thereof, or combinations thereof. In some embodiments, the semiconductor material or the semiconductor photodetector comprises a p-n junction. In some embodiments, the semiconductor material or the semiconductor photodetector comprises Si, Ge, InGaAs, GaAs, InP, Ge, SiGe, InGaN, GaN, or combinations thereof. In some embodiments, the detector comprises a silicon photomultiplier (SiPM) detector. In some embodiments, the piercing element is configured to transmit light within the piercing element towards the analyte binding probe. In some embodiments, the piercing element is configured to guide light emitting from the analyte binding probe out of the piercing element. In some embodiments, the piercing element is configured to transmit light using a reflective metal coating on a surface within the piercing element, optionally, wherein the reflective metal coating comprises Ag or Au. In some embodiments, the piercing element is made of a reflective metal configured to reflect light, optionally, wherein the reflective metal comprises stainless steel, Ti, Au Ag, or combinations thereof. In some embodiments, the piercing element comprise a polymer, a plastic polymer, or polymer coated with reflective metal, or combinations thereof, optionally wherein the reflective metal is optionally Ag, Au, or combinations thereof. In some embodiments, the reflective metal coating is configured to increases an efficiency of light coupling from a top of the piercing element towards the analyte binding probe within the piercing element. In some embodiments, the reflective metal coating is configured to increases an efficiency of light coupling from the analyte binding probe towards the detector. In some embodiments, the piercing element is configured to guide light using a dielectric material comprised within the piercing element. In some embodiments, the dielectric material is a dielectric waveguide with a core and cladding. In some embodiments, the dielectric waveguide is an optical fiber. In some embodiments, the second waveguide guides an excitation light towards the analyte binding probe, and an emission light from the analyte binding probe towards the detector. In some embodiments, the analyte binding probe is located above the piercing elements. In some embodiments, the piercing element comprises a plurality of piercing members held together by a base. In some embodiments, the plurality of piercing members is at least partially hollow. In some embodiments, at least one of the plurality of piercing members provides a fluorescence signal of known magnitude to establish a reference signal as to the change in optical signal from the analyte binding probe under a given biological condition. In some embodiments, the given biological conditions comprise a pH value, a temperature, a salt concentration, or combinations thereof. In some embodiments, at least two of the piercing members comprise a same analyte binding probe. In some embodiments, at least two of the piercing members comprise a same analyte binding probe in a same concentration. In some embodiments, at least two of the piercing members comprise two different analyte binding probes that detect two different analytes. In some embodiments, the change in optical signal when the analyte binding probe comes in contact with the analyte is detected using fluorescence resonance energy transfer (FRET) or a time resolved fluorescence (TRF) or change in optical emission intensity. In some embodiments, the change in analyte concentration when the analyte binding probe comes in contact with the analyte is detected using a change in intensity of the fluorescence. In some embodiments, the analyte binding probe comprises a quantum dot. In some embodiments, the analyte binding probe comprises an aptamer conjugated to a quantum dot. In some embodiments, the optical coupler is an optical grating. In some embodiments, the optical grating is a diffraction element configured to guide light from a free space into the waveguide, or from the waveguide into a free space. In some embodiments, the optical grating is configured to direct light from the waveguide toward the piercing element. In some embodiments, the optical grating is configured to direct light from the piercing element towards the waveguide. In some embodiments, the piercing element is separable from the device. In some embodiments, the piercing element is configured to store the biological sample for subsequent analysis.

Aspects disclosed herein provide a method for sensing an analyte in a biological sample of a subject, comprising: piercing a skin of the subject to contact a biological sample, and bringing the biological sample in contact with an analyte binding probe; inducing a conformational change in the analyte binding probe by binding a target analyte with the analyte binding probe; applying a light source to the analyte binding probe to produce an optical signal; measuring a presence, a lack of presence, an increase, or a decrease of the optical signal to determine the presence or concentration of the target analyte in the sample. In some embodiments, the method includes passing light through an optical waveguide from a light source to the analyte binding probe. In some embodiments, the method includes passing light through an optical waveguide from the analyte binding probe to a detector. In some embodiments, applying the light source to the analyte binding probe comprises transmitting light through an optical excitation path comprising a waveguide and a light coupler and: i) transmitting light through one or more focusing elements and focusing light from a light source towards the light coupler, ii) transmitting light through a waveguide and reflecting it within the waveguide using a reflective cladding layer surrounding the waveguide, thereby guiding the light toward the piercing element or iii) transmitting light from a light source, through the light coupler, and into the waveguide. In some embodiments, measuring a presence, a lack of presence, an increase, or a decrease of the optical signal comprises transmitting light through an optical emission path comprising: i) apertures in a reflective cladding layer surrounding a waveguide, transmitting light through the apertures towards the detector, or ii) one or more focusing elements configured to focus emission light from the analyte binding probe towards the detector, transmitting lights through the one or more focusing elements towards the detector. In some embodiments, applying a light source to the analyte binding probe to produce an optical signal comprises transmitting light about an optical excitation path comprising a waveguide, and an optical emission path comprising the waveguide, the waveguide transmitting light from the light source to the analyte binding probe, and the transmitting light through the waveguide from the analyte binding probe to a detector. In some embodiments, applying the light source to the analyte binding probe and/or measuring a presence, a lack of presence, an increase, or a decrease of the optical signal comprises the waveguide transmitting light from a light source to the analyte binding probe, and the waveguide transmitting light from the analyte binding probe to the detector. In some embodiments, the analyte binding probe is comprised in a sensing domain comprising a hydrogel matrix comprising one or more particles comprising the analyte binding probe. In some embodiments, the analyte binding probe has a dissociation constant of at least 1 pM with respect to the analyte. In some embodiments, piercing the skin of the subject comprises piercing the skin of the subject with a piercing element that is removable from a device. In some embodiments, piercing the skin of the subject comprises storing the biological sample in the piercing element for subsequent analysis. In some embodiments, measuring the presence, the lack of presence, the increase, or the decrease of the optical signal to determine the presence or concentration of the target analyte in the sample occurs using a device coupled to a piercing element. In some embodiments, measuring the presence, lack of presence, increase of optical signal, or decrease of optical signal to determine the concentration of the target analyte in the biological sample occurs while the piercing element is attached to the body of a subject. In some embodiments, measuring the presence, lack of presence, increase of optical signal, or decrease of optical signal to determine the concentration of the target analyte in the biological sample occurs while the piercing element is removed from the body of a subject.

Provided herein is a device for sensing an analyte in a biological sample of a subject, comprising: a support; a piercing element coupled to the support, wherein the piercing element is configured to pierce a body surface of the subject when the device is coupled to the body surface, to thereby bring the piercing element in contact with the biological sample; an analyte binding probe on or within the piercing element, wherein the analyte binding probe is configured to provide a change in an optical signal when the analyte binding probe comes in contact with the analyte in the biological sample of the subject; and a detector operatively coupled to the support, wherein the detector is configured to detect the optical signal. In some embodiments, the device further comprises a light source. In some embodiments, the device is configured to be placed in optical communication with an external light source. In some embodiments, the device further comprises two or more analyte binding probes on or within the piercing element, each of the two or more analyte binding probes configured to provide a change in an optical signal when the two or more analyte binding probes contact a second analyte in the biological sample of the subject. In some embodiments, the device further comprises a multiplexed array of analyte binding probes on or within the piercing element, each of the multiplexed array of analyte binding probes configured to provide a change in an optical signal when the multiplexed array of analyte binding probe contacts a subsequent analyte in the biological sample of the subject. In some embodiments, the subsequent analyte is a different analyte, the multiplexed array of analyte binding probes is configured to detect a plurality of analytes in the biological sample of the subject. In some embodiments, the piercing element comprises a plurality of piercing elements. In some embodiments, the plurality of piercing elements defines subsets of piercing elements, wherein each subset of piercing elements comprises a different analyte binding probe configured to detect a different analyte in the biological sample of the subject. In some embodiments, the subsets of piercing elements comprising the different analyte binding probe comprises the multiplexed array of analyte binding probes. In some embodiments, the support comprises an optical light guide, or an optical waveguide. In some embodiments, the optical light guide comprises a 2-dimensional array of light guides. In some embodiments, the optical light guide comprises a light guide core. In some embodiments, the optical light guide comprises a light guide core. In some embodiments, the optical light guide comprises a coupling region. In some embodiments, the optical light guide comprises a coupling region where the optical light guide contacts the microneedle. In some embodiments, the optical light guide comprises a coupling region positioned at a base of the microneedle. In some embodiments, the coupling region is in contact with the base of the microneedle, or is adjacent to the base of the microneedle. In some embodiments, light passes through the coupling region to the analyte binding probe. In some embodiments, the coupling region comprises a higher refractive index than the light guide core. In some embodiments, the coupling region comprises a higher refractive index than the light guide core, and refracts light towards the aptamer binding probe. In some embodiments, the coupling region comprises a lower refractive index than the light guide core, and refracts light towards the detector. In some embodiments, the coupling region comprises a same refractive index as the light guide core. In some embodiments, the optical light guide comprises one or more reflectors. In some embodiments, the reflectors are positioned in contact with a base of the piercing element. In some embodiments, the reflectors surround a base of the piercing element. In some embodiments, the reflectors form an array about a base of the piercing element. In some embodiments, the reflectors are adjacent to a base of the piercing element. In some embodiments, the reflectors are configured to reflect light towards the piercing element. In some embodiments, the reflectors are configured focus light towards the analyte binding probe. In some embodiments, the reflectors comprise a reflective material on a sidewall of a structure. In some embodiments, the 2-dimensional array comprises dichroic mirrors. In some embodiments, the 2-dimensional array comprises gratings. In some embodiments, the 2-dimensional array is etched. In some embodiments, the light guide comprises a glass or a polymer. In some embodiments, the optical light guide comprises a polymer glassy matrix comprising dispersed photoluminescent particles. In some embodiments, the polymer comprises silicones, polysiloxanes, silsequioxanes, or combinations thereof. In some embodiments, the polymer comprises: polymethylmethacrylate (PMMA), polystyrene (PS), polycarbonate (PC), polyurethane (PU), epoxy resin, deuterated and halogenated polyacrylates, fluorinated polyimides, perfluorocyclobutyl (PFCB) aryl ether polymers, nonlinear optical polymers, benzocylcobutene (BCB), perfluorovinyl ether cyclopolymer (CYTOP), tetrafluoroethylene and perfluorovinyl ether copolymer (Teflon AF), silicone, fluorinated poly(arylene ether sulfide), poly(pentafluorostyrene), fluorinated dendrimers, fluorinated hyperbranched polymers, or combinations thereof. In some embodiments, the optical light guide is configured to: couple to a light source, to guide at least a portion of light from the light source along a length of the optical light guide, and to divert at least a portion of the light from the light guide to the piercing element. In some embodiments, the support comprises an optical light guide is configured to provide a light transmission efficiency of at least 1, 5, 10, 15, 20, 25, 30, 35, 40, 45, 50, 50, 60, 65, 70, 75, 80, 85, 90, 95, or 99% transmission efficiency. In some embodiments, the support comprises an optical light guide is configured to provide a light transmission efficiency of at least 1, 5, 10, 15, 20, 25, 30, 35, 40, 45, 50, 50, 60, 65, 70, 75, 80, 85, 90, 95, or 99% transmission efficiency from the light source to the piercing element. In some embodiments, the optical light guide is configured to collect an emission light of the optical reporter from the analyte binding probe, to guide at least a portion of the emission light to the detector. In some embodiments, the support comprises an optical light guide is configured to provide an essentially losses light transmission from the piercing element to the detector. In some embodiments, the support comprises an optical light guide is configured to provide a light transmission efficiency of at least 1, 5, 10, 15, 20, 25, 30, 35, 40, 45, 50, 50, 60, 65, 70, 80, 85, 90, 95, or 99% transmission efficiency from the piercing element to the detector. In some embodiments, the optical light guide defines a plurality of paths from the light source to the piercing element. In some embodiments, the light source is configured to provide light in different wavelengths. In some embodiments, the light source comprises a plurality of light sources each configured to provide a different wavelength of light. In some embodiments, the device is configured to be coupled to an external light source each configured to provide a different wavelength of light. In some embodiments, the plurality of paths from the light source to the piercing element comprises one or more distinct paths from the light source to the multiplexed array of analyte binding probes. In some embodiments, multiplexed array of analyte binding probes is spatially multiplexed across the piercing element. In some embodiments, at least one of the plurality of paths is configured to guide light from one of the plurality of light sources with a specific wavelength of light to one of the analyte binding probes in the multiplexed array of analyte binding probes which is configured to be responsive to the specific wavelength of light. In some embodiments, the plurality of paths from the light source to the piercing element comprises one or more distinct paths from the light source to the subsets of piercing elements. In some embodiments, at least one of the plurality of paths is configured to guide light from one of the plurality of light sources with a specific wavelength of light to one of the analyte binding probes in the subsets of piercing elements. In some embodiments, the optical light guide comprises one or more switches configured to block one or more of the plurality of paths. In some embodiments, the piercing element is coupled to the support using one or more holes. In some embodiments, the piercing element is coupled to the support using one or more insertable elements configured to attach to a corresponding one or more receiving elements. In some embodiments, the piercing element is coupled to the support using a lock and key attachment. In some embodiments, the piercing element is coupled to the support using a mortise and tenon attachment. In some embodiments, the piercing element is coupled to the support using a dovetail attachment. In some embodiments, the piercing element is coupled to the support using a magnetic attachment. In some embodiments, the piercing element is coupled to the support using an adhesive. In some embodiments, the piercing element is coupled to the support using one or more elastically deformable attachment elements. In some embodiments, the piercing element is coupled to the support using one or more elastically deformable attachment elements configured to rebound once inserted into the support. In some embodiments, the piercing element is removably coupled to the support. In some embodiments, the piercing element comprises a microneedle array which is removably coupled to the support. In some embodiments, the optical light guide is removably coupled to the support. In some embodiments, the optical light guide is removably coupled to the support, and is removable from the support while remaining coupled to the light guide. In some embodiments, the optical light guide comprises a first portion and a second portion, wherein the first portion is removably coupled to the support, and the second portion is coupled to the piercing element. In some embodiments, the optical light guide comprises a first portion and a second portion removably coupled to each other. In some embodiments, the second portion is removably coupled to the support, wherein the second portion is coupled to the piercing element. In some embodiments, the second portion is removable from the first portion. In some embodiments, the support does not comprise an optical light guide. In some embodiments, the device comprises a free space optical system. In some embodiments, the device comprises a free space optical system configured to transfer light from the light source to the analyte binding probe. In some embodiments, the device comprises a free space optical system configured to transfer light from the analyte binding probe to the detector. In some embodiments, the free space optical system comprises a light source coaxially aligned with the analyte binding probe. In some embodiments, the free space optical system comprises a light source vertically integrated with the analyte binding probe. In some embodiments, the free space optical system comprises a light source directly coupled to the piercing element. In some embodiments, the detector is directly coupled to the piercing element. In some embodiments, there is a light path between the analyte binding probe and the detector. In some embodiments, a light source is directly coupled to the analyte binding probe. In some embodiments, there is a light path between the analyte binding probe and the light source. In some embodiments, there is an unobstructed light path between the analyte binding probe and the light source. In some embodiments, the light source is a plurality of light-emitting diodes (LEDs) or lasers. In some embodiments, the light source is a plurality of light-emitting diodes (LEDs) or lasers, each of the plurality of light-emitting diodes (LEDs) or lasers configured to deliver a different wavelength of light. In some embodiments, the light source has wavelength of at least about 200 nanometers. In some embodiments, the light source has wavelength of at most about 2 micrometers. In some embodiments, the analyte binding probe is coupled to an optical reporter. In some embodiments, the optical reporter is a fluorophore or a quencher. In some embodiments, the analyte binding probe coupled to the optical reporter is an oligonucleotide probe. In some embodiments, the oligonucleotide probe is an aptamer. In some embodiments, the aptamer is coupled to a displacement strand, wherein the displacement strand is partially complementary to the aptamer. In some embodiments, the displacement strand is coupled to a second optical reporter. In some embodiments, the second optical reporter is a fluorophore or a quencher. In some embodiments, the aptamer is coupled to a linker moiety placed between the aptamer and the displacement strand. In some embodiments, the linker moiety is a nucleotide acid moiety, a peptide nucleic acid (PNA) moiety, a peptide moiety, a disulfide bond, a phosphodiester linkage, or a polymer. In some embodiments, the analyte binding probe coupled to the optical reporter is a polynucleotide probe. In some embodiments, the analyte binding probe comprises an antibody. In some embodiments, the analyte binding probe is configured to undergo a conformational change when the analyte interacts with the analyte binding probe. In some embodiments, the conformation is configured to provide the change in the optical signal. In some embodiments, the change in the optical signal is in a function of a concentration of the analyte. In some embodiments, the optical signal is the emission light. In some embodiments, the analyte binding probe is configured to detect one or plurality of analytes. In some embodiments, the analyte is an antibody. In some embodiments, the analyte is a oligonucleotide, mRNA, RNA, DNA, cDNA, a lipid, lipid particle, an exosome, a viral particle, or combinations thereof. In some embodiments, the analyte is a protein. In some embodiments, the analyte is a small molecule. In some embodiments, the small molecule is a drug. In some embodiments, the piercing element is a needle. In some embodiments, the piercing element is a microneedle. In some embodiments, the needle is configured to penetrate a stratum corneum of the subject. In some embodiments, the piercing element is configured to penetrate into a dermis of the subject. In some embodiments, one or more sidewalls of the piercing element are reflective. In some embodiments, one or more sidewalls of the needle are reflective. In some embodiments, the needle comprises a structural domain, a barrier domain, and a sensing domain. In some embodiments, the structural domain is positioned on a surface of the support and extends outward from the surface to define a needle, and defines an interior space, wherein the sensing domain is contained within the interior space. In some embodiments, the needle comprises a well. In some embodiments, the sensing domain is contained within the well. In some embodiments, the barrier domain coats an exterior surface of the structural domain. In some embodiments, the structural domain defines one or more opening on a lateral face of the needle. In some embodiments, the structural domain defines pyramidal needles. In some embodiments, the structural domain defines pyramidal needles comprising an opening on each face of the pyramidal needles. In some embodiments, the barrier domain coats the openings. In some embodiments, the barrier domain contacts a portion of the sensing domain. In some embodiments, the barrier domain contacts a portion of the sensing domain at the openings. In some embodiments, the needle comprises a structural domain, and the sensing domain. In some embodiments, the structural domain encapsulates the barrier domain. In some embodiments, the structural domain encloses the sensing domain. In some embodiments, the sensing domain encapsulates the analyte binding probe within a matrix of the sensing domain, wherein the barrier domain comprises a hydrogel, a polymer, or combinations thereof. In some embodiments, the sensing domain comprises the analyte binding probe. In some embodiments, the sensing domain comprise the analyte binding probe in a hydrogel matrix. In some embodiments, the sensing domain encapsulates the analyte binding probe in a hydrogel matrix. In some embodiments, the analyte binding probe is attached to hydrogel by conjugation methods comprising: DBCO-Azide, BCN-Tetrazine, biotin-streptavidin, EDC, NHS/EDC, thiol maleimide, DBCO-N3, DBCO-DHPA, BCN-N3, or any combination thereof. In some embodiments, the hydrogel is produced from Cu-click reactions. In some embodiments, the hydrogel is produced from Cu-free click reaction. In some embodiments, the sensing domain encapsulates the analyte binding probe within a matrix of the sensing domain. In some embodiments, the barrier domain comprises a hydrogel, a polymer, or combinations thereof. In some embodiments, the structural domain encapsulates the sensing domain, wherein the sensing domain is configured to control transfer of the analyte to analyte binding probe. In some embodiments, the barrier domain coats a portion of the sensing domain, wherein the barrier domain is configured to control transfer of the analyte to sensing domain. In some embodiments, the barrier domain is configured to control transfer of the analyte to sensing domain via diffusion. In some embodiments, the sensing domain is configured to control transfer of the analyte to analyte binding probe via diffusion. In some embodiments, the sensing domain comprises a plurality of pores. In some embodiments, the barrier domain comprises a plurality of pores. In some embodiments, the structural domain comprises one or more openings on an exterior surface of the structural domain. In some embodiments, the one or more openings is configured to allow the analyte to contact the sensing domain. In some embodiments, the sensing domain defines a passage connecting the one or more openings to the analyte binding probe. In some embodiments, the needle comprises a plurality of openings. In some embodiments, the needle comprises a structural domain comprising a hollow region of the needle. In some embodiments, the hollow region is orientated in a longitudinal direction. In some embodiments, the plurality of openings are positioned on a lateral face of the needle. In some embodiments, the plurality of openings are positioned on opposing lateral faces of the needle. In some embodiments, the sensing domain extends longitudinally into the needle. In some embodiments, the sensing domain extends longitudinally into the needle and defines a passage connecting the one or more openings to the analyte binding probe. In some embodiments, there is one opening on a lateral surface of the needle. In some embodiments, the structural domain is directly in contact with the sensing domain. In some embodiments, the structural domain and the sensing domain extends longitudinally from the device. In some embodiments, the sensing domain is positioned orthogonally to a longitudinal axis of the needle. In some embodiments, the sensing domain is positioned orthogonally to a longitudinal axis of the needle, wherein the sensing domain is positioned parallel to a longitudinal axis of the needle. In some embodiments, the sensing domain is positioned on the exterior surface of the structural domain. In some embodiments, the barrier domain is positioned on the exterior surface of the structural domain, and wherein the sensing positioned within an interior space of the structural domain. In some embodiments, the barrier domain is positioned on the exterior surface of the structural domain, positioned within an interior space of the structural domain, and wherein the sensing domain is positioned within the structural domain an in contact with the barrier domain positioned within an interior space of the structural domain. In some embodiments, the barrier domain is positioned on the exterior surface of the structural domain and wherein the barrier domain is positioned within an interior space of the structural domain, and wherein the sensing domain is positioned within the structural domain orthogonally to a longitudinal axis of the needle, and is in contact with the barrier domain positioned within an interior space of the structural domain. In some embodiments, the barrier domain is positioned on the exterior surface of the structural domain and wherein the barrier domain is positioned within an interior space of the structural domain, and wherein the sensing domain is positioned throughout a matrix of the barrier domain. In some embodiments, the barrier domain is partially within an interior space of the structural domain. In some embodiments, the sensing domain is within an interior space of the structural domain and is exposed to an exterior surface of the needle through the one or more openings, and wherein the analyte binding probe is positioned throughout a matrix of the sensing domain. In some embodiments, the barrier domain is positioned on the exterior surface of the structural domain and wherein the sensing domain is positioned within an interior space of the structural domain, and wherein the analyte binding probe is positioned throughout a matrix of the sensing domain, wherein there are at least two opening on opposing lateral faces of the needle. In some embodiments, the analyte binding probe is contained within the sensing domain at a concentration of about 1 nM to about 1 mM. In some embodiments, the analyte binding probe is contained within the sensing domain at a concentration of about 1 nM to about 1 uM. In some embodiments, the analyte binding probe is distributed substantially uniformly dispersed throughout the barrier domain. In some embodiments, the needle has a length of at least about 3 millimeters. In some embodiments, the needle has a length of at least about 1 millimeter. In some embodiments, the needle has a length of at least about 500 micrometers. In some embodiments, the needle has a length of at least about 100 micrometers. In some embodiments, the needle is a 3-dimensional printed needle. In some embodiments, the needle is a hydrogel needle. In some embodiments, the needle is a polymer. In some embodiments, the needle comprises a cavity filled with a hydrogel matrix. In some embodiments, the barrier domain comprises a hydrogel matrix. In some embodiments, wherein the microneedle is solid. In some embodiments, the microneedle has a hollow core. In some embodiments, the microneedle is porous. In some embodiments, the microneedle is a swellable microneedle. In some embodiments, the device comprises a plurality of piercing elements, wherein the plurality of piercing elements comprises the piercing element. In some embodiments, at least one piercing element of the plurality of piercing element is coupled to a control reference probe. In some embodiments, the device is configured to perform a single time-point measurement of the analyte. In some embodiments, the device is configured to perform continuous, real-time measurement of the analyte. In some embodiments, the device is configured to present some information related to the analyte. In some embodiments, the information includes a presence of the analyte. In some embodiments, the information includes a concentration of the analyte. In some embodiments, the detector comprises a semiconductor material. In some embodiments, the detector comprises a semiconductor photodetector. In some embodiments, the detector comprises a semiconductor photodetector comprising a silicon photomultiplier chip, an avalanche photodiode, a metal-semiconductor-metal photodiode, a CMOS sensor array, a CCDs (charge coupled device), a lateral semiconductor photodiode, an array of photodetectors, or combinations thereof. In some embodiments, the semiconductor material or the semiconductor photodetector comprises an p-n junction. In some embodiments, the semiconductor material or the semiconductor photodetector comprises Si, Ge, InGaAs, GaAs, InP, Ge, SiGe, InGaN, GaN, or combinations thereof. In some embodiments, the detector comprises a silicon photomultiplier (SiPM) detector. In some embodiments, the SiPM detector has a dimension up to about 1 cm. In some embodiments, the SiPM detector has a dimension up to about 3 millimeters. In some embodiments, the device further comprises a battery. In some embodiments, the device further comprises a wireless communication configured to communicate with an external device to exchange the information. In some embodiments, the device is a skin patch. In some embodiments, the skin patch is removable. In some embodiments, the device is configured to emit the optical signal when the analyte contacts the analyte binding probe. In some embodiments, the device is configured to result in a decrease in optical signal when the analyte binding probe is bound to the analyte. In some embodiments, the device is configured to emit the optical signal in a default configuration when not in contact with the analyte. In some embodiments, the analyte binding probe emits the optical signal, and does not emit the optical signal when bound to the analyte. In some embodiments, the analyte binding probe emits the optical signal, and undergoes the conformational change when bound to the analyte as to not emit the optical signal. In some embodiments, the analyte binding probe emits the optical signal, and undergoes the conformational change when bound to the analyte as to emit a reduced optical signal. In some embodiments, the device measures a concentration of the analyte in the biological sample of the subject by measuring a decrease in the optical signal. In some embodiments, the device further comprises an LED array. In some embodiments, the device further comprises an LED driver. In some embodiments, the device further comprises a temperature sensor. In some embodiments, the device further comprises an MCU, a Bluetooth low energy model, or a CMOS image sensor, or combinations thereof.

Provided herein is a method for sensing an analyte in a biological sample of a subject, comprising: (a) piercing a skin of the subject to contact a biological sample; (b) bringing the biological sample in contact with an analyte binding probe; (c) inducing a conformational change in the analyte binding probe by binding a target analyte with the analyte binding probe; (d) applying a light source to the analyte binding probe to produce an optical signal, and e measuring a presence, a lack of presence, an increase, or a decrease of the optical signal to determine the presence or concentration of the target analyte in the sample. In some embodiments, the method further comprises passing light through an optical waveguide from a light source to the analyte binding probe. In some embodiments, the method further comprises passing light through the optical waveguide from the analyte binding probe to a detector.

Another aspect of the present disclosure provides a non-transitory, computer-readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

FIGS. 2A-2B represents a top view of an exemplary device of an array (FIG. 2A) comprising a light source, a detection circuit, and a photodetector (FIG. 2B).

FIGS. 4A-4H illustrate different microneedle configurations comprising a structural domain, a barrier domain, a sensing domain, and one or more analyte binding sensors.

In FIG. 5A shown is a coupling embodiment between the light guide and the microneedle where the coupling region of the microneedle is substantially index-matched with the light guide core; as light bounces around it continues to travel without deflection into the microneedles and reaches the sensing domain in the microneedles. In FIG. 5B shown is a coupling embodiment between the light guide and the microneedle where the coupling region of the microneedle has a higher index material than the core of the light guide, turning the light inward toward the microneedle. In FIG. 5C, reflective sidewalls about a base of a light guide base aid in directing more light toward the detector situated at the top of the waveguide through reflection from the sidewalls.

FIGS. 6A-6C show an exemplary device to detect analytes of interest with exemplary removable sensing portions. In FIG. 6A, the light guide is part of the reusable sensor hardware; in FIG. 6B the light guide is part of disposable microneedle array; and in FIG. 6C the light guide is partially in both sensor hardware and in the microneedle array.

FIG. 38A shows the front view of the sensor. FIG. 38B shows the back view of the sensor.

FIG. 39A shows the packaged reusable part from the backside. FIG. 39B shows an exploded view of the main layers and components inside the reusable part of the sensor.

FIG. 40 shows a cross sectional view of the reusable and disposable parts of the sensor depicted in FIG. 38.

FIG. 41 shows a magnified view of FIG. 40 with more detailed depictions of the layers and showing all of the layers described in detail in the disclosure.

FIG. 42 shows a slightly tilted view of the sensor depicted in FIG. 40 with the same layers depicted in FIG. 41.

FIG. 48 is an exploded view of the components inside the reusable sensor.

DETAILED DESCRIPTION

Overview

Figure 1:
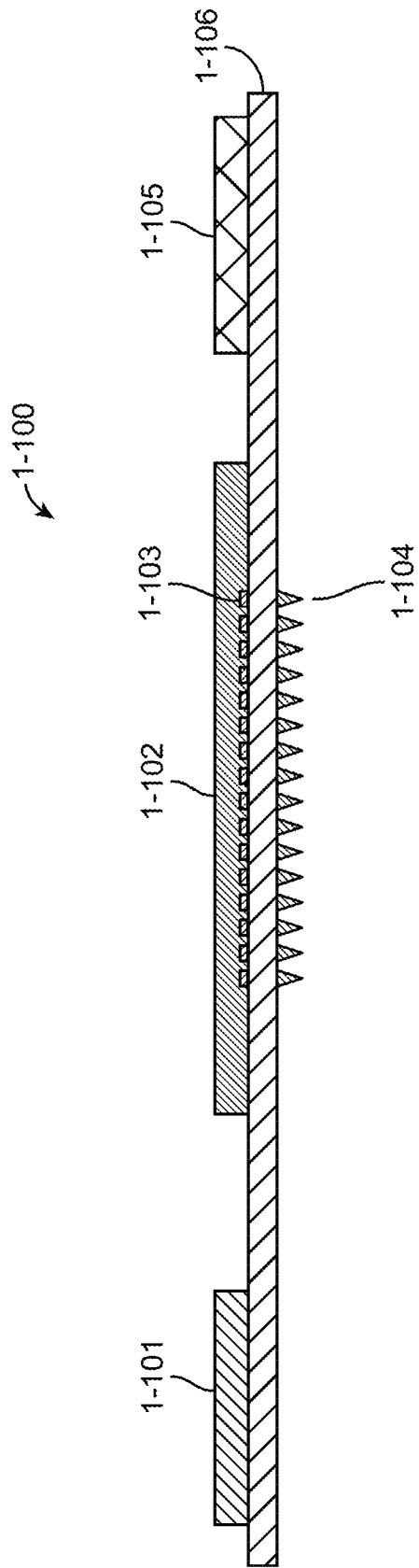
FIG. 1 represents an exemplary device to detect analyte(s) of interest, wherein the support does not include a waveguide, in accordance with an example embodiment.

Responsive to the unmet need for improved biosensors which can perform an assay for analyte detection at the point of care which can deliver a result to a subject shortly following sample collection, and improved biosensors which can perform multiplexed or continuous assays for ongoing monitoring of an analyte; disclosed herein are biosensors for minimally invasive, continuous, real-time measurement of one or more target analytes in the body of a subject from a biological sample, and monitoring of concentration of one or more target analytes in the body of a subject from a biological sample. The present disclosure provides devices for detection of one or more analytes at the point of care, and for ongoing monitoring of analytes at the point of care. The device may utilize optical detection modalities to detect the presence and concentration of an analyte in a sample, and provide for structures to distribute light to a detection element of the device for detection of one or more target analytes. Various aspects of the present disclosure describe a system and method to monitor analytes in a subject from a bodily fluid of a subject, for example, from skin interstitial fluid (ISF). The detection of these analytes (e.g., biomarkers) may include a plurality of piercing elements that can penetrate into the skin, a support attached to the piercing element, and an analyte binding probe.

In the present disclosure, solutions to the problem of detecting small concentrations of analytes in the interstitial fluid utilizing a wearable patch with an optical sensor are presented. Previous implementations of wearable patches with optical sensors have suffered from a low quantity of light, and a loss of light during transmission about optical excitation and optical emission paths, resulting in lower sensitivity of analyte detection. The present disclosure proposes solutions to this problem by improving the optical coupling efficiency in the optical sensor. For example, some embodiments optimize the optical excitation path by utilizing a waveguide and an optical coupler and comprising one or more focusing elements configured to focus light from a light source towards the light coupler. Some embodiments optimize the optical excitation path with a reflective cladding layer surrounding the waveguide, which is configured to reflect the light back inside the waveguide and guide the light toward the piercing element. Some embodiments optimize the optical excitation path by configuring the light coupler to couple light from a light source into the waveguide.

Some embodiments of the present disclosure optimize the optical emission path, and allow the detection of very small levels of emission light, which is in some cases orders of magnitude small than an excitation light. In some embodiments, apertures in a reflective cladding layer surrounding a waveguide are configured to transmit an emission light from the analyte probe towards the detector. In some embodiments, one or more focusing elements are configured to focus emission light from the analyte binding probe towards the detector. In some embodiments, the optical excitation path and the optical emission path are configured to minimize interference with each other. In some embodiments, optical filters in combination transmit emission light while substantially blocking light which is a same wavelength as excitation light. The present disclosure also provides solutions to the problem of how to develop a sensor that is sufficiently small enough to comprise a wearable patch. In some embodiments, a solution to this problem is to design a waveguide that can transmit both excitation and emission light in one device. This allows for the sensor to be more effectively miniaturized and compacted. However, utilizing a waveguide which is both a component of the optical emission path and optical excitation path presents problems associated with the detection of the emission light, which is in some cases orders of magnitude small than an excitation light. In some cases, the waveguide transmits light from a light source to the analyte binding probe, and waveguide is configured to permit light to be transmitted through the waveguide from the analyte binding probe to the detector. In some cases, the waveguide transmits light from a light source to the analyte binding probe through a directed path in the wave guide, in which light is reflected using one or more reflective walls. In some cases, the waveguide transmits light from the analyte binding probe to a detector using an optical emission path that is directly aligns the analyte binding probe with the detector about the optical emission path.

The present disclosure also provides solutions to problems related to detecting analytes in more flexible or sensitive ways. In some embodiments, the analyte binding probes that bind to the analyte can be attached to one or more particles within a hydrogel matrix inside the piercing element. Having the particles physically entrapped by the hydrogel solves the problem of decoupling any conjugation chemistry compatibility requirements between the hydrogel and the aptamers. In addition, the user can QC/QA the particles prior to inserting into the device, which has advantages for reproducibility and consistency during the manufacturing process.

Previous implementations of wearable patches with optical sensors have suffered from a low quantity of light and a loss of light, resulting in lower sensitivity of analyte detection. Optimizing the optical excitation path is one feature in the present disclosure that provides the beneficial technical effect of improving the optical coupling efficiency in the optical sensor. Improving the optical coupling efficiency has the beneficial technical effect of decreasing the power level and battery size needed in the device. In some embodiments, the optical excitation path is optimized by utilizing a waveguide and an optical coupler and comprising one or more focusing elements configured to focus light from a light source towards the light coupler. Some embodiments optimize the optical excitation path with a reflective cladding layer surrounding the waveguide, which is configured to reflect the light back inside the waveguide and guide the light toward the piercing element. Some embodiments optimize the optical excitation path by configuring the light coupler to couple light from a light source into the waveguide.

Optimizing the optical emission path can provide the beneficial technical effect of allowing the device to detect smaller amounts of emission light. This allows for a smaller detector, which would allow for the beneficial technical effect of improving the miniaturizability and compactness of the device. In some embodiments, apertures in a reflective cladding layer surrounding a waveguide are configured to transmit emission light from the analyte probe towards the detector. In some embodiments, one or more focusing elements are configured to focus emission light from the analyte binding probe towards the detector. In some embodiments, the optical excitation path and the optical emission path are configured to minimize interference with each other. In some embodiments, optical filters in combination transmit emission light while substantially blocking light which is a same wavelength as excitation light.

In some embodiments, the present disclosure comprises a waveguide that can transmit both excitation and emission light in a single device. This has the beneficial technical effect of allowing for the sensor to be more efficiently miniaturized and compacted, and possibly creating a sensor that is sufficiently small enough to comprise a wearable patch. However, utilizing a waveguide which is both a component of the optical emission path and optical excitation path presents problems associated with the detection of the emission light, which is in some cases orders of magnitude small than an excitation light. In some cases, the waveguide transmits light from a light source to the analyte binding probe, and waveguide is configured to permit light to be transmitted through the waveguide from the analyte binding probe to the detector. In some cases, the waveguide transmits light from a light source to the analyte binding probe through a directed path in the wave guide, in which light is reflected using one or more reflective walls. In some cases, the waveguide transmits light from the analyte binding probe to a detector using an optical emission path that is directly aligns the analyte binding probe with the detector about the optical emission path.

The present disclosure also provides beneficial technical effects related to detecting analytes in more flexible or sensitive ways. In the present disclosure, the analyte binding probes that bind to the analyte can be attached to one or more particles within a hydrogel matrix inside the piercing element. Having the particles physically entrapped by the hydrogel provides the beneficial technical effect of decoupling any conjugation chemistry compatibility requirements between the hydrogel and the aptamers. In addition, the user can QC/QA the particles prior to inserting into the device, which has beneficial technical effects of reproducibility and consistency during the manufacturing process.

In some embodiments, the piercing element may be removable, interchangeable, or disposable. In some embodiments, the piercing element may comprise needles. In some embodiments, the needle may comprise microneedles. In some embodiments, the piercing element is configured to pierce a body surface of the subject when the device is coupled to the body surface, to thereby bring the piercing element in contact with the biological sample. In some embodiments, the piercing element comprises an analyte binding probe on or within the piercing element, wherein the analyte binding probe is configured to provide a change in an optical signal when the analyte binding probe comes in contact with the analyte in the biological sample of the subject. In some embodiments, the device comprises a detector operatively coupled to the support, wherein the detector is configured to detect the optical signal. In some embodiments, the device may comprise two or more analyte binding probes within the piercing element, where each of the two or more analyte binding probes provides a change in an optical signal when the two or more analyte binding probes contacts a second analyte in the biological sample of the subject. In some embodiments, the device uses a multiplexed array of analyte binding probes on or within the piercing element, each of the multiplexed array of analyte binding probes configured to provide a change in an optical signal when the multiplexed array of analyte binding probe contacts a subsequent analyte in the biological sample of the subject. In some embodiments, the subsequent analyte is a different analyte, and the multiplexed array of analyte binding probes is configured to detect a plurality of analytes in the biological sample of the subject. In some embodiments, the piercing element comprises a plurality of piercing elements which defines subsets of piercing elements, wherein each subset of piercing elements comprises a different analyte binding probe configured to detect a different analyte in the biological sample of the subject. In some embodiments, the subsets of piercing elements comprising the different analyte binding probes comprises the multiplexed array of analyte binding probes. The multiplexed array of analyte binding probes can be spatially multiplexed within the piercing element.

The device may comprise a light source, configured to shine one or more beams of light of one or more wavelengths to the analyte binding probe. The support may comprise an optical light guide or an optical waveguide, which can guide or collect a portion of optical signal (e.g., light) to and from the piercing element. The optical signal detected may comprise a) fluorescence intensity b) FRET ratio, c) time-resolved fluorescence (via phosphorescence), d) decay curve monitoring (detecting the lifetime of the phosphorescence reporter), or e) combinations thereof. The optical light guide or optical waveguide may define one or more optical paths connecting the light source to the analyte binding probe, and the analyte binding probe to the detector. In another embodiment, the support may attach directly to the piercing element, and the light source may attach directly to the piercing element, and there may not be an optical light guide or optical waveguide. The optical waveguide may comprise a 2-dimensional array of light guides. The 2-dimensional array may comprise dichroic mirrors, and the 2-dimensional array may comprise gratings, or be etched. The optical waveguide may comprise a polymer glassy matrix comprising dispersed photoluminescent particles. The polymers may include: polysiloxanes, silsequioxanes, polymethylmethacrylate (PMMA), polystyrene (PS), polycarbonate (PC), polyurethane (PU), epoxy resin, deuterated and halogenated polyacrylates, fluorinated polyimides, perfluorocyclobutyl (PFCB) aryl ether polymers, nonlinear optical polymers, benzocylcobutene (BCB), perfluorovinyl ether cyclopolymer (CYTOP), tetrafluoroethylene and perfluorovinyl ether copolymer (Teflon AF), silicone, fluorinated poly(arylene ether sulfide), poly(pentafluorostyrene), fluorinated dendrimers, fluorinated hyperbranched polymers, or combinations thereof. The optical waveguide may couple to a light source, to guide at least a portion of light from the light source along a length of the optical light guide, and to divert at least a portion of the light from the light guide to the piercing element. The optical light guide may provide a light transmission efficiency of 1, 5, 10, 15, 20, 25, 30, 35, 40, 45, 50, 55, 60, 65, 70, 75, 80, 85, 90, 95, or 99% transmission efficiency, and may provide the same from the light source to the piercing element. The optical waveguide may collect an emission light of the optical reporter from the analyte binding probe, to guide at least a portion of the emission light to the detector. The optical waveguide may provide an essentially lossless light transmission from the piercing element to the detector, or provide a light transmission efficiency of at least 10% transmission efficiency from the piercing element to the detector. The optical waveguide may provide an essentially lossless light transmission from the piercing element to the detector, or provide a light transmission efficiency of 1, 5, 10, 15, 20, 25, 30, 35, 40, 45, 50, 55, 60, 65, 70, 75, 80, 85, 90, 95, or 99 from the piercing element to the detector.

The optical waveguide may define a plurality of paths from the light source to the piercing element. The light source may provide light in different wavelengths, and the light source may have a plurality of light sources each configured to provide a different wavelength of light. The optical light guide may include a plurality of paths from the light source to the piercing element and comprises one or more distinct paths from the light source to the multiplexed array of analyte binding probes. The at least one of the plurality of paths may guide light from one of the plurality of light sources with a specific wavelength of light to one of the analyte binding probes in the multiplexed array of analyte binding probes which is responsive to the specific wavelength of light. The plurality of paths from the light source to the piercing element may include one or more distinct paths from the light source to the subsets of piercing elements. The plurality of paths may guide light from one of the plurality of light sources with a specific wavelength of light to one of the analyte binding probes in the subsets of piercing elements. The optical waveguide may include one or more switches configured to block one or more of the plurality of paths.

The device may have the piercing element coupled to the support using one or more holes, one or more insertable elements configured to attach to a corresponding one or more receiving elements, a lock and key attachment, a mortise and tenon attachment, a dovetail attachment, a magnetic attachment, an adhesive, one or more elastically deformable attachment elements, the elastically deformable attachment elements rebounding once inserted into the support. The piercing element may be removably coupled to the support.

The light source may include light-emitting diodes (LEDs) or lasers; or a plurality of light-emitting diodes (LEDs) or lasers, each of the plurality of light-emitting diodes (LEDs) or lasers configured to deliver a different wavelength of light.

The analyte binding probe may be coupled to an optical reporter, where the optical reporter is a fluorophore or a quencher. The analyte binding probe may be an oligonucleotide probe, or an aptamer. The aptamer may be coupled to a displacement strand, wherein the displacement strand is partially complementary to the aptamer. The displacement strand may be coupled to a second optical reporter, where the second optical reporter is a fluorophore or a quencher, and wherein the aptamer is coupled to a linker moiety placed between the aptamer and the displacement strand. The linker moiety can be a nucleotide acid moiety, a peptide nucleic acid (PNA) moiety, a peptide moiety, a disulfide bond, a phosphodiester linkage, or a polymer. The analyte binding probe may undergo a conformational change when the analyte interacts with the analyte binding probe, thereby providing a change in optical signal, for example, an emission light, or an emission light which is a function of a concentration of the analyte.

The piercing element may include a structural domain, a barrier domain, a sensing domain, and the analyte binding probe. The structural domain can encapsulate the barrier domain, and the barrier domain can encapsulate the analyte binding probe, for example, within a matrix of the barrier domain, where the barrier domain includes a hydrogel, a polymer, or combinations thereof. The barrier domain may control transfer of the analyte to analyte binding probe, for example, via diffusion. A variety of configurations may be utilized for the piercing element and the structural domain, the barrier domain, and the analyte binding probe, for example: where the structural domain includes one or more openings on an exterior surface of the structural domain; where the one or more openings are configured to allow the analyte to contact the barrier domain; where the barrier domain defines a passage connecting the one or more openings to the analyte binding probe; where the needle includes a structural domain with a plurality of openings; where the needle includes a structural domain comprising a hollow region of the needle; where the hollow region is orientated in a longitudinal direction; where the plurality of openings are positioned on a lateral face of the needle; where the plurality of openings are positioned on opposing lateral faces of the needle; where the barrier domain extends longitudinally into the needle; where the barrier domain extends longitudinally into the needle and defines a passage connecting the one or more openings to the analyte binding probe; where there is one opening on a lateral surface of each needle; where the structural domain is directly in contact with the analyte binding probe; where the structural domain and the analyte binding probe extend longitudinally from the device; where the analyte binding probe is positioned orthogonally to a longitudinal axis of the needle; the analyte binding probe is positioned orthogonally to a longitudinal axis of the needle, where the barrier domain is positioned parallel to a longitudinal axis of the needle; the barrier domain is positioned on the exterior surface of the structural domain; where the barrier domain is positioned on the exterior surface of the structural domain, and positioned within an interior space of the structural domain; where the barrier domain is positioned on the exterior surface of the structural domain, positioned within an interior space of the structural domain, and where the analyte binding probe is positioned within the structural domain and in contact with the barrier domain positioned within an interior space of the structural domain; where the barrier domain is positioned on the exterior surface of the structural domain and where the barrier domain is positioned within an interior space of the structural domain, and where the analyte binding probe is positioned within the structural domain orthogonally to a longitudinal axis of the needle, and is in contact with the barrier domain positioned within an interior space of the structural domain; where the barrier domain is positioned on the exterior surface of the structural domain and where the barrier domain is positioned within an interior space of the structural domain, and where the analyte binding probe is positioned throughout a matrix of the barrier domain; where the barrier domain is within an interior space of the structural domain, and where the analyte binding probe is positioned throughout a matrix of the barrier domain; where the barrier domain is within an interior space of the structural domain and is exposed to an exterior surface of the needle through the one or more openings, and where the analyte binding probe is positioned throughout a matrix of the barrier domain; where the barrier domain is positioned on the exterior surface of the structural domain and where the barrier domain is positioned within an interior space of the structural domain, and where the analyte binding probe is positioned throughout a matrix of the barrier domain, where there are at least two openings on opposing lateral faces of the needle, or combinations thereof. The analyte binding probe is comprised within the barrier domain at a concentration of about 1 nM to about 1 μmM, and at a about 1 nM to about 1 uM. In some cases, the analyte binding probe is substantially uniformly dispersed throughout the barrier domain.

In some cases, the device may have a signal off configuration where the device is configured to not emit an optical signal when the analyte does not contact the analyte binding probe, or will emit a reduced signal when the analyte contacts the analyte binding probe. For example, the analyte binding probes may emit an optical signal in a default configuration when not in contact with an analyte; undergo a conformational change when bound to an analyte as to not emit an optical signal or will undergo a conformational change when bound to an analyte as to emit a reduced optical signal; and the device can measure a concentration of the analyte in the biological sample of the subject by measuring a decrease in the optical signal.

The reader device can detect a change in an optical signal when an analyte binds to the analyte binding probe. In some embodiments, the device may include its own optical sensor, control electronics, and a communication system to exchange data. The analyte information (e.g., analyte concentration, presence) can be sent from the reader to a display device. The display device could be, for example, a wearable, laptop, desktop, handheld, or tablet computer, a mobile phone, or a subsystem of such a device, such as CPU or a display. In some embodiments, the device may comprise the display. The display device can store the data received from the reader, perhaps process the data, and generate display(s) based on the received and/or processed data. In some embodiments, the device may comprise a computer-readable medium configured to induce operation of the device and record the results of one or more tests. The device may comprise a battery, capacitor, a hybrid electrochemical cell or any other suitable power source to provide power to the various components of the device.

The device may be utilized to detect a variety of target analytes for a number of varying consumer and commercial purposes. For instance, the device may be configured as to detect glucose as a measure of metabolic health, fitness, or diabetes; cortisol as a measure of stress, sleep, fitness, or meditation; potassium or sodium as a measure of kidney function or dehydration; bilirubin or bile acids as a measure of liver health; lactate as a measure of fitness, infection, metabolic health, or sepsis; 3-hydroxybutyrate as a measure of ketosis; creatinine as a measure of dehydration, kidney function/health; serum amyloid A (SAA) as a general marker of inflammation, infection, or sepsis; uric acid as a measure of gout, dehydration, kidney health; urea as a measure of liver health, kidney health, dehydration, or fitness; concentration of a therapeutic agent in a patient; hydration levels, and other analytes for various purposes.

Example Systems

FIG. 1 is a block diagram of a device 1-100 for sensing an analyte in a biological sample of a subject, comprising: a support 1-106; a power source 1-101; an array of piercing elements 104 coupled to said support, wherein said piercing element can be configured to pierce a body surface of said subject when said device is coupled to said body surface, thereby bringing said piercing element in contact with said biological sample. Each piercing element can be further coupled to a sensor interface module 1-103 comprising a light source 1-108, a detection circuitry 1-110 and a photodetector 1-105. When an analyte binds to a binding probe, the analyte binding probe may be configured to provide a change in an optical signal. The generated optical signal may be detected by the detector 1-102, and notifies the wearer of the presence of the analyte via a controller 1-102.

Figure 3:
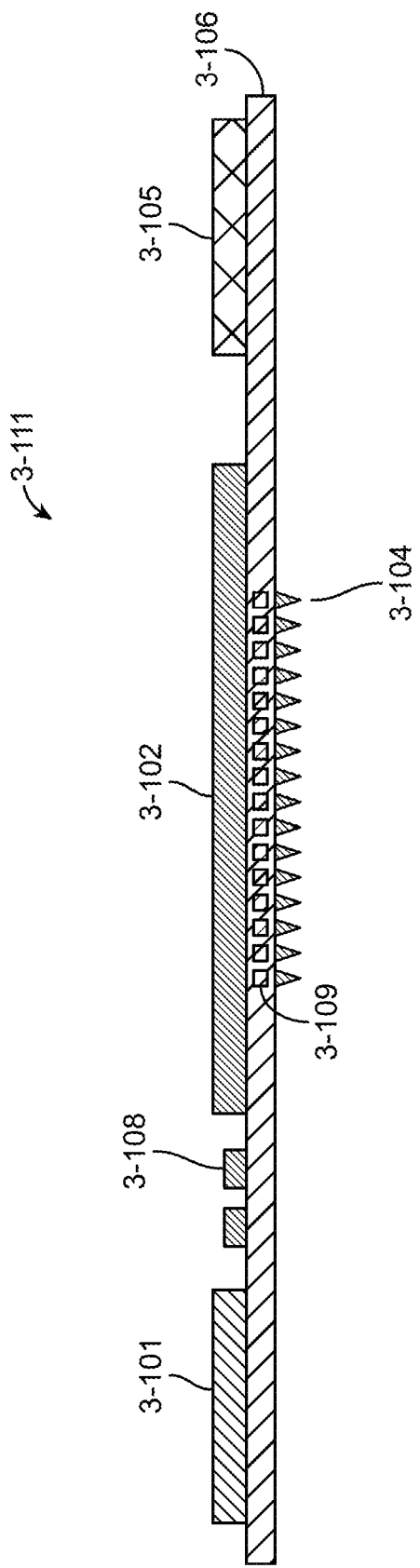
FIG. 3 represent an exemplary device to detect analytes of interest with a waveguide.
Figure 4D:
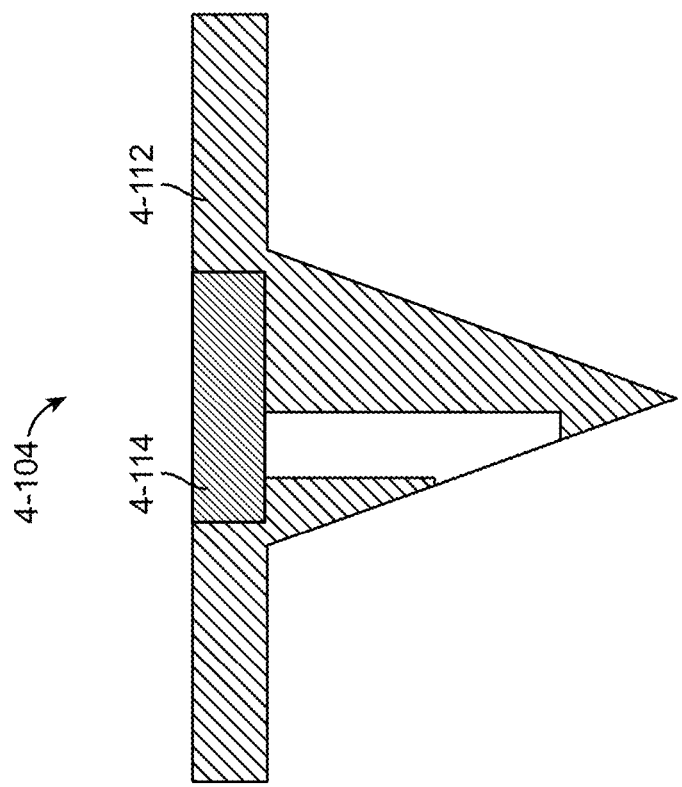
Figure 4C:
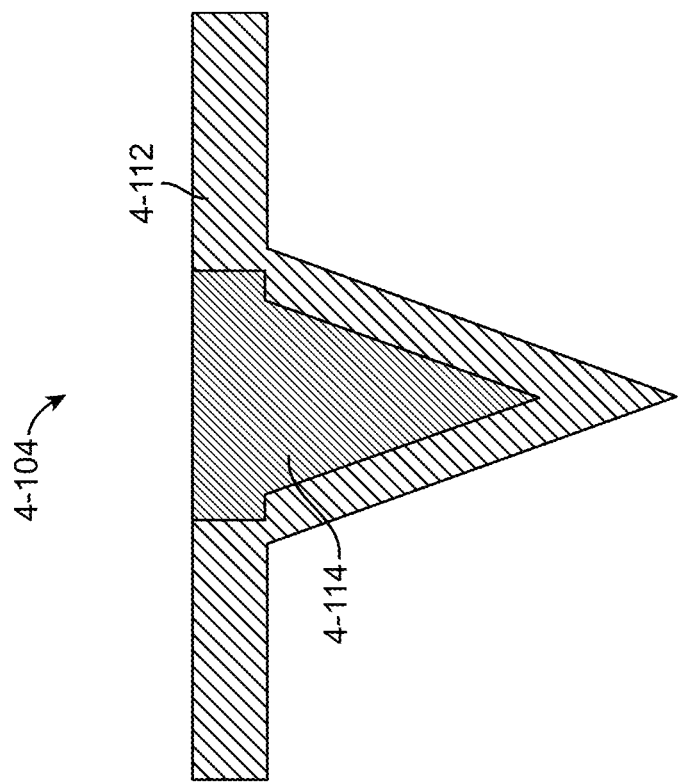
Figure 4F:
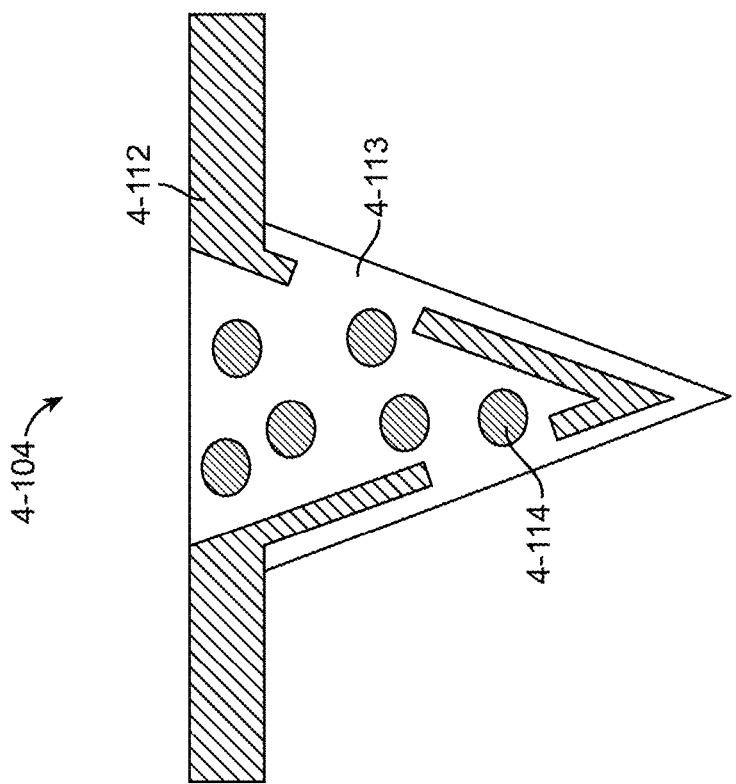
Figure 4E:
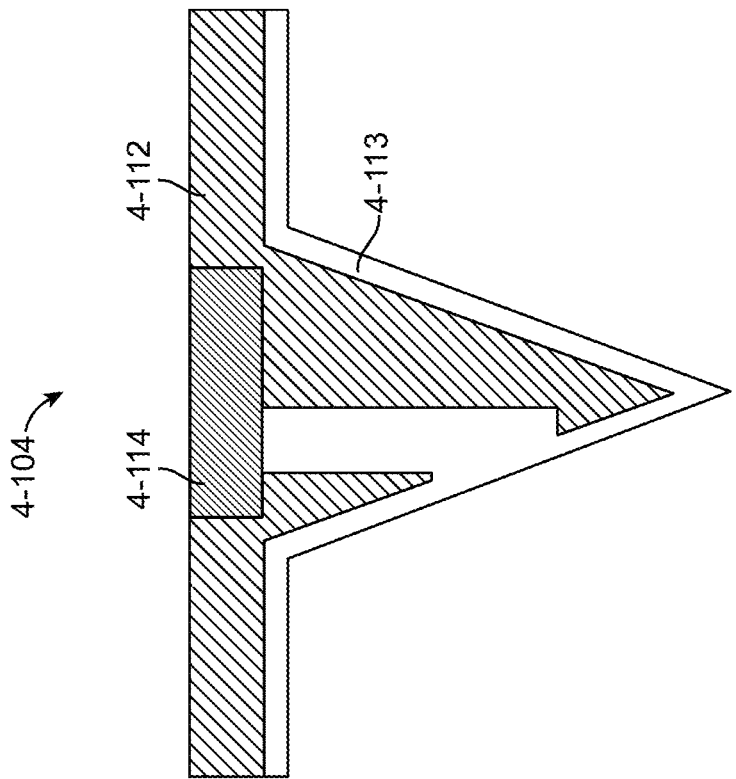
Figure 4H:
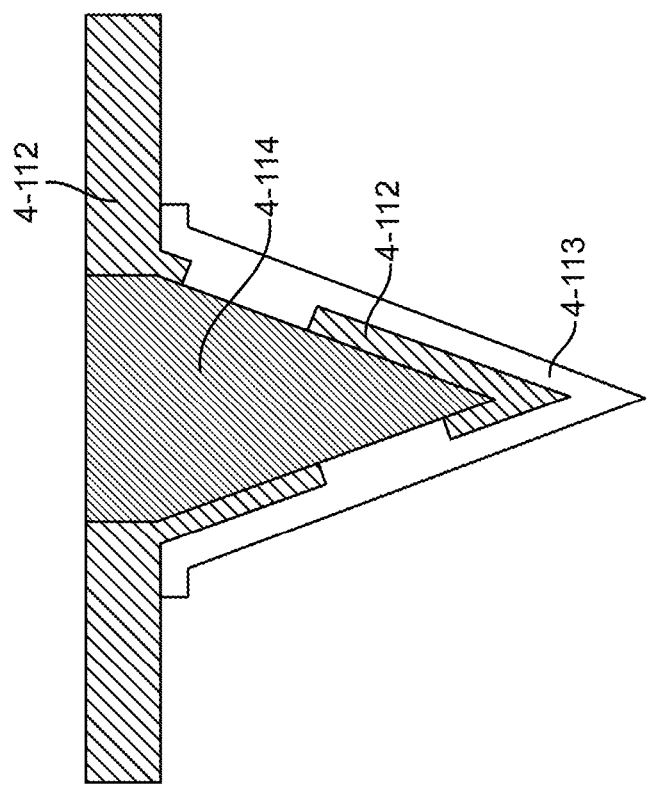
Figure 4G:
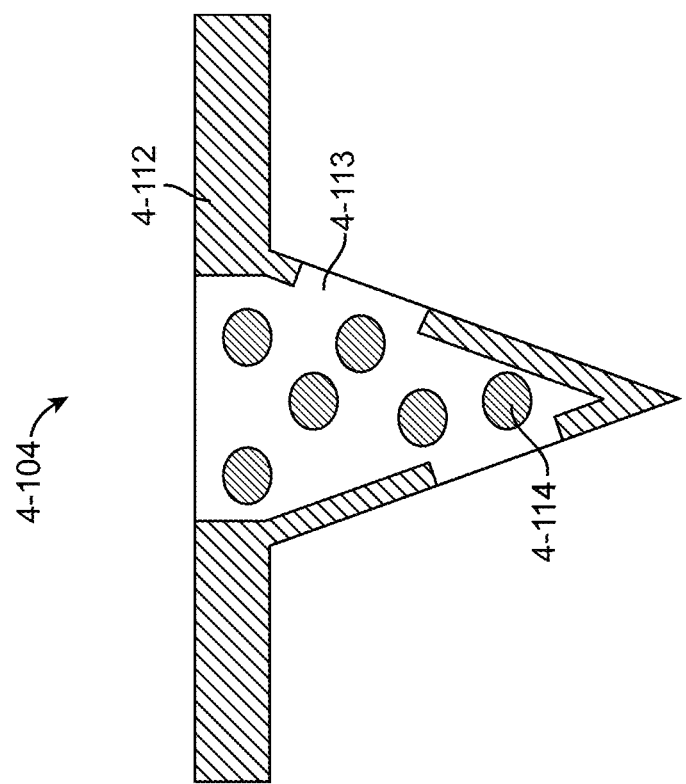

FIG. 3 is a block diagram of a device 3-111 for sensing an analyte in a biological sample of a subject, comprising; a support 3-106; a power source 3-101; an array of piercing elements 3-104 coupled to said support, wherein said piercing element can be configured to pierce a body surface of said subject when said device can be coupled to said body surface, to thereby bring said piercing element in contact with said biological sample. Each piercing element can be coupled to an analyte binding probe on or within said piercing element, wherein said analyte binding probe can be configured to provide a change in an optical signal when said analyte binding probe comes in contact with said analyte in said biological sample of said subject; and a detector 3-102 operatively coupled to said support, wherein said detector can be configured to detect said optical signal. For example, the analyte binding probe may undergo a conformational change from a first configuration to a second configuration when it binds to a particular analyte, and the analyte binding probe may be fluorescent when exposed to light in the second configuration. The device further comprises an optical waveguide 3-109 coupled to said support. The optical waveguide defines a light path between the light source and the analyte binding probe, and from the analyte binding probe to the detector. A light source 3-108 from within the device can be illuminated and applied to optical waveguide, which applies the light source to the analyte binding sensor operatively coupled to a fluorophore and generate optical signal. The generated optical signal can be detected by the detector 3-102, and notifies the wearer of the presence of the analyte via a controller 3-102.

The piercing element 3-104 may comprise a structural domain 3-112, a barrier domain 3-113, and one or more analyte binding sensors 3-114 with various configurations as shown in FIGS. 4A-4H.

Piercing Element

The present disclosure provides a device which includes a plurality of piercing elements having a base end and a tip wherein the piercing elements are configured to penetrate into the skin to contact interstitial fluid, or other bodily fluids. In some embodiments, the piercing element may include one or more skin insertion objects, such as needles, microneedles, lancets, blades, knives, protrusions, or other suitable objects.

In some embodiments, the piercing element may comprise an analyte binding sensor having a detectable optical label and configured to interact with a target analyte present in interstitial fluid, and a structural domain. In some embodiments, the piercing element may comprise an analyte binding sensor, a structural domain, and a barrier domain. The barrier domains are configured such that the interstitial fluid can readily diffuse into the microneedle and interact with the analyte binding probe that may be dispersed throughout the microneedles or contained in a polymer matrix within an interior hollow space of the microneedles. In some embodiments, it is advantageous for the assay components to have a restricted diffusion in order to minimize their loss from the substrates into the bloodstream. This can be achieved by ensuring that the biodegradable material has a pore size that permits the diffusion of low molecular weight analytes such as glucose, but not diffusion of the assay components themselves. The assay components may be of high molecular weight, such as proteins or polymers, in order to restrict their loss from the sensor.

The piercing element may comprise a structural domain, a sensing domain, a barrier domain, and/or analyte binding domain and may be configured in various geometries. The structural domain can be positioned on a surface of the support and extend outward from the surface to define a needle, and define an interior space, wherein the sensing domain is contained within the interior space. The needle can define a well within, where the sensing domain is contained within the well. The barrier domain may comprise a thin layer of a higher molecular weight hydrogel, and the barrier domain can coat an exterior surface of the structural domain. The structural domain can define one or more openings on a lateral face of the needle. In some embodiments, the sensing domain encapsulates the analyte binding probe. In some embodiments, the sensing domain entraps the analyte binding probe. In some embodiments, the structural domain encapsulates the analyte binding probe within a matrix of the sensing domain within a polymer or hydrogel matrix. Any suitable polymer may be used including hydrogels. As used herein, the term "entrap" and variations thereof is used interchangeably with "encapsulate" and is used to mean that the aptamer is immobilized within or on the constituents of the matrix. As used herein, "matrix" refers to essentially a three-dimensional environment which has at least one antigen binding probe immobilized therein for the purpose of measuring a detectable signal from analyte-analyte binding probe interaction. The relationship between the constituents of the matrix and the analyte binding probes includes, but are not limited to, covalent, ionic, and Van der Waals interactions and combinations thereof. The spatial relationship between the matrix and the aptamers includes heterogeneous and homogeneous distribution within and/or upon any or all of the matrix volume.

In some embodiments, the structural domain encapsulates said barrier domain, wherein said barrier domain can be configured to control transfer of said analyte to analyte binding probe. In some embodiments, the structural domain comprises one or more openings on an exterior surface of the structural domain. The one or more openings can be configured to allow said analyte to contact said barrier domain. In some embodiments, the barrier domain defines a passage connecting the one or more openings to the analyte binding probe. In some embodiments, the needle comprises a structural domain with a plurality of openings. In some embodiments, the needle comprises a structural domain comprising a hollow region of the needle. In some embodiments, the hollow region can be orientated in a longitudinal direction. In some embodiments, the plurality of openings can be positioned on a lateral face of the needle. In some embodiments, the plurality of openings can be positioned on opposing lateral faces of the needle. In some embodiments, the sensing domain extends longitudinally into the needle. In some embodiments, the sensing domain extends longitudinally into the needle and defines a passage connecting the one or more openings to the sensing domain with one opening on a lateral surface of the needle. In some embodiments, the structural domain can be directly in contact with the sensing domain. In some embodiments, the structural domain and the sensing domain extend longitudinally from the device. In some embodiments, the sensing domain can be positioned orthogonally to a longitudinal axis of the needle. In some embodiments, the sensing domain can be positioned orthogonally to a longitudinal axis of the needle, wherein the barrier domain can be positioned parallel to a longitudinal axis of the needle. In some embodiments, the barrier domain can be positioned on the exterior surface of the structural domain. In some embodiments, the barrier domain can be positioned on the exterior surface of the structural domain, and positioned within an interior space of the structural domain. In some embodiments, the barrier domain can be positioned on the exterior surface of the structural domain, positioned within an interior space of the structural domain, and wherein the sensing domain can be positioned within the structural domain in contact with the barrier domain positioned within an interior space of the structural domain. In some embodiments, the barrier domain can be positioned on the exterior surface of the structural domain, positioned within an interior space of the structural domain, and wherein the sensing domain can be positioned within the structural domain orthogonally to a longitudinal axis of the needle, and can be in contact with the barrier domain positioned within an interior space of the structural domain. In some embodiments, the barrier domain can be positioned on the exterior surface of the structural domain, positioned within an interior space of the structural domain, and wherein the sensing domain can be positioned throughout a matrix of the barrier domain. In some embodiments, the barrier domain can be within an interior space of the structural domain, and wherein the sensing domain can be positioned throughout a matrix of the barrier domain. In some embodiments, the barrier domain can be within an interior space of the structural domain and can be exposed to an exterior surface of the needle through the one or more openings, and wherein the sensing domain can be positioned throughout a matrix of the barrier domain. In some embodiments, the barrier domain can be positioned on the exterior surface of the structural domain, positioned within an interior space of the structural domain, and wherein the sensing domain can be positioned throughout a matrix of the barrier domain, wherein there are at least two opening on opposing lateral faces of the needle.

In some embodiments, the piercing element may be a microneedle. The microneedle can have straight or tapered shafts. In some embodiments, the diameter of the microneedle can be greatest at the base end of the microneedle and taper to a point or tip at the end distal to the base. The micro-needle can also be fabricated to have a shaft that includes both a straight (untapered) portion and a tapered portion. In some cases, the microneedle comprises a beveled edge to improve insertion into the skin.

In some embodiments, the length of the microneedle can be about 50 μm to about 5 mm. In some embodiments, the length of the microneedle can be about 50 μm to about 100 μm, about 50 μm to about 200 μm, about 50 μm to about 400 μm, about 50 μm to about 600 μm, about 50 μm to about 800 μm, about 50 μm to about 1 mm, about 50 μm to about 1.5 mm, about 50 μm to about 2 mm, about 50 μm to about 3 mm, about 50 μm to about 4 mm, about 50 μm to about 5 mm, about 100 μm to about 200 μm, about 100 μm to about 400 μm, about 100 μm to about 600 μm, about 100 μm to about 800 μm, about 100 μm to about 1 mm, about 100 μm to about 1.5 mm, about 100 μm to about 2 mm, about 100 μm to about 3 mm, about 100 μm to about 4 mm, about 100 μm to about 5 mm, about 200 μm to about 400 μm, about 200 μm to about 600 μm, about 200 μm to about 800 μm, about 200 μm to about 1 mm, about 200 μm to about 1.5 mm, about 200 μm to about 2 mm, about 200 μm to about 3 mm, about 200 μm to about 4 mm, about 200 μm to about 5 mm, about 400 μm to about 600 μm, about 400 μm to about 800 μm, about 400 μm to about 1 mm, about 400 μm to about 1.5 mm, about 400 μm to about 2 mm, about 400 μm to about 3 mm, about 400 μm to about 4 mm, about 400 μm to about 5 mm, about 600 μm to about 800 μm, about 600 μm to about 1 mm, about 600 μm to about 1.5 mm, about 600 μm to about 2 mm, about 600 μm to about 3 mm, about 600 μm to about 4 mm, about 600 μm to about 5 mm, about 800 μm to about 1 mm, about 800 μm to about 1.5 mm, about 800 μm to about 2 mm, about 800 μm to about 3 mm, about 800 μm to about 4 mm, about 800 μm to about 5 mm, about 1 mm to about 1.5 mm, about 1 mm to about 2 mm, about 1 mm to about 3 mm, about 1 mm to about 4 mm, about 1 mm to about 5 mm, about 1.5 mm to about 2 mm, about 1.5 mm to about 3 mm, about 1.5 mm to about 4 mm, about 1.5 mm to about 5 mm, about 2 mm to about 3 mm, about 2 mm to about 4 mm, about 2 mm to about 5 mm, about 3 mm to about 4 mm, about 3 mm to about 5 mm, or about 4 mm to about 5 mm. In some embodiments, the length of the microneedle can be about 50 μm, about 100 μm, about 200 μm, about 400 μm, about 600 μm, about 800 μm, about 1 mm, about 1.5 mm, about 2 mm, about 3 mm, about 4 mm, or about 5 mm. In some embodiments, the length of the microneedle can be at least about 50 μm, about 100 μm, about 200 μm, about 400 μm, about 600 μm, about 800 μm, about 1 mm, about 1.5 mm, about 2 mm, about 3 mm, or about 4 mm. In some embodiments, the length of the microneedle can be at most about 100 μm, about 200 μm, about 400 μm, about 600 μm, about 800 μm, about 1 mm, about 1.5 mm, about 2 mm, about 3 mm, about 4 mm, or about 5 mm.

The cross-sectional dimensions of the micro-needles can be about 1 μm to about 500 am. The cross-sectional dimensions of the micro-needles can be about 1 μm to about 50 μm, about 1 μm to about 100 μm, about 1 μm to about 150 μm, about 1 μm to about 200 μm, about 1 μm to about 250 μm, about 1 μm to about 300 μm, about 1 μm to about 350 μm, about 1 μm to about 400 μm, about 1 μm to about 450 μm, about 1 μm to about 500 μm, about 50 μm to about 100 am, about 50 μm to about 150 μm, about 50 μm to about 200 μm, about 50 μm to about 250 μm, about 50 μm to about 300 μm, about 50 μm to about 350 μm, about 50 μm to about 400 μm, about 50 μm to about 450 μm, about 50 μm to about 500 μm, about 100 μm to about 150 μm, about 100 μm to about 200 μm, about 100 μm to about 250 μm, about 100 μm to about 300 μm, about 100 μm to about 350 μm, about 100 μm to about 400 μm, about 100 μm to about 450 μm, about 100 μm to about 500 μm, about 150 μm to about 200 μm, about 150 μm to about 250 μm, about 150 μm to about 300 μm, about 150 μm to about 350 μm, about 150 μm to about 400 μm, about 150 μm to about 450 μm, about 150 μm to about 500 μm, about 200 μm to about 250 μm, about 200 μm to about 300 μm, about 200 μm to about 350 μm, about 200 μm to about 400 μm, about 200 μm to about 450 μm, about 200 μm to about 500 μm, about 250 μm to about 300 μm, about 250 μm to about 350 μm, about 250 μm to about 400 μm, about 250 μm to about 450 μm, about 250 μm to about 500 μm, about 300 μm to about 350 μm, about 300 μm to about 400 μm, about 300 μm to about 450 μm, about 300 μm to about 500 μm, about 350 μm to about 400 μm, about 350 μm to about 450 μm, about 350 μm to about 500 μm, about 400 μm to about 450 μm, about 400 μm to about 500 μm, or about 450 μm to about 500 am. The cross-sectional dimensions of the micro-needles can be about 1 μm, about 50 μm, about 100 μm, about 150 μm, about 200 μm, about 250 μm, about 300 μm, about 350 μm, about 400 μm, about 450 μm, or about 500 μm. The cross-sectional dimensions of the micro-needles can be at least about 1 μm, about 50 μm, about 100 μm, about 150 μm, about 200 μm, about 250 μm, about 300 μm, about 350 μm, about 400 μm, or about 450 μm. The cross-sectional dimensions of the micro-needles can be at most about 50 μm, about 100 μm, about 150 μm, about 200 μm, about 250 μm, about 300 μm, about 350 μm, about 400 μm, about 450 μm, or about 500 μm. The length can be selected for the particular application, accounting for both an inserted and uninserted portion, and the target bodily fluid to be assayed.

An array of microneedles can include a mixture of microneedles having, for example, various lengths, outer diameters, inner diameters, cross-sectional shapes, and spacings between the microneedles, for example, varying depending on the target patient, target fluid, or target assay. Generally, the microneedles are sized to avoid or minimize contact with nerve endings in the biological tissue, such as the dermis, thereby eliminating or reducing pain when the microneedles are inserted, for example into the skin. The array of microneedles may penetrate into a dermis of the subject.

The microneedles can be oriented perpendicular or at an angle to the substrate. In some embodiments, the microneedles are oriented perpendicular to the substrate to provide structural strength and to permit ease of insertion into the tissue. An array of microneedles can include a mixture of microneedle orientations, heights, spacings, or other parameters. This variation in an array can be useful, for example, if different microneedles are to provide different sensing or insertion functions.

In another embodiment, the microfabricated microneedles can be formed from a polymer that includes the analyte binding probe. The microneedles of the device can be constructed from a variety of polymeric materials, including biocompatible and/or biodegradable polymers. Representative polymers include, without limitation, biodegradable polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polymethacrylic acid, ethylenevinyl acetate, polytetrafluoroethylene (TEFLON™), and polyesters. In one embodiment, the micro-needles can be constructed from materials that are optically transparent and do not interfere with the optical detection of target analytes.

The piercing element may be a removable and replaceable element of the device. Different piercing elements may comprise different analyte binding probes for detection of different analytes using the same device. In some cases, it may be desirable for the piercing element to be a replaceable part of the device as to permit optimal analyte detection over an extended period. In some cases, there may be a foreign body response to the piercing element, which may negatively impact the ability of the analyte binding probe to detect the target analyte. In such cases, it may be desirable to utilize a replaceable piercing element as to permit for highly specific detection of the target analyte which is not negatively impacted by a foreign body response to the piercing element.

The piercing element may comprise an adhesive to aid in attaching the device to the skin of the user. The adhesive may surround the microneedle array such that when adhered to the skin a light-tight seal is formed around the array to prevent inadvertent excitation of the fluorophore in the microneedles. In some embodiments, the device may further comprise an adhesive on one or more surfaces of the device in contact with a skin of the user.

Hydrogel Polymers

In some embodiments, the structural domain, sensing domain and/or the barrier domain may comprise a polymer matrix. The structural domain may comprise a higher molecular and higher density weight hydrogel, as compared to the barrier domain. The barrier domain may comprise a higher molecular and higher density weight hydrogel, as compared to the sensing domain.

The polymer matrix can be in any desirable form or shape including one or more of disk, fiber, cylinder, patch, nanoparticle, microsphere, porous polymer, open cell foam, and combinations thereof providing it permits permeability to analyze. The polymer matrix may additionally prevent leaching of the analyte binding domain from the sensing mechanism. In some cases, the polymer matrix is substantially transparent and permits light from optical sources or any other interrogating signals to or from the reporter group bound to the aptamer to pass through the biosensor. When used in an in vivo application, the biosensor will be exposed to a substantially physiological range of analyte and determination or detection of a change in analyte concentration would be desired whereas the determination or detection includes continuous, programmed, and episodic detection means.

In some embodiments, the polymer matrix comprises an optical transmittance of about 10% to about 99%. In some embodiments, the polymer matrix comprises an optical transmittance of about 10% to about 15%, about 10% to about 25%, about 10% to about 50%, about 10% to about 75%, about 10% to about 80%, about 10% to about 85%, about 10% to about 90%, about 10% to about 95%, about 10% to about 97%, about 10% to about 98%, about 10% to about 99%, about 15% to about 25%, about 15% to about 50%, about 15% to about 75%, about 15% to about 80%, about 15% to about 85%, about 15% to about 90%, about 15% to about 95%, about 15% to about 97%, about 15% to about 98%, about 15% to about 99%, about 25% to about 50%, about 25% to about 75%, about 25% to about 80%, about 25% to about 85%, about 25% to about 90%, about 25% to about 95%, about 25% to about 97%, about 25% to about 98%, about 25% to about 99%, about 50% to about 75%, about 50% to about 80%, about 50% to about 85%, about 50% to about 90%, about 50% to about 95%, about 50% to about 97%, about 50% to about 98%, about 50% to about 99%, about 75% to about 80%, about 75% to about 85%, about 75% to about 90%, about 75% to about 95%, about 75% to about 97%, about 75% to about 98%, about 75% to about 99%, about 80% to about 85%, about 80% to about 90%, about 80% to about 95%, about 80% to about 97%, about 80% to about 98%, about 80% to about 99%, about 85% to about 90%, about 85% to about 95%, about 85% to about 97%, about 85% to about 98%, about 85% to about 99%, about 90% to about 95%, about 90% to about 97%, about 90% to about 98%, about 90% to about 99%, about 95% to about 97%, about 95% to about 98%, about 95% to about 99%, about 97% to about 98%, about 97% to about 99%, or about 98% to about 99%, including increments therein. In some embodiments, the polymer matrix comprises an optical transmittance of about 10%, about 15%, about 25%, about 50%, about 75%, about 80%, about 85%, about 90%, about 95%, about 97%, about 98%, or about 99%. In some embodiments, the polymer matrix comprises an optical transmittance of at least about 10%, about 15%, about 25%, about 50%, about 75%, about 80%, about 85%, about 90%, about 95%, about 97%, or about 98%. In some embodiments, the polymer matrix comprises an optical transmittance of at most about 15%, about 25%, about 50%, about 75%, about 8000, about 85%, about 90%, about 95%, about 97%, about 98%, or about 99%.

The polymer matrix may be prepared from biocompatible materials or incorporate materials capable of minimizing adverse reactions with the body. Adverse reactions for implants include inflammation, protein fouling, tissue necrosis, immune response and leaching of toxic materials.

Hydrogels as polymers are particularly useful. As used herein, the term "hydrogel" is used to indicate a water-insoluble, water-containing polymer network. Numerous hydrogels may be used in the present invention. The hydrogels may be, for example, polysaccharides such as agarose, dextran, carrageenan, alginic acid, starch, cellulose, or derivatives of these such as, e.g., carboxymethyl derivatives, or a water-swellable organic polymer such as, e.g., polyvinyl alcohol, polyacrylic acid, polyacrylamide, polyethylene glycol, copolymers of styrene and maleic anhydride, copolymers of vinyl ether and maleic anhydride and derivates thereof. Derivatives providing for covalently crosslinked networks are preferred. Synthesis and biomedical and pharmaceutical applications of hydrogels have been described by a number of researchers. An exemplary hydrogel matrix derived from a water-soluble, UV crosslinkable polymer comprises poly(vinyl alcohol), N-methyl-4(4'-formylstyryl) pyridinium methosulphate acetal (CAS Reg. No. [107845-59-0]) available from PolyScience Warrington, Pa.

The polymers that are to be used in the hydrogel matrices may be functionalized. That is, the polymers or monomers comprising the polymers can possess reactive groups such that the hydrogel matrices are amenable to chemical reactions, e.g., covalent attachment. As used herein, a "reactive group" is a chemical group that can chemically react with a second group. The reactive group of the polymer or monomers comprising the polymer may itself be an entire chemical entity or it may be a portion of an entire chemical entity, including, but not limited to, single atoms or ions. Further, the second group with which the reactive group can be capable of reacting can be the same or different from the reactive group of the polymer or monomers comprising the polymers. Examples of reactive groups include, but are not limited to, halogens, amines, amides, aldehydes, acrylates, vinyls, hydroxyls and carboxyls. In one embodiment, the polymers or monomers comprising the polymers of the hydrogel should be functionalized with carboxylic acid, sulfate, hydroxy or amine groups. In some embodiments, the polymers or monomers comprising the polymers of the hydrogel are functionalized with one or more acrylate groups. In some embodiments, the acrylate functional groups are terminal groups. The reactive groups of the polymers or monomers comprising the polymers of the matrix may be reactive with any component of the matrix portion of the biosensor, such as, but not limited to, another polymer or monomer within the matrix, a binding protein, and an additive.

Suitable polymers which may be used in the present disclosure include, but are not limited to, one or more of the polymers selected from the group consisting of poly(vinyl alcohol), polyacrylamide, poly (N-vinyl pyrolidone), poly (ethylene oxide) (PEO), hydrolyzed polyacrylonitrile, polyacrylic acid, polymethacrylic acid, poly(hydroxyethyl methacrylate), polyurethane polyethylene amine, poly(ethylene glycol) (PEG), cellulose, cellulose acetate, carboxy methyl cellulose, alginic acid, pectinic acid, hyaluronic acid, heparin, heparin sulfate, chitosan, carboxymethyl chitosan, chitin, collagen, pullulan, gellan, xanthan, carboxymethyl dextran, chondroitin sulfate, cationic guar, cationic starch as well as salts and esters thereof. The polymers of the hydrogel matrix may also comprise polymers of two or more distinct monomers. Monomers used to create copolymers for use in the matrices include, but are not limited to, acrylate, methacrylate, methyl methacrylate, methacrylic acid, alkylacrylates, phenylacrylate, hydroxyalkylacrylates, hydroxyalkylmethacrylates, aminoalkylacrylates, aminoalkylmethacrylates, alkyl quaternary salts of aminoalkylacrylamides, alkyl quaternary salts of aminoalkylmethacrylamides, and combinations thereof. Polymer components of the matrix may, of course, include blends of other polymers.

In some embodiments, the hydrogel can be comprised of poly(ethylene glycol) dimethacrylate (PEGDMA). PEGDMA is commercially available in a variety of molecular weights. For example, PEGDMA is available from at least Aldrich Chemical Co. (Milwaukee, Wis. USA) and from Polysciences, Inc. (Warrington, Pa., USA) and can be synthesized in an assortment of molecular weights. In some embodiments, the hydrogel can be comprised of polymers formed from Cu-click reactions, copper free click reactions (e.g. DBCO-Azide, BCN-Tetrazine), EDC, NHS/EDC, thiol maleimide, etc.), DBCO-N3, DBCO-DHPA, BCN-N3 f, or combinations thereof.

In some embodiments, the hydrogels comprise PEGDMA and at least one acrylate. As used herein, the term acrylate is well understood in the art. Specifically, acrylates are compounds, including but not limited to, polymers, comprising the acrylic group (HC2=CH—C(=O). Examples of acrylates include, but are not limited to, acrylic acid, ethyl acrylate, methacrylic acid, methyl methacrylic acid and acrylamides. In another specific embodiment, the hydrogels comprise more than one acrylate. In a more specific embodiment, the hydrogels comprise a mixture of methacrylate and methyl methacrylate.

The polymers used in the hydrogel matrices can be modified to contain nucleophilic or electrophilic groups. In some embodiments, the polymers may further comprise polyfunctional small molecules that do not contain repeating monomer units but are polyfunctional, i.e., containing two or more nucleophilic or electrophilic functional groups. These polyfunctional groups may readily be incorporated into conventional polymers by multiple covalent bond-forming reactions. For example, PEG can be modified to contain one or more amino groups to provide a nucleophilic group. Examples of other polymers that contain one or more nucleophilic groups include, but are not limited to, polyamines such as ethylenediamine, tetramethylenediamine, pentamethylenediamine, hexamethylenediamine, bis-(2-hydroxyethyl)amine, bis-(2-aminoethyl)amine, and tris-(2-aminoethyl)amine. Examples of electrophilic groups include, but are not limited to, succinimide esters, epoxides, hydroxybenzotriazole esters, oxycarbonylimidazoles, nitrophenyl carbonates, tresylates, mesylates, tosylates, carboxylates, and isocyanates. In one embodiment, the composition comprises a bis-amine-terminated poly(ethylene) glycol.

In some embodiments, the polymers may be crosslinked, either physically or chemically, to form a hydrogel. Physical crosslinking includes, but is not limited to, such nonchemical processes as radiation treatment such as electron beams, gamma rays, x-rays, ultraviolet light, anionic and cationic treatments. The crosslinking of the polymers may also comprise chemical crosslinking, such as covalent crosslinking. For example, a chemical crosslinking system may include, but is not limited to, the use of enzymes, which is well-known in the art. Another example of the chemical covalent crosslinking comprises the use of peroxide. Chemical crosslinking may occur when a crosslinking reagent reacts with at least two portions of a polymer to create a three-dimensional network. Covalent crosslinking may also occur when multifunctional monomers are used during the crosslinking process. For example, an acrylate monomer may be polymerized with a bifunctional acrylate monomer to form a crosslinked polymer. Any crosslinking reagent will be suitable for the present invention, provided the crosslinking reagent will at least partially dissolve in water or an organic solvent and can form the crosslinked polymer. For example, if the polymer is an amine-terminated PEG, the crosslinking reagent should be capable of reacting with the PEG-amine groups and be substantially soluble in water. In another example, (hydroxyethyl methacrylate) and methacrylic acid monomers can be polymerized with poly(ethylene glycol)-bis-alkylacrylate crosslinking agent in water or in dimethylformide to form polymeric hydrogels.

If the crosslinked polymers are functionalized with nucleophilic groups, such as amines (primary, secondary and tertiary), thiols, thioethers, esters, nitrites, and the like, the crosslinking reagent can be a molecule containing an electrophilic group. Examples of electrophilic groups have been described herein. Likewise, if polymers to be crosslinked are functionalized with electrophilic groups, the crosslinking reagent can be a molecule containing a nucleophilic group. It is understood that one skilled in the art can exchange the nucleophilic and electrophilic functional groups as described above without deviating from the scope of the present embodiment. It is also understood that the binding molecule can provide the requisite nucleophilic and electrophilic functional groups. For example, where the binding molecule is a protein, the nucleophilic and electrophilic functional groups may be present as naturally occurring amino acids in the protein, or may be introduced to the protein using chemical techniques described herein. Other general methods for preparing or crosslinking polymers to form hydrogel matrices are well known in the art.

In some embodiments, the analyte binding probe can be encapsulated within a hydrogel (e.g., entrapped within a hydrogel). In some cases, analyte binding probe can be held within hydrogel through steric interactions and/or intermolecular forces. In some cases, the analyte binding probe is covalently bound to the hydrogel. The attachment of the analyte binding probes to the hydrogel should not interfere with the binding of the analyte binding probes to the target ligand. Furthermore, the attachment of the analyte binding probes to the hydrogel should be resistant to degradation. The functional group in one embodiment, a polymer or other component of the hydrogel, serves to couple the analyte binding probe to the hydrogel. The coupling of the analyte binding probe to the hydrogel can be accomplished in any number of ways. For example, coupling reactions between the hydrogel and binding molecule include, but are not limited to, diazonium coupling, isothiocyano coupling, hydrazide coupling, amide formation, disulfide coupling, maleic anhydride coupling, thiolactone coupling, and dichlotriazine coupling. These coupling reactions between two functional groups are well documented, and are considered well known to those skilled in the art. For example, an amino functional group in an analyte binding probe can be covalently coupled to a carboxyl functional group of one or more components of a hydrogel using coupling agents such as 1-ethyl-3-(3-dimethylaminopropyl) carbodiimide hydrochloride (EDC) or dicyclohexylcarbodiimide (DCC). It is understood that the amino and carboxyl functional groups of the binding molecule and one or more components of the hydrogel as described above can be transposed without deviating from the scope of the embodiment.

In some embodiments, the analyte binding probes may be bound encapsulated non-covalently within polymer matrix or scaffold by any suitable means that allows analyte-induced conformational change of the analyte binding probes, retention of the analyte binding probes within the polymer to prevent loss or leaching of the analyte binding probe, and to provide a stable, continuous and reversible sensor response to changing concentrations of the target analyte of interest. For instance, well-established processes for enzyme immobilization in hydrogels may be used.

In some embodiments, the substrate can be made of a biodegradable material or polymer. In another embodiment, the substrate can be coated or embedded within a matrix of biodegradable material or polymer. In some embodiments, the substrate can be retained by an envelope of biodegradable material or polymer, or may be separately covered with biodegradable material or polymer.

In some embodiments, the substrate is suspended within the matrix which comprises the analyte binding probe for detecting or measuring analytes in interstitial fluid. In some embodiments, low molecular weight analytes, such as glucose, can freely diffuse into the matrix from the surrounding interstitial fluid.

Alternatively, the substrate can be made from a solid or gel-like polymer biodegradable material within which the sensor components are mounted or distributed. When injected or implanted cutaneously this solid polymer sensor hydrates and swells, and target analyte penetrates through the structure to encounter the substrate.

Biodegradable materials suitable for use in the coating of the substrate or the construction of the substrate include cross-linked proteins such as human albumin, fibrin gels, polysaccharides such as starch or agarose, polylactides (PLA) such as poly (DL-lactide), polyglycolides (PGA) such as poly (DL-glycolide), poly(lactide-co-glycolides) (PLGA), polyanhydrides, polyorthoesters, fatty acid/cholesterol mixtures that form semi-solid derivates, hyaluronates and liquid crystals of monoolein and water. These materials have the advantage that they are broken down into biologically acceptable molecules which are metabolized and removed from the body via normal pathways.

Microneedle Configuration

Figure 7A:
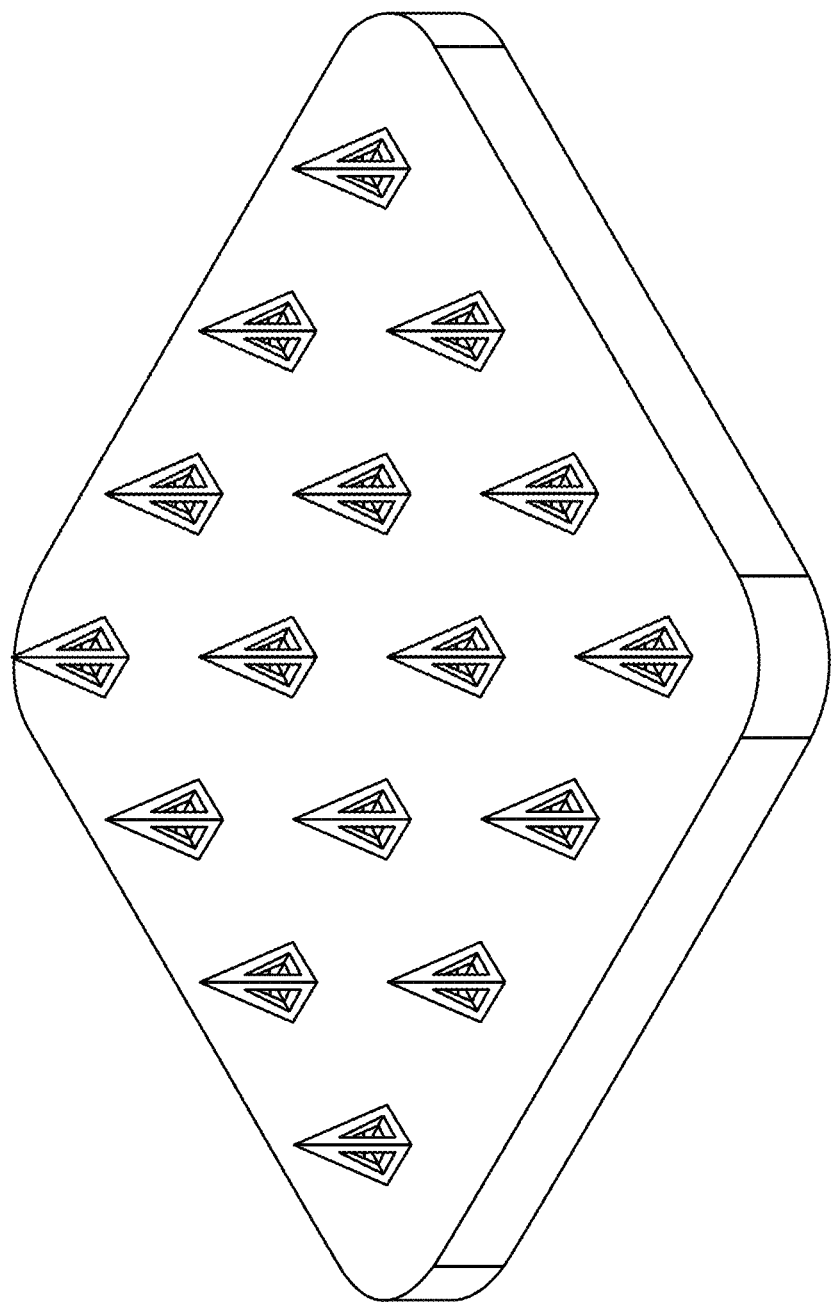
FIGS. 7A-7B show exemplary piercing elements.
Figure 7B:
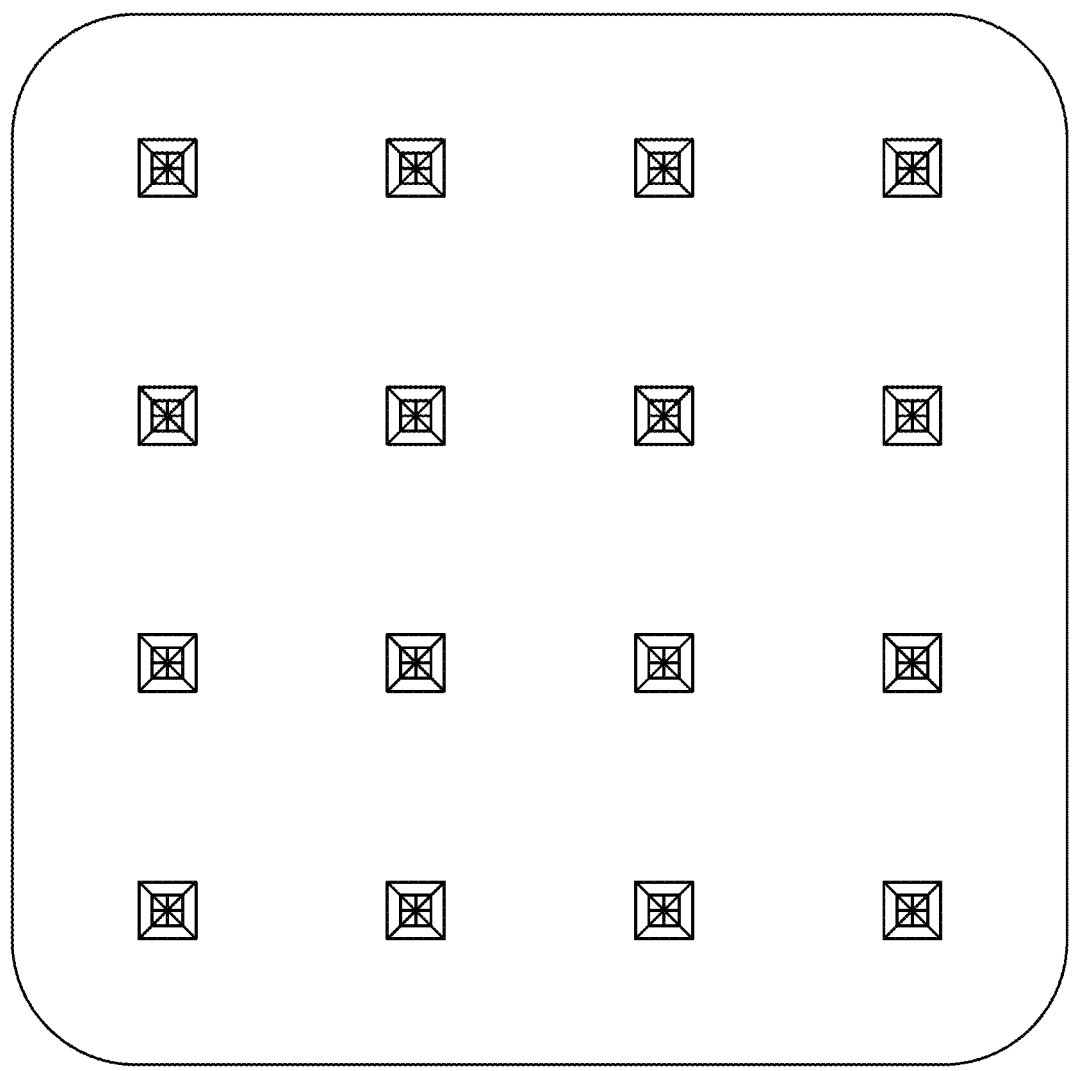

In another embodiment, the device may comprise a piercing element which may include an array of microfabricated microneedles. The microneedles may comprise a well or have an interior hollow space, wherein the analyte binding probes are encapsulated in a polymer matrix contained in the hollow interior space. The polymer matrix of the hollow interior space can be the same or different from the polymer forming the microneedles. The analyte binding probe can be bound covalently or non-covalently to the wall of the hollow interior space or to the polymer matrix within the hollow interior space. In some cases, the analyte binding probe can be sterically trapped within the matrix. In some cases, the analyte binding probe can be held within the matrix with a combination of different interactions (e.g., Van der Waals forces, other intermolecular interactions). In some cases, the microneedles may comprise a pyramidal structure which define a plurality of faces about the exterior surface of the microneedles. In some cases, the microneedles may comprise opening about the plurality of faces about the exterior surface of the microneedles, for example, as illustrated in FIGS. 7A-7B.

In some embodiments, each microneedle can be associated with a plurality of types of analyte binding probes, each type directed to a specific target analyte, to provide a spatially defined microneedle array to allow for the detection of a multitude of different analytes, such as Na+, K+, glucose, etc., in a controlled spatial array. In some embodiments, the interaction with the target analyte can occur in or on the microneedle. In some embodiments, the analyte binding sensor is located in the microneedle and contacts the interstitial fluid containing the analyte. The detectable change may be indicated optically, e.g., based on fluorescence emitted by the nanosensors when optically interrogated. The analyte binding probe can be located inside the surface of a porous microneedle, and/or embedded within the microneedle but exposed to interstitial fluid. In another embodiment, the microneedle array having an analyte binding probe can be readily removed by simply removing it from the transdermal patch (e.g., consumable). The piercing element can be coupled to the support using one or more holes, using one or more insertable elements configured to attach to a corresponding one or more receiving elements, using a lock and key attachment, using a mortise and tenon attachment, using a dovetail attachment, using a magnetic attachment, using an adhesive, using one or more elastically deformable attachment elements, using one or more elastically deformable attachment elements configured and rebound once inserted into the support, or combinations thereof. In some embodiments, the piercing element alone is removable from the device, as is illustrated in FIG. 6A. In some embodiments, both the light guide and the piercing element are removably coupled to the support, for example, as illustrated in FIG. 6B where the light guide is coupled to the piercing element, and the light guide is removable from the support. In some embodiments, the light guide comprises first portion and a second portion, where the second portion is coupled to the piercing element, and wherein the first portion and the second portion are separable from one another as to remove the piercing element and the second portion of the light guide from the support, as is illustrated in FIG. 6C.

Analyte Binding Probe

The present disclosure provides sensors for analyte detection. An analyte binding probe can comprise polypeptide or nucleic acid sequences, antibodies, peptides, proteins, physiochemical detectors, enzymes, artificial binding proteins, or combinations thereof. In some embodiments, the analyte sensor comprises a polypeptide or peptide sequence such as an antibody. For example, an analyte sensor may comprise single stranded deoxyribonucleic acid, double stranded DNA (dsDNA), ribonucleic acid (RNA), nucleic acids in some cases with modified bases, and the like. The analyte sensor may be an oligonucleotide probe and the analyte may be a complementary target nucleic acid. In another embodiment, the binding domain can be a dsDNA strand specific to a target enhancer protein target. In some embodiments, the analyte sensor may comprise a nucleic acid sequence comprising an aptamer.

Antigen Binding Probe: Aptamers

Sometimes referred to as "synthetic antibodies," aptamers may be pre-selected single-stranded oligonucleotide (e.g., DNA or RNA) or peptide molecules that bind to specific target molecules including proteins and peptides with affinities and specificities that are comparable to antibodies. These molecules can assume a variety of shapes due to their propensity to form helices and single-stranded loops with specific binding pockets, explaining their versatility in binding to diverse targets. Their specificity and characteristics are not directly determined by their primary sequence but by their tertiary structure which can be analogous to the globular shape of tRNA. Aptamers have a wide range of applications including diagnostics and therapeutics and can be chemically synthesized using known techniques. Furthermore, aptamers can offer a number of advantages over traditional antibodies including avoiding the need to specifically know the precise epitopes or biomarkers themselves. Finally, aptamers may be typically non-immunogenic, easy to synthesize, characterize, modify, and exhibit high specificity and affinity for their target antigen.

The aptamer may be nucleic acid or peptide molecules that bind to a specific target molecule. In some embodiments, binding of the target analyte to the aptamer induces conformational changes in the aptamer. In some embodiments, the aptamer may bind to various molecular targets, for example, small molecules, macromolecules, metabolites, proteins, carbohydrates, metals, nucleic acids, cells, tissues, and organisms.

By using a variety of selection techniques, aptamers can be selected to find targets, e.g., on a surface or inside a cell of interest, without the need to identify the precise biomarker or epitopes themselves. In many cases, the aptamer identification process can begin with a large random pool of oligonucleotides or peptides that are systematically subjected to negative and positive rounds of selection against a target, e.g., a protein molecule, to filter out low affinity or unspecific binders. The remaining aptamers can be collected and propagated, e.g., PCR amplified, and used in subsequent rounds of selection. This selection process, referred to as Systemic Evolution of Ligands by Exponential Enrichment or SELEX, is commonly used for selecting and identifying highly targeted aptamers. A variant of this methodology, known as cell-SELEX, has been developed for aptamers that are capable of recognizing whole living cells.

Aptamer Switch

In some embodiments, the antigen binding probe may comprise at least one of the four elements: a single-stranded oligonucleotide; a short, complementary DNA sequence to the oligonucleotide; a linking moiety that conjugates the oligonucleotide with the DNA sequence; and luminescent molecules.

In some embodiments, the single oligonucleotide has a first and second terminus, wherein the first terminus can be attached to a luminescent molecule and a second terminus attached to a piercing element. In some embodiments, the single oligonucleotide further comprises a short, partially complementary DNA sequence, wherein the short, partially complementary DNA sequence further comprises a second luminescent molecule.

In some embodiments, the single-stranded oligonucleotide has a first and second terminus, where the first terminus can be attached to the linking moiety. The linking moiety can be also attached to the first terminus of a short DNA strand having a partially complementary sequence to the oligonucleotide, where the short DNA strand has a first and second terminus. Luminescent molecules are attached to the second termini of the oligonucleotide and the short DNA strand.

In some embodiments, the oligonucleotide can be an aptamer. Aptamers are nucleic acid molecules that bind to a specific target molecule such as small molecules, proteins, nucleic acids, cells, tissues, and organisms. In some embodiments, aptamers are single-stranded oligonucleotides exhibiting high affinity and specificity toward any given target molecule. The aptamer disclosed herein may be any suitable size.

In some embodiments, the size of the aptamer as disclosed herein can be about 5 nucleotides to about 250 nucleotides. In some embodiments, the size of the aptamer as disclosed herein can be about 5 nucleotides to about 25 nucleotides, about 5 nucleotides to about 50 nucleotides, about 5 nucleotides to about 75 nucleotides, about 5 nucleotides to about 100 nucleotides, about 5 nucleotides to about 125 nucleotides, about 5 nucleotides to about 150 nucleotides, about 5 nucleotides to about 175 nucleotides, about 5 nucleotides to about 200 nucleotides, about 5 nucleotides to about 225 nucleotides, about 5 nucleotides to about 250 nucleotides, about 25 nucleotides to about 50 nucleotides, about 25 nucleotides to about 75 nucleotides, about 25 nucleotides to about 100 nucleotides, about 25 nucleotides to about 125 nucleotides, about 25 nucleotides to about 150 nucleotides, about 25 nucleotides to about 175 nucleotides, about 25 nucleotides to about 200 nucleotides, about 25 nucleotides to about 225 nucleotides, about 25 nucleotides to about 250 nucleotides, about 50 nucleotides to about 75 nucleotides, about 50 nucleotides to about 100 nucleotides, about 50 nucleotides to about 125 nucleotides, about 50 nucleotides to about 150 nucleotides, about 50 nucleotides to about 175 nucleotides, about 50 nucleotides to about 200 nucleotides, about 50 nucleotides to about 225 nucleotides, about 50 nucleotides to about 250 nucleotides, about 75 nucleotides to about 100 nucleotides, about 75 nucleotides to about 125 nucleotides, about 75 nucleotides to about 150 nucleotides, about 75 nucleotides to about 175 nucleotides, about 75 nucleotides to about 200 nucleotides, about 75 nucleotides to about 225 nucleotides, about 75 nucleotides to about 250 nucleotides, about 100 nucleotides to about 125 nucleotides, about 100 nucleotides to about 150 nucleotides, about 100 nucleotides to about 175 nucleotides, about 100 nucleotides to about 200 nucleotides, about 100 nucleotides to about 225 nucleotides, about 100 nucleotides to about 250 nucleotides, about 125 nucleotides to about 150 nucleotides, about 125 nucleotides to about 175 nucleotides, about 125 nucleotides to about 200 nucleotides, about 125 nucleotides to about 225 nucleotides, about 125 nucleotides to about 250 nucleotides, about 150 nucleotides to about 175 nucleotides, about 150 nucleotides to about 200 nucleotides, about 150 nucleotides to about 225 nucleotides, about 150 nucleotides to about 250 nucleotides, about 175 nucleotides to about 200 nucleotides, about 175 nucleotides to about 225 nucleotides, about 175 nucleotides to about 250 nucleotides, about 200 nucleotides to about 225 nucleotides, about 200 nucleotides to about 250 nucleotides, or about 225 nucleotides to about 250 nucleotides. In some embodiments, the size of the aptamer as disclosed herein can be about 5 nucleotides, about 25 nucleotides, about 50 nucleotides, about 75 nucleotides, about 100 nucleotides, about 125 nucleotides, about 150 nucleotides, about 175 nucleotides, about 200 nucleotides, about 225 nucleotides, or about 250 nucleotides. In some embodiments, the size of the aptamer as disclosed herein can be at least about 5 nucleotides, about 25 nucleotides, about 50 nucleotides, about 75 nucleotides, about 100 nucleotides, about 125 nucleotides, about 150 nucleotides, about 175 nucleotides, about 200 nucleotides, or about 225 nucleotides. In some embodiments, the size of the aptamer as disclosed herein can be at most about 25 nucleotides, about 50 nucleotides, about 75 nucleotides, about 100 nucleotides, about 125 nucleotides, about 150 nucleotides, about 175 nucleotides, about 200 nucleotides, about 225 nucleotides, or about 250 nucleotides. In some embodiments, the probe may further comprise a short, complementary DNA sequence that, in the absence of a target analyte, can hybridize with complete or partial complementary to a portion of the aptamer. In some embodiments, the aptamer and complementary DNA sequence described herein may have one or more mismatched nucleotides. One or more mismatched nucleotide may be 1 or more mismatched nucleotides; 2 or more mismatched nucleotides; 3 or more mismatched nucleotides; 4 or more mismatched nucleotides; 5 or more mismatched nucleotides; 6 or more mismatched nucleotides; 7 or more mismatched nucleotides; 8 or more mismatched nucleotides; 9 or more mismatched nucleotides; 10 or more mismatched nucleotides; 12 or more mismatched nucleotides; 14 or more mismatched nucleotides; 16 or more mismatched nucleotides; 18 or more mismatched nucleotides; or 20 or more mismatched nucleotides. The length of a short, complementary DNA sequence can be about 2 nucleotides to about 45 nucleotides. The length of a short, complementary DNA sequence can be about 2 nucleotides to about 4 nucleotides, about 2 nucleotides to about 6 nucleotides, about 2 nucleotides to about 8 nucleotides, about 2 nucleotides to about 10 nucleotides, about 2 nucleotides to about 15 nucleotides, about 2 nucleotides to about 20 nucleotides, about 2 nucleotides to about 25 nucleotides, about 2 nucleotides to about 30 nucleotides, about 2 nucleotides to about 35 nucleotides, about 2 nucleotides to about 40 nucleotides, about 2 nucleotides to about 45 nucleotides, about 4 nucleotides to about 6 nucleotides, about 4 nucleotides to about 8 nucleotides, about 4 nucleotides to about 10 nucleotides, about 4 nucleotides to about 15 nucleotides, about 4 nucleotides to about 20 nucleotides, about 4 nucleotides to about 25 nucleotides, about 4 nucleotides to about 30 nucleotides, about 4 nucleotides to about 35 nucleotides, about 4 nucleotides to about 40 nucleotides, about 4 nucleotides to about 45 nucleotides, about 6 nucleotides to about 8 nucleotides, about 6 nucleotides to about 10 nucleotides, about 6 nucleotides to about 15 nucleotides, about 6 nucleotides to about 20 nucleotides, about 6 nucleotides to about 25 nucleotides, about 6 nucleotides to about 30 nucleotides, about 6 nucleotides to about 35 nucleotides, about 6 nucleotides to about 40 nucleotides, about 6 nucleotides to about 45 nucleotides, about 8 nucleotides to about 10 nucleotides, about 8 nucleotides to about 15 nucleotides, about 8 nucleotides to about 20 nucleotides, about 8 nucleotides to about 25 nucleotides, about 8 nucleotides to about 30 nucleotides, about 8 nucleotides to about 35 nucleotides, about 8 nucleotides to about 40 nucleotides, about 8 nucleotides to about 45 nucleotides, about 10 nucleotides to about 15 nucleotides, about 10 nucleotides to about 20 nucleotides, about 10 nucleotides to about 25 nucleotides, about 10 nucleotides to about 30 nucleotides, about 10 nucleotides to about 35 nucleotides, about 10 nucleotides to about 40 nucleotides, about 10 nucleotides to about 45 nucleotides, about 15 nucleotides to about 20 nucleotides, about 15 nucleotides to about 25 nucleotides, about 15 nucleotides to about 30 nucleotides, about 15 nucleotides to about 35 nucleotides, about 15 nucleotides to about 40 nucleotides, about 15 nucleotides to about 45 nucleotides, about 20 nucleotides to about 25 nucleotides, about 20 nucleotides to about 30 nucleotides, about 20 nucleotides to about 35 nucleotides, about 20 nucleotides to about 40 nucleotides, about 20 nucleotides to about 45 nucleotides, about 25 nucleotides to about 30 nucleotides, about 25 nucleotides to about 35 nucleotides, about 25 nucleotides to about 40 nucleotides, about 25 nucleotides to about 45 nucleotides, about 30 nucleotides to about 35 nucleotides, about 30 nucleotides to about 40 nucleotides, about 30 nucleotides to about 45 nucleotides, about 35 nucleotides to about 40 nucleotides, about 35 nucleotides to about 45 nucleotides, or about 40 nucleotides to about 45 nucleotides. The length of a short, complementary DNA sequence can be about 2 nucleotides, about 4 nucleotides, about 6 nucleotides, about 8 nucleotides, about 10 nucleotides, about 15 nucleotides, about 20 nucleotides, about 25 nucleotides, about 30 nucleotides, about 35 nucleotides, about 40 nucleotides, or about 45 nucleotides. The length of a short, complementary DNA sequence can be at least about 2 nucleotides, about 4 nucleotides, about 6 nucleotides, about 8 nucleotides, about 10 nucleotides, about 15 nucleotides, about 20 nucleotides, about 25 nucleotides, about 30 nucleotides, about 35 nucleotides, or about 40 nucleotides. The length of a short, complementary DNA sequence can be at most about 4 nucleotides, about 6 nucleotides, about 8 nucleotides, about 10 nucleotides, about 15 nucleotides, about 20 nucleotides, about 25 nucleotides, about 30 nucleotides, about 35 nucleotides, about 40 nucleotides, or about 45 nucleotides.

Linking Moieties

In some embodiments the analyte sensor may further comprise a flexible linker region that attaches the oligonucleotides (e.g., aptamer) to the short DNA sequence. In some cases, the linker moiety can be a nucleotide acid moiety that does not bind to either the oligonucleotide, the short DNA sequence, a peptide nucleic acid (PNA) moiety, a peptide moiety, a disulfide bond, a phosphodiester linkage, or a polymer such as a polyethylene glycol (PEG) moiety. The linker region disclosed herein can be about 2 residues in length to about 45 residues in length. The linker region disclosed herein can be about 2 residues in length to about 4 residues in length, about 2 residues in length to about 6 residues in length, about 2 residues in length to about 8 residues in length, about 2 residues in length to about 10 residues in length, about 2 residues in length to about 15 residues in length, about 2 residues in length to about 20 residues in length, about 2 residues in length to about 25 residues in length, about 2 residues in length to about 30 residues in length, about 2 residues in length to about 35 residues in length, about 2 residues in length to about 40 residues in length, about 2 residues in length to about 45 residues in length, about 4 residues in length to about 6 residues in length, about 4 residues in length to about 8 residues in length, about 4 residues in length to about 10 residues in length, about 4 residues in length to about 15 residues in length, about 4 residues in length to about 20 residues in length, about 4 residues in length to about 25 residues in length, about 4 residues in length to about 30 residues in length, about 4 residues in length to about 35 residues in length, about 4 residues in length to about 40 residues in length, about 4 residues in length to about 45 residues in length, about 6 residues in length to about 8 residues in length, about 6 residues in length to about 10 residues in length, about 6 residues in length to about 15 residues in length, about 6 residues in length to about 20 residues in length, about 6 residues in length to about 25 residues in length, about 6 residues in length to about 30 residues in length, about 6 residues in length to about 35 residues in length, about 6 residues in length to about 40 residues in length, about 6 residues in length to about 45 residues in length, about 8 residues in length to about 10 residues in length, about 8 residues in length to about 15 residues in length, about 8 residues in length to about 20 residues in length, about 8 residues in length to about 25 residues in length, about 8 residues in length to about 30 residues in length, about 8 residues in length to about 35 residues in length, about 8 residues in length to about 40 residues in length, about 8 residues in length to about 45 residues in length, about 10 residues in length to about 15 residues in length, about 10 residues in length to about 20 residues in length, about 10 residues in length to about 25 residues in length, about 10 residues in length to about 30 residues in length, about 10 residues in length to about 35 residues in length, about 10 residues in length to about 40 residues in length, about 10 residues in length to about 45 residues in length, about 15 residues in length to about 20 residues in length, about 15 residues in length to about 25 residues in length, about 15 residues in length to about 30 residues in length, about 15 residues in length to about 35 residues in length, about 15 residues in length to about 40 residues in length, about 15 residues in length to about 45 residues in length, about 20 residues in length to about 25 residues in length, about 20 residues in length to about 30 residues in length, about 20 residues in length to about 35 residues in length, about 20 residues in length to about 40 residues in length, about 20 residues in length to about 45 residues in length, about 25 residues in length to about 30 residues in length, about 25 residues in length to about 35 residues in length, about 25 residues in length to about 40 residues in length, about 25 residues in length to about 45 residues in length, about 30 residues in length to about 35 residues in length, about 30 residues in length to about 40 residues in length, about 30 residues in length to about 45 residues in length, about 35 residues in length to about 40 residues in length, about 35 residues in length to about 45 residues in length, or about 40 residues in length to about 45 residues in length. The linker region disclosed herein can be about 2 residues in length, about 4 residues in length, about 6 residues in length, about 8 residues in length, about 10 residues in length, about 15 residues in length, about 20 residues in length, about 25 residues in length, about 30 residues in length, about 35 residues in length, about 40 residues in length, or about 45 residues in length. The linker region disclosed herein can be at least about 2 residues in length, about 4 residues in length, about 6 residues in length, about 8 residues in length, about 10 residues in length, about 15 residues in length, about 20 residues in length, about 25 residues in length, about 30 residues in length, about 35 residues in length, or about 40 residues in length. The linker region disclosed herein can be at most about 4 residues in length, about 6 residues in length, about 8 residues in length, about 10 residues in length, about 15 residues in length, about 20 residues in length, about 25 residues in length, about 30 residues in length, about 35 residues in length, about 40 residues in length, or about 45 residues in length.

In some embodiments, a linker can be a homopolymeric polynucleotide. An intramolecular linker can be about 5 nucleotides to about 60 nucleotides. An intramolecular linker can be about 5 nucleotides to about 10 nucleotides, about 5 nucleotides to about 15 nucleotides, about 5 nucleotides to about 20 nucleotides, about 5 nucleotides to about 25 nucleotides, about 5 nucleotides to about 30 nucleotides, about 5 nucleotides to about 35 nucleotides, about 5 nucleotides to about 40 nucleotides, about 5 nucleotides to about 45 nucleotides, about 5 nucleotides to about 50 nucleotides, about 5 nucleotides to about 55 nucleotides, about 5 nucleotides to about 60 nucleotides, about 10 nucleotides to about 15 nucleotides, about 10 nucleotides to about 20 nucleotides, about 10 nucleotides to about 25 nucleotides, about 10 nucleotides to about 30 nucleotides, about 10 nucleotides to about 35 nucleotides, about 10 nucleotides to about 40 nucleotides, about 10 nucleotides to about 45 nucleotides, about 10 nucleotides to about 50 nucleotides, about 10 nucleotides to about 55 nucleotides, about 10 nucleotides to about 60 nucleotides, about 15 nucleotides to about 20 nucleotides, about 15 nucleotides to about 25 nucleotides, about 15 nucleotides to about 30 nucleotides, about 15 nucleotides to about 35 nucleotides, about 15 nucleotides to about 40 nucleotides, about 15 nucleotides to about 45 nucleotides, about 15 nucleotides to about 50 nucleotides, about 15 nucleotides to about 55 nucleotides, about 15 nucleotides to about 60 nucleotides, about 20 nucleotides to about 25 nucleotides, about 20 nucleotides to about 30 nucleotides, about 20 nucleotides to about 35 nucleotides, about 20 nucleotides to about 40 nucleotides, about 20 nucleotides to about 45 nucleotides, about 20 nucleotides to about 50 nucleotides, about 20 nucleotides to about 55 nucleotides, about 20 nucleotides to about 60 nucleotides, about 25 nucleotides to about 30 nucleotides, about 25 nucleotides to about 35 nucleotides, about 25 nucleotides to about 40 nucleotides, about 25 nucleotides to about 45 nucleotides, about 25 nucleotides to about 50 nucleotides, about 25 nucleotides to about 55 nucleotides, about 25 nucleotides to about 60 nucleotides, about 30 nucleotides to about 35 nucleotides, about 30 nucleotides to about 40 nucleotides, about 30 nucleotides to about 45 nucleotides, about 30 nucleotides to about 50 nucleotides, about 30 nucleotides to about 55 nucleotides, about 30 nucleotides to about 60 nucleotides, about 35 nucleotides to about 40 nucleotides, about 35 nucleotides to about 45 nucleotides, about 35 nucleotides to about 50 nucleotides, about 35 nucleotides to about 55 nucleotides, about 35 nucleotides to about 60 nucleotides, about 40 nucleotides to about 45 nucleotides, about 40 nucleotides to about 50 nucleotides, about 40 nucleotides to about 55 nucleotides, about 40 nucleotides to about 60 nucleotides, about 45 nucleotides to about 50 nucleotides, about 45 nucleotides to about 55 nucleotides, about 45 nucleotides to about 60 nucleotides, about 50 nucleotides to about 55 nucleotides, about 50 nucleotides to about 60 nucleotides, or about 55 nucleotides to about 60 nucleotides. An intramolecular linker can be about 5 nucleotides, about 10 nucleotides, about 15 nucleotides, about 20 nucleotides, about 25 nucleotides, about 30 nucleotides, about 35 nucleotides, about 40 nucleotides, about 45 nucleotides, about 50 nucleotides, about 55 nucleotides, or about 60 nucleotides. An intramolecular linker can be at least about 5 nucleotides, about 10 nucleotides, about 15 nucleotides, about 20 nucleotides, about 25 nucleotides, about 30 nucleotides, about 35 nucleotides, about 40 nucleotides, about 45 nucleotides, about 50 nucleotides, or about 55 nucleotides. An intramolecular linker can be at most about 10 nucleotides, about 15 nucleotides, about 20 nucleotides, about 25 nucleotides, about 30 nucleotides, about 35 nucleotides, about 40 nucleotides, about 45 nucleotides, about 50 nucleotides, about 55 nucleotides, or about 60 nucleotides.

Photoluminescent Label

A photoluminescent label (e.g., fluorophore label) can be any chemical moiety that exhibits an absorption maximum at or beyond 280 nm, and when covalently attached to the analyte binding probe or other reagent retains its spectral properties. In some embodiments, the photoluminescent label can be any molecule that provides luminescent indication of analyte sensor and target molecule binding. In some cases, the luminescent molecule is a fluorophore, quencher, fluorescence resonance energy transfer (FRET) or FRET pair. A fluorophore molecule may be a molecule that has the ability to absorb energy from light, transfer this energy internally, and emit the energy as light within a characteristic wavelength range. In some embodiments, an analyte binding probe may comprise a fluorophore and a quencher, which absorbs excitation energy from a fluorophore. Suppression of emission from a fluorophore may occur as a result of the formation of a complex between the fluorophore and the quencher, where the absorption spectra of the two molecules change upon formation of the complex. When the two molecules are not in close proximity with each other, fluorescence emission may be restored. In some embodiments, the quencher may be another fluorophore or a nonfluorescent molecule. Fluorophores of the present disclosure include, without limitation; a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine a carbostyryl, a porphyrin, a salicylate, an anthranilate, an azulene, a perylene, a pyridine, a quinoline, a borapolyazaindacene (including any corresponding compounds disclosed, a xanthene, an oxazine or a benzoxazine, a carbazine, a phenalenone, a coumarin (including an corresponding compounds; a benzofuran and benzphenalenone and derivatives thereof. As used herein, oxazines include resorufins, aminooxazinones, diaminooxazines, and their benzo-substituted analogs. When the fluorophore is a xanthene, the fluorophore is optionally a fluorescein, or a rhodamine. As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171, incorporated by reference). Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

Fluorophores for use in the present disclosure include, but are not limited to, xanthene (rhodol, rhodamine, fluorescein and derivatives thereof) coumarin, cyanine, pyrene, oxazine and borapolyazaindacene. Sulfonated xanthenes, fluorinated xanthenes, sulfonated coumarins, fluorinated coumarins and sulfonated cyanines are useful. The choice of the fluorophore will determine the absorption and fluorescence emission properties of the aptamer conjugate. Physical properties of a fluorophore label include spectral characteristics (absorption, emission and Stokes shift), fluorescence intensity, lifetime, polarization and photo-bleaching rate all of which can be used to distinguish one fluorophore from another.

Typically the fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

Specific examples of fluorophore labels are selected from the group consisting of fluorescein, coumarins, rhodamines, 5-TMRIA (tetramethylrhodamine-5-iodoacetamide), (9-(2 (or 4)-(N-(2-maleimdylethyl)-sulfonamidyl)-4 (or 2)-sulfophenyl)-2,3,6,7,12,13,16,17-octahydro-(1-H,5H,11H,15H-xantheno(2,-3,4-ij:5,6,7-i'j')diquinolizin-18-ium salt) (TEXAS RED), 2-(5-(1-(6-(N-(2-maleimdylethyl)-amino)-6-oxohexyl)-1,3-dihydro-3,3-dimet-hyl-5-sulfo-2H-indol-2-ylidene)-1,3-propyldienyl)-1-ethyl-3,3-dimethyl-5-s-ulfo-3H-indolium salt (Cy3), N,N'-dimethyl-N-(iodoacetyl)-N'-(7-nitrobenz-2-oxa-1,3-diazol-4-yl)ethyle-nediamine (IANBD amide), N-((2-(iodoacetoxy)ethyl)-N-methyl) amino-7-nitrobenz-2-oxa-1,3-diazole (IANBD ester), 6-acryloyl-2-dimethylaminonaphthalene (acrylodan), pyrene, 6-amino-2,3-dihydro-2-(2-((iodoacetyl)amino) ethyl)-1,3-dioxo-1H-benz(de)i-soquinoline-5,8-disulfonic acid salt (lucifer yellow), 2-(5-(1-(6-(N-(2-maleimdylethyl)-amino)-6-oxohexyl)-1,3-dihydro-3,3-dimet-hyl-5-sulfo-2H-indol-2-ylidene)-1,3-pentadienyl)-1-ethyl-3,3-dimethyl-5-su-lfo-3H-indolium salt (Cy™5), 4-(5-(4-dimethylaminophenyl)oxazol-2-yl)phenyl-N-(2-bromoacetamidoethyl)sulfonamide (Dapoxyl® (2-bromoacetamidoethyl)sulfonamide)), (N-(4,4-difluoro-1,3,5,7-tetramethyl-4-bora-3a,4a-diaza-s-indacene-2-yl)iodoacetamide (BODIPY 507/545 IA), N-(4,4-difluoro-5,7-diphenyl-4-bora-3a,4a-diaza-s-indacene-3-propionyl)-N-'-iodoacetylethylene diamine (BODIPY 530/550 IA), 5-((((2-iodoacetyl)amino)ethyl)amino)napthalene-1-sulfonic acid (1,5-IAEDANS), and carboxy-X-rhodamine, 5/6-iodoacetamide (XRIA 5,6). Another example of a label is BODIPY-FL-hydrazide. Other luminescent labels include lanthanides such as europium (Eu3+) and terbium (Tb3+), as well as metal-ligand complexes of ruthenium [Ru(II)], rhenium [Re(I)], or osmium [Os(II)], typically in complexes with diamine ligands such as phenanthroline. Additional fluorophores not specifically disclosed herein may also be utilized in embodiments of the present disclosure.

Antigen Binding Probe: Peptides

In some embodiments, an analyte sensor may be a polypeptide-based probe employing intramolecular signal transduction. In some embodiments, the polypeptide-based probe contains at least one of the following elements: a polypeptide with an antigen binding region, a linking moiety, and a luminescent molecule. In some embodiments, the polypeptide-based probe is a protein-based affinity reagent. In some embodiments, the polypeptide-based probe comprises nanobodies, antibody fragments, peptides, cysteine-knot proteins (knottins), or combinations thereof.

In some embodiments, a polypeptide with an antigen binding domain is further conjugated with a luminescent molecule. In some embodiments, a polypeptide with an antigen binding domain is attached to a linking moiety. The linking moiety can be also attached to a second polypeptide with another antigen binding domain, and the luminescent molecules are attached to the first and second polypeptides. In some cases, when the two antigen binding domains bind to the molecular target, they become closer in proximity and can alter the optical signal via a fluorophore/quencher or FRET-type interaction to produce an optical signal.

Antibody fragments which recognize specific epitopes can be generated by known techniques. Antibody fragments are antigen binding portions of an antibody, such as F(ab')2, Fab', F(ab)2, Fab, Fv, scFv and the like. F(ab')2 fragments can be produced by pepsin digestion of the antibody molecule and Fab' fragments can be generated by reducing disulfide bridges of the F(ab')2 fragments. Alternatively, Fab' expression libraries can be constructed (Huse et al., 1989, Science, 246:1274-1281) to allow rapid and easy identification of monoclonal Fab' fragments with the desired specificity. F(ab)2 fragments may be generated by papain digestion of an antibody.

In some embodiments, the polypeptide is a single-chain polypeptide. In some embodiments of any of the single-chain polypeptides described herein, the single-chain polypeptide can be or include a BiTe, a (scFv)2, a nanobody, a nanobody-HSA, a DART, a TandAb, a scDiabody, a scDiabody-CH3, scFv-CH-CL-scFv, a HSAbody, scDiabody-HSA, or a tandem-scFv.

In some embodiments, the polypeptide is a multi-chain polypeptide. In some embodiments, the multi-chain polypeptide can be or can include an antibody, a Dual scFab, a F(ab')2, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IgG, a IgG(H)-scFv, a scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, an Intrabody, a dock and lock, a lmmTAC, an IgG-IgG conjugate, a Cov-X-Body, or a scFv1-PEG-scFv2.

In some embodiments, the antigen-binding domain is humanized or human.

The antibodies of use can be of various isotypes, such as human IgG1, IgG2, IgG3, or IgG4. The antibodies or fragments thereof can be chimeric human-mouse, humanized (human framework and murine hypervariable (CDR) regions), or fully human, as well as variations thereof, such as half-IgG4 antibodies (referred to as "unibodies"). The antibodies or fragments thereof may be designed or selected to comprise human constant region sequences that belong to specific allotypes, which may result in reduced immunogenicity when administered to a human subject. Preferred allotypes for administration include a non-G1 m1 allotype (nG1m1), such as G1m3, G1m3,1, G1m3,2, or G1m3,1,2. More preferably, the allotype is selected from the group consisting of the nG1m1, G1m3, nG1m1,2, and Km3 allotypes.

In some embodiments, non-limiting examples of analyte binding probe includes a DARPin, an affibody, a monobody, a nanobody, a diabody, an antibody (including a monospecific or bispecific antibody); a cell-targeting oligopeptide including but not limited to RGD integrin-binding peptides, de novo designed binders, a bicycle peptide, conotoxins, small molecules such as folic acid, and a virus that binds to the cell surface.

Analyte Detection

In some embodiments, the analyte binding domain can change its conformation (e.g., Aptamer Switch) upon binding to a target analyte. In some embodiments, an analyte sensor may be an antibody switch sensor or any other sensor that may undergo conformational rearrangement upon interaction with one or more analytes that modulates the optical signal. Suitable optical signals which can be used as an assay readout include any optical signal which can be generated by a proximity assay, such as those generated by fluorescence resonance energy transfer (FRET), fluorescence polarization, fluorescence quenching, phosphorescence technique, luminescence enhancement, luminescence quenching, diffraction or plasmon resonance, all of which are known techniques.

For example, in the absence of a target molecule, the analyte detection is in a position such that a first label (e.g., fluorophore) is in close proximity to a second label (e.g., quencher), the detectable optical read-out is quenched (e.g., reduced) by the second label. Conversely, when the analyte binding domain binds to its target molecule, the binding between binding domain and target molecule induces a conformational change, such that the first label (e.g., fluorophore) is away from the second label (e.g., quencher) resulting in the increase of detectable optical read-out.

Efficient and complete quenching of the fluorescence emitted from the fluorophore by the quencher depends in part on the overlap between the fluorophore emission and quencher absorption spectra. For example, the fluorophore coumarin emits at emission wavelength around 472 nm and can be paired with quencher (QSY35) which absorbs at a wavelength of around 475 nm. In another example, fluorophore Alexa 532 emits at emission wavelength around 554 nm and can be paired with quencher QSY7 which absorbs at wavelength around 560 nm. In yet another example, fluorophore Alex 647 emits at an emission wavelength around 665 nm and can be paired with quencher QSY 21 which absorbs at wavelength around 661 nm.

In some embodiments, the substrate incorporates assay components that generate an optical readout using FRET. In this assay format, a pair of fluorophores are used wherein one serves as a donor chromophore and the other acts as an acceptor chromophore. With respect to the fluorescence emission spectrum, the emission spectrum of the donor chromophore overlaps with the absorption spectrum of the acceptor chromophore, such that when the donor and acceptor chromophores are brought into close proximity, a proportion of the energy which normally would produce fluorescence emitted by the donor chromophore (following irradiation with incident radiation of a wavelength absorbed by the donor chromophore) will be non-radiatively transferred to the adjacent acceptor chromophore, a process known in the art as fluorescence resonance energy transfer, with the result that a proportion of the fluorescent signal emitted by the donor chromophore is quenched, that the lifetime of the fluorescence is changed, and, in some instances, that the acceptor chromophore emits fluorescence. The acceptor chromophore may, however, be a non-fluorescent dye. Fluorescence resonance energy transfer generally only occurs when the donor and acceptor chromophores are brought into close proximity by the binding of, for instance, an analyte to an aptamer, which causes a conformational change which brings the donor and acceptor chromophores together. Thus, in the presence of analyte, the amount of quenching can be increased (resulting in a measurable decrease in the intensity of the fluorescent signal emitted by the donor chromophore or an increase in the intensity of the signal emitted by the acceptor chromophore). The intensity or lifetime of the fluorescent signal emitted from the donor chromophore thus correlates with the concentration of target analyte in the interstitial fluid bathing the sensor.

The sensor can be adapted for the detection or quantitative measurement of any target analyte present in interstitial fluid such as glucose (in connection with the long-term monitoring of diabetics), urea (in connection with kidney disease or dysfunction), lactate (in connection with assessment of muscle performance in sports medicine), ions such as sodium, calcium or potassium and therapeutic drugs whose concentration in the blood must be closely monitored, such as, for example, digoxin, theophylline or immunosuppressant drugs. The above analytes are listed by way of example only and it is to be understood that the precise nature of the analyte to be measured is not material.

The sensor can be interrogated transcutaneously using optical means, for example, no physical connection may be required between the sensor and the optical means. When the sensor incorporates the technique of fluorescence resonance energy transfer, the optical means can supply a first beam of incident radiation at a wavelength within the absorption spectrum of the donor chromophore and a second beam of incident radiation at a wavelength within the absorption spectrum of the acceptor chromophore. In addition, the optical means can be capable of measuring optical signals generated in the sensor at two different wavelengths; wavelength 1 within the emission spectrum of the donor chromophore (the signal generated in connection with the measurement of analyte and wavelength 2 in the emission spectrum of the acceptor chromophore (which could be the analyte signal or the internal reference or calibration signal).

Optical means suitable for use in remote interrogation of the sensor can include a simple high-throughput fluorimeter comprising an excitation light source such as, for example, a light-emitting diode (for example blue, green or red), an excitation light filter (for example a dichroic, dye filter) and a fluorescent light detector for example (PIN diode, Silicon photo-multiplier, Avalanche photodiode, image sensor configuration).

Figure 8:
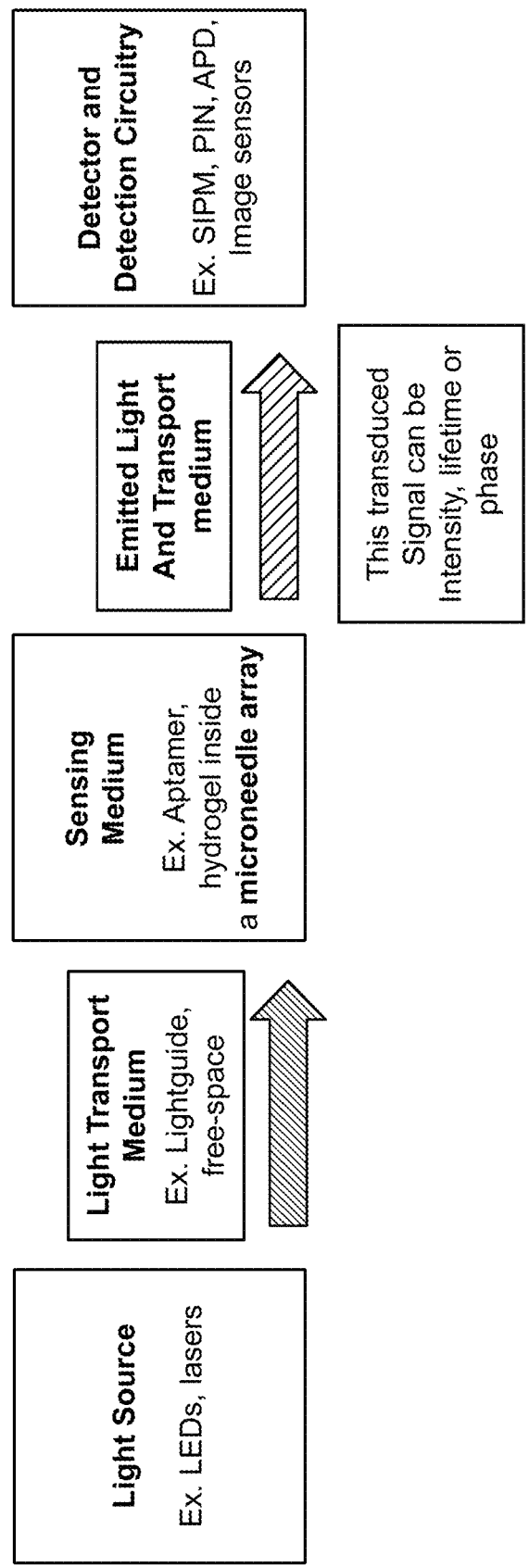
FIG. 8 shows a flowchart illustrating exemplary detection methods using the devices of the present disclosure.
Figure 9:
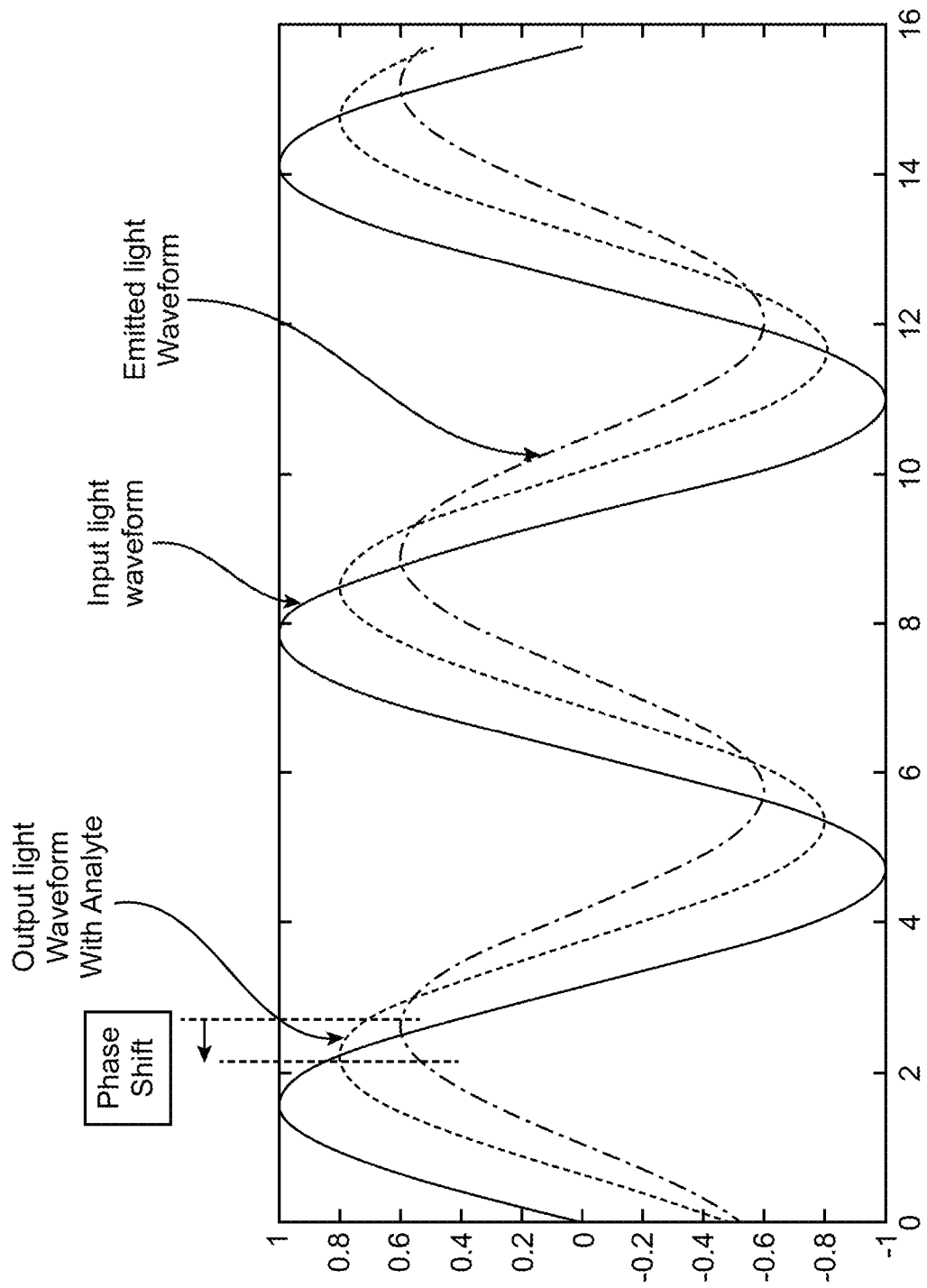
FIG. 9 shows a graph illustrating the phase shift of output light which may be produced from an exemplary device when used to detect an analyte as compared to the emitted light waveform without an analyte response, and input light waveform.
Figure 10:
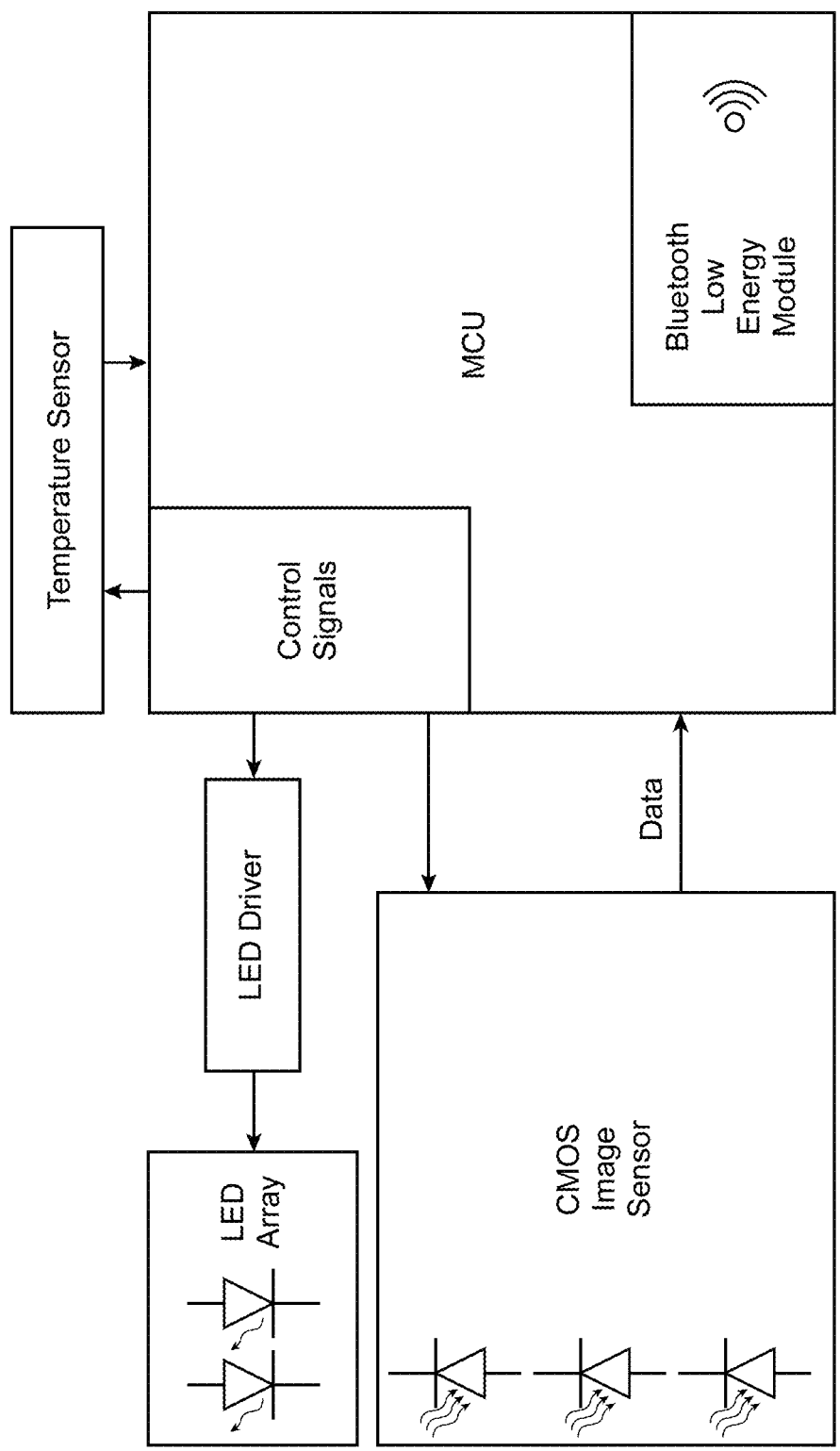
FIG. 10 depicts an exemplary circuit diagram showing electrical couplings between various components of the device.

FIG. 8 shows the basic sensor block diagram. A source light excites a sensor domain under the skin. The sensing domain emits light at a different wavelength, which is typically redshifted. The sensor domain modulates any of the numerous possible properties of the emitted light depending on the target analyte concentration and the required sensitivity. Different properties of emitted light can be used to constitute different detection schemes. In one embodiment, the modulated and detected property of the light is the intensity, leading to an intensity detection implementation. In another embodiment, the modulated and tracked property of emitted light is the lifetime of the excited light emitting molecule. Here a pulse of light is launched and the decay time is monitored. In yet another embodiment the transduced light property is the phase of the emitted light wave. FIG. 9 shows an example wave diagram, where the phase of the emitted light is transduced based on the concentration of the analyte. The detection circuitry in this case is built to detect the phase difference, which is then used to calculate the target analyte concentration.

Calibration & Controls

In some embodiments, the device of the present disclosure may comprise a plurality of analyte binding domains which serve as a control to assist in target analyte detection. For example, one or more portions of the piercing element may comprise a portion with a known concentration of the target analyte present in the piercing element to produce a signal with a known strength relative to a known concentration of the target analyte. Further, the piercing elements with the known concentration may be isolated from the ISF so as not to alter the control concentrations. For instance, the piercing element may comprise microneedles without openings or holes on the microneedle such that it is isolated from any biological fluid. In other embodiments, different instances of control with one or more piercing elements and which may simultaneously or uniquely exist in the same device as other controls can comprise of a piercing element with fluorophore only.

In other embodiments, the device may utilize control molecules or compounds which provide a signal of a known strength with regard to the analyte binding probe, for example, a control may comprise a fluorophore used in the analyte binding probe. In some cases, the control may be incorporated into the piercing element, or a microneedle. In some cases, the control may be incorporated directly into the device or detector, or proximal to the detector. In some cases, the control may be utilized to account for noise in the signal provided by the analyte binding probe. In some cases, the control may be utilized to correct for noise in the signal from the analyte binding probe resulting: from pH affecting the signal provided by the analyte binding probe; temperature affecting the signal provided by the analyte binding probe; photobleaching or change in fluorophore concentration; chemical bleaching which may impact the fluorophore optical properties; free radicals from the body which may impact the fluorophore optical properties; biofouling of the piercing element, sensing domain, or analyte binding probe; other biological agents which may result in damage to the analyte binding probe (e.g., nucleases); any other source of noise in the signal from the analyte binding probe; or combinations thereof.

Above examples of controls are only provided to elucidate the concept of control and should not be interpreted narrowly as the only types of controls possible. Using a single or plurality of controls of one or different types in a single sensor device along with the sensing domains of one or more analytes allows correction from spurious and unwanted effects such as variation in temperature, pH, and active fluorophore concentration, It can also allow correction from possible misalignment of the analyte binding probe to the waveguide or light source, variation in the power of the light source, or other effects which could result in spurious detection of the target analyte in a particular application of the device. In some embodiments, the device may comprise one or more controls which correspond to the target analyte(s) to be detected by the analyte binding probe. In some embodiments, the analyte binding probe may contain one or more reference groups or elements. The reference group may have a luminescence signal that is substantially unchanged upon binding of the target analyte to the analyte binding probe. The luminescence signal from the reference group may provide an internal optical standard that can be used to correct for optical artifacts due to, for example, electronic drift in the optical system or to motion of the sample or optical conduit. The reference group can also be used for calibration. The reference group can be attached to any number of components of a device including the analyte binding probe, a polymer matrix, a biomolecule that is not an analyte of interest, or a piercing element(s). In some embodiments, the reference group may be attached to a binding analyte of interest that has been engineered to show little or no significant response to the analyte at physiologically relevant concentrations. In some embodiments, the analyte binding probe may include additional luminescent reference groups that are optionally attached to biomolecules, polymers, or organic molecules for the purpose of providing a reference or calibration signal.

Light Source & Waveguide

Figure 5A:
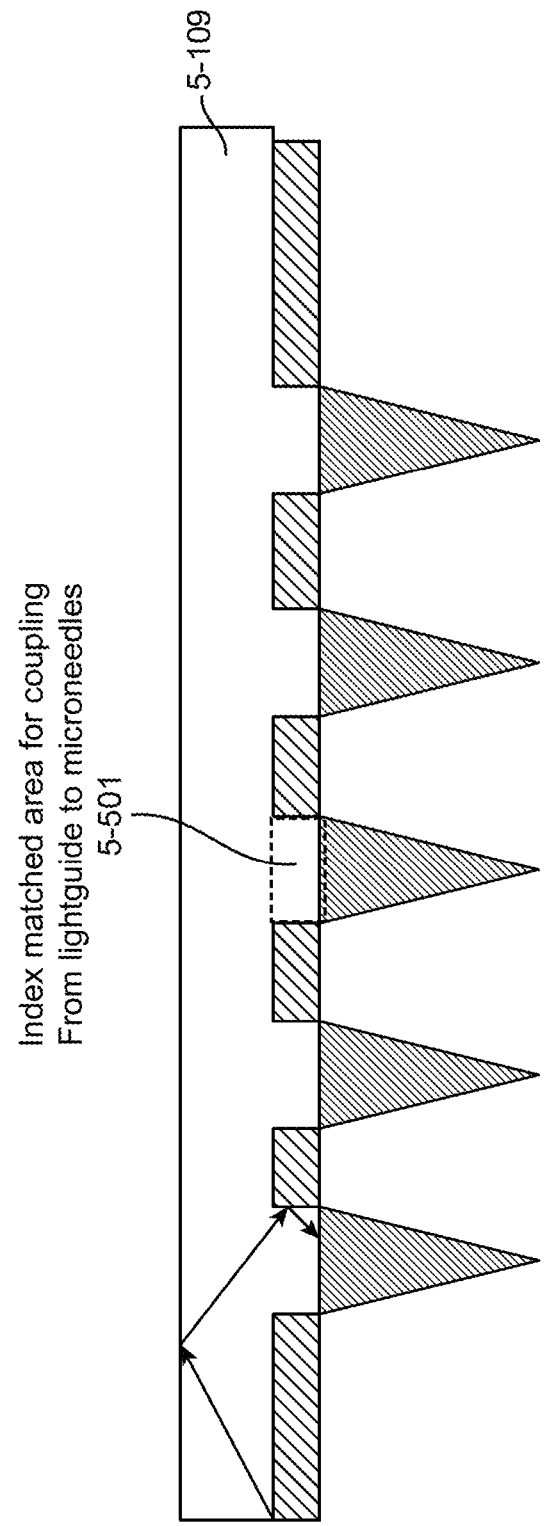
FIGS. 5A-5C show an exemplary device to detect analytes of interest with exemplary waveguides.
Figure 5B:
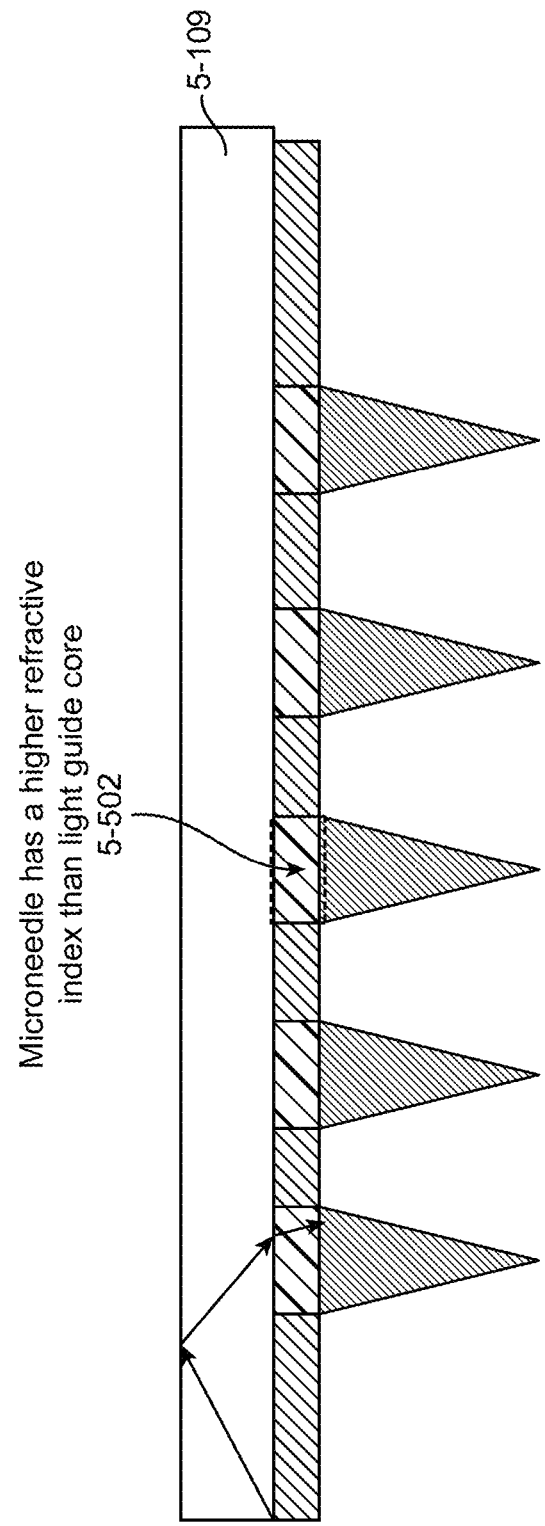
Figure 5C:
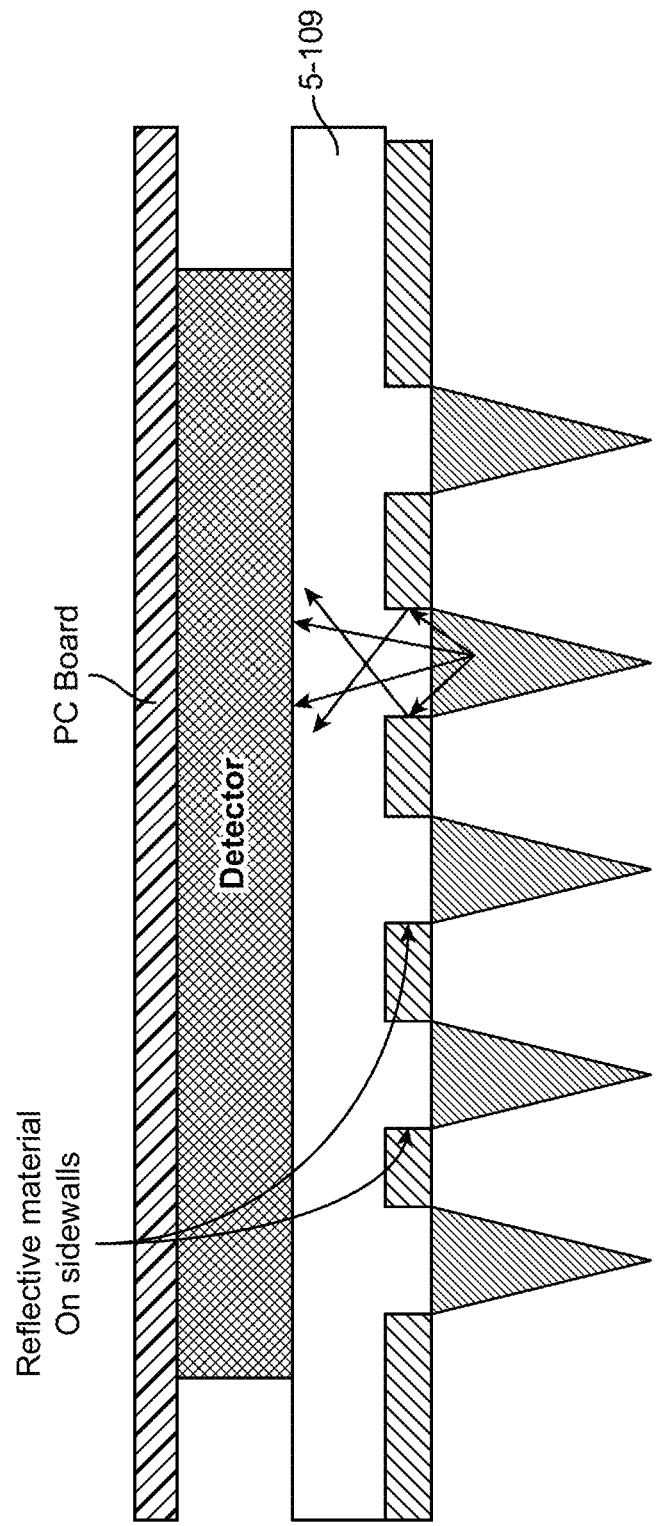

In general, the devices for generating light described herein include a means for spatially distributing primary light and a photoluminescent material for at least partially absorbing the spatially distributed light and emitting phosphorescence and/or fluorescence as secondary emission. In some embodiments, the means for spatially distributing primary light may comprise a waveguide (e.g., optical waveguide or semiconductor waveguide) or a light guide. The optical waveguide may be configured to couple in light from a primary light source, to at least partially guide the coupled-in light in the core of the waveguide along a length of the waveguide, and to leak the coupled-in, guided primary light out of the waveguide core in a controlled manner, e.g., to leak the guided light out of the core gradually or continuously along the length of the waveguide, or at particular or discrete regions of the waveguide. The light that has been leaked out of the waveguide core comprises a spatially distributed light source that has been created from the incident primary light source. The leaked, spatially distributed light can then incident upon a photoluminescent material, which may in some variations comprise a combination of materials. The photoluminescent material can be configured to at least partially absorb, for example, and be pumped by the leaked light. After it absorbs the incident leaked light, the photoluminescent material emits a secondary light emission, for example, by phosphorescence and/or fluorescence. The primary light that has been leaked out of the waveguide core may or may not leak out of the waveguide generally, e.g., in some cases a cladding of the waveguide may comprise a photoluminescent material that absorbs the primary light that has been leaked out of the core. The secondary light emission from the photoluminescent material may be in a desired wavelength range, e.g., visible and/or infrared. In one example, the secondary light emission from the devices may comprise red, green, blue, yellow, infrared, and/or white light. The devices may be configured for use with an external light source, for example, a light source which is applied to the device, and which generates an optical signal which determines a result that is then electronically stored by the device. The optical system may comprise an optoelectronic chip and may comprise one or more optical paths for delivering light from the light source to the detector molecules, and from the detector molecules to a detection element within the device. The optical system may comprise an optoelectronic chip and may comprise one or more optical paths for delivering light from the light source to the detector molecules, and from the detector molecules to a detection element within the device. The waveguide may comprise an optical surface which can be configured to engage with one or more interchangeable or replaceable piercing elements. The waveguide may comprise a coupling region which is configured to direct light into the piercing element. The coupling region may comprise a higher refractive index then the core of the waveguide so as to steer light into the piercing element, for example, as illustrated in FIG. 5B. The coupling region may comprise a same refractive index as the core of the waveguide so as to steer light into the piercing element, for example, as illustrated in FIG. 5A. The waveguide may comprise one or more reflective bases proximal to, adjacent to, or in contact with coupling region, where the reflective base is configured to reflect into and out of the piercing element, for example, as illustrated in FIG. 5C. The reflective bases may comprise a reflective coating, or may be made from a reflective material. In some cases, the optical light guide may be a lossy optical transmission path which transmits light from the light source to the analyte binding probe. In some cases, the optical light guide may comprise an optical waveguide. In some cases, the optical waveguide may provide for lossless or substantially lossless transmission of light from the analyte binding probe to the detector. In some cases, the transmission of light from analyte to detector can either be in free-space or can be guided. The light guide can be configured to deliver illumination to a detector molecule. The light guide may consist of a material having the lowest possible optical absorption. In some embodiments, the light guide can comprise of polymer, plastic, glass or quartz.

In some embodiment, a support (e.g., waveguide or light guide) can be about 5% to about 100% transparent. In some embodiment, the support can be about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 5% to about 100%, about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 10000, or about 90% to about 100% transparent. In some embodiments, the support can be about 5%, about 10%, about 20%, about 30%, about 40%, about 50%, about 60%, about 70%, about 80%, about 90%, or about 100% transparent. In some embodiment, the support can be at least about 5%, about 10%, about 20%, about 30%, about 40%, about 50%, about 60%, about 70%, about 80%, or about 90% transparent. In some embodiment, support can be at most about 10%, about 20%, about 30%, about 40%, about 50%, about 60%, about 70%, about 800%, about 90%, or about 100% transparent.

The primary light source used with the devices may be any suitable type of light source. For example, one or more lasers, e.g., laser diodes, LEDs, lamps, e.g., arc lamps, discharge lamps, fluorescent lamps, and the like may be used. In some variations, a primary light source may comprise more than one light source or more than one type of light source, e.g., more than one laser, more than one LED, or a laser and an LED. Primary light sources may be either continuous (e.g., continuous wave (CW) lasers) or pulsed (e.g., flashlamp-pumped, mode-locked, Q-switched, or cavity-dumped lasers). Shutters or optical choppers and the like may also be used to temporally modulate the primary light source. A primary light source may be part of a light-emitting device, e.g., adjoined as a component to a light-emitting device, or as an integral component of the light-emitting device.

In variations of light-emitting devices in which the primary light source comprises a laser, a semiconductor laser described herein, now known, or later developed may be used. In many variations, lasers having a relatively high electrical-to-optical conversion efficiency may be used to improve the overall efficiency of the light-emitting devices, and/or external light sources. For example, lasers having an electrical-to-optical conversion efficiency of at least about 40%, at least about 50%, or at least 60%, or even higher, e.g., at least about 70%, may be used. For example, a laser comprising GaN or a GaN alloy as a lasing medium may be used. In other variations, other direct band gap semiconductor lasers such as GaAs, AlGaAs, GaP, InGaAs, GaInNAs, InGaAsP, InP, and GaInP lasers may be used. In certain variations, a ZnO laser, e.g., a ZnO photonic crystal laser, may be used as a primary light source. Lasers used in the light-emitting devices described herein may have a variety of configurations. For example, in some variations, a semiconductor laser used as a primary light source may be an edge-emitting laser, or in-plane laser. In other variations, a semiconductor laser may be a surface-emitting laser. A semiconductor laser such as an edge-emitting or surface-emitting semiconductor laser may be separate from the light-emitting device, or may be part of the device itself, e.g., as an adjoined component, or as an integral component.

In some variations of devices, the primary light source may comprise one or more LEDs. The LEDs may be any suitable type of LED described herein, now known, or later developed, and may have any suitable composition and any suitable configuration. For example, LEDs may be GaN LEDs or GaN alloy LEDs. In other variations, LEDs may be AlGaAs, AlInGaP, InGaN, InP, GaInP, InGaAs, GaInNAs, ZnSe, or ZnO LEDs. An LED may be a component that is part of a light-emitting device, e.g., as an adjoined component or as an integral component.

The primary light source may emit light of any suitable wavelength that is at least partially absorbed by the photoluminescent molecules. In some variations, the primary light source may emit light that has a wavelength in a range from about 200 nm to about 500 nm, e.g., about 250 nm, about 300 nm, about 350 nm, about 400 nm, about 450 nm, or about 500 nm. A semiconductor diode laser or a LED emitting over this wavelength range may be used. For example, a GaN or GaN alloy diode laser capable of emitting about 100 mW, about 200 mW, about 300 mW, or even more power, of blue-violet light having a wavelength of about 400 nm, about 410 nm, about 420 nm, about 430 nm, about 440 nm, about 450 nm, about 460 nm, about 470 nm, about 480 nm, about 490 nm, or about 500 nm may be used. GaN or GaN alloy LEDs or other LEDs emitting in the blue-violet range, e.g., about 400 nm, about 410 nm, about 420 nm, about 430 nm, about 440 nm, about 450 nm, about 460 nm, about 470 nm, or about 480 nm, about 490 nm, or about 500 nm may be used. In some embodiments, the disclosure described herein may be coupled to a tunable-wavelength light source (e.g., a tunable laser) to emit light of any suitable wavelength. In some embodiments, the disclosure described herein may have multiple light sources, each operating independently and operating at the same and/or different wavelengths.

An optical waveguide used herein may be any suitable type of waveguide. The optical waveguide may comprise a single mode waveguide region, e.g., for those devices in which the primary light source comprises a laser. In other variations, the optical waveguide may comprise a multi-mode waveguide region, e.g., a large core multi-mode waveguide region. Large core multi-mode waveguides may, for example, be used in those devices in which the primary light source is a light source emitting light with low coherence, such as an LED. The optical waveguide may comprise a combination of waveguide types, e.g., a waveguide may comprise a taper region wherein a large core region of the optical waveguide is tapered to a smaller core region of the optical waveguide. In some embodiments, the large core region that is tapered into a smaller core region may be a multi-mode waveguide. In some cases, the optical waveguide functions as path for light which distributes light from the light source(s) to each of the microneedles within the microneedle array, acting as a photonic integrated circuit where the waveguide enables dense interconnection with the microneedles, which can serve to permit miniaturization of the device a traditional light path (e.g., fiber optic cables), and permit for the design and construction of a device which can be worn on the skin of a user.

Any suitable means or technique may be used to couple light from the primary light source into the waveguide. In some variations, the light source may be coupled into a waveguide by abutting the light source against a waveguide. This butt-coupling technique may be used for example, if the primary light source is a surface-mounted light source such as a laser diode and the waveguide is a planar or rectangular waveguide disposed on the identical or an adjacent surface, or an optical fiber that can be abutted against a surface-mounted light source. In certain variations, the devices may further comprise a coupler that can be configured to couple the light from the primary light source into the waveguide. Any suitable coupler described herein, now known, or later developed may be used. Non-limiting examples of couplers include those selected from the group consisting of ball lens couplers, aspheric lens couplers, grating couplers, butt couplers, index couplers, reverse core waveguide taper couplers, direct couplers, e.g., Namiki-type spherical or cylindrical lensed fiber couplers, and combinations thereof.

The waveguide may be configured to spatially distribute the in-coupled, guided primary light. For example, a waveguide may comprise one or more optical loss regions, e.g., disposed along its length, wherein each optical loss region can be configured to divert at least a portion of the coupled-in, guided light out of the core of the optical waveguide to create spatially-distributed light.

Waveguides may comprise a variety of types and configurations of optical loss regions to divert at least a portion of the coupled-in, guided primary light out of the core of the waveguide, so that the diverted or leaked light may be used to pump a photoluminescent material. The amount of optical loss associated with each optical loss region or group of optical loss regions may be tuned for a particular application and/or photoluminescent material. Further, a spatial distribution of optical loss regions along or around a waveguide may be adjusted for certain applications and/or photoluminescent materials. In many variations, it may be desired to illuminate a photoluminescent material with a peak intensity and/or peak power below a damage threshold of the photoluminescent material and/or a matrix material comprising the photoluminescent material, e.g., a polymer or glassy matrix comprising dispersed photoluminescent particles. In some embodiments, the polymer may be polymethylmethacrylate (PMMA), polystyrene (PS), polycarbonate (PC), polyurethane (PU), epoxy resin, deuterated and halogenated polyacrylates, fluorinated polyimides, perfluorocyclobutyl (PFCB) aryl ether polymers, nonlinear optical polymers, benzocylcobutene (BCB), perfluorovinyl ether cyclopolymer (CYTOP), tetrafluoroethylene and perfluorovinyl ether copolymer (Teflon AF), silicone, fluorinated poly(arylene ether sulfide), poly(pentafluorostyrene), fluorinated dendrimers, or fluorinated hyperbranched polymers. To increase system efficiency and/or reduce the probability for pump-induced damage, a photoluminescent material may be pumped with a peak power and/or peak intensity that is below a saturation threshold of the photoluminescent material. Any type of optical waveguide may be used in the methods, e.g., single mode, multi-mode, planar waveguides, rectangular waveguides, optical fibers, hollow lightpipes, photonic crystal fibers, or a combination thereof.

A variety of types of optical loss regions may be provided in a waveguide to spatially distribute in-coupled, guided light out of a core of a waveguide in a controlled manner. For example, waveguides may comprise one or more optical splitters and/or taps, so that the waveguide can be configured to split at least a portion of the guided primary light into multiple beams. At least one of the split-off beams may be diverted from a core of the optical waveguide to pump a photoluminescent material. In some embodiments, optical loss regions may comprise one or more scattering regions that are configured to scatter at least a portion of the guided primary light out of the core of the waveguide to excite a photoluminescent material. Such scattering regions may comprise one or more roughened regions and/or one or more graded index regions, where each graded index region can be configured to scatter light out of the core of the waveguide. In some embodiments, optical loss regions may comprise one or more bend regions, where light can be leaked out of the core of the waveguide in a controlled manner in the bend regions. In some embodiments, waveguides may comprise a taper region, where a large core multi-mode region is tapered into a smaller core region, and light that is not coupled into the small core region, e.g., certain modes that do not couple into the smaller core, may be diverted out of the core of the waveguide and used to pump a photoluminescent material.

In one embodiment, the sensor hardware consisting of electronics and optics can be detachable from the microneedle array carrying the sensing domain. This allows the expensive sensor to be reused with a new, microneedle array, when the inexpensive microneedle array has to be disposed at the end of its life. When the sensor is attached to the microneedle array, provisions are made to self-align it with the microneedle array.

In yet another specific embodiment of above configuration, the sensor hardware comprises of a light guide or a waveguide, in which a light source at a specific wavelength is coupled into the light guide. The illuminating light source can be on one or both sides of the light guide. It can be edge coupled or surface coupled and for example may consist of LEDs of wavelengths from 300 nm to 800 nm. In one case, the light guide may be wholly part of the reusable sensor architecture. In another embodiment, the light guide is part of the microneedle array and gets disposed with the microneedle. In yet another embodiment, the light guide may be partially in sensor hardware and partially in the microneedle array (FIGS. 6A-6C)

It is also proposed that in the configuration where source light is coupled into the microneedle array using light guide, there can be single or multiple light guides covering a row of microneedles. Similarly, a single, several, or all rows of microneedles can be covered by a single light guide. The choice can be dictated by the necessity of having control microneedles and/or multiple analytes.

In some embodiments, the light source or sources may be positioned directly above the molecular sensing domain, with no light guide present. The light sources may be individually addressable, so that illumination can be controlled locally rather than globally. In some embodiments of this configuration, the signal for each individual piercing element in an array of piercing elements may be able to be turned on and off.

Light Coupling into the Microneedle

In one embodiment, the source light is coupled with the phosphorescence molecule in the sensing domain using index matching between the light guide and the microneedle pockets. Herein, the refractive index of the light guide and the pocket is substantially similar to FIG. 5A, which allows light to continue into the microneedle. In one of the embodiments, the sidewalls of the base of the microneedle array (FIG. 5C) can be substantially reflective or are coated with a reflective material. This allows the light hitting the sides of the microneedle to be reflected and ultimately be captured by the above-situated photodetectors. The deposition could use, for example, any of the myriad techniques such as PVD, sputtering evaporation, dip coating, plating, etc. In another embodiment, the light guide has additional periodic protrusion structures, which align to and fit into the microneedle, providing a substantially similar refractive index as the light guide.

In another embodiment, the refractive index of the part of the microneedle material interfacing with the light guide has a higher refractive index than the light guide, forcing the light to turn toward the microneedle (FIG. 5B) when it crosses form waveguide into the microneedle.

Multiplexing Several Analytes

In one embodiment, multiple analyte detection is possible. By immobilizing a plurality of aptamers of different binding specificity to target analytes, simultaneous multiple target analyte determinations can be made, thereby providing clinicians with deeper insight into the identification and assessment of health state and disease progression. The use of spectral filters and/or alternative light sources as the interrogation signal can be used to excite the label, e.g., fluorophores and detect light, e.g., fluorescent light, from the different analyte binding probes, and thereby determine the contribution of each analyte binding probes to the total fluorescent properties of the sample. In other embodiments, the different analyte binding probes can be spatially multiplexed or use Space Division Multiplexing (SDM) to identify signals which correspond to analyte binding probes, wherein different analyte binding probes are provided in different microneedles.

In one embodiment several different analytes can be sensed by a single sensor using multiplexing. This can be achieved either using spatial multiplexing where the detector is able to distinguish between signals in different locations. In another embodiment, multiple analytes are sensed using time division multiplexing (TDM) where a set of microneedles corresponding to a particular analyte are illuminated at once. This is followed sequentially in time by illumination of a different set of microneedles corresponding to a different analyte. Enough volume of each analyte needs to be ensured.

In yet another multiplexing implementation, wavelength division multiplexing (WDM) can be used to sense multiple analytes. Here, slightly varying wavelengths are launched at the same time, and each wavelength may correspond a particular analyte, with particular analyte binding probes responding to different wavelengths of light.

Optical Filters and Detectors

In one of the embodiments, the detector sensing the light coming from the light emitting sensor domain has an optical filter in front of it. The purpose of this filter is to eliminate the source light coupling into the detector. In one embodiment, the filters can be dielectric filters which are designed to have high rejection ratios for a wide range of incidence angles of the source light.

In one embodiment, the detectors themselves can be made of silicon. Further, any of the following types of detectors can be used: PIN, PN, APD, single photon multipliers. They can also be combined into possibly a CMOS image sensor or any of the several different types of light sensors that may be used in other applications.

Operations

In some embodiments, the present disclosure provides a method for operating a system including a substrate and a reader to measure an analyte concentration within interstitial fluid in the skin. The method may include receiving, by a substrate, a signal from a reader device, a signal from a reader device, wherein the substrate includes a sensor comprising aptamer conjugates and can be implanted into the skin; performing, by the sensor, in response to the signal, a measurement related to an analyte in the interstitial fluid; and communicating, by the substrate, data indicative of the measurement to the reader device.

In some embodiments, the signal can be an optical signal and the data indicative of the measure comprising at least one of optical absorption, reflectivity, transmission, or fluorescence. For example, the concentration of the analyte can be calculated based on the change in the optical signal by fluorescence or phosphorescence within the microneedle when candidate analytes are captured by the analyte binding probe. The change in optical signal strength (e.g., bound vs unbound state of the analyte binding probe) can be an increase or decrease in fluorescence or phosphorescence signal intensity compared to unbound state. In some embodiments, it can be an increase or decrease in fluorescence or phosphorescence lifetime. In some embodiments, the change in the optical signal may include fluorescence intensity, FRET ratio, time-resolved fluorescence, or decay curve monitoring for detecting the lifetime of the phosphoresce reporter.

In another embodiment, the method may further include: transmitting, by a reader device, a signal to a substrate implanted in the skin, the substrate comprising a sensor, the sensor comprising aptamer conjugates, wherein the sensor can be configured to obtain one or more measurements related to an analyte in interstitial fluid; and receiving, by the reader device, a responsive signal from the substrate, wherein the responsive signal may indicate the one or more measurements related to the analyte in the interstitial fluid, from which the concentration of an analyte in the interstitial fluid may be determined.

In some embodiments, the substrate may include an antenna and a sensor. The signal and the responsive signal may be radio frequency (RF) signals. In some embodiments, the responsive signal includes data indicative of one or more measurements related to the analyte obtained by the sensor. In some embodiments, the responsive signal may indicate the concentration of one or more analytes in interstitial fluid.

In some embodiments, the signal and the responsive signal may be optical signals. The substrate may include a sensor comprising aptamer conjugates which can be configured to undergo an optically-detectable change related to the analyte. In some examples, the optically-detectable change may involve a change in at least one of optical absorption, reflectivity, transmission, or fluorescence. In some embodiments the responsive signal indicates the presence or absence of an analyte and/or amount, level, or concentration of the analyte in interstitial fluid. The responsive signal that is generated can be due to the presence of the analyte in the interstitial fluid of the subject and these interstitial fluid analyte levels are related to the blood analyte levels in the subject. In general, the interstitial fluid analyte levels are directly related to the blood analyte levels of the subject. Thus, in one embodiment, the interstitial fluid analyte levels serve as a surrogate for the blood analyte levels of the subject. In another embodiment, the interstitial fluid analyte levels may be correlated to the blood analyte levels.

Exemplary Systems

Figure 40:
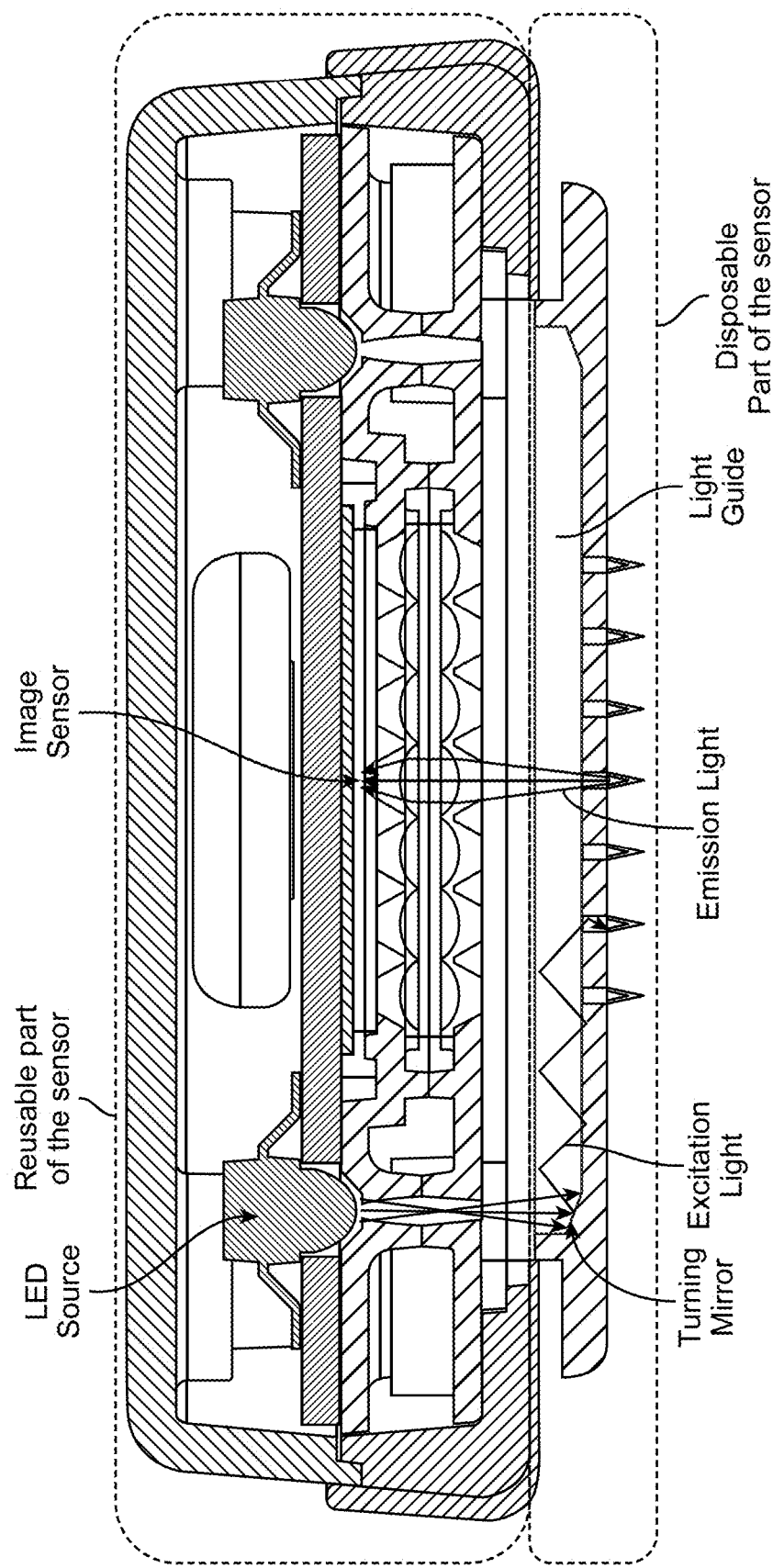
FIGS. 40-42 show cross sectional views of all of the layers of both the reusable and disposable parts of the sensor depicted in FIG. 38.

Referring now to FIG. 40, shown and described is an exemplary system. The light is provided from a light source and directed through one or more apertures in an opaque material about an optical excitation path. In some embodiments, there may be a plurality of light sources. The optical excitation path may comprise one or more filters, for example a dicrotic filter or an absorptive filter, configure configured to preferentially transmit light of a particular wavelength, thereby reducing an interference signal or background noise from light otherwise present within the device. The optical excitation path may further comprise one or more focusing elements within the optical excitation path, focusing the excitation light towards from a light source towards a light coupler in the optical excitation path. The optical excitation path may further comprise an optical wave guide which is a component of the optical excitation path. In some embodiments, the excitation light is passed through one or more optical filters, through one or more focusing elements, into the light coupler, and into the optical wave guide. In some embodiments, the excitation light is directed through one or more focusing elements into the light coupler, and transmitted to the wave guide, and from the wave guide into one or more piercing elements.

The optical wave guide may comprise a of cladding layer surrounding the wave guide configured to reflect the light back inside the wave guide and guide the light towards the piercing element. In some embodiments, the optical excitation path may comprise a light coupler, the light coupler being configured to couple light from the light source and into the wave guide, increasing the optical coupling efficiency of the optical excitation path. Once, the reflective clotting layer comprises an air gap. In some embodiments, at least a portion of the air gap is positioned between a base of the piercing element and the optical wave guide. In some cases, the air gap is configured to reflect light towards the piercing element. The air gap may have a lower refractive index than the wave guide, thereby enhancing the reflection of the light towards the piercing element. There are wave guide may have a refractive index of greater than one. In some cases, the waveguide comprises a geometrical core that is made of a dielectric material, with the reflective cladding layer surrounding the dielectric core. In some cases, the reflective cladding layer is made of metal, glass, or another reflective material, and in cases where the reflective clotting layer is made of metal, the metal may comprise aluminum, silver, titanium, or another reflective metal. In some cases, the wave guide is configured to direct light to the analyte binding probe.

The wave guide may be in optical communication with the piercing element. The piercing element may comprise the analyte binding probe therein. The piercing element may be comprised of a barrier domain, a structural domain, and a sensing domain. The piercing element may comprise a hydrogel material forming the sensing domain, with a plurality of particles comprising the analyte binding probe on a surface of the particles dispersed therein.

The present disclosure also provides solutions to problems related to detecting analytes in more flexible or sensitive ways. In some embodiments, the analyte binding probes that bind to the analyte can be attached to one or more particles within a hydrogel matrix inside the piercing element. Having the particles physically entrapped by the hydrogel solves the problem of decoupling any conjugation chemistry compatibility requirements between the hydrogel and the aptamers. In addition, the user can QC/QA the particles prior to inserting into the device, which has advantages for reproducibility and consistency during the manufacturing process.

Once contacted with the analyte, the analyte binding probes may undergo a conformational change, thereby inducing a change in optical signal, indicating the presence of the analyte. In some cases, an emission light is then produced as a result of the conformational change with the analyte binding probe, and the emission light is then transmitted about an optical emission path towards the detector.

For example, some embodiments optimize the optical excitation path by utilizing a waveguide and an optical coupler and comprising one or more focusing elements configured to focus light from a light source towards the light coupler. Some embodiments optimize the optical excitation path with a reflective cladding layer surrounding the waveguide, which is configured to reflect the light back inside the waveguide and guide the light toward the piercing element. Some embodiments optimize the optical excitation path by configuring the light coupler to couple light from a light source into the waveguide.

In some cases, the emission path may comprise a first portion which is positioned within the piercing element transmitting light to the optical wave guide, through one or more apertures in a reflective cladding layer surrounding the optical wave guide, towards one or more focusing elements, one or more optical filters, a second focusing element, and towards the detector. The detector may be physically aligned with the piercing element and the analyte binding probe in order to minimize the degree of optical coupling necessary to transmit the emission light to the detector. The emission light may be transmitted through a same portion of the waveguide which transmits the excitation light. The emission light may be transmitted through the wave guide, through one or more apertures in a reflective clotting layer surrounding the optical waveguide, towards one or more focusing elements which are configured to collimate the light into a beam and pass the light through one or more optical filters. The optical filters may be a dicrotic filter, an absorptive filter, or another filter which is configured to preferentially transmit light of a particular wavelength, for example, light that is the same wavelength as the emission light, which is a different wavelength than the excitation light. And some embodiments, there may be a plurality of optical filters in the emission path. In some cases, the plurality of filters in the optical emission path are configured to substantially blocked transmission of light which is not the same wavelength as the emission light. In some cases, 99%, 99.99%, 99.9999%, 99.99999% of all light which is not of the same wavelength of light as the emission light is blocked by the one or more optical filters. After passing through the one or more optical filters, the filtered emission light may then be passed through a second focusing element focusing the emission light onto one or more pixels of a detector configure to detect the change in optical signal.

Some embodiments of the present disclosure optimize the optical emission path, and allow the detection of very small levels of emission light, which is in some cases orders of magnitude small than an excitation light. In some embodiments, apertures in a reflective cladding layer surrounding a waveguide are configured to transmit an emission light from the analyte probe towards the detector. In some embodiments, one or more focusing elements are configured to focus emission light from the analyte binding probe towards the detector. In some embodiments, the optical excitation path and the optical emission path are configured to minimize interference with each other. In some embodiments, optical filters in combination transmit emission light while substantially blocking light which is a same wavelength as excitation light.

The present disclosure also provides solutions to the problem of how to develop a sensor that is sufficiently small enough to comprise a wearable patch. In some embodiments, a solution to this problem is to design a waveguide that can transmit both excitation and emission light in one device. This allows for the sensor to be more effectively miniaturized and compacted. However, utilizing a waveguide which is both a component of the optical emission path and optical excitation path presents problems associated with the detection of the emission light, which is in some cases orders of magnitude small than an excitation light. In some cases, the waveguide transmits light from a light source to the analyte binding probe, and waveguide is configured to permit light to be transmitted through the waveguide from the analyte binding probe to the detector. In some cases, the waveguide transmits light from a light source to the analyte binding probe through a directed path in the wave guide, in which light is reflected using one or more reflective walls. In some cases, the waveguide transmits light from the analyte binding probe to a detector using an optical emission path that is directly aligns the analyte binding probe and the detector.

In some embodiments, the device further comprises a light source, wherein the light source emits light at wavelengths of 600 nm to 750 nm. In some embodiments, the optical waveguide is configured to transmit light at wavelengths of 350 nm to 1500 nm. In some embodiments, the light source emits light within a 50 nm band within the wavelengths of 600 nm to 750 nm. In some embodiments, the light source emits light within a 50 nm band within the wavelengths of 350 nm to 1500 nm.

In some embodiments, the optical emission path is configured to reject light from the optical excitation path. In some embodiments, the optical emission path is configured to reject at least 75% of light from the optical excitation path. In some embodiments, the optical emission path is configured to reject light that is a higher wavelength than the light emitted by the light source. In some embodiments, the optical emission path is configured to reject light that is a higher wavelength than the light transmitted by the optical waveguide.

In some embodiments, the optical excitation path and the optical emission path are configured to minimize interference with each other. In some embodiments, the optical excitation path and the optical emission path are partially co-located within the optical waveguide. In some embodiments, the excitation path is configured to transmit light in a vertical direction and a horizontal direction. In some embodiments, the emission path is configured to transmit light in a vertical direction. In some embodiments, the emission path is configured to transmit light only in a vertical direction.

Optimizing the optical excitation and emission paths are one features in the present disclosure that provides the beneficial technical effect of improving the optical coupling efficiency in the optical sensor. Improving the optical coupling efficiency has the beneficial technical effect of decreasing the power level and battery size needed in the device. In some embodiments, the optical excitation path is optimized by utilizing a waveguide and an optical coupler and comprising one or more focusing elements configured to focus light from a light source towards the light coupler. Some embodiments optimize the optical excitation path with a reflective cladding layer surrounding the waveguide, which is configured to reflect the light back inside the waveguide and guide the light toward the piercing element. Some embodiments optimize the optical excitation path by configuring the light coupler to couple light from a light source into the waveguide.

Provided herein is a device for sensing an analyte in a biological sample of a subject, comprising: a support; a piercing element coupled to the support, wherein the piercing element is configured to pierce a body surface of the subject when the device is coupled to the body surface, to thereby bring the piercing element in contact with the biological sample; an analyte binding probe on or within the piercing element, wherein the analyte binding probe is configured to provide a change in an optical signal when the analyte binding probe comes in contact with the analyte in the biological sample of the subject; a detector operatively coupled to the support, wherein the detector is configured to detect the optical signal; a waveguide; an optical excitation path comprising the waveguide; an optical emission path comprising the waveguide, wherein the waveguide transmits light from a light source to the analyte binding probe, and wherein the waveguide is configured to permit light to be transmitted through the waveguide from the analyte binding probe to the detector. In some embodiments, the light coupler is configured to couple light from the light source into the waveguide. In some embodiments, the waveguide comprises a dielectric core, wherein the reflective cladding surrounds the dielectric core. In some embodiments, the reflective cladding comprises an aperture between the light source and the light coupler and the aperture is defined by the absence of the reflective cladding. In some embodiments, the piercing element comprises a reflective material about a base of the piercing element, wherein the optical excitation path guides light from a light source through the protruding portion of waveguide and to the reflective material about the base of the piercing element, wherein the reflective material about the base of the piercing element reflects the light to the analyte binding probe. In some embodiments, the optical emission path further comprises apertures in a reflective cladding layer surrounding the waveguide configured to transmit an emission light from the analyte probe towards the detector. In some embodiments, the optical emission path further comprises one or more focusing elements configured to focus emission light from the analyte binding probe towards the detector. In some embodiments, one or more focusing elements comprises a first focusing element configured to focus at least part of the emission light from the analyte binding probe into a first beam, and a second focusing element configured to focus the first beam towards the detector. In some embodiments, a diameter of the second beam coming from the second focusing element is configured to be a smaller size diameter than the first beam when the second beam crosses the plane of the detector and is incident on one or more pixels of the detector, thereby improving the signal to noise ratio of the detector. In some embodiments, the portion of the light blocked from transmission by filter has a wavelength which is a same wavelength as the light source. In some embodiments, the first focusing element transmits light to the optical filter at an angle within approximately +/−25 degrees with respect to a surface normal vector of the filter. In some embodiments, the optical emission path is configured to reject emission light from the analyte binding probe which does not enter the waveguide at a critical angle between ±20 degrees as measured from a vector normal to a base of the piercing element. In some embodiments, the analyte binding probe is comprised in a sensing domain comprising a hydrogel matrix comprising one or more particles comprising the analyte binding probe. In some embodiments, the analyte binding probe comprises a fluorophore conjugated to an aptamer configured to bind to the analyte, wherein the aptamer is configured to undergo a conformation change resulting in a shift in optical signal upon contacting the analyte. In some embodiments, the analyte binding probe is comprised in a sensing domain comprising a hydrogel matrix comprising one or more particles comprising the analyte binding probe. In some embodiments, the particles comprise a diameter of about 1 micron to about 50 microns. In some embodiments, the piercing element comprises a plurality of microneedles, wherein a number of particles in any one of the plurality of microneedle is at least $10^3$ particles. In some embodiments, the concentration of analyte binding probes on a surface of the one or more particles is about at least $10^6$ analyte binding probes per $cm^2$.

In some embodiments, the reflective cladding layer comprises an air gap. In some embodiments, the air gaps provide for a total internal reflection methods of light transmission. In some embodiments, at least a portion of the air gap is positioned between a base of the piercing element and the optical waveguide. In some embodiments, the air gap is configured to reflect light towards the piercing element. In some embodiments, the air gap has a lower refractive index than the waveguide. In some embodiments, the waveguide comprises a refractive index of greater than 1. In some embodiments, the waveguide comprises a geometrical core that is made of a dielectric material, wherein the reflective cladding surrounding the dielectric core is a reflective metal or glass, optionally, wherein the metal comprises Al or Ag. In some embodiments, the waveguide comprises a geometrical cross section that is a rectangle. In some embodiments, the two dimensions of the rectangle range from 100 microns to 5 mm. In some embodiments, the optical waveguide is configured to only transmit the excitation light to the piercing element, and wherein the optical waveguide is a dielectric waveguide comprising the reflective cladding, wherein light is configured to enter the optical waveguide within a narrow range of angles around the surface normal of the top, light-source facing side of the waveguide. In some embodiments, the range of the angles is 40-50 degrees as measured from the surface normal of the bottom coupling surface of the waveguide. In some embodiments, the device further comprises a light coupler. In some embodiments, the light coupler is configured to transmit light from the light source to a waveguide. In some embodiments, the waveguide comprises a dielectric core, wherein the reflective cladding surrounds the dielectric core. In some embodiments, the reflective material comprises a metal, Al, or Ag. In some embodiments, the reflective cladding comprises an aperture between the light source and the light coupler. In some embodiments, the dielectric core surrounded by the reflective cladding is configured to confine light within the waveguide. In some embodiments, the waveguide comprises a protruding portion which extends into a base of the piercing element. In some embodiments, the waveguide comprises a connecting material that optically extracts light from the waveguide towards the piercing element and the analyte probe. In some embodiments, the connecting material is an extension of the dielectric core material of the waveguide. In some embodiments, the connecting material is different from the core of the waveguide and comprises a substantially similar refractive index as the core of the wave guide, and, optionally, comprises multiple layers. In some embodiments, the piercing element comprises a reflective material about a base of the piercing element. In some embodiments, the optical excitation path guides light from a light source through the protruding portion of waveguide and to the reflective material about the base of the piercing element, wherein the reflective material about the base of the piercing element reflects the light to the analyte binding probe on or within the piercing element. In some embodiments, the waveguide comprises a polymer glassy matrix comprising dispersed photoluminescent particles. In some embodiments, the polymer comprises silicones, polysiloxanes, silsequioxanes, or combinations thereof. In some embodiments, the polymer comprises: polymethylmethacrylate (PMMA), polystyrene (PS), polycarbonate (PC), polyurethane (PU), epoxy resin, deuterated and halogenated polyacrylates, fluorinated polyimides, perfluorocyclobutyl (PFCB) aryl ether polymers, nonlinear optical polymers, benzocylcobutene (BCB), perfluorovinyl ether cyclopolymer (CYTOP), tetrafluoroethylene and perfluorovinyl ether copolymer (Teflon AF), silicone, fluorinated poly(arylene ether sulfide), poly(pentafluorostyrene), fluorinated dendrimers, fluorinated hyperbranched polymers, or combinations thereof.

In some embodiments, the optical excitation path is configured to reject light which does not enter the optical excitation path at a critical angle. In some embodiments, the critical angle is between 80-100 degrees as measured from a vector normal to a base of the piercing element. In some embodiments, the critical angle is an angle which is not approximately 90 degrees. In some embodiments, the device further comprises an opaque layer comprising apertures, wherein light must enter the optical excitation path at the critical angle to pass through the apertures. In some embodiments, the optical excitation path further comprises an optical filter between the light source and the light coupler. In some embodiments, the optical filter is a dichroic filter or an absorptive filter. In some embodiments, the analyte binding probe is an aptamer, or an antibody. In some embodiments, the light coupler comprises a faceted mirror. In some embodiments, the faceted mirror is configured to direct light towards the waveguide. In some embodiments, the faceted mirror is configured to direct light from a section of free space optics towards the waveguide. In some embodiments, the faceted mirror is partially metalized. In some embodiments, the faceted mirror is fully metalized. In some embodiments, the faceted mirror is non-metalized. In some embodiments, the device further comprises an optoelectronics system, the optoelectronics system comprising the detector, wherein the optoelectronics system is operatively coupled to the support, and wherein the optoelectronic system is configured to detect the change in the optical signal using the detector. In some embodiments, the device further comprises an excitation light source. In some embodiments, the excitation light source comprises a laser, or an LED. In some embodiments, the device further comprises an electrical system coupled to the detector that processes the change and generates an electrical signal related to the concentration of the analyte. In some embodiments, the optical excitation path comprises a section of free space optics between a light source and the waveguide.

In some embodiments, the optical emission path comprises a first focusing element configured to focus the emission light from the analyte binding probe into a first beam. In some embodiments, the first beam comprises light rays that are substantially parallel to each other and substantially perpendicular to the surface of the first focusing element. In some embodiments, the first beam is configured to be incident on one or more pixels of the detector. In some embodiments, the device further comprises a second focusing element configured to focus the first beam towards the detector. In some embodiments, a diameter of the second beam is configured to be a similar size diameter as one or more pixels on the detector, and improves a signal to noise ratio of the detector. In some embodiments, an optical path of the first beam is isolated from an optical path of the excitation light. In some embodiments, the device further comprises an optical filter between the first beam and the detector which does not transmit a portion of light directed to the filter. In some embodiments, a diameter of the second beam is configured to be a similar size diameter as the first beam when the second beam crosses the plane of the detector and is incident on one or more pixels of the detector, thereby improving the signal to noise ratio of the detector. In some embodiments, the optical filter is a dichroic filter or an absorptive filter. In some embodiments, the first focusing element transmits light to the filter at an angle of approximately +/−25 degrees with respect to the beam. In some embodiments, the first focusing element transmits light to the filter at an angle of approximately 0 degrees with respect to the surface normal vector of the filter. In some embodiments, the portion of light not transmitted comprises wavelengths of light less than 700 nm in wavelength. In some embodiments, the optical filter transmits emission light while substantially blocking light which is a same wavelength as excitation light. In some embodiments, the optical filter is configured to block at least 99, 99.9, 99.99, 99.999, 99.9999, 99.99999, 99.99999% of light from the excitation path. In some embodiments, the optical filter is configured to maximize the rejection of excitation light from an optical excitation path. In some embodiments, the device further comprises a second optical filter, wherein the second optical filter is a dichroic filter or an absorptive filter. In some embodiments, the first optical filter and the second optical filter in combination transmit emission light while substantially blocking light which is a same wavelength as excitation light. In some embodiments, the device further comprises a light source. In some embodiments, the light source is a downward firing light source positioned above the pierceable member. In some embodiments, the device further comprises an opaque layer comprising apertures, wherein light must enter the optical excitation path at the critical angle to pass through the apertures. In some embodiments, the light source is positioned on a first side of the opaque layer, and wherein the detector is positioned on a opposite side of the opaque layer. In some embodiments, the device further comprises an opaque material with an aperture in the emission path that is configured to block transmission of excitation light that does not strike the optical filter within approximately +/−25 degrees with respect to a vector normal to the surface of the optical filter. In some embodiments, the optical emission path comprises a section of free space optics between a waveguide and the detector. In some embodiments, the device further comprises a battery. In some embodiments, the light source is configured to increase a single battery cycle life of the device. In some embodiments, the detector is configured to increase a single battery cycle life of the device. In some embodiments, the optical excitation path is configured to increase light coupling efficiency from the excitation light source to the analyte probe, and is configured to increase a single battery cycle life of the device. In some embodiments, the optical excitation path is configured to increase light coupling efficiency from the excitation light source to the analyte probe, and is configured to increase a single battery cycle life of the device. In some embodiments, the optical excitation path is configured to increased light coupling efficiency, and is configured to increase a single battery cycle life of the device. In some embodiments, the optical emission path is configured to increased light coupling efficiency, and is configured to increase a single battery cycle life of the device. In some embodiments, the piercing element comprises a structural domain, a barrier domain, and a sensing domain. In some embodiments, the analyte binding probe is comprised of a hydrogel matrix in the sensing domain. In some embodiments, the analyte binding probe is comprised of one or more particles comprised by the hydrogel matrix. In some embodiments, the particles comprise a polymer, optionally, wherein the polymer is polystyrene. In some embodiments, the particles are magnetic. In some embodiments, the particles comprise a diameter of about 100 nm to about 100 microns. In some embodiments, the particles comprise a diameter of at least 100 nm. In some embodiments, the particles comprise a diameter of up to about 100 microns. In some embodiments, the device further comprises a light source. In some embodiments, the device is configured to be placed in optical communication with an external light source. In some embodiments, the device further comprises two or more analyte binding probes on or within the piercing element, each of the two or more analyte binding probes configured to provide a change in an optical signal when the two or more analyte binding probes contact a second analyte in the biological sample of the subject. In some embodiments, the device further comprises two or more analyte binding probes on or within the piercing element, each of the two or more analyte binding probes configured to provide a change in an optical signal when the two or more analyte binding probes contact a second analyte in the biological sample of the subject. In some embodiments, the analyte binding probe comprises a fluorophore conjugated to an aptamer configured to bind to the analyte, wherein the analyte binding probe is configured to contact the biological sample of the subject and provide the change in an optical signal when the piercing element is inserted into a skin of a subject. In some embodiments, the device further comprises a multiplexed array of analyte binding probes on or within the piercing element, each of the multiplexed array of analyte binding probes configured to provide a change in an optical signal when the multiplexed array of analyte binding probe contacts a subsequent analyte in the biological sample of the subject. In some embodiments, the subsequent analyte is a different analyte, the multiplexed array of analyte binding probes is configured to detect a plurality of analytes in the biological sample of the subject. In some embodiments, the piercing element comprises a plurality of piercing elements. In some embodiments, the plurality of piercing elements defines subsets of piercing elements, wherein each subset of piercing elements comprises a different analyte binding probe configured to detect a different analyte in the biological sample of the subject. In some embodiments, the subsets of piercing elements comprising the different analyte binding probes comprise the multiplexed array of analyte binding probes.

In some embodiments, the piercing element is coupled to the support using a lock and key attachment. In some embodiments, the piercing element is coupled to the support using a mortise and tenon attachment. In some embodiments, the piercing element is coupled to the support using a dovetail attachment. In some embodiments, the piercing element is coupled to the support using a magnetic attachment. In some embodiments, the piercing element is coupled to the support using an adhesive. In some embodiments, the piercing element is coupled to the support using one or more elastically deformable attachment elements. In some embodiments, the piercing element is coupled to the support using one or more elastically deformable attachment elements configured to rebound once inserted into the support. In some embodiments, the piercing element is removably coupled to the support. In some embodiments, the piercing element comprises a microneedle array which is removably coupled to the support. In some embodiments, the optical light guide is removably coupled to the support.

In some embodiments, the piercing element is configured to transmit light within the piercing element towards the analyte binding probe. In some embodiments, the piercing element is configured to guide light emitting from the analyte binding probe out of the piercing element. In some embodiments, the piercing element is configured to transmit light using a reflective metal coating on a surface of the piercing element. In some embodiments, the piercing element is made of a reflective metal configured to reflect light, optionally, wherein the reflective metal comprises stainless steel, Ti, Ag, or combinations thereof. In some embodiments, the piercing element comprise a polymer, a plastic polymer, or combinations thereof. In some embodiments, the reflective metal coating is configured to increases an efficiency of light coupling from a top of the piercing element towards the analyte binding probe. In some embodiments, the reflective metal coating is configured to increases an efficiency of light coupling from the analyte binding probe towards the detector. In some embodiments, wherein the piercing element is configured to guide light using a dielectric material comprised within the piercing element.

In some embodiments, the piercing element is configured to transmit light within the piercing element towards the analyte binding probe. In some embodiments, the piercing element is configured to guide light emitting from the analyte binding probe out of the piercing element. In some embodiments, the piercing element is configured to transmit light using a reflective metal coating on a surface within the piercing element, optionally, wherein the piercing element comprises Ag or Au. In some embodiments, the piercing element is made of a reflective metal configured to reflect light, optionally, wherein the reflective metal comprises stainless steel, Ti, Ag, or combinations thereof. In some embodiments, the piercing element comprise a polymer, a plastic polymer, or combinations thereof. In some embodiments, the reflective metal coating is configured to increases an efficiency of light coupling from a top of the piercing element towards the analyte binding probe within the piercing element. In some embodiments, the reflective metal coating is configured to increases an efficiency of light coupling from the analyte binding probe towards the detector. In some embodiments, the piercing element is configured to guide light using a dielectric material comprised within the piercing element. In some embodiments, the dielectric material is a dielectric waveguide with a core and cladding. In some embodiments, the dielectric waveguide is an optical fiber. In some embodiments, the second waveguide guides an excitation light towards the analyte binding probe, and an emission light from the analyte binding probe towards the detector. In some embodiments, the analyte binding probe is located above the piercing elements. In some embodiments, the piercing element comprises a plurality of piercing members held together by a base. In some embodiments, the plurality of piercing members is at least partially hollow. In some embodiments, at least one of the plurality of piercing members provides a fluorescence signal of known magnitude to establish a reference signal as to the change in optical signal from the analyte binding probe under a given biological condition. In some embodiments, the given biological conditions comprise a pH value, a temperature, a salt concentration, or combinations thereof. In some embodiments, at least two of the piercing members comprise a same analyte binding probe. In some embodiments, at least two of the piercing members comprise a same analyte binding probe in a same concentration. In some embodiments, at least two of the piercing members comprise two different analyte binding probes that detect two different analytes.

In some embodiments, the piercing element is a microneedle array. In some embodiments, one or more sidewalls of each microneedle of the microneedle array are reflective. In some embodiments, the piercing element comprises a structural domain, a barrier domain, and a sensing domain. In some embodiments, the structural domain is positioned on a surface of the support and extends outward from the surface to define a needle, and defines an interior space, wherein the sensing domain is contained within the interior space. In some embodiments, the structural domain encapsulates the barrier domain. In some embodiments, the structural domain encloses the sensing domain. In some embodiments, the sensing domain encapsulates the analyte binding probe within a matrix of the sensing domain, wherein the barrier domain comprises a hydrogel, a polymer, or combinations thereof. In some embodiments, the sensing domain comprises the analyte binding probe. In some embodiments, the sensing domain comprises the analyte binding probe in a hydrogel matrix. In some embodiments, the analyte binding probe is bound to one or more beads in the hydrogel matrix. In some embodiments, the barrier domain comprises a hydrogel, a polymer, or combinations thereof. In some embodiments, the structural domain encapsulates the sensing domain, wherein the sensing domain is configured to control transfer of the analyte to the analyte binding probe. In some embodiments, the barrier domain is configured to control transfer of the analyte to sensing domain via diffusion. In some embodiments, the sensing domain and/or the barrier domain comprise a plurality of pores. In some embodiments, the analyte binding probe is contained within the sensing domain at a concentration of about 1 nM to about 1 mM. In some embodiments, the analyte binding probe is contained within the sensing domain at a concentration of about 1 nM to about 1 uM.

In some embodiments, the piercing element is configured to store the biological sample for subsequent analysis. In some embodiments, the structural domain encapsulates the barrier domain. In some embodiments, the structural domain encloses the sensing domain. In some embodiments, the sensing domain encapsulates the analyte binding probe within a matrix of the sensing domain, wherein the barrier domain comprises a hydrogel, a polymer, or combinations thereof. In some embodiments, the sensing domain comprises the analyte binding probe. In some embodiments, the sensing domain comprises the analyte binding probe in a hydrogel matrix. In some embodiments, the analyte binding probe is bound to one or more beads in the hydrogel matrix. In some embodiments, the barrier domain comprises a hydrogel, a polymer, or combinations thereof. In some embodiments, the structural domain encapsulates the sensing domain, wherein the sensing domain is configured to control transfer of the analyte to the analyte binding probe. In some embodiments, the barrier domain is configured to control transfer of the analyte to sensing domain via diffusion. In some embodiments, the sensing domain and/or the barrier domain comprise a plurality of pores. In some embodiments, the analyte binding probe is contained within the sensing domain at a concentration of about 10 pM to about 1 mM. In some embodiments, the analyte binding probe is contained within the sensing domain at a concentration of about 1 nM to about 1 uM. In some embodiments, a concentration of particles in the sensing domain ranges from $10^3$ particles to $10^9$ particles/mL. In some embodiments, a concentration of particles in the sensing domain ranges from $10^5$ particles to $10^8$ particles/mL. In some embodiments, the concentration of analyte binding probes on a surface of the one or more particles is about $10^6$ to about $5*10^{13}$ analyte binding probes per $cm^2$. In some embodiments, the concentration of analyte binding probes on a surface of the one or more particles is about $10^{10}$ to about $10^{13}$ analyte binding probes per $cm^2$. In some embodiments, the analyte binding probe is an aptamer, wherein the concentration of analyte binding probes on a sur-face of the one or more particles is about $10^6$ to about $5*10^3$ aptamers per $cm^2$. In some embodiments, the analyte binding probe is an aptamer, wherein the concentration of analyte binding probes on a surface of the one or more particles is about $10^{10}$ DNA aptamers/$cm^2$ to about $10^{13}$ DNA ap-tamers/$cm^2$. In some embodiments, the analyte binding probe is an aptamer, wherein an average spacing of the analyte binding probes ranges from about 1.4 nm to about 10 micrometers between aptamers. In some embodiments, the analyte binding probe is an aptamer, wherein an average spacing of the analyte binding probes ranges from about 3 nm to about 100 nm between aptamers.

In some embodiments, the analyte binding probe coupled to the optical reporter is an oligonucleotide probe. In some embodiments, the oligonucleotide probe is an aptamer. In some embodiments, the aptamer is coupled to a displacement strand, wherein the displacement strand is partially complementary to the aptamer. In some embodiments, the displacement strand is coupled to a second optical reporter. In some embodiments, the second optical reporter is a fluorophore or a quencher. In some embodiments, the aptamer is coupled to a linker moiety placed between the aptamer and the displacement strand. In some embodiments, the linker moiety is a nucleotide acid moiety, a peptide nucleic acid (PNA) moiety, a peptide moiety, a disulfide bond, a phosphodiester linkage, or a polymer. In some embodiments, one or more sidewalls of the piercing element are reflective.

In some embodiments, the detector comprises a semiconductor material. In some embodiments, the detector comprises a semiconductor photodetector. In some embodiments, the detector comprises a semiconductor photodetector comprising a silicon photomultiplier chip, an avalanche photodiode, a metal-semiconductor-metal photodiode, a CMOS sensor array, a CCD (charge coupled device), a lateral semiconductor photodiode, an array of photodetectors, or combinations thereof. In some embodiments, the semiconductor material or the semiconductor photodetector comprises a p-n junction. In some embodiments, the semiconductor material or the semiconductor photodetector comprises Si, Ge, InGaAs, GaAs, InP, Ge, SiGe, InGaN, GaN, or combinations thereof. In some embodiments, the detector comprises a silicon photomultiplier (SiPM) detector.

In some embodiments, the dielectric material is a second waveguide. In some embodiments, the second waveguide guides an excitation light towards the analyte binding probe, and an emission light from the analyte binding probe towards the detector. In some embodiments, the analyte binding probe is located above the piercing elements. In some embodiments, the piercing element comprises a plurality of piercing members held together by a base. In some embodiments, the plurality of piercing members is at least partially hollow. In some embodiments, at least one of the plurality of piercing members provides a fluorescence signal of known magnitude to establish a baseline signal as to the change in optical signal from the analyte binding probe under a given biological condition. In some embodiments, the given biological conditions comprise a pH value, a temperature, a salt concentration, or combinations thereof. In some embodiments, at least two of the piercing members comprise a same analyte binding probe. In some embodiments, at least two of the piercing members comprise a same analyte binding probe in a same concentration.

In some embodiments, the change in optical signal when the analyte binding probe comes in contact with the analyte is detected using a time resolved fluorescence technique. In some embodiments, the change in optical signal when the analyte binding probe comes in contact with the analyte is detected using an intensity of the fluorescence. In some embodiments, the analyte binding probe comprises a quantum dot.

In some embodiments, the analyte binding probe comprises an aptamer conjugated to a quantum dot. In some embodiments, the optical coupler is an optical grating. In some embodiments, the optical grating is a diffraction element configured to guide light from a free space into the waveguide, or from the waveguide into a free space. In some embodiments, the optical grating is configured to direct light from the waveguide toward the piercing element. In some embodiments, the optical grating is configured to direct light from the piercing element towards the waveguide. In some embodiments, the piercing element is separable from the device. In some embodiments, the detector comprises a semiconductor material. In some embodiments, the detector comprises a semiconductor photodetector. In some embodiments, the detector comprises a semiconductor photodetector comprising a silicon photomultiplier chip, an avalanche photodiode, a metal-semiconductor-metal photodiode, a CMOS sensor array, a CCD (charge coupled device), a lateral semiconductor photodiode, an array of photodetectors, or combinations thereof. In some embodiments, the semiconductor material or the semiconductor photodetector comprises a p-n junction. In some embodiments, the semiconductor material or the semiconductor photodetector comprises Si, Ge, InGaAs, GaAs, InP, Ge, SiGe, InGaN, GaN, or combinations thereof. In some embodiments, the detector comprises a silicon photomultiplier (SiPM) detector.

In some embodiments, the change in optical signal when the analyte binding probe comes in contact with the analyte is detected using a fluorescence resonance energy transfer (FRET) or a time resolved fluorescence (TRF) technique. In some embodiments, the change in analyte concentration when the analyte binding probe comes in contact with the analyte is detected using a change in intensity of the fluorescence. In some embodiments, the analyte binding probe comprises a quantum dot. In some embodiments, the analyte binding probe comprises an aptamer conjugated to a quantum dot. In some embodiments, the optical coupler is an optical grating. In some embodiments, the optical grating is a diffraction element configured to guide light from a free space into the waveguide, or from the waveguide into a free space. In some embodiments, the optical grating is configured to direct light from the waveguide toward the piercing element. In some embodiments, the optical grating is configured to direct light from the piercing element towards the waveguide. In some embodiments, the piercing element is separable from the device. In some embodiments, the piercing element is configured to store the biological sample for subsequent analysis.

The devices and systems disclosed herein may also be used in method for sensing an analyte in a biological sample of a subject, comprising: piercing a skin of the subject to contact a biological sample, and bringing the biological sample in contact with an analyte binding probe; inducing a conformational change in the analyte binding probe by binding a target analyte with the analyte binding probe; applying a light source to the analyte binding probe to produce an optical signal; measuring a presence, a lack of presence, an increase, or a decrease of the optical signal to determine the presence or concentration of the target analyte in the sample. In some embodiments, passing light through an optical waveguide from a light source to the analyte binding probe. In some embodiments, passing light through an optical waveguide from the analyte binding probe to a detector. In some embodiments, applying the light source to the analyte binding probe comprises transmitting light through an optical excitation path comprising a waveguide and a light coupler and: i) transmitting light through one or more focusing elements and focusing light from a light source towards the light coupler, ii) transmitting light through a waveguide and reflecting it within the waveguide using a reflective cladding layer surrounding the waveguide, thereby guiding the light toward the piercing element or iii) transmitting light from a light source, through the light coupler, and into the waveguide. In some embodiments, measuring a presence, a lack of presence, an increase, or a decrease of the optical signal comprises transmitting light through an optical emission path comprising: i) apertures in a reflective cladding layer surrounding a waveguide, transmitting light through the apertures towards the detector, or ii) one or more focusing elements configured to focus emission light from the analyte binding probe towards the detector, transmitting lights through the one or more focusing elements towards the detector. In some embodiments, applying a light source to the analyte binding probe to produce an optical signal comprises transmitting light about an optical excitation path comprising a waveguide, and an optical emission path comprising the waveguide, the waveguide transmitting light from the light source to the analyte binding probe, and the transmitting light through the waveguide from the analyte binding probe to a detector. In some embodiments, applying the light source to the analyte binding probe and/or measuring a presence, a lack of presence, an increase, or a decrease of the optical signal comprises the waveguide transmitting light from a light source to the analyte binding probe, and the waveguide transmitting light from the analyte binding probe to the detector. In some embodiments, the analyte binding probe is comprised in a sensing domain comprising a hydrogel matrix comprising one or more particles comprising the analyte binding probe. In some embodiments, the analyte binding probe has a dissociation constant of at least 1 pM with respect to the analyte. In some embodiments, piercing the skin of the subject comprises piercing the skin of the subject with a piercing element that is removable from a device. In some embodiments, piercing the skin of the subject comprises storing the biological sample in the piercing element for subsequent analysis. In some embodiments, measuring the presence, the lack of presence, the increase, or the decrease of the optical signal to determine the presence or concentration of the target analyte in the sample occurs using a device coupled to a piercing element. In some embodiments, measuring the presence, lack of presence, increase of optical signal, or decrease of optical signal to determine the concentration of the target analyte in the biological sample occurs while the piercing element is attached to the body of a subject. In some embodiments, measuring the presence, lack of presence, increase of optical signal, or decrease of optical signal to determine the concentration of the target analyte in the biological sample occurs while the piercing element is removed from the body of a subject.

Computer Systems

Figure 11:
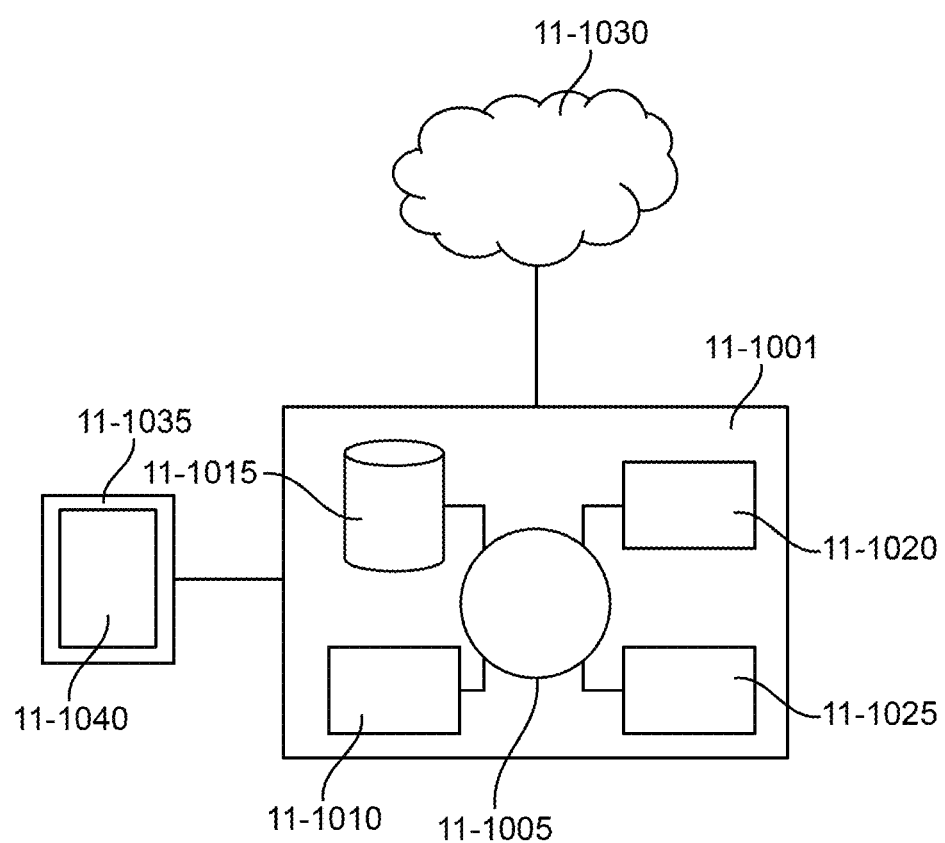
FIG. 11 depicts computer systems that are programmed to implement methods of the disclosure.

The present disclosure provides computer systems that are programmed to implement methods of the disclosure. FIG. 11 shows a computer system 11-1001 that is programmed or otherwise configured to manipulate an analyte detection parameter or to calculate concentration of one or more analytes, or a plurality thereof. The computer system 11-1001 can regulate various aspects of analyte detection parameter or concentration calculation, such as, for example, selecting analyte of interest to measure by manipulating wavelength of the light source, calculating concentration of the analyte by measuring the changes in the optical signal, or any combination thereof. The computer system 11-1001 can be an electronic device of a user or a computer system that is remotely located with respect to the electronic device. The electronic device can be a mobile electronic device. The computer system 11-1001 includes a central processing unit (CPU, also "processor" and "computer processor" herein) 11-1005, which can be a single core or multi core processor, or a plurality of processors for parallel processing. The computer system 11-1001 also includes memory or memory location 11-1010 (e.g., random-access memory, read-only memory, flash memory), electronic storage unit 11-1015 (e.g., hard disk), communication interface 11-1020 (e.g., network adapter) for communicating with one or more other systems, and peripheral devices 11-1025, such as cache, other memory, data storage and/or electronic display adapters. The memory 11-1010, storage unit 11-1015, interface 11-1020 and peripheral devices 11-1025 are in communication with the CPU 11-1005 through a communication bus (solid lines), such as a motherboard. The storage unit 11-1015 can be a data storage unit (or data repository) for storing data. The computer system 11-1001 can be operatively coupled to a computer network ("network") 11-1030 with the aid of the communication interface 11-1020. The network 11-1030 can be the Internet, an internet and/or extranet, or an intranet and/or extranet that is in communication with the Internet The network 11-1030 in some cases is a telecommunication and/or data network. The network 11-1030 can include one or more computer servers, which can enable distributed computing, such as cloud computing. The network 11-1030, in some cases with the aid of the computer system 11-1001, can implement a peer-to-peer network, which may enable devices coupled to the computer system 11-1001 to behave as a client or a server.

The CPU 11-1005 can execute a sequence of machine-readable instructions, which can be embodied in a program or software. The instructions may be stored in a memory location, such as the memory 11-1010. The instructions can be directed to the CPU 11-1005, which can subsequently program or otherwise configure the CPU 11-1005 to implement methods of the present disclosure. Examples of operations performed by the CPU 11-1005 can include fetch, decode, execute, and writeback.

The CPU 11-1005 can be part of a circuit, such as an integrated circuit. One or more other components of the system 11-1001 can be included in the circuit. In some cases, the circuit is an application specific integrated circuit (ASIC).

The storage unit 11-1015 can store files, such as drivers, libraries and saved programs. The storage unit 11-1115 can store user data, e.g., user preferences and user programs. The computer system 11-1001 in some cases can include one or more additional data storage units that are external to the computer system 11-1001, such as located on a remote server that is in communication with the computer system 11-1001 through an intranet or the Internet.

The computer system 11-1001 can communicate with one or more remote computer systems through the network 11-1030. For instance, the computer system 11-1001 can communicate with a remote computer system of a user (e.g., hand-held device). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 11-1001 via the network 11-1030.

Methods as described herein can be implemented by way of machine (e.g., computer processor) executable code stored on an electronic storage location of the computer system 11-1001, such as, for example, on the memory 11-1010 or electronic storage unit 11-1015. The machine executable or machine readable code can be provided in the form of software. During use, the code can be executed by the processor 11-1005. In some cases, the code can be retrieved from the storage unit 11-1015 and stored on the memory 11-1010 for ready access by the processor 11-1005. In some situations, the electronic storage unit 11-1015 can be precluded, and machine-executable instructions are stored on memory 11-1010.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine-readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer-readable media may be involved in carrying one or more sequences of one or more instructions to a processor for execution.

The computer system 11-1001 can include or be in communication with an electronic display 11-1035 that comprises a user interface (UI) 11-1040 for providing, for example, concentration of the analyte of interest. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 11-1005.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

The following examples are included for illustrative purposes only and are not intended to limit the scope of the invention.

Example 1: Preparation of Aptamer Switches

Provided is an example method for converting existing aptamers into optically responsive structure switching aptamer switches. Since the majority of aptamers are not selected to undergo a reversible binding-induced conformational change, the majority of aptamer switches are therefore created via a post-selection engineering approach.

The first step of the process starts with the selection of a parent aptamer, which can be selected using one of the numerous aptamer selection techniques. Examples include SELEX, Cell-SELEX, CE-SELEX, Particle Display, Capture-SELEX, and microarray-based selection techniques. Next, a displacement strand is identified which can be displaced from binding to the parent aptamer by the aptamer's molecular target in a concentration-dependent manner. The selection of displacement strand regions can be done randomly, or via rational design aided by computationally predicted secondary structures. Typically, the displacement strands target the hypothesized binding pockets or stem regions within the aptamer sequence.

In order to experimentally confirm the ability of the displacement strand to de-hybridize from the parent aptamer upon target addition, the parent aptamer is labeled with a fluorophore (e.g. FAM, Cy3, Cy5) and the displacement strand with a quencher (e.g. Dabcyl, BHQ). The ability of the displacement strand to bind and quench the signal from the fluorophore is first confirmed by titrating in various concentrations of the displacement strand while maintaining a constant concentration of the fluorescently-labeled parent aptamer. The binding of the displacement strand is observed as a reduction in fluorescent intensity. Once this is complete, a concentration of the displacement strand where ~90-95% of the parent aptamer is bound is selected. Next, the target molecule is added to confirm the ability of the target to induce a conformational change in the parent aptamer structure, which results in ejection of the displacement strand, and thus results in an increase in fluorescent signal.

Once a displacement strand region is identified, the aptamer switch can be constructed. This is typically done by creating constructs that are labeled at the 5' end with a fluorophore, then include the aptamer sequence, followed by a poly T linker, displacement strand sequence, and finally a 3' quencher (or FRET acceptor). Typically, several constructs are synthesized, and then optimized over several rounds of synthesis, experimentation, and analysis. Optimization can include, but are not limited to, changing the length of the poly T linker strands, and changing the composition of the displacement strand by adding, subtracting, or including base-pairing mismatches. For example, a poly T linker of 15 nucleotides may be chosen, and then 5 constructs of different length displacement strands (which are designed from the initial displacement strand) can be used in an initial test where target is added to a fixed concentration of the aptamer switch constructs and evaluated for an increase in optical signal. From the initial tests, the best candidate can be selected and further optimized by introducing mismatches into the displacement strand, or by changing the length of the linker.

Example 2: Integration of Aptamer Switches into Piercing Element

Provided are 4-arm PEG-DBCO, MW 10K (creative PEGWorks, PSB-4070); 4-arm PEG-Azide, MW 10K (creative PEGWorks, PSB-328); an Aptamer switch (with fluorophore and quencher) with 5' DBCO group; Artificial ISF (aISF) buffer; and 3D printed microneedles. Using these materials, the aptamer switches may be integrated into a hydrogel matrix of a microneedle array, for example, by:
  Mixing 50 mg/mL solution of PEG-DBCO in aISF;
  Mixing a stock of 100 uM aptamer switch in aISF;
  Mixing a solution containing 50 mg/mL solution of PEG-Azide in aISF with 1 uM aptamer switch;
  Permitting the mixture to set for 30 minutes to allow reactants to conjugate;
  Mixing well 500 uL of the 50 mg/mL solution of PEG-DBCO and 500 uL of the 50 mg/mL of the PEG containing aptamer switch; and
  Immediately loading the mixture into the microneedles. The solution can be loaded many different ways, but can be pipetted or put into a mold in which the MN is placed. If being pipetted directly into the MN, it can be done from below the MN or above the MN through holes which are present at the base of the MN patch.

The mixture can then be allowed to set for an additional 15 minutes. Over this time the hydrogel forms crosslinks and becomes a gel. Gelation time is roughly 5-7 minutes.

Once this is complete the hydrogel with aptamer is loaded into the microneedles.

Although this example utilized a DBCO/Azide hydrogel system, many other hydrogel systems could also be utilized. For example, PVA hydrogels that are chemically crosslinked using glutaraldehyde or PEGDMA systems that are UV-crosslinked.

The microneedle filled with hydrogel will then be characterized. The mechanical properties can then be evaluated using compression tests on an Instron mechanical testing system. The function of the integrated aptamers can be examined by exposing the needles to different concentrations of analyte and examining the change in optical signal within the microneedle using standard laboratory equipment such as fluorescent microscopy or microplate readers. Mechanical properties of the microneedle can establish the ability of the microneedle to penetrate the dermis multiple times without undergoing inelastic deformation. Functional testing utilizing fluorescent microscopy or microplate readers can establish that the aptamers and hydrogel respond sufficiently when in the dermal tissue via the microneedle, provide a fluorescent signal in a concentration dependent manner; and can be further used to characterize the change in signal with respect to analyte concentration, kinetics as to the rate of signal and signal change between the aptamer and an analyte, sensitivity (photon emission) of the aptamer, and dynamic range.

Example 3: Preparation of a Device for Detection of Analyte

Provided is a device for sensing an analyte in a biological sample of a subject, comprising: a support; a piercing element coupled to said support, wherein said piercing element is configured to pierce a body surface of said subject when said device is coupled to said body surface, to thereby bring said piercing element in contact with said biological sample; an analyte binding probe on or within said piercing element, wherein said analyte binding probe is configured to provide a change in an optical signal when said analyte binding probe comes in contact with said analyte in said biological sample of said subject; and a detector operatively coupled to said support, wherein said detector is configured to detect said optical signal. The device comprises an optical waveguide coupled to said support. The optical waveguide defines a light path between the light source and the analyte binding probe, and from the analyte binding probe to the detector. In some cases, the said optical waveguide comprises a 2-dimensional array of said waveguides, said 2-dimensional array comprises dichroic mirrors, said 2-dimensional array comprises gratings, said waveguide comprises a glass or a polymer, said 2-dimensional array is etched, and said optical waveguide is configured to collect an emission light of said optical reporter from said analyte binding probe, to guide at least a portion of said emission light to said detector. A light source from within the device is illuminated and applied to an optical waveguide, which applies the light source to the aptamer with the free fluorophore, to produce an optical signal. The waveguide is also in contact with the aptamer and defines a light path between the aptamer with the free fluorophore and the detector, and transfers the optical signal to the detector. The generated optical signal is detected by the detector, and notifies the wearer of the presence of the analyte.

The device is positioned on the skin of a wearer. The analyte selective sensor is deployed such that a sensing element contained within the analyte-selective sensor penetrates the stratum corneum of the skin and becomes positioned in the viable epidermis or dermis of the wearer. The sensing element is configured to penetrate the stratum corneum and in contact with one or more physiological analytes in a biological sample. The analyte of interest binds to an aptamer within the analyte-selective sensor inducing a conformational change of the aptamer. The conformational change of the aptamer which results in a change in luminescence via the change in distance between two optical reporters, a fluorophore and quencher, or FRET pair, allowing optical signal to be generated. A light source from within the device is illuminated and applied to the aptamer with the optical reporters, to produce an optical signal, by shining the light though the optical waveguide which defines a path between the light source and the two optical reporters. The waveguide is in contact with the light source, the analyte binding probe, and the detector, and is positioned in between the light source, the detector; and the analyte binding probe. There is a light path between the aptamer with the two optical reporters and the detector through the waveguide, and a light path between the light source and the aptamer with the free fluorophore. The generated optical signal is detected by the detector, and notifies the user of information (e.g., presence or concentration) about the analyte. The analyte may be glucose, 3-hydroxybutyrate, lactate, cortisol, uric acid, creatinine, potassium, urea, sodium, or serum amyloid A; and the device may detect multiple analytes.

Example 4: Preparation of a Device for Detection of Analyte ("Off Configuration")

Provided is a device for sensing an analyte in a biological sample of a subject, comprising: a support; a piercing element coupled to said support, wherein said piercing element is configured to pierce a body surface of said subject when said device is coupled to said body surface, to thereby bring said piercing element in contact with said biological sample; an analyte binding probe on or within said piercing element, wherein said analyte binding probe is configured to provide a change in an optical signal when said analyte binding probe comes in contact with said analyte in said biological sample of said subject; and a detector operatively coupled to said support, wherein said detector is configured to detect said optical signal. The device comprises an optical waveguide coupled to said support. The optical waveguide defines a light path between the light source and the analyte binding probe, and from the analyte binding probe to the detector. In some cases, the said optical waveguide comprises a 2-dimensional array of said waveguides, said 2-dimensional array comprises dichroic mirrors, said 2-dimensional array comprises gratings, said waveguide comprises a glass or a polymer, said 2-dimensional array is etched, and said optical waveguide is configured to collect an emission light of said optical reporter from said analyte binding probe, to guide at least a portion of said emission light to said detector. A light source from within the device is illuminated and applied to an optical waveguide, which applies the light source to the aptamer with the two optical reporters, to produce an optical signal. In this embodiment, the aptamer provides an optical signal in its first configuration, and provides a reduced or no optical signal when bound to the target analyte. The waveguide is also in contact with the aptamer and defines a light path between the aptamer with two optical reporters and the detector, and transfers the optical signal, or the lack thereof, to the detector. The optical signal is detected by the detector, and notifies the wearer of the presence of the analyte based on the reduction of optical signal measured by the detector. The device may also comprise a plurality of control modules which comprises one or more control molecules (which may be a fluorophore, a fluorophore just conjugated to a poly T strand, or a fluorophore directly conjugated another polymer), and defines a light path between the control molecules with the optical reporter and the detector, and transfers the optical signal to the detector, where the control modules are configured to not come into contact with the biological sample, as to provide an indication of the optical signal in the default or "off" configuration where there is no analyte bound to the aptamer.

The device is positioned on the skin of a wearer. The analyte selective sensor is deployed such that a sensing element contained within the analyte-selective sensor penetrates the stratum corneum of the skin and becomes positioned in the viable epidermis or dermis of the wearer. The sensing element is configured to be positioned in the viable epidermis and in contact with one or more physiological analytes in a biological sample. The analyte of interest binds to an aptamer within the analyte-selective sensor inducing a conformational change of the aptamer. The conformational change of the aptamer which results in a change in luminescence via the change in distance between two optical reporters, a fluorophore and quencher, or FRET pair, allowing optical signal to be generated. A light source from within the device is illuminated and applied to the aptamer A light source from within the device is illuminated and applied to the aptamer with the optical, to produce an optical signal, by shining the light though the optical waveguide which defines a path between the light source and the optical reporter. The analyte of interest binds to an aptamer within the analyte-selective sensor inducing a conformational change of the aptamer. The conformational change of the aptamer binds the fluorophore to the quencher, reducing or eliminating the production of the optical signal. The waveguide is in contact with the light source, the analyte binding probe, and the detector, and is positioned in between the light source, the detector; and the analyte binding probe. There is a light path between the aptamer with the free fluorophore and the detector through the waveguide, and a light path between the light source and the aptamer with the free fluorophore. The reduction or lack of the optical signal relative to the control is detected by the detector, and notifies the information (e.g., presence or concentration) about the analyte. The analyte may be glucose, 3-hydroxybutyrate, lactate, cortisol, uric acid, creatinine, potassium, urea, sodium, or serum amyloid A; and the device may detect multiple analytes.

While various embodiments of the disclosure have been shown and described herein, it will be obvious to those skilled in the art that such embodiments are provided by way of example only. Numerous variations, changes, and substitutions may occur to those skilled in the art without departing from the disclosure. It should be understood that various alternatives to the embodiments of the disclosure described herein may be employed.

Example 5: Detailed Description of an Exemplary Device Utilizing Direct Light

This example details and provides a design, structure, and methods of optical coupling for optically probed molecular sensors. The structure described herein positions a light source or sources directly above a molecular sensing domain. The structural layers of the solution may comprise a light delivery system to the sensing apparatus from the light source, a light carrying apparatus from the sensing apparatus to the detection system, and a detection system. Thus, the structure described herein provides a durable device that both measures the light emitted by each sensing domain as well as provides the means for optical stimulation of the sensing domain or domains. The structural layers, advantageously miniaturized, and their relative arrangement in a biosensor, interrogated using light and relying on fluorescence, are described herein. The term direct light refers to line of sight exposure light or line of sight light.

This example describes an implementation of an exemplary device that utilizes direct light, with no light guide. In some embodiments of the device, a light source or sources may be positioned directly above an array of piercing elements, in this case a microneedle array, with no light guide present, allowing for an increase in the total number of excitation photons in each microneedle. Eliminating the light guide and positioning the light source directly above the microneedle array allows for the delivery of uniform, high intensity light to each needle. The light sources may be individually addressable, so that illumination can be controlled locally rather than globally. In some embodiments of this configuration, the signal for each individual piercing element in an array of piercing elements may be able to be turned on and off.

Figure 12:
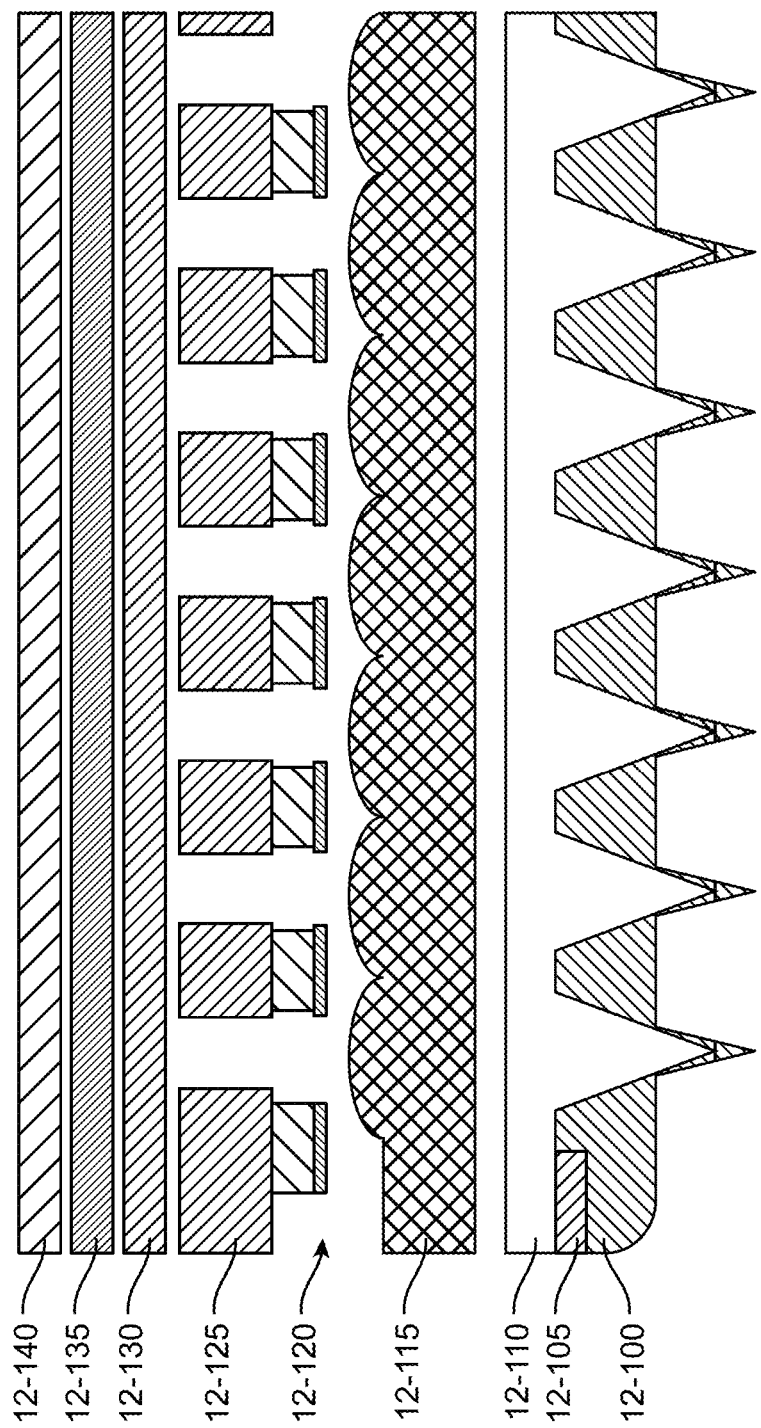
FIG. 12 depicts an exploded cross-sectional view of an exemplary device where the light source is positioned directly above a molecular sensing domain, without a light guide.

FIG. 12 depicts an example of this type of embodiment. It shows an exploded cross-sectional view of the different layers present in the structure, some of which are shown separated from each other for illustration purposes only. 12-100 depicts the array of microneedles. 12-105 depicts an adhesive patch. 12-110 depicts a patch window. 12-115 depicts a sensor window. 12-120 depicts an excitation filter. 12-125 depicts an LED board with LEDs. 12-130 depicts a long pass emission filter. 12-135 depicts an image sensor. 12-140 depicts a sensor board. 12-100, 12-105, and 12-110 may comprise a disposable portion of the embodiment, which may be inexpensive allowing it to be disposed to reduce the cost of ownership of the sensor. 12-115, 12-120, 12-125, 12-130, 12-135, and 12-140 may comprise a durable portion of the sensor which may be reused. The excitation light comes from the LED array and is directed toward the microneedles which locally hold the sensing material in the sensing domain. The excitation light may be focused by the micro lenses in either the patch or the sensor windows. Some of the emitted light from the microneedle array is collected by the sensor depicted in 12-135 and 12-140. Optical structures such as micro lenses may also be used to help collimate this light toward the sensor.

In FIG. 12, 12-120 depicts an excitation filter. In some embodiments this excitation filter may be a filter which has periodically varying properties. These properties are such that right below the LED, the filter serves as a short pass filter to filter out any spectral impurity in longer wavelengths, whereas in the spatial areas where the light coming out from the sensing domain needs to pass through to the detection assembly, the filter properties are different so as to allow the red shifted light to pass through. In some embodiments, the filter has periodically shifting properties under the LED and in areas where light from the sensing domain needs to pass through.

In FIG. 12, 12-125 illustrates an LED mounted on an LED board. This layer also contains the LED drivers in addition to the LED array. The holes are cut out in this board to let the sensing light coming from the piercing elements to pass through the detecting board, above which an image sensor may be present as a detector. 12-130 depicts an emission filter. In some embodiments this may be a long pass emission filter which does not allow the excitation light to couple into the detection assembly. In some embodiments it may be a dichroic filter. In some embodiments it may be a color filter or an absorptive filter. 12-135 depicts an image sensor that is pixelated and detects the light coming from the sensing molecules. In some embodiments, this layer may contain other types of photodetection devices.

In some embodiments, some of the layers portrayed in FIG. 12 may not be present in the sensor. For example, the excitation filter may be present if the particular LED source has an undesirable emission at the longer wavelength which interferes with the emitted wavelength from the analyte binding probe comprised in the hydrogel matrix. The excitation filter may be present in a different shape or at a different location. In some embodiments, some of the layers may have a different shape than shown. For example, the lenses shown in 12-115, which have the purpose of focusing LED light into the microneedle and helping to collimate the emitted light from the analyte binding probe comprised in the hydrogel matrix in the microneedles, may not be present, or could take a different shape or form than shown here. Similarly, 12-110 is shown as a planar layer without any micro lenses. In some embodiments, this layer may have its own micro lenses in order to further improve performance or to provide more design options to optimize LED light focusing as well as sensing light collimation through the LED board holes. In some embodiments, there may be an intentional air gap between some of the layers. For example, the boundary between 12-110 and 12-115, which in some embodiments may be the boundary between the disposable and non-disposable portions of the structure, there may be an intentional air gap so that the layers do not get scratched. In some embodiments, the LED board may be transparent to the light emitted by the sensing domain in the microneedle, which may obviate the need for having holes through the LED board. In some embodiments, the emission filter may be buried inside the LED board through a recess in the LED board. In some embodiments, layers 12-100 to 12-110 may not be separable from layers 12-115 to 12-140, and the entire structure may be applied as a sensor to a skin surface at the same time.

Figure 13:
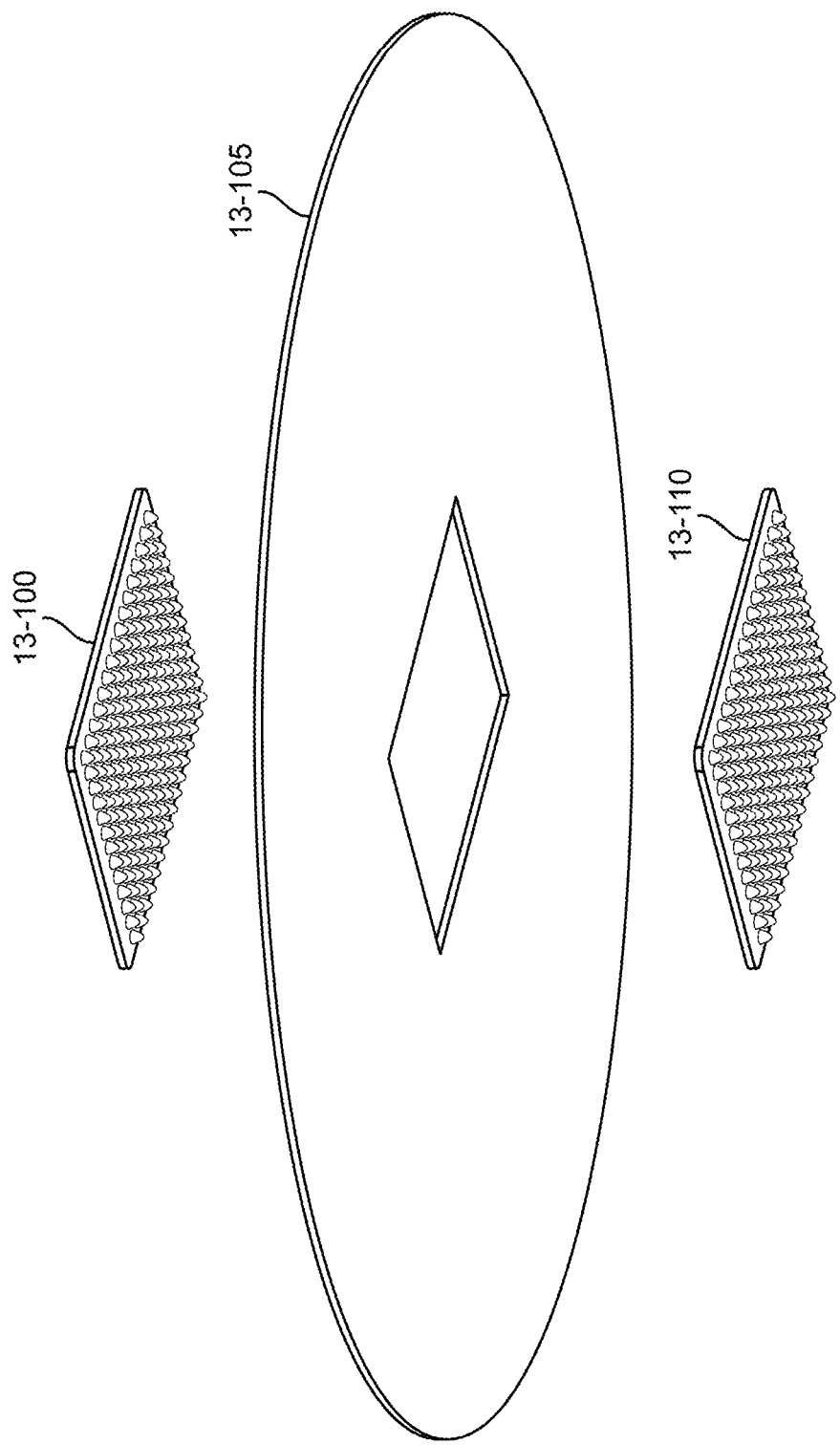
FIG. 13 depicts the construction of an exemplary disposable microneedle array patch, which includes an array, a window, and an adhesive patch.

FIG. 13 depicts an exemplary disposable microneedle patch, which includes a microneedle array (13-110), a window (13-100), and an adhesive patch (13-105).

Figure 14:
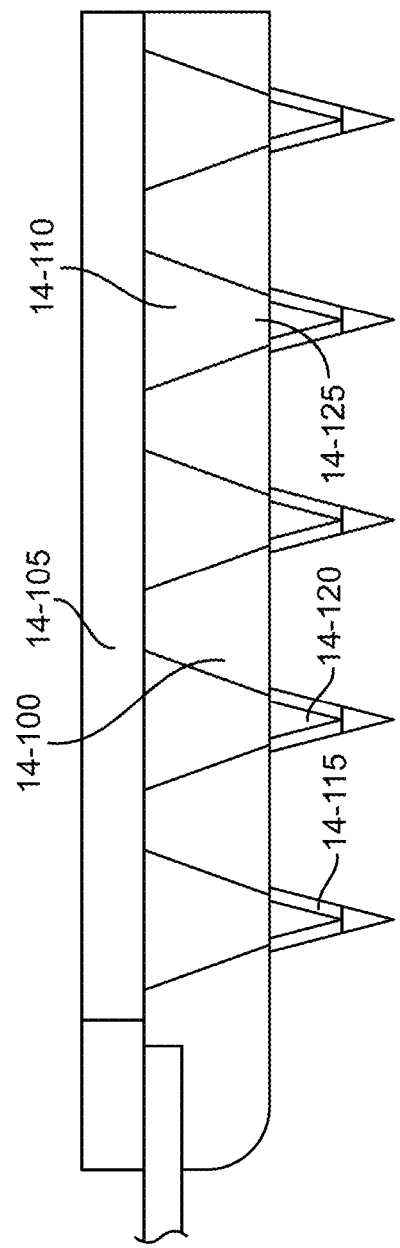
FIG. 14 depicts a cross section of the patch in FIG. 13, comprising an array base with microneedles, an analyte binding probe comprised in the hydrogel matrix in each needle, and a transparent window with conical features that seal the top of the needles and optically couple to the gel.

FIG. 14 depicts a cross section of this patch, showing an array base with microneedles, analyte binding probe comprised in the hydrogel matrix in each microneedle, and a transparent window with conical features that seal the top of the needles and optically couple to the hydrogel matrix. The draft angle of the conical features in the exemplary patch is chosen to optimize the coupling of light from the LEDs to the hydrogel matrix and also to optimize the emitted light between the microneedles and the sensor. In this figure, 14-100 indicates the draft angle, 14-105 indicates the patch window, 14-110 indicates a conical projection, 14-115 indicates a microneedle, 14-120 indicates a molecular sensing domain, and 14-125 indicates a wetted contact.

Figure 15:
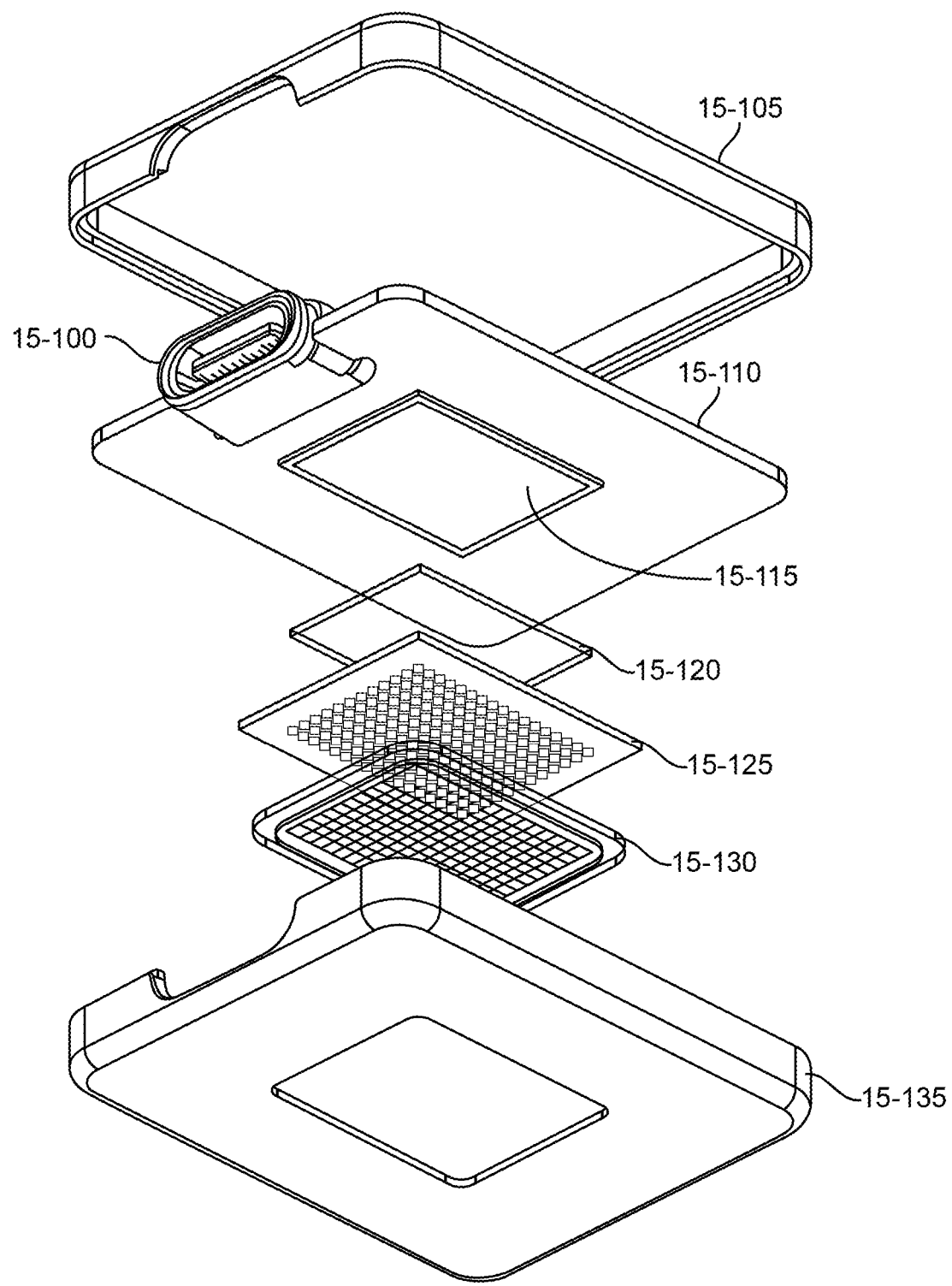
FIG. 15 depicts an exploded view of an exemplary durable sensor device that comprises an enclosure, an image sensor board, an optical filter, an LED board with apertures, and a sensor window.

FIG. 15 depicts an exploded view of an exemplary durable sensor device, which includes an enclosure, an image sensor board, an optical filter, an LED board with apertures, and a sensor window. The sensor device is placed inside a sealed enclosure and the optical interface to the microneedle array patch is a transparent window at the bottom of the enclosure. Here, 15-100 indicates the sensor power and data, 15-105 indicates the sensor cover, 15-110 indicates the sensor board, 15-115 indicates the image sensor, 15-120 indicates the filter, 15-125 indicates the LED board, 15-130 indicates the sensor window, and 15-135 indicates the sensor base.

Figure 16:
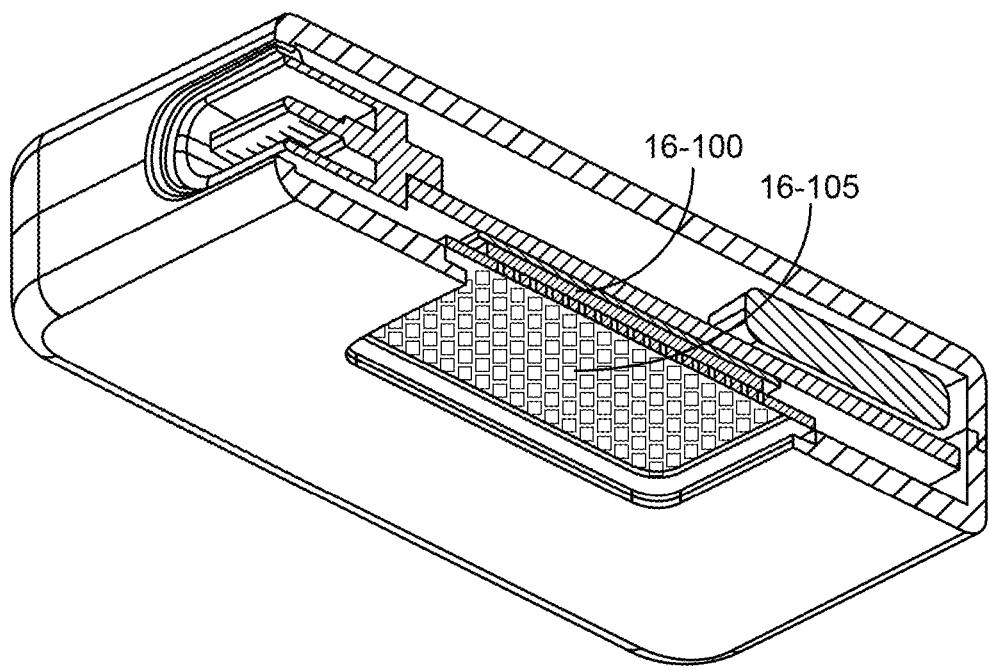
FIG. 16 depicts an isomeric cross section of an assembled sensor device as shown in FIG. 15.

FIG. 16 depicts an isomeric cross section of the exemplary assembled sensor device shown in FIG. 15. 16-100 indicates the image sensor and 16-105 indicates the LED array.

Figure 17:
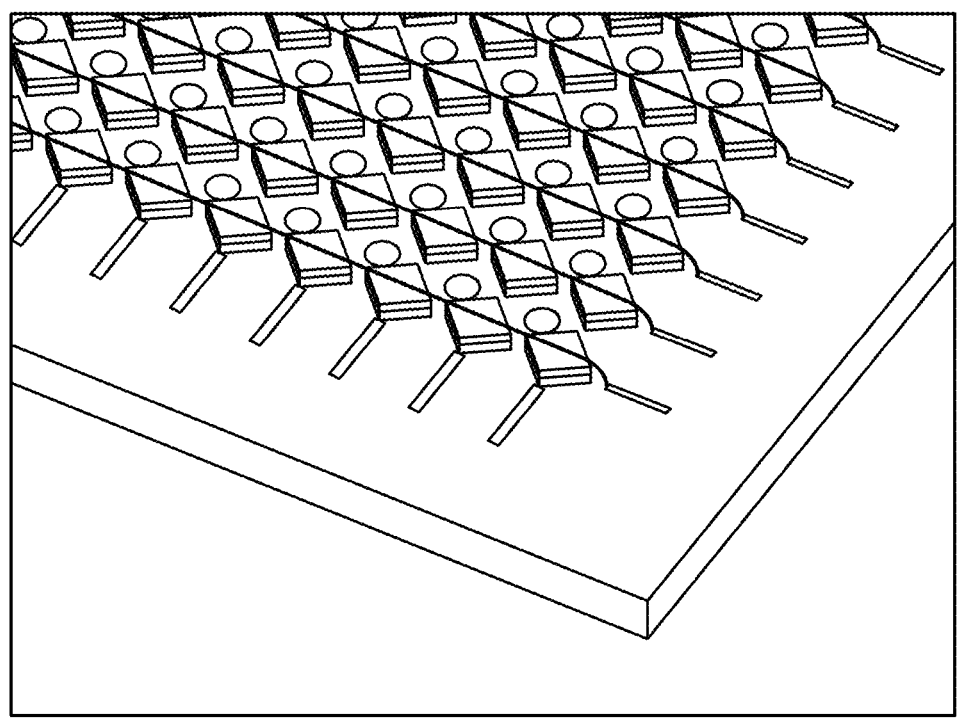
FIG. 17 depicts a portion of the LED array on the LED board, and the row and column lines used for addressing the LEDs.

FIG. 17 depicts an example of a portion of an LED array on an LED board, with row and column lines that are used to add an address to each LED. The board has an array of apertures interspersed between the LEDs that align with the microneedles and allow the light emitted by the hydrogel matrix in each needle to pass through the board and filter to reach the image sensor. Each aperture is surrounded by four LEDs, and adjacent needles share LEDs between them. In this exemplary arrangement, each needle receives light from the four surrounding needles. In another embodiment, each needle may be illuminated by two adjacent LEDs. In another embodiment, each needle may be illuminated by one adjacent LED. Illumination by two or one adjacent LEDs reduces the number of LEDs in the array, resulting in lower cost, complexity, power consumption, and heat generation. FIG. 17 also depicts a matrix of electrical conductors connecting the anodes and cathodes of the LEDs in rows and columns. The conductors allow the activation of individual LEDs in numerous combinations, allowing flexible operation of the LED matrix. A single LED is activated by allowing current to flow through the LED's associated row and column conductors. Multiple LEDs may be activated by allowing current to flow through all the conductors for that group. In another embodiment, a different LED addressing system may allow for more flexible addressing. In another embodiment, a different LED addressing system may allow for less flexible addressing. FIG. 17 shows the LED row conductors as electrical traces on the LED board printed circuit (PCB) and the column conductors as stitch bond wires across the top of the LEDs. This is a convenient method of connecting to the top contact of the LED die shown. In some embodiments, LEDs may be employed that have both contacts on the bottom. These embodiments may implement both the row and column lines as PCB traces, eliminating the need for wire bonding.

Figure 18:
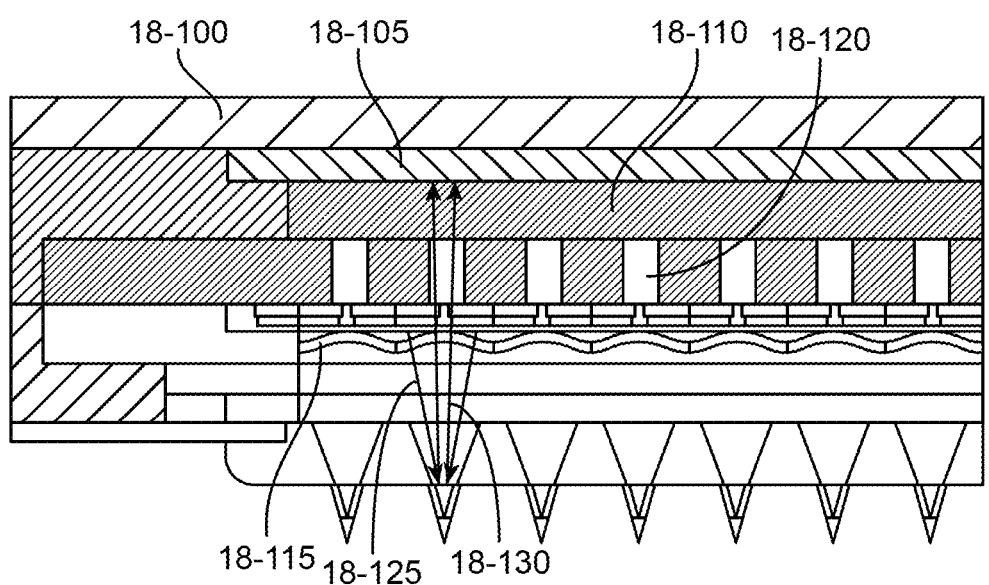
FIG. 18 depicts a cross section of a sensor device as shown in FIG. 15. This figure particularly shows the arrangement of the optical elements and the paths of the illumination and emission light.

FIG. 18 depicts a cross section of the exemplary sensor device, highlighting the arrangement of optical elements and the paths of the illumination and emission light. This figure is another view of FIG. 12. FIG. 18 shows the holes in the LED board and a filter positioned between the LED board and the image sensor. The filter blocks LED stimulus light from reaching the image sensor, ensuring that only the red shifted light emitted from the needle hydrogel matrix is detected. The holes serve to limit the incident angle of light reaching the filter in order to improve the rejection of stimulus light from the LEDs. The holes also allow the flexibility to, in some embodiments, use an absorptive LED board so that light from the needle hydrogel matrix can still pass through it. In some embodiments, the filtering surface may face toward the image filter. In some embodiments, the filtering surface may face away from the image filter. FIG. 18 also shows the position of lens elements used to concentrate stimulus light from the LEDs into the microneedles and to focus light emitted by the analyte binding probe comprised in the hydrogel matrix onto the image sensor. Some embodiments may have additional optical elements to concentrate LED light into the needles and concentrate emitted light onto the image sensor. Some embodiments may have no concentrating optical elements and may contain just a flat window. Some embodiments may include light blocking features between adjacent positions to prevent light from one position from reaching adjacent positions. In this figure, 18-100 indicates the sensor board, 18-105 indicates the image sensor, 18-110 indicates the long pass filter, 18-115 indicates the lens elements, 18-120 indicates the position apertures, 18-125 indicates the excitation light, and 18-130 indicates the emission light.

Figure 19:
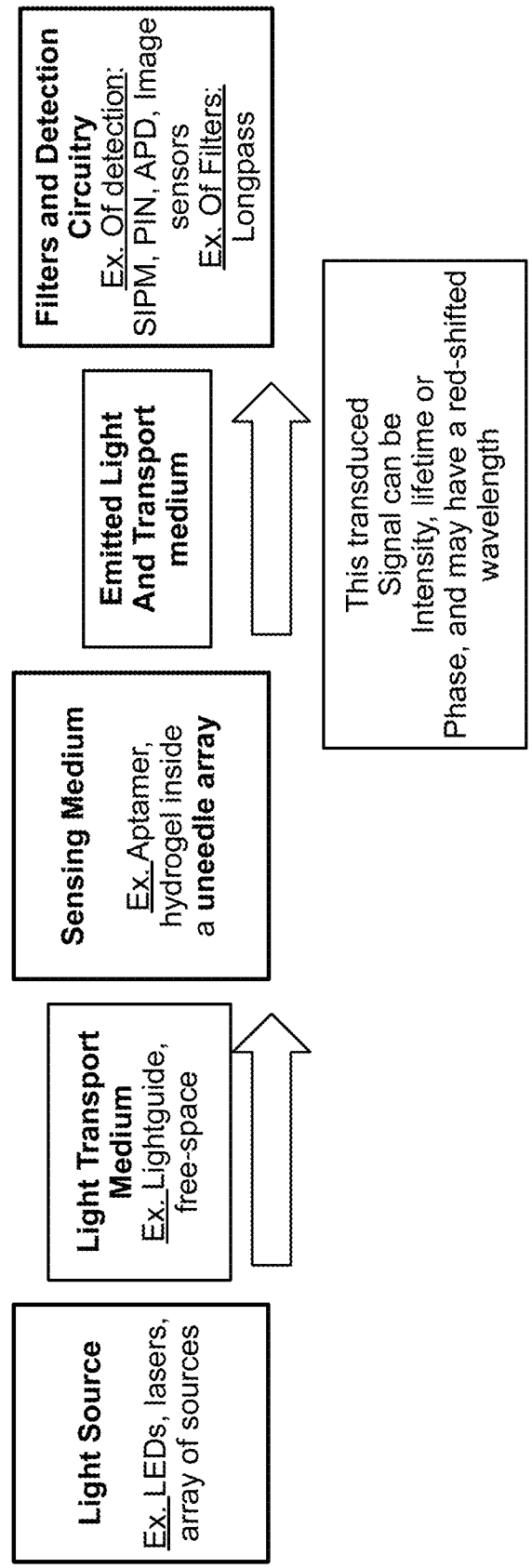
FIG. 19 shows the schematic of the optical sensor with generic building blocks.
Figure 20:
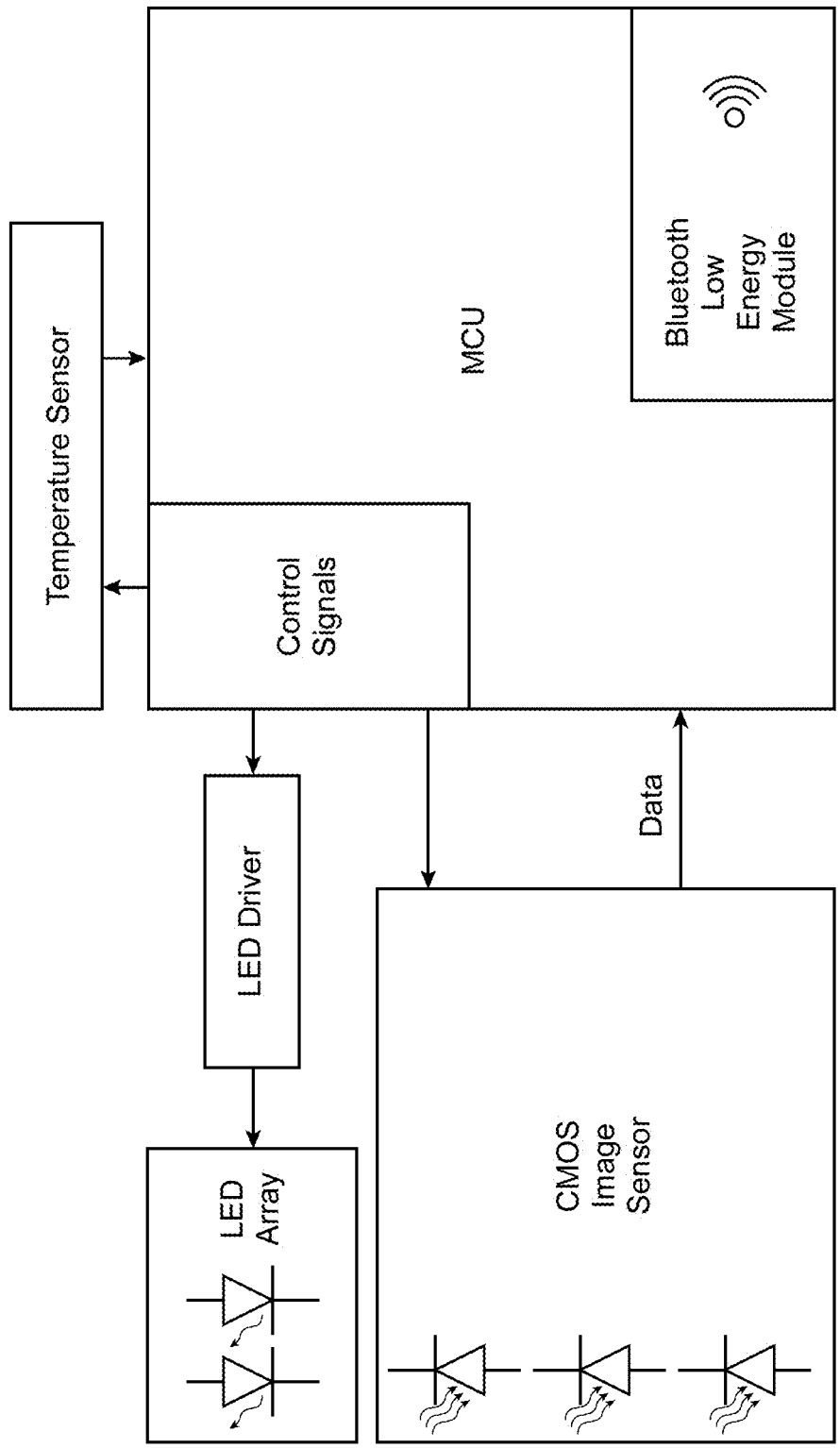
FIG. 20 shows a schematic circuit diagram of one possible embodiment of a detection system, with generic building blocks.

Example 6: Optical Coupling Mechanisms for Optically Probed Molecular Sensors In this example, theoretical and practical principles for designing optical systems are explored. FIG. 19 shows a basic schematic of the optical system. It comprises an optical source or a multitude of optical sources and a scheme to transport the optical signal from the source or sources to the molecular sensor. The molecular sensor comprises synthetic analyte binding probes. In some embodiments, these synthetic molecules are aptamers, which among other things have a fluorophore and a quencher attached to them. The fluorophores go through a change in the emitted optical signal depending on whether the aptamer they are attached to binds with the target molecule. The mechanism entails a shape change in the aptamer switch upon target binding, which in turn modulates the distance between the quencher and the fluorophore, resulting in a change in fluorophore emission properties. In some embodiments, these molecular sensors may be housed inside a microneedle array. The emitted light from the fluorophore of the molecular sensors is typically red shifted compared to the excitation wavelength. Among other attributes, the detection scheme can be based on one or more of the three types of signal change: intensity of emission, lifetime of the fluorophore under pulsed illumination, and phase of the emitted light. Depending on the need and the available signal to noise ratio, the detectors are designed to detect one of the above attributes and changes in it. The emitted light is then transported through an efficient optical system to the detection system. One possible embodiment of the detection system is shown in FIG. 20.

A key requirement of these sensors is to design an efficient optical system that carries the excitation light from the light source to the sensor molecule and also carries the emitted light and its accompanying attribute changes from the fluorophores to the detector system. The efficiency of the coupling in both directions is critical to the performance of the sensor in terms of dictating its sensitivity and dynamic range.

Figure 21:
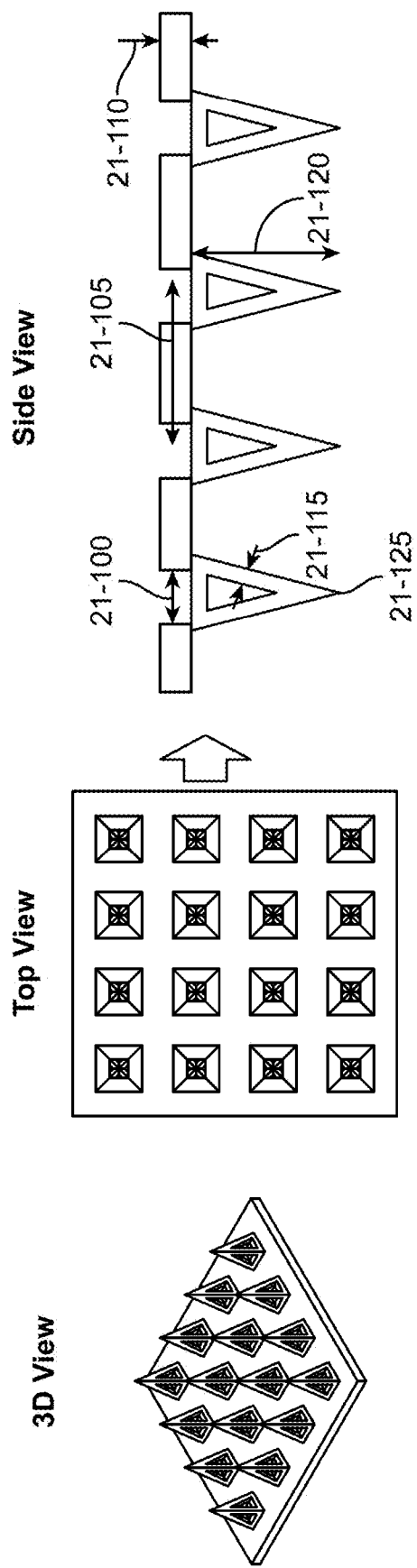
FIG. 21 shows the microneedle array for one embodiment.

In one embodiment, the sensor apparatus comprises a microneedle array, which in turn may hold the aptamer or fluorophore combinations locally in the sensing medium, such as under the skin. FIG. 21 shows a possible microneedle array with relevant dimensions. This array has a base layer as well as actual microneedles. FIG. 21 shows a simple shape as an example; however, the shape of the microneedle can vary from simple hollow structures which open up to the outside through holes all the way to more complicated lattice structures. The shapes are dictated by requirements related to the ability to hold the maximum volume of the molecular sensor while retaining critical mechanical strength. In addition, the shapes should be conducive to pain-free insertion through the skin. The array can comprise one row and one column up to multiple rows and columns. The rows and columns do not have to be equal. The array can span the area of the sensor, ranging from a few mm by a few mm to several tens of mm by tens of mm. The array can be in any shape such as a square, circle, or rectangle. In one embodiment, this can be a rectangular array of about 10 mm by 10 mm or less. The microneedles are meant to penetrate skin and can be characterized by geometrical attributes such as depth, shape, base width, base thickness, and base wall angle. The microneedles are also characterized by material properties such as base material surface reflectivity, transparency, and refractive index. In FIG. 21, 21-100 indicates the base width, 21-105 indicates the needle pitch, 21-110 indicates the base thickness, 21-115 indicates the strut thickness, 21-120 indicates the needle depth, and 21-125 indicates the needle sharpness.

The excitation can be an LED, a laser, or other light sources, characterized by either monochromatic spanning wavelengths from UV to infrared, non-monochromatic sources, or white light with different wavelengths. There can also be a multitude of excitation sources.

In the embodiment described herein, the source light is carried in a guided fashion using lightguides or waveguides. In general, the emitted light can be a different wavelength than the excitation light, and in most cases the emitted light will be red shifted compared to the source light.

Figure 22:
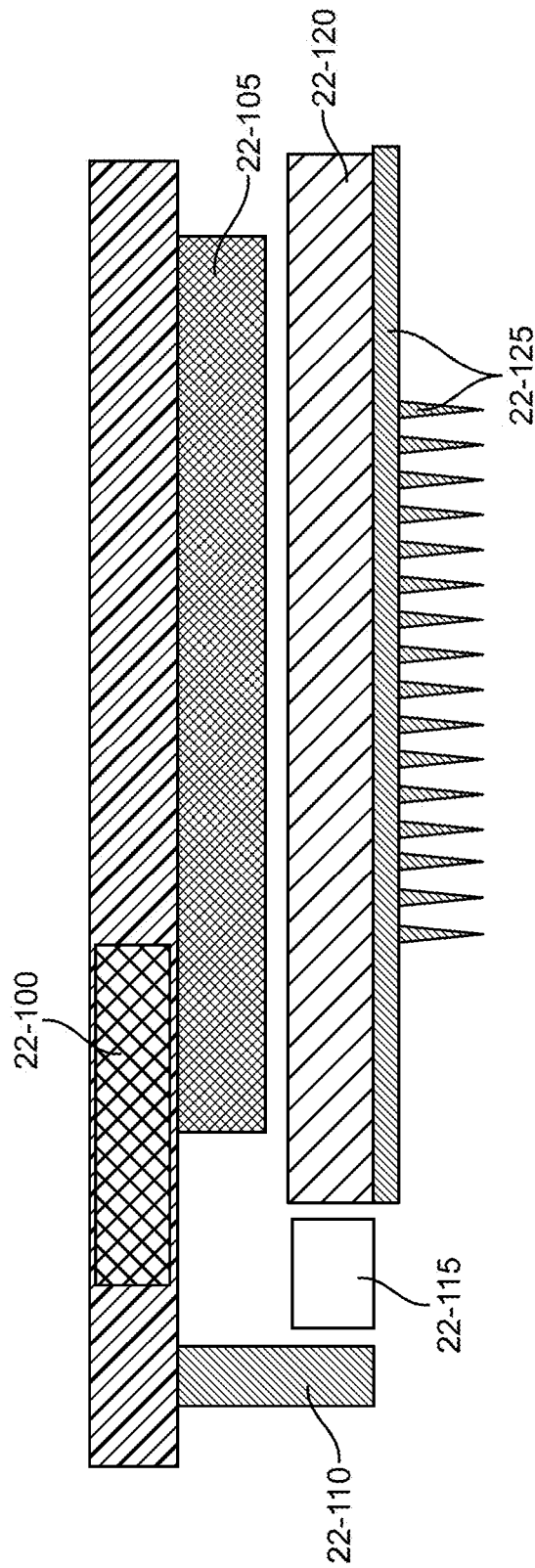
FIG. 22 is a schematic block diagram showing different components of the optical sensor.

FIG. 22 shows a very high-level schematic of a possible guided wave system for coupling the light source into the microneedle array carrying the aptamer/fluorophore combination. In this embodiment, an edge-coupled LED is used to couple light into a lightguide supporting multiple propagation modes. A geometrical coupler structure may be used between the LED and the lightguide to ensure efficient coupling. This coupler is shown as a high-level schematic. The coupler may comprise a gradual taper from the LED source to the lightguide. In some embodiments, other types of light sources or coupling schemes are possible, including surface coupling of the LEDs from above the lightguide as opposed to edge coupling, or other light sources such as lasers. The light guide can be made from a myriad of materials, including but not limited to polymers and glass. The light guide is substantially transparent and comprises a higher refractive index material, referred hereafter as the "core", surrounded by a lower refractive index, which can be referred to as cladding, to provide it with light guiding properties. In one embodiment, the cladding can be air. The mode travels substantially inside the core. The excitation wavelength can range from UV to infrared, from 200 nm to 2 μm in wavelength. The excitation source is connected to the sensor PC board, which houses drivers and other electronics components, such as shown in FIG. 19. Some of the light coming from the analyte-sensing hydrogel matrix in the microneedles escapes out of the lightguide and travels toward the detector attached to the sensor PC board. There can be either optical, geometrical filters and/or micro lenses between the lightguide and the detector. The purpose of the optical and geometrical filter is to ensure no source light is back coupled into the detector. The purpose of the micro lenses is to increase the photon density of the sense light at the detector. These micro lenses can also be designed to aid in making the optical filter more effective in filtering out the source light, as optical filters are better near surface normal incidence. In FIG. 22, 22-100 indicates the sensor PC board, 22-105 indicates the detector/optical/geometric filter micro lenses, 22-110 indicates the LED or LED array, 22-115 indicates the optical coupler, 22-120 indicates the light guide, and 22-125 indicates the microneedle array with its base.

In one embodiment, the light guide sits on top of the microneedle array. In one embodiment, the light guide is on the top and is abutting the microneedle array, and has periodically protruding structures at its bottom. This is shown in Area 1 of FIG. 23 (23-120). These periodic structures are designed to fit into the microneedle holes in the base, substantially complimenting the hollow base of the microneedles and occurring at the same pitch as the microneedles. The protruding structure can be part of the lightguide itself or can be part of the microneedle array.

Figure 23:
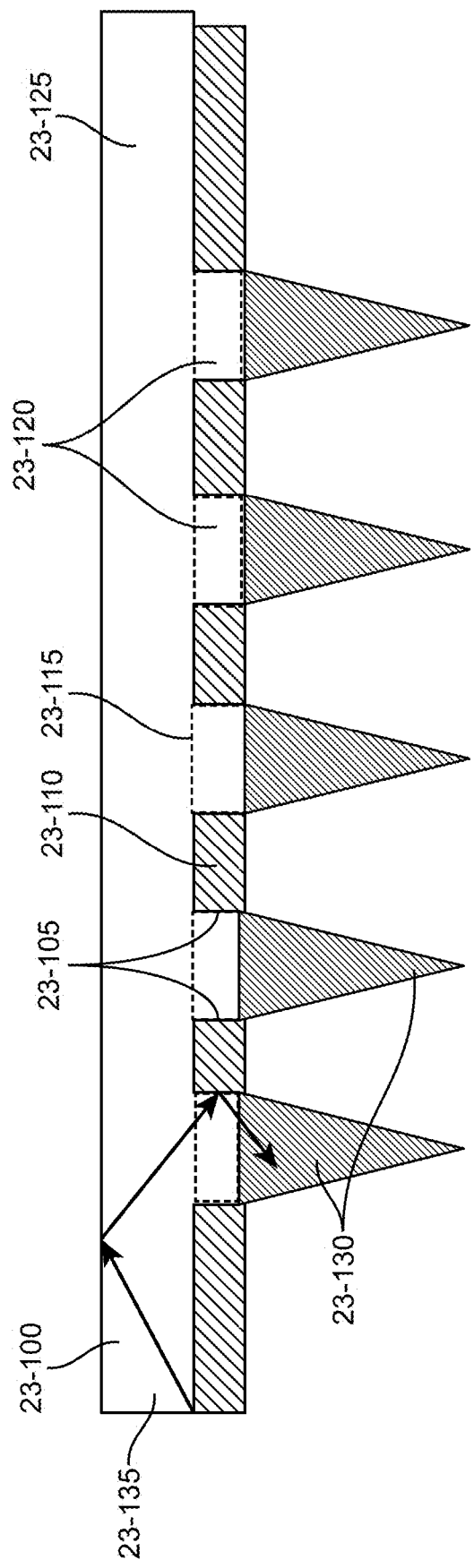
FIG. 23 shows a method of coupling the optical modes in the lightguide with the needle sensing domains.

The basic principle of coupling using these structures is described in FIG. 23. This figure shows critical interfaces and structures that elucidate the operational principle. Since several modes are supported by the light guide, the guided mode light strikes at different angles at the interface of core and cladding corresponding to a mode and gets totally internally reflected (TIR). Different modes are characterized by different incidence angles at this interface. Even though the bottom interface of the lightguide is the interface between the lightguide core and the microneedle base material, in practice there will be an air interface between the two materials. This will ensure a good TIR at the bottom interface as well. During its travel through the lightguide, the light periodically hits the bottom interface, where there is a discontinuity in the cladding that is substituted instead by the protruding structures. This is shown in Area 1 in FIG. 23. The refractive index of the protruding structures is designed so that the light continues to travel in the same direction without being substantially reflected. This light continues into the protruded structures and will eventually hit the interface of the protrusion and the base surface of the microneedle arrays, as shown in Area 2 of FIG. 23 (23-105), or it may directly couple into the sensing area, as shown in Area 3 of FIG. 23 (23-130). Area 2 is designed to substantially reflect the light back toward Area 3. In one embodiment, this is achieved by having a slight amount of air at the interface between the protrusion and the base. This can provide TIR at Area 2. If care has been taken to have no air at the interface, then TIR has to be carefully orchestrated using the right choice of refractive indices. The efficiency of the aforementioned coupling scheme relies on several geometrical and material design parameters. These parameters include the refractive index of the protrusions, the base thickness of the microneedle array, the base width of the microneedle array, the aspect ratio of the base of the microneedle array defined at the thickness to width ratio of the base, the angle of the base wall of the microneedle array, and the reflectivity of the base wall. The reflectivity of the base wall can be designed using myriad techniques. If TIR is used as the reflective mechanism and care is taken to have no air at this interface, then the refractive index of the base with respect to the protrusion is a critical parameter that dictates the reflectivity of this interface. In FIG. 23, 23-100 indicates the core of the lightguide, 23-105 indicates Area 2, the protrusion/base sidewall interface, 23-110 indicates the base of the microneedle array, 23-115 indicates the core/protrusion interface, 23-120 indicates Area 1, the protrusion area, 23-125 indicates the optical light guide, 23-130 indicates Area 3, the microneedle sensing domain that is an aptamer/fluorophore combination, and 23-135 indicates the path of a light mode inside the lightguide.

Table 1 tabulates some of the combinations creating different embodiments that entail perpendicular sidewalls. In some embodiments, the base can have non-perpendicular sidewalls. For each of the embodiments listed in Table 1, non-perpendicular sidewalls can be used when required by the design to maximize efficiency of coupling. In addition, for each of the embodiments, geometrical design such as aspect ratio and base depth and width will be optimized as required. Tradeoffs with respect to geometries are detailed for some embodiments below.

TABLE 1

Tabular description of examples of categories of embodiments

| Protrusion Region Refractive Index | Sidewall Angle | Base Sidewall Reflectivity/Absorptivity |
|---|---|---|
| Same as core of lightguide | Substantially perpendicular | Substantially absorptive |
| Same as core of lightguide | Substantially perpendicular | Substantially reflective at all angles |
| Same as core of lightguide | Substantially perpendicular | Substantially reflective at a range of certain incidence angles due to TIR |
| Same as core of lightguide | Substantially perpendicular | Interspersed combination of above cases |
| Higher than core of lightguide | Substantially perpendicular | Substantially absorptive |
| Higher than core of lightguide | Substantially perpendicular | Substantially reflective at all angles |
| Higher than core of lightguide | Substantially perpendicular | Substantially reflective at a range of certain incidence angles due to TIR |

TABLE 1-continued

Tabular description of examples of categories of embodiments

| Protrusion Region Refractive Index | Sidewall Angle | Base Sidewall Reflectivity/Absorptivity |
|---|---|---|
| Higher than core of lightguide | Substantially perpendicular | Interspersed combination of above |

The impact of these parameters on design as well as some of the ensuing embodiments are discussed.

In one embodiment, the protrusion material that fits into the micro needles has the same refractive index as the core of the light guide and the base wall is near perpendicular or perpendicular to the plane of the lightguide. With this choice of the refractive index, light travels through into the protrusion area without being substantially reflected or disturbed at the interface between the core of the lightguide and the protrusion areas. This is shown in Area 1 of FIG. 23.

Within this embodiment, three embodiments that depend on the reflectivity of the base wall are discussed. These embodiments can be further combined in various ways to create more variations and embodiments.

Figure 24:
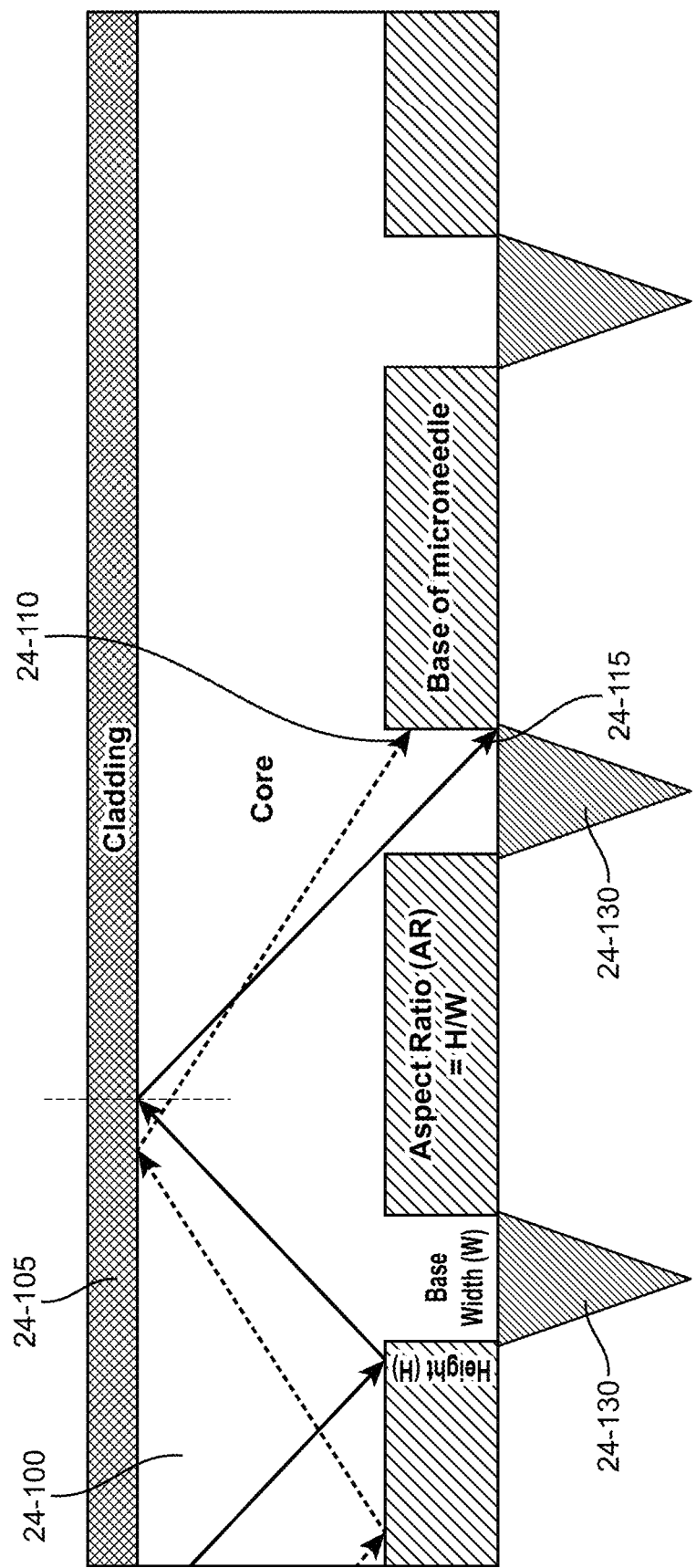
FIG. 24 shows a specific embodiment of FIG. 23, where the sidewall of the base is substantially absorptive and only light rays at a substantially non-grazing angle at the core/cladding interface directly couple into the microneedle sensing domain.

In one embodiment, the base wall is substantially absorptive, for example 30% to 100%. The motivation for an absorptive sidewall may be desirable for several reasons. These reasons could be related to stopping any spurious coupling of the source light directly to the detector above the lightguide. Spurious coupling of source light to the detector may overwhelm the emitted light signal from the analyte sensing molecules, creating false readings. In this embodiment, the majority of the light that eventually will couple into the microneedles has to come at an angle that is steep enough so as to not strike the base wall but rather to directly couple with the sensing region. This is shown in FIG. 24. FIG. 24 is a specific embodiment of FIG. 23, wherein the sidewall of the base (Area 2) is substantially absorptive, and only light rays at a substantially non-grazing angle at the core/cladding interface directly couple into Area 3. In FIG. 24, 24-100 indicates the ncore (core refractive index), 24-105 indicates the nclad (cladding refractive index), 24-110 indicates light absorbed at the sidewall of the base of the microneedle, 24-115 indicates direct coupling into Area 3, and 24-130 indicates Area 3, the microneedle sensing domain aptamer/fluorophore combination. In this scenario, if the light ray is to avoid hitting the sidewall of the base and is to directly couple into Area 3, the incidence angle at the top core cladding interface a has to be smaller than a threshold angle dictated by the height to width ratio (aspect ratio) of the base of the microneedle. This aspect ratio is defined in FIG. 24.

$$\propto \frac{1}{\sqrt{1 + AR^2}}$$

For total internal reflection to occur at the core cladding interface at the top of the lightguide, the following condition also needs to be satisfied:

$$\sin\sin\alpha > \frac{n_{clad}}{n_{core}}$$

Combining the above two equations results in the following preferred requirement from a design perspective for this embodiment:

$$\frac{1}{\sqrt{1 + AR^2}} > \frac{n_{clad}}{n_{core}}$$

Thus, $$AR < \sqrt{\left(\frac{n_{clad}}{n_{core}}\right)^2 - 1}$$

For example, for a core index of approximately 1.5 and air cladding ($n_{clad}$ of approximately 1), AR (the height to width ratio of the base) must be lower than approximately 1.11 to have any guided rays strike directly onto Area 3. Some light reflected from the base sidewall will also couple, depending on the absorption strength of the base wall as well as specularity of the reflection from this interface.

In another embodiment, the protrusion material has a substantially similar refractive index as the core, the base walls are perpendicular, and the sidewalls of the base of the microneedles are substantially reflective at all angles. This may be achieved by coating with a film that provides substantially high reflectivity. This high reflectivity can for example be achieved by coating a thin reflective metal film deposited on the sidewall of the base using myriad deposition schemes such as PVD, selective plating (electroless or electroplating), dip coating, screen printing, or stencil printing. The coated metal is highly reflective and substantially smooth to provide largely specular reflection. For example, this metal can be copper, aluminum, silver, gold, or any of the reflective metals. The light that strikes this interface is substantially redirected into the sensing area (Area 3 of FIG. 23).

Figure 25:
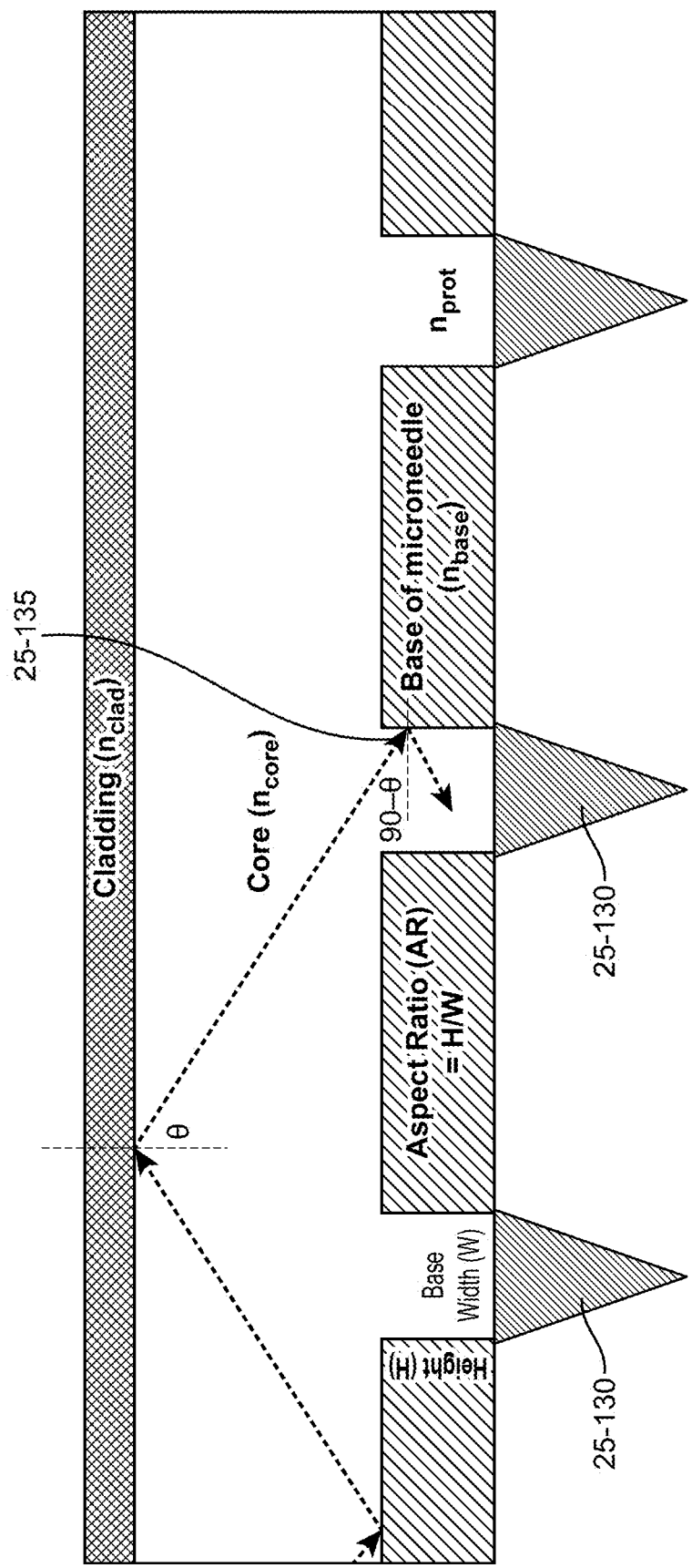
FIG. 25 shows total internal reflectance at the protrusion area and the base sidewall.

In another embodiment where the refractive index of the protrusion material is substantially similar to that of the core, and the base walls are again substantially perpendicular to the lightguide plane, the base walls provide substantial total internal reflectance (TIR) to divert the source light into the sensing area (FIG. 23). In this scenario, the choice of the refractive index of the core (with the protrusion material being substantially similar to the core), the base of the microneedles, and the cladding of the light guide are critical in maximizing coupling into Area 3 of FIG. 23. In FIG. 25, 25-130 indicates Area 3, the microneedle sensing domain aptamer/fluorophore combination, and 25-135 indicates the sidewall of the base TIR.

For total internal reflection (TIR) from the base wall of the microneedle (FIG. 25), the following condition must be satisfied:

$$\sin(90 - \theta) > \sin\beta_c$$

where $\beta_c$ is the critical angle for TIR at the microneedle base and protrusion interface, and is given by $$\sin\sin\beta_c = \frac{n_{base}}{n_{prot}}$$

The minimum $\theta_{min}$ at the core/cladding interface of the lightguide has to be small enough such that 90−θ at the microneedle/protrusion interface is greater than $\beta_c$.

$$\sin\theta_{min} = \frac{n_{clad}}{n_{core}}$$

Hence, $$\cos\theta_{min} > \sin\beta_c$$

Hence, $$\frac{\sqrt{n_{core}^2 - n_{clad}^2}}{n_{core}} > \frac{n_{base}}{n_{prot}}$$

Finally, $$n_{base} < n_{prot}\sqrt{1 - \frac{n_{clad}^2}{n_{core}^2}}$$

The above formula is generic for any protrusion refractive index ($n_{prot}$) and base refractive index. In the above embodiment, we consider $n_{prot}$ to be the same as the lightguide core refractive index ($n_{core}$). If $n_{prot}=n_{core}$ in the above formula, we get $$n_{base} < \sqrt{n_{core}^2 - n_{clad}^2}$$

For the specific case of the core index being the same as the protrusion index and cladding of the lightguide as well as the base index is 1. This may happen if there is air at the interface of the cladding index and between the protrusion area and the base. In this scenario, the above formulation requires the core index to be greater than $\sqrt{2}$. In general, the protrusion refractive index may be different, specifically higher than the core refractive index, and such cases are represented by the more generic formulation above.

To maximize light coupling into Area 3 of FIG. 23, the conditions mentioned on the base refractive index ($n_{base}$) above should be met more strictly than barely meeting it. This ensures that a larger fraction of light hitting the base sidewall goes through total internal reflection (TIR) and eventually gets coupled into the sensing area.

Other related embodiments can be created from the condition where the refractive index of the protrusion material is substantially similar to that of the core of the light guide, and the base walls are substantially perpendicular to the plane of the lightguide. These embodiments entail a combination of the above conditions, where the sidewall of the base is partially absorptive and partially reflective. One of the many possible ways to make this is by making the base using different materials. The absorptive part of the sidewall can be closer to micro needles or closer to the light guide. In addition, in a general case, there can be multiple smaller absorptive segments interspersed between the reflective segments, achieved by the combination of materials. Such structures are designed to provide design flexibility to maximize the coupling of source light into the sensing domain. The reflective segments can be reflective because of TIR or use other methods to be reflective. In addition to the coupling of the source light into the microneedles, the choice of the aforementioned design also plays a critical role in dictating the efficiency of coupling emission light from the sensor region to the detector. Hence, both design considerations must be taken into account when designing the sensor. Thus, the design flexibility offered by the above embodiments may be critical.

Figure 26:
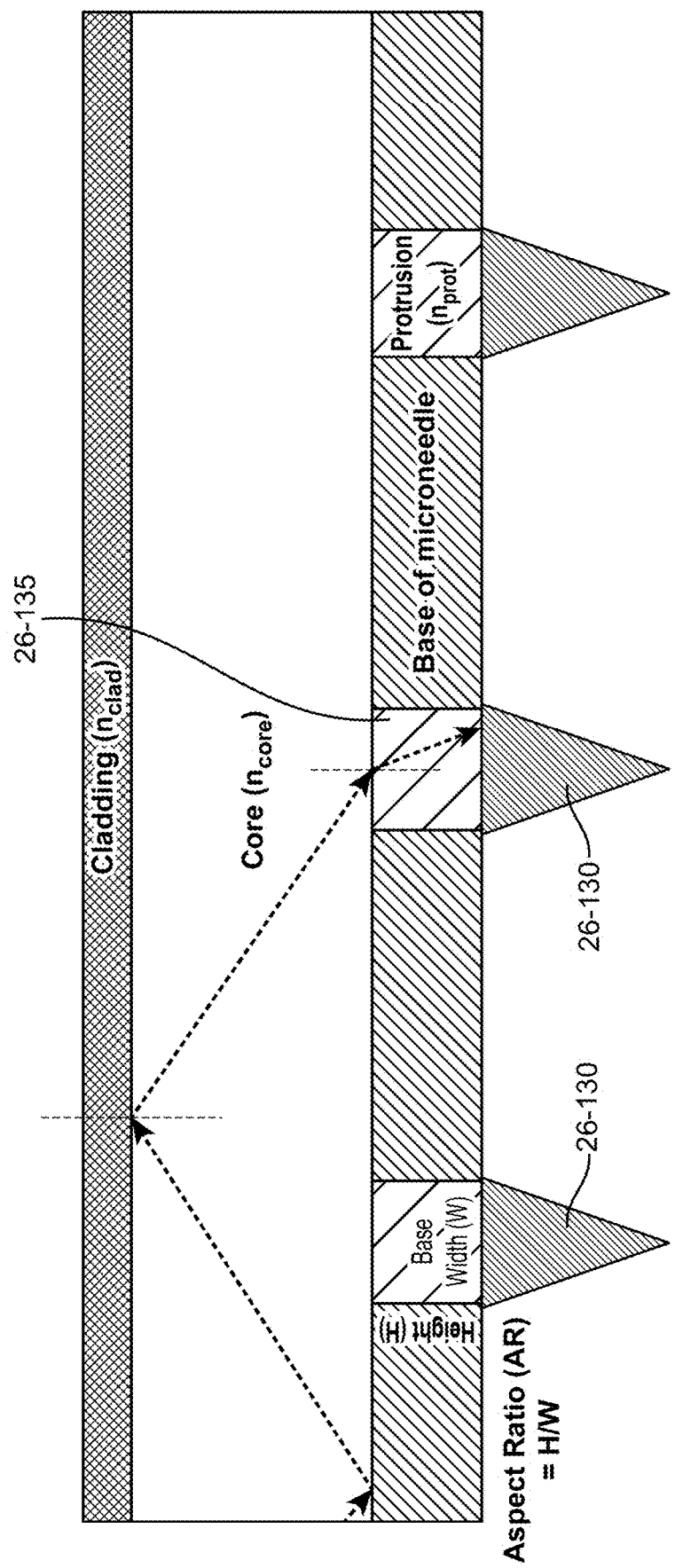
FIG. 26 shows an embodiment where the protrusion area refractive index is higher than the refractive index of the core of the lightguide.

In another category of embodiments, the refractive index of the protrusion material is higher than the refractive index of the core of the lightguide. This allows the mode of the light striking the interface between the core and the protrusion material to bend inward toward the micro needles (FIG. 26). This can potentially increase coupling of the source light with the aptamer/fluorophores. This also minimizes interaction of the incoming source light with the sidewall in case the sidewall is not substantially reflective, as is the case for the absorptive sidewall or in the TIR case where TIR is not as strong. In FIG. 26, 26-135 indicates that nprot>ncore, which bends the light inward toward Area 3. This can substantially avoid interaction with the base needle wall. 26-130 indicates Area 3. This category of embodiments may in turn be used with any of the aforementioned subcategories, including when the wall of the base of the microneedles is substantially absorptive, substantially reflective with thin film like metal thin films, and substantially reflective using TIR. In addition, a combination of the above three states of the sidewall of the microneedle base can also be used along with this category of embodiments where the refractive index of the protrusion is higher than the refractive index of the core of the lightguide. In the most general sense, this will entail the three possible states of the sidewall being interspersed with each other to create the most efficient coupling combination for both source coupling into the microneedles as well as coupling of emitted light from the microneedles into the detector.

The potential advantage of this category of embodiments where the refractive index of the protrusion region is higher than the core may be prevalent for the cases where the sidewall of the base is not as reflective. This will occur when the sidewall is substantially absorptive and/or for the case where the total internal reflection (TIR) is not as strong. In these scenarios, it is more desirable that the incoming source light does not interact with the sidewall and directly couples into the sensing area.

In the above embodiments, the sidewall of the base region of the microneedles is substantially perpendicular to the plane of microneedles. However, for all of the above embodiments, it is possible to have substantially non-perpendicular sidewalls as a design parameter, creating a draft angle of the base sidewall. This design parameter may be used to increase coupling either on the source side to the sensing area, or the emitted light from the sensing area into the detector. The perpendicularity of the sidewall as a parameter can also be used to minimize the spurious direct coupling of the source into the detector.

Figure 27:
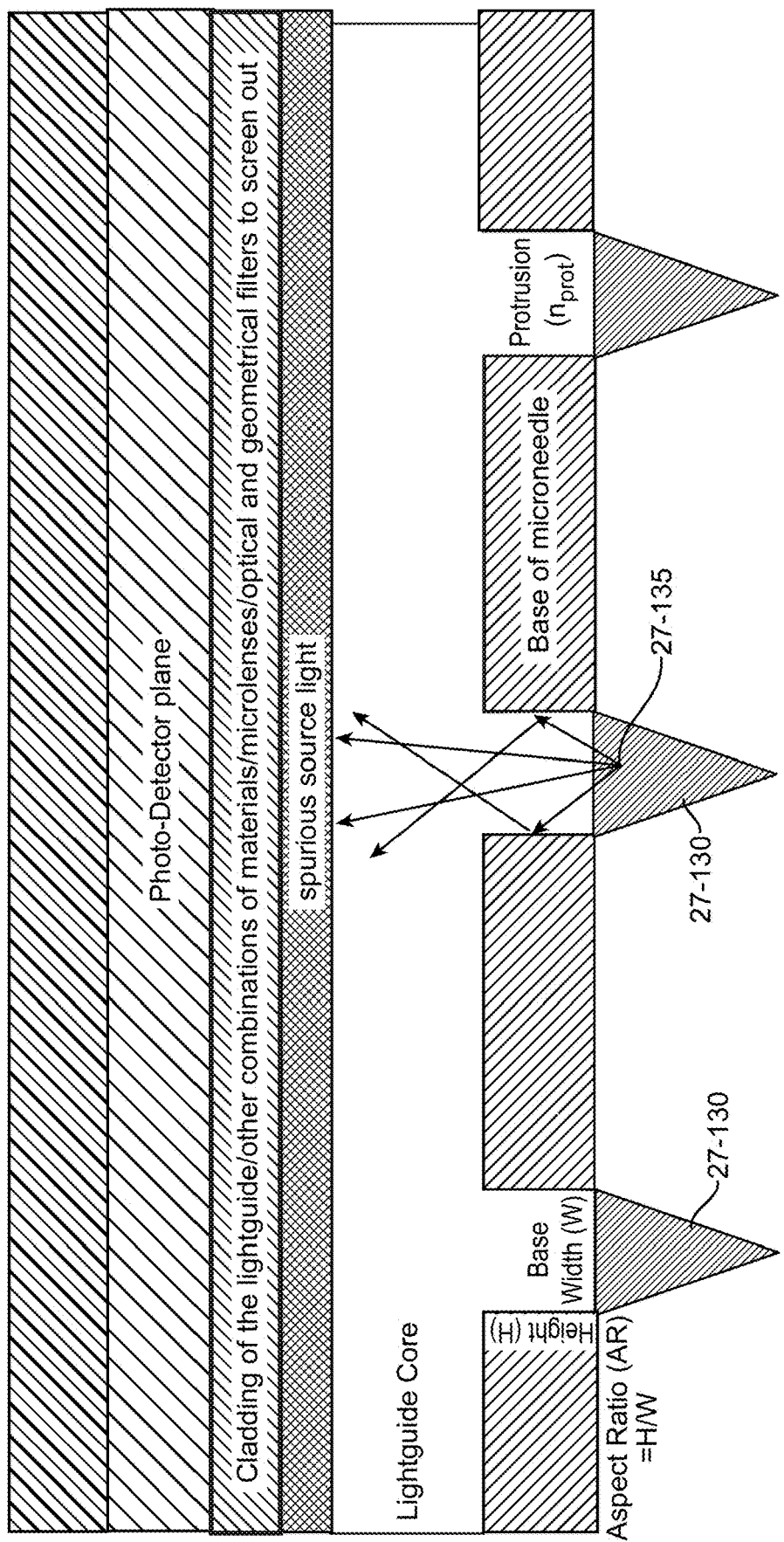
FIG. 27 shows light being emitted from the microneedle sensing molecules toward the photodetector and Sensing PC board.

FIG. 27 shows a specific embodiment and potential structures that provide coupling of the emitted light from the aptamers or fluorophores in the microneedles into the detector. In this figure, 27-130 represents Area 3, and 27-135 indicates the emitted light from the fluorophores in Area 3. The physical layers relevant to this pathway as shown are the sensing molecules of the microneedles, the base of the microneedles, the core of the lightguide, the cladding of the lightguide, and any other combination of materials above the cladding for light manipulation (to maximize coupling in the detector) and detection. The layers above the lightguide may include: the optical filters for selecting emission wavelengths but rejecting direct source coupling wavelengths; the geometrical filters to cut off steep angles; micro lenses to increase intensity and to substantially collimate light; the detector plane for capturing emitted light; and the PC board to convert the signal from the optical detectors into a readable signal for sensing. The objectives of the positioning of the geometrical structures between the lightguide and the detector plane, the dimensions of the geometrical structures, and the choice of their material properties such as refractive indices, absorption properties, and transparency are substantially two-fold: first, to maximize the coupling of the emitted light from the microneedles into the detector; and second, to minimize the coupling of the direct source light back into the detector.

Figure 28:
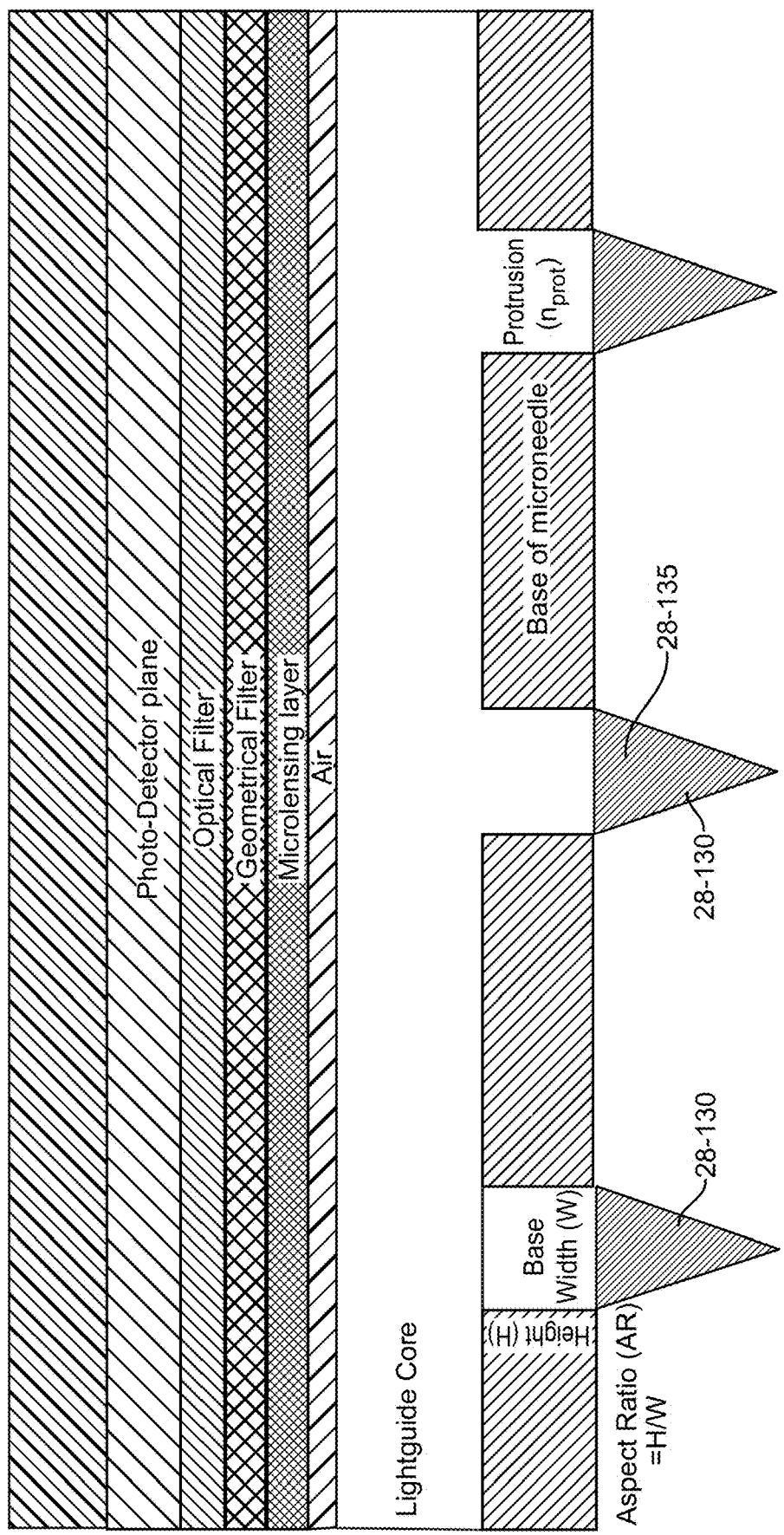
FIG. 28 shows light being emitted from the microneedle sensing molecules toward the photodetector and Sensing PC board, with a possible geometrical stack for capturing the emitted light.

The emitted light from the aptamer/fluorophore sensing area in general is emitted in random directions (which may be substantially Lambertian), and the geometrical and material parameters impact the collection efficiency. Additionally, the spurious or unwanted source light can either be reflected from any of the various materials or interfaces or be backscattered in random directions by molecules in different areas. FIG. 28 shows a block diagram of one possible geometrical apparatus/stack for capturing the sensor emitted light. In this figure, 28-130 indicates Area 3, and 28-135 indicates the emitted light from the fluorophores in Area 3. The figure should not be interpreted in a limited sense and serves only as an example. In general, some of the layers between the detector and the lightguide may not be present, or the order in which they appear may be different from the order shown in FIG. 28.

A subset of the layers in this embodiment is substantially similar or equivalent to the geometrical arrangement in FIG. 23 for source in-coupling into the microneedles. In addition to features that are common with source coupling apparatuses, there is a detector apparatus which is situated above the waveguide/lightguide that is designed specifically to capture the light that is emitted from the sensing area (Area 3 in FIG. 23). This detector apparatus may comprise a photodetector or image sensor (for example, a CMOS image sensor) with all the accompanying electronics that convert optical signal into electrical signal. The electronics and detector choices are designed to maximize signal to noise ratio and dynamic range. The detector and its electronics, along with other electronics components, may be held by a PC board that is located above the detector.

In general, the detector may span the entire microneedle array to be able to capture all the emitted light from each of the microneedles, and may be larger in area than the microneedle array to make sure that the light from the end needles are coupled into it. The detector may also be pixelated with a myriad of pixels spanning a single microneedle. For example, this may be the case for CMOS image sensors. In addition, the detector may be separated from or abutted to the top of the lightguide. In case it is separated from the top of the light guide, the material in between the detector and the lightguide can be air, another material, or a combination of air and another material. The choice of the material/air combination is dictated by design considerations such as light guiding properties as well as outcoupling of the emitted light and the maximum angle that it comes out at. For example, the angles at which the light travels in these layers can be critical from the perspective of filtering out the spurious direct source light coupling.

In general, the space between the lightguide and the detector can be occupied by optical filters. These filters in general are wavelength selective filters that are designed to block the direct spurious source light and let through the emitted light from the microneedle to minimize background offset due to undesired signal. In one embodiment, these optical filters can be dielectric film combination filters that are designed to block lower wavelengths and let through higher wavelengths. Such long-pass filters are ideal in case the emitted light is red-shifted compared to the source light. The cut-off wavelength is thus designed to be in between the source and the sensor emitted wavelengths. A larger separation between these wavelengths, depending on the design of the aptamer/fluorophore systems, may make the filter design easier.

One of the possible shortcomings of these filters can be that they work efficiently if the incidence angles are substantially perpendicular to their surface. However, they may not be as efficient in filtering incidence light that comes at shallower or substantially grazing angles. To mitigate this, these filters can be used in combination with spatial filters (also shown in FIG. 28). Spatial filters will reject the substantially grazing angles to the optical filter surface, thus making optical filters more efficient. The spatial filters can be through holes in a solid film, with the aspect ratio of the holes dictating the angles that are allowed vs. rejected. Further, the order of the spatial and optical filters may be swapped.

There are several design considerations that may maximize the coupling of the emitted light from the sensing area into the detector (the signal), while minimizing the coupling of any spurious source light into the detector (the noise). In addition, the design choices have to simultaneously be aware of the requirement of maximizing source light coupling into the sensing area. Maximizing the capture of the emitted signal light from the sensing area and minimizing source back-coupled light in turn depends on how much light as a fraction of the total emitted light from the sensor area exits out of the lightguide toward the detector as well as the angle at which it exits and eventually strikes the detector surface. The angle of exiting light may be important, as it may dictate the ability to minimize the amount of spurious source-light into the detector (the noise).

Figure 29:
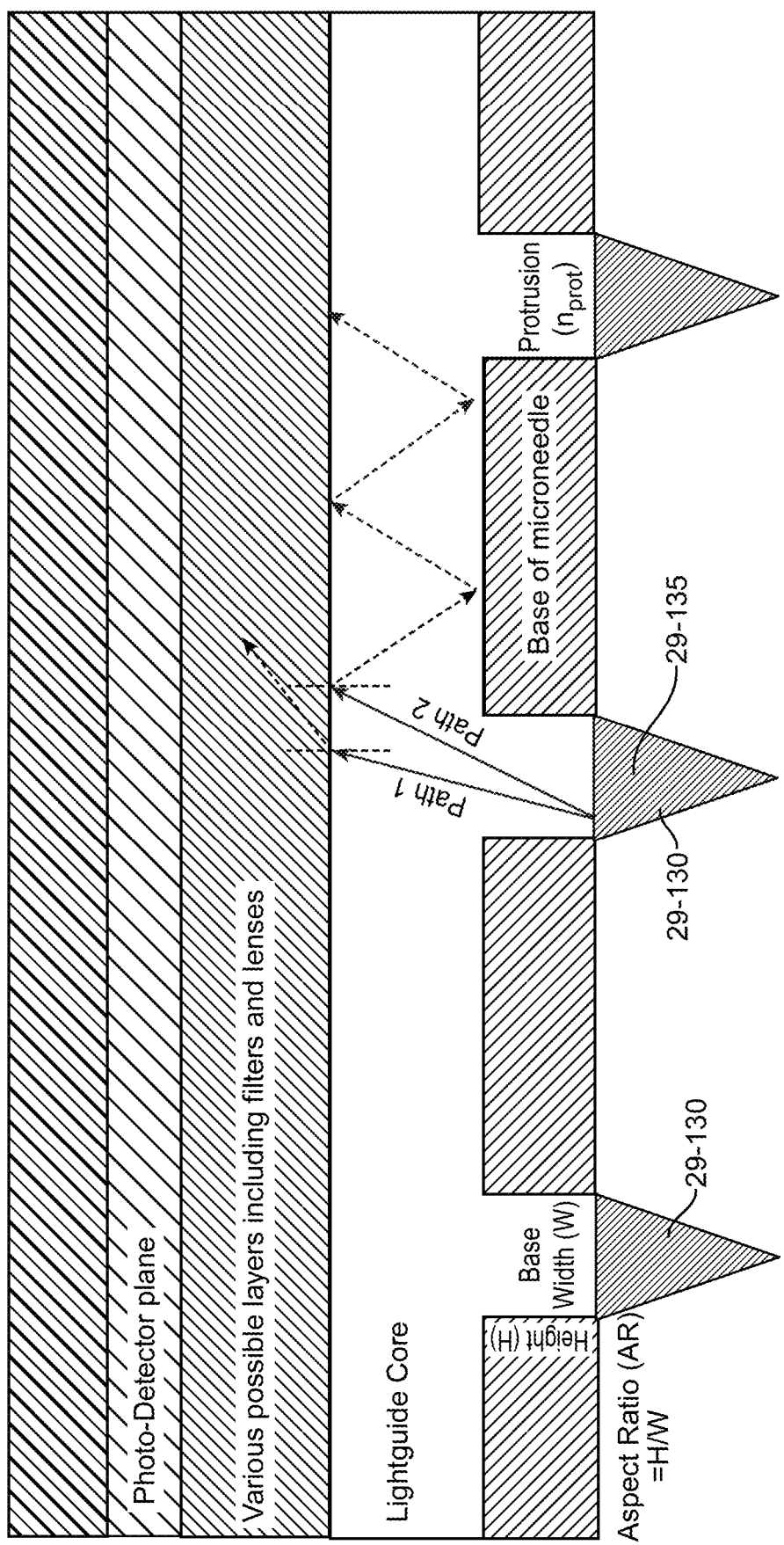
FIG. 29 shows different paths the emitted light can take depending on the incidence angle at the upper core/cladding interface and their relative refractive indices.

There are several considerations involved in dictating the fraction of the total emitted light from the sensor area that exits out of the lightguide. First, one of the design considerations is the core/upper cladding refractive indices of the lightguide. FIG. 29 shows a few possible paths of the emitted light from the sensing area toward the detector. In this figure, 29-130 represents Area 3 and 29-135 represents the emitted light from the fluorophores in Area 3. These examples and possible paths are only shown specifically for the case where the protrusion area refractive index is substantially the same as the core of the lightguide. It serves only as an example and should not be interpreted in the limited sense. One possible path (Path 1, FIG. 29) entails having the emitted light hit the core/upper cladding interface at an incidence angle that is smaller than the critical angle for total internal reflection (TIR) at this interface. In this case, the light will not TIR and will continue to travel toward the detector plane, albeit at a refractive angle that is higher than the incidence angle. A different possible light path comprises an incidence angle of the emitted light and/or the scattered or reflected spurious source light, which is higher than the critical angle for TIR at this interface (Path 2, FIG. 29). In this case the light will not go toward the detector but will be totally internally reflected back into the core of the lightguide. The critical incidence angle at the core/upper cladding interface, below which the light will move toward the detector, is given by $$\sin(\theta_{crit}) = \frac{n_{clad}}{n_{core}}$$

As an example, for a typical core refractive index of approximately 1.5 and an example upper cladding of air ($n_{clad}=1$), the critical angle for TIR is approximately 42 degrees. If the cladding index is higher than that of air for the same core refractive index, the critical angle will be higher. Hence, more of the light will escape out of the lightguide toward the detector. Similarly, if the core refractive index is higher than 1.5 for the same cladding, the critical angle will be smaller, and less of the emitted light will be coupled toward the detector. Thus, core and upper cladding refractive indices are critical design parameters for maximizing emitter light signal that is captured by the detector. These design considerations pertaining to capturing a large fraction of the emitted light into the detector should be carefully weighed against the source light coupling from the light source (such as an LED) into the lightguide as well as scattering and loss in the guided modes of the lightguide.

Another design consideration that goes into dictating the amount of light signal that comes out of the lightguide and is captured by the detector pertains to the properties of the sidewalls of the base of the microneedle array. As discussed earlier in the context of source light coupling into the sensing area, some possibilities for the state of the sidewall are that they can be fully absorptive layers, substantially reflective due coated layers (for example, metal layers), be a dielectric interface between the protrusion area and the base of the microneedle doing at least a partial TIR depending on the refractive index of the protrusion and the base or protrusion area and air interface, or a combination of any of the above possibilities.

Figure 30:
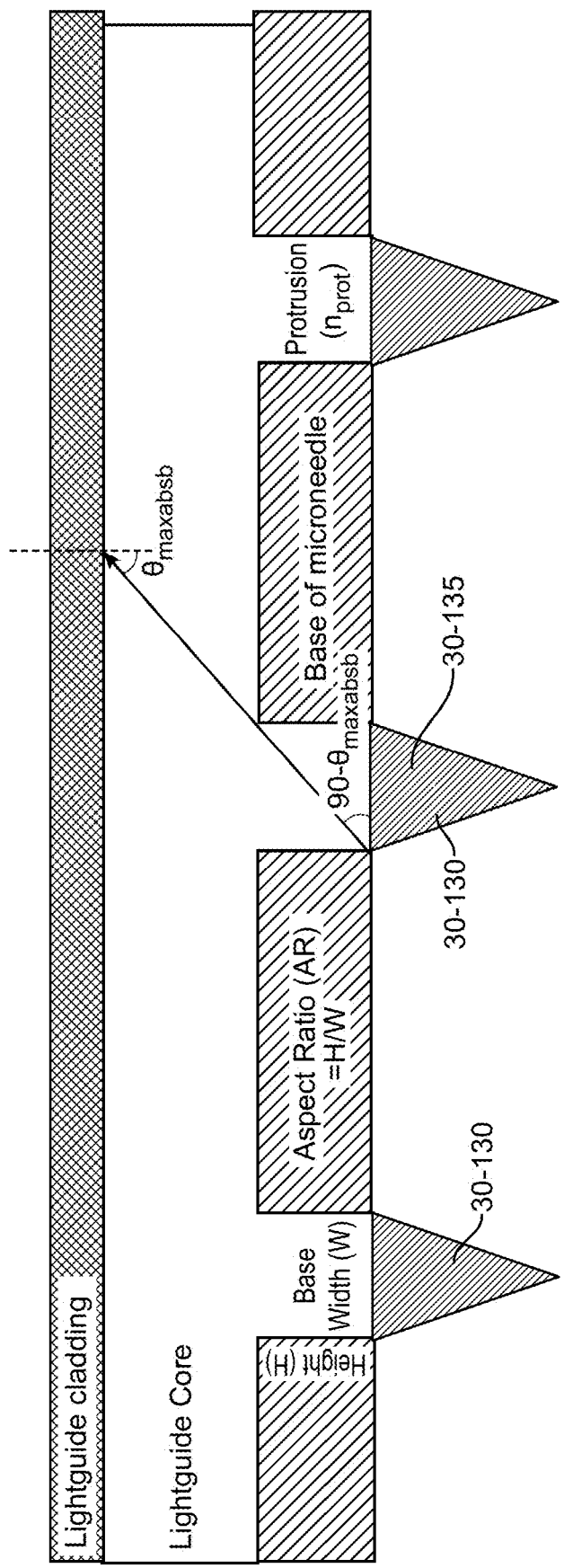
FIG. 30 shows an embodiment where the sidewall of the base of the microneedles is substantially absorptive.

For the case where the sidewall is substantially absorptive, the incidence angle of the emitted light reaching the lightguide core and upper cladding interface will have a maximum incidence angle at the interface, depending on the aspect ratio (AR) of the base of the microneedle (FIG. 30). In this figure, 30-130 represents Area 3 and 30-135 again represents the emitted light from the fluorophores in Area 3. This maximum angle, $\theta_{max,\,absb}$, is given by the following condition:

$$\tan\tan(90 - \theta_{max,absb}) = AR$$

Thus, $$\sin(\theta_{max,absb}) = \frac{1}{\sqrt{1+AR^2}}$$

At lower ARs, the only angles that will hit the sidewall of the base and get absorbed would have hit the upper core/cladding index at an angle that would TIR. However, as the AR of the sidewall of the base increases, there is a critical AR above which the light rays that would have refracted toward the detector would also now be absorbed by the sidewall, thereby decreasing the amount of emitted light that makes it to the detector plane. This critical AR is given by the condition:

$$\sin(\theta_{max,absb}) = \sin(\theta_{crit}) = \frac{n_{clad}}{n_{core}}$$

Thus, $$\frac{1}{\sqrt{1+AR_{max}^2}} = \frac{n_{clad}}{n_{core}}$$

Thus, $$AR_{max} = \sqrt{\left(\frac{n_{clad}}{n_{core}}\right)^2 - 1}$$

For example, if $n_{core}$ is approximately 1.4 and $n_{clad}$ is approximately 1 (air), the maximum AR beyond which the light collected by the detector will start getting reduced is approximately 1.11.

In some embodiments of the substantially absorptive sidewalls, it may be desirable to have an aspect ratio (AR)>$AR_{max}$. This may be the case if there is a need to filter out/eliminate the spurious scattered source light that comes at a substantially non-normal angle to the detector plane. In this case, the sidewall of the base of the needle itself serves as a spatial/angular filter. The motivation for spatial/angular filtering is that the wavelength-based optical filters may not be able to effectively filter out substantially non-normal incident light. Hence, this subset needs to be filtered out using spatial filters so as to not introduce a large, undesirable background signal at the detector. However, this comes at a cost of also filtering out the substantially non-normal light wavelength emitted from the sensing area (Area 3 in FIG. 23), thus also reducing the signal. Hence, the design must be carefully considered to maximize the signal to noise ratio. In addition, the source light coupling into the sensing area is also impacted by the aspect ratio (AR), as outlined earlier in this example. Source coupling must also be factored in while designing the optimal aspect ratio.

Figure 31:
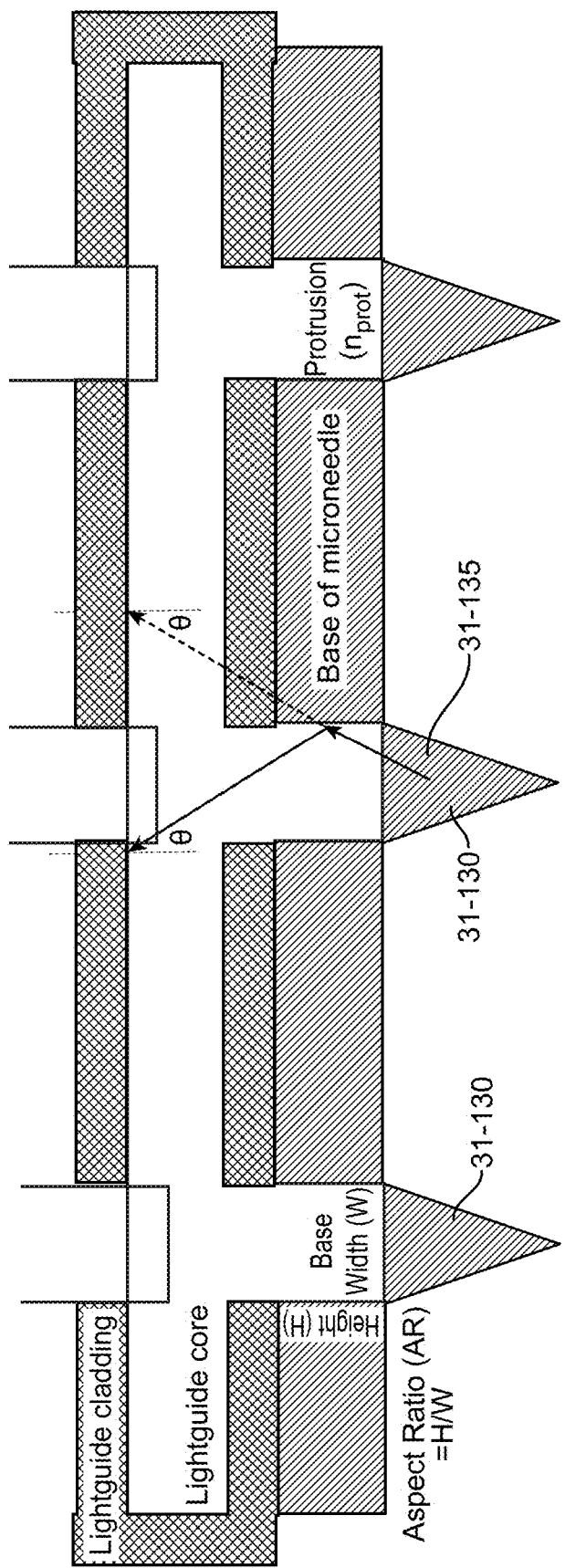
FIG. 31 shows an embodiment where the sidewall of the base of the microneedles is substantially reflective and specular.

In another embodiment, the wall of the base of microneedles is substantially reflective (FIG. 31), possibly due to a reflective material coating, as well as substantially specular. In this embodiment, light will be hit on the core/upper cladding interface of the lightguide at a similar array of angles, up to the critical TIR angle, as if the sidewall is not present. In this embodiment, the cladding layer completely surrounds the core layer. The cladding layer must have a lower refractive index than the core layer, but the cladding layer can be made of any material. When the cladding layer has a lower refractive index than the core, it is a dielectric waveguide. In some embodiments, the cladding layer is a metallic, refractive coating, which is a metallic waveguide.

In this figure, 31-130 represents Area 3 and 31-135 represents the emitted light from the fluorophores in Area 3. Effectively, there is a direct line of sight between the emission region and the core/upper cladding interface. The angles will span normal to substantially grazing angles, with the ones larger than the critical angle given above dong TIR. Another possible variant of this embodiment may entail a reflective sidewall with a non-specular (for example, Lambertian) reflection or a reflection characteristic which is a mix of specular and Lambertian emission.

Figure 32:
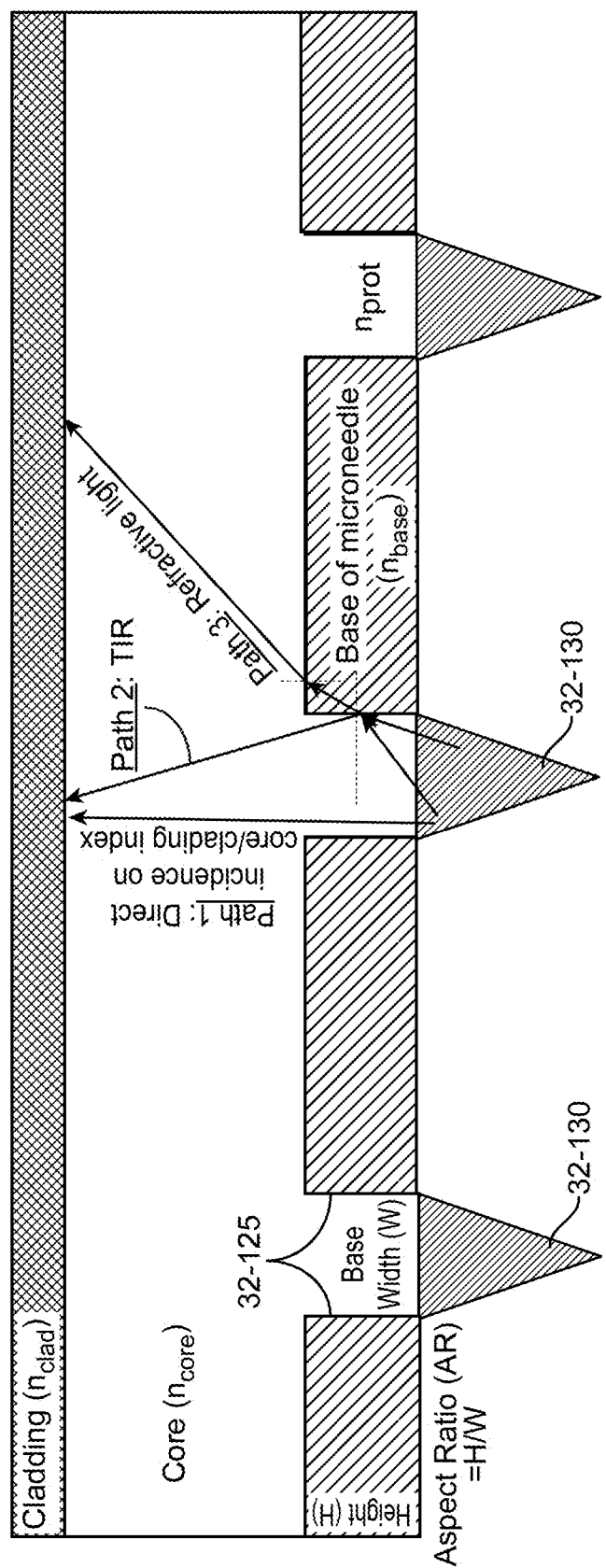
FIG. 32 shows an embodiment where the sidewall of the base of the microneedle is a dielectric stack capable of both refraction and TIR.

For the case where the sidewall of the base of the microneedle is a dielectric stack (FIG. 32) between the protrusion index and the base index, the emitted light from the sensing region (the signal) and the scattered spurious light (noise) will experience partial TIR and partial refraction at the sidewall of the base. In this figure, 32-130 represents Area 3, and 32-125 represents the sidewall of the base of the microneedle. One special case of this embodiment is when there is air at the interface between the protrusion area and the base. The light that will undergo TIR at the sidewall will strike the core/upper cladding interface, similarly to the above substantially reflective case. However, the transmitted light which did not TIR and went through into the base material will also eventually strike the core/upper cladding interface similarly.

In another embodiment, it is also possible to have sidewalls of the base of the microneedles that are non-normal to the core/upper cladding interface. This angle of the sidewall can be used to alter the angles at which the emitter light is striking the core/cladding interface, thus in turn controlling how much of it escapes the lightguide toward the detector plane.

In summary, there are at least two high-level factors that dictate the amount of sensor-emitted light that makes it out of the lightguide and strikes the detector. First, there are design parameters that determine the critical incidence angle at the core/upper cladding interface, below which the emitted light from the sensor will escape out of the lightguide toward the detector plane. These design parameters are the core and upper cladding refractive indices. Second, there are parameters that dictate a range of incidence angles for the light coming out of the sensing area, as well as the spurious backscattered/reflected source light, with respect to the surface normal of the core/cladding interface. These parameters comprise the sidewall of the base of the microneedles and/or its perpendicularity with respect to the core/cladding interface of the lightguide, and/or the aspect ratio of the base of the microneedles. Ultimately, the amount of sensor light (and spurious backscattered source light) making it to the detector is dictated by the above two sets of considerations.

In addition to the amount of light exiting out from the lightguide toward the detector, it may also be critical to control the angle at which the light comes out of the lightguide toward the detector. This is relevant because of the general difficulty of the optical wavelength filters (that in one instance is designed to selectively pass longer wavelengths and attenuate shorter wavelengths) not being as effective at substantially non-normal incidence angles. Thus, the spurious source light, which in a preferred embodiment is at a smaller wavelength than the sensor area emitted light, may get through the optical filters at substantially non-normal incidence angles, causing a degradation in signal to noise ratio.

To prevent this, in one set of embodiments, the optical wavelength filter stack can be placed just before the detector. In addition, it may be preferable for the light striking the optical filters, placed before the light goes into the detector, to not consist of substantially non-normal incidence angles. This may be achieved in multiple ways.

In a simplistic scenario, this can be controlled by eliminating substantially non-normal angles, using the sidewall of the base of the microneedle itself as the angular/spatial filter for the absorptive base-sidewall case.

Figure 33:
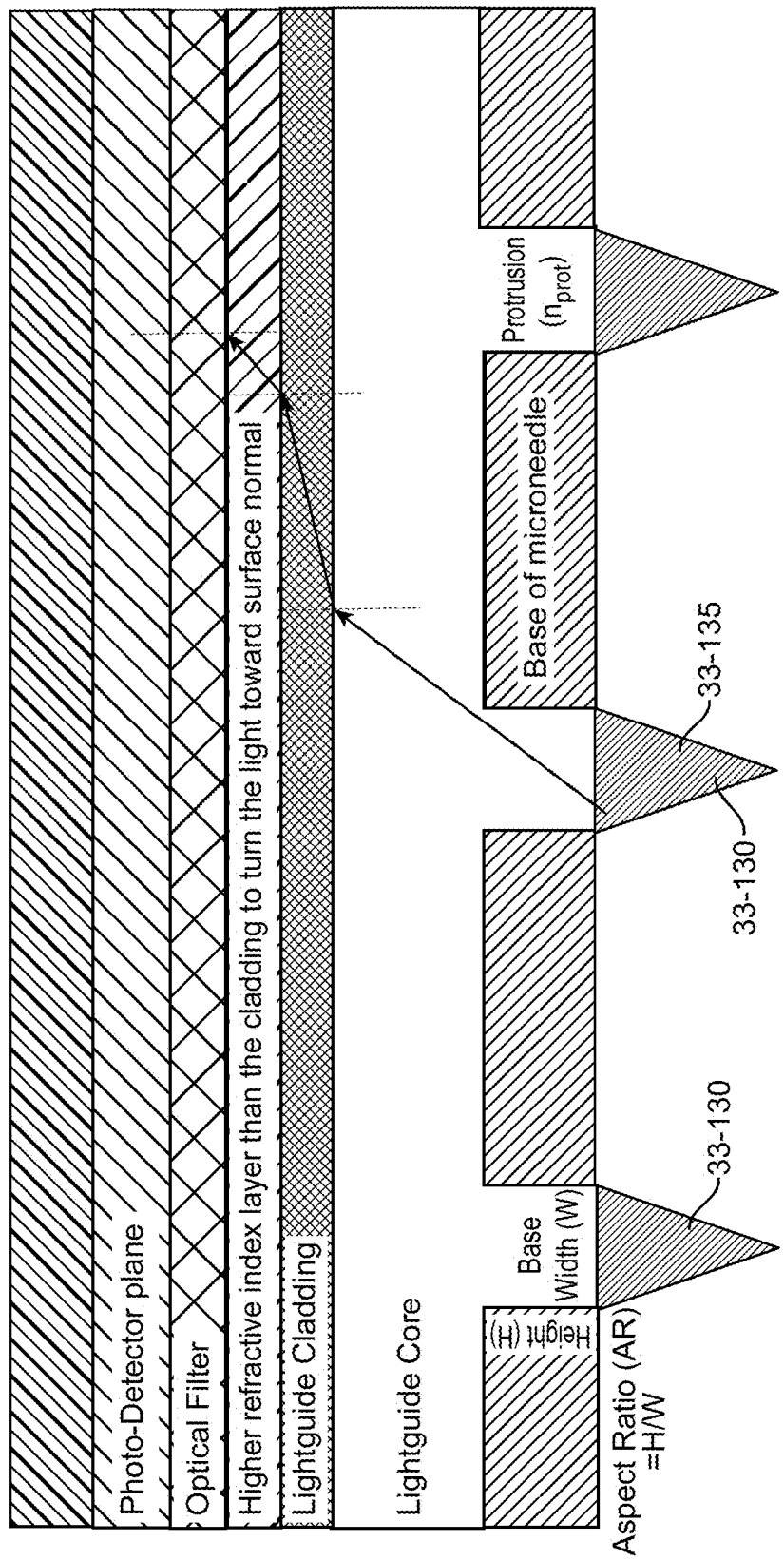
FIG. 33 is a diagram of the sensing light collection stack above the lightguide core.

In another approach, steep angles emerging out of the lightguide can be refracted toward more normal incidence by stacking a layer of material that has a higher refractive index than the cladding of the lightguide (FIG. 33). In this figure, 33-130 represents Area 3 and 33-135 represents the emitted light from the fluorophores in Area 3. This will allow the light to strike the optical wavelength filter closer to a normal incidence angle.

Figure 34:
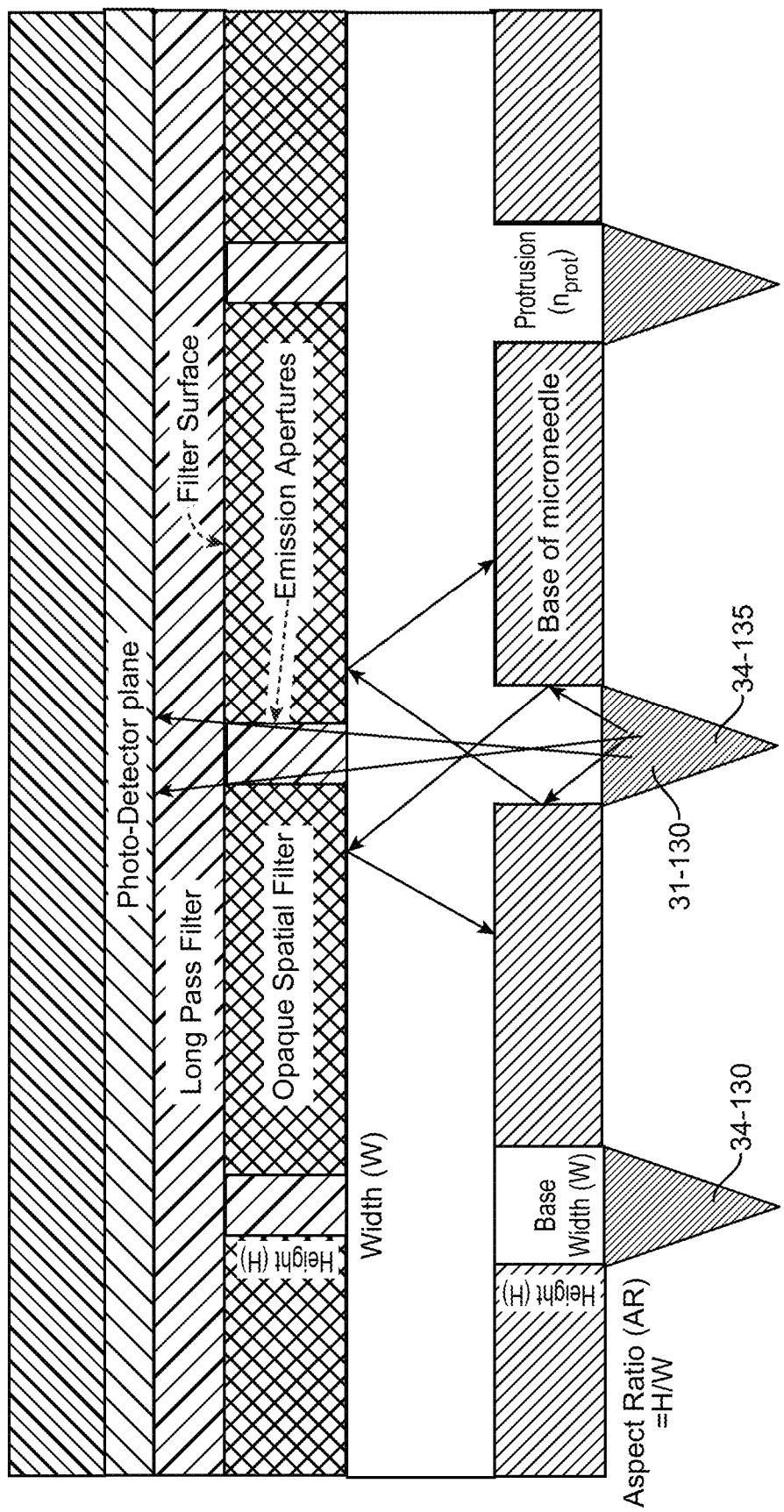
FIG. 34 shows the addition of a spatial filter above the lightguide and before the optical long-pass filter.

In another approach, a spatial/angular filter at the exit side of the light, above the lightguide but before the optical wavelength filter, may be added. This spatial/angular filter may comprise a high aspect ratio hole array (FIG. 34). In this figure, 34-130 represents Area 3 and 34-135 represents the emitted light from the fluorophores in Area 3. There may be an optimization in signal to noise ratio as a function of the aspect ratio (AR) of this structure. A higher AR hole array will eliminate more non-normal incidence angles for both noise (source light) and for signal light coming from the sensing area. This in turn will reduce not only undesirable background signals but also the main signal; it therefore needs to be optimized appropriately. In one embodiment, the hole structure can be absorptive.

In another embodiment, to increase signal to noise ratio, the light exiting the lightguide may be collimated using, for example, micro lenses before it strikes the optical filter. This makes the optical filter a lot more effective at eliminating spurious source light. The potential advantage of this structure entails retaining all the signal light as opposed to rejecting some of it, thus getting a stronger signal at the detector.

In addition, a combination of above approaches can also be deployed before the optical wavelength filter in order to make the incidence angle at its interface substantially normal or close to normal.

Figure 35:
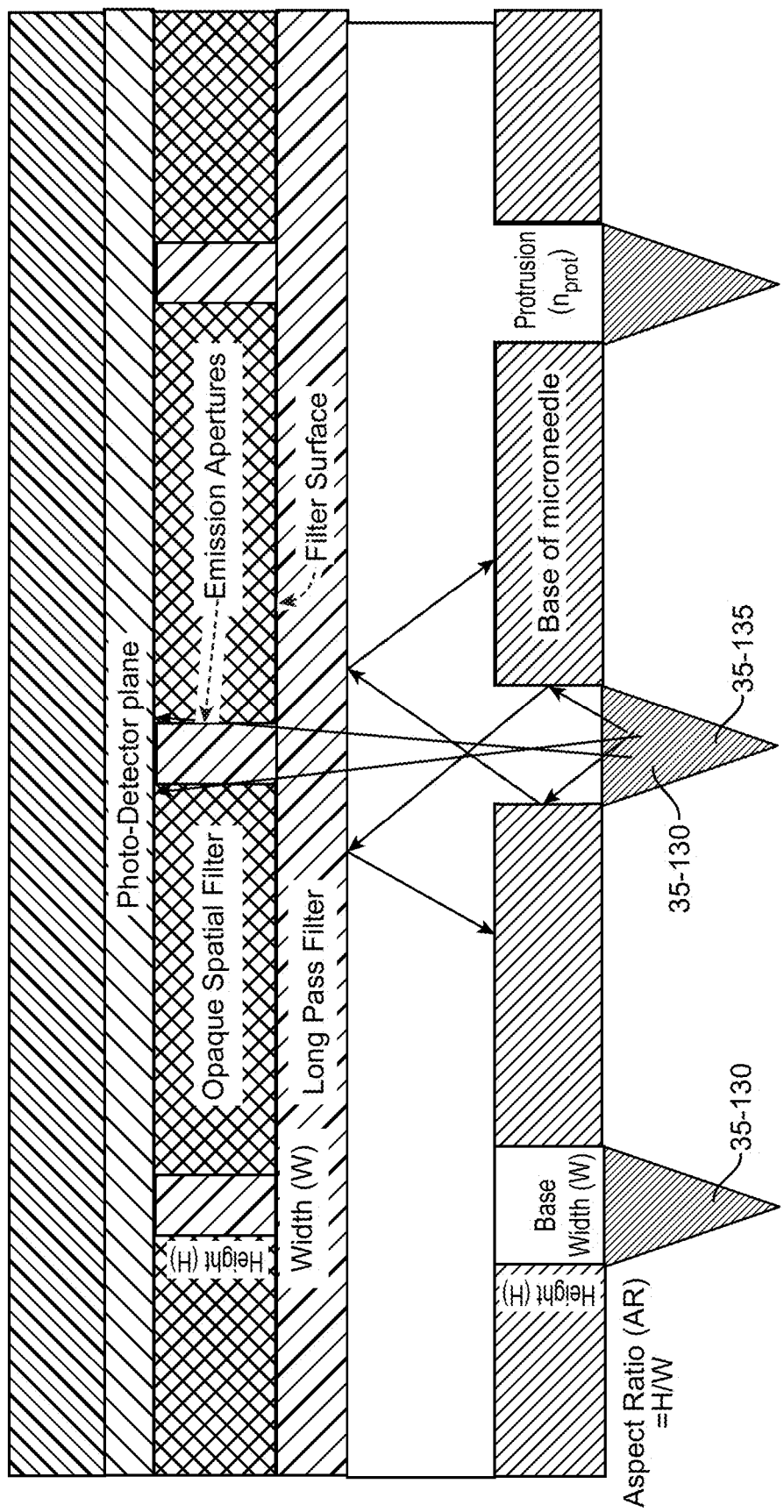
FIG. 35 shows an embodiment where the spatial filter used to cutoff substantially non-normal angles is placed after the optical long-pass filter.

In another set of embodiments, the method to eliminate noise coming from source light back-coupling into the detector may comprise eliminating substantially non-normal incident light after the optical filter. This scenario may contain a similar high AR hole array structure that was used before the optical detector but after the optical filter (FIG. 35). In this figure, 35-130 represents Area 3 and 35-135 represents the emitted light from the fluorophores in Area 3. The rationale is that after the optical wavelength filter, the substantially near normal incident angles for the spurious source light will be eliminated and only the substantially non-normal angles will be present. These non-normal angles can then be eliminated using geometrical structures after the filter but right before the light strikes the detector.

The key optimization in this design entails maximizing the signal light from the sensing area into the detector, maximizing the source light coupling into the sensing area, and minimizing the spurious source light (backscattered or reflected) in the detector, so as to keep a high signal fidelity without the spurious background signal from the source. There are several design parameters which simultaneously impact the above objectives, including various refractive indices (core, upper cladding, protrusion area, and base area), the optical filter cutoff and its performance with off-normal incidence angles, the wavelength shift between the source wavelength and the fluorophore-emitted wavelength, the aspect ratio of the base of the microneedles, as well as the angle of the sidewall. Given the complexity of these interactions, there is a need to develop a systematic approach.

It is important to realize that maximizing the sensing signal light into the detector depends on the ability to capture the largest possible incidence angles at the core/upper cladding interface. The limitation in this cutoff angle comes from two constraints. The first constraint is the ratio of cladding to the core refractive index. This ratio dictates the maximum angle that will escape the lightguide (and not TIR) toward the detector, and may be dictated by other requirements related to light coupling from the source into the lightguide.

Figure 36:
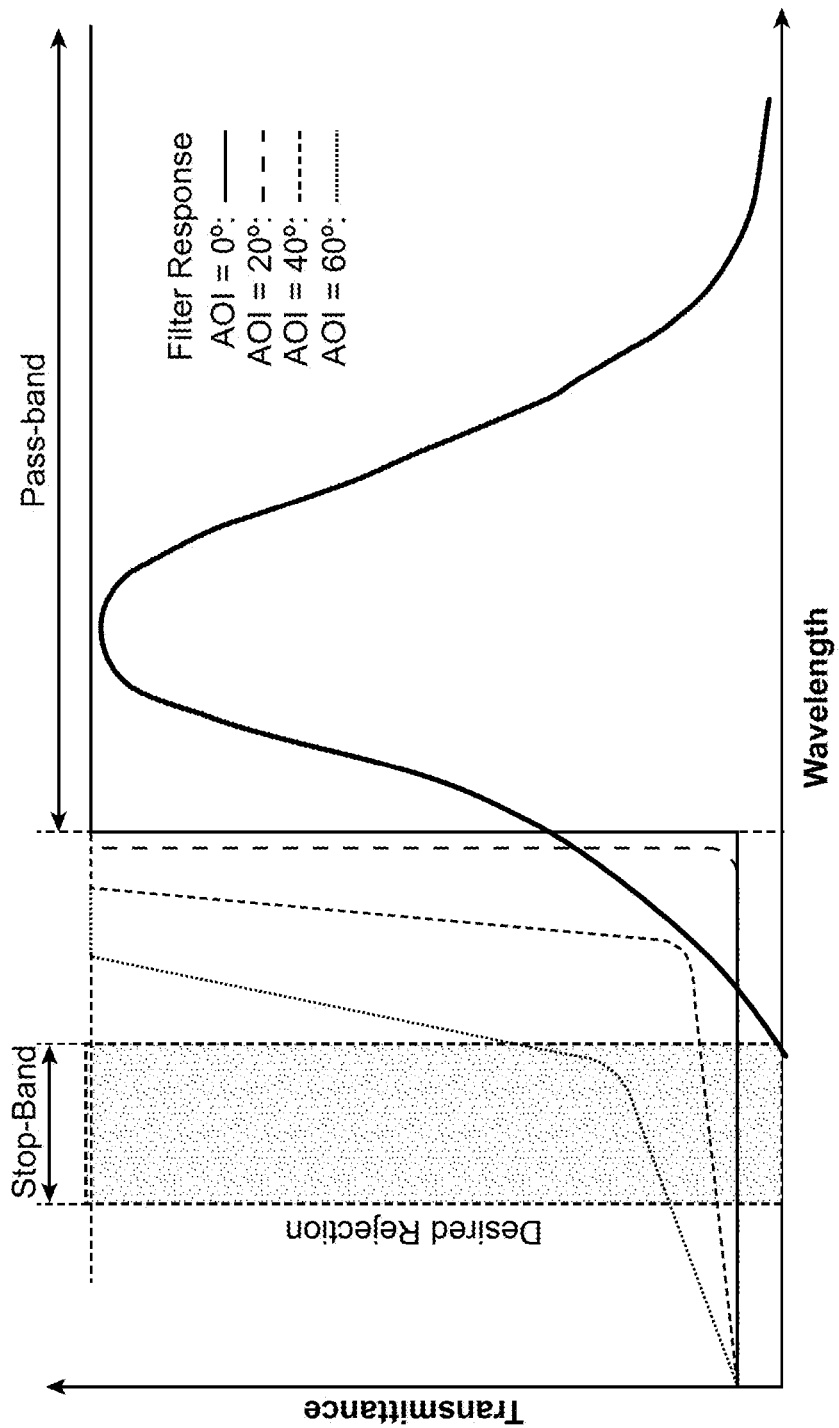
FIG. 36 shows the optical filter characteristics at various angles.

The second constraint comes from a limitation on the maximum incidence angle on the optical filter. This depends on the separation between the source wavelength and the emitted wavelength from the sensing area as well as the quality and ability of the optical wavelength filter to yield a good extinction ratio at substantially non-normal incidence. FIG. 36 elucidates the second constraint. As an example only, it shows one of the many possible optical filter characteristics at an off-normal incidence angle, along with the source light wavelength and emitted wavelength from a particular fluorophore. Other types of fluorophores with different excitation and emission profiles are possible, along with other types of filter characteristics. If we insert a layer of material before the optical filter and after the cladding of the lightguide, which has the same refractive index as the core of the lightguide, the incidence angle at the optical filter will be the same as the incidence angle at the core/upper cladding interface of the lightguide. Alternatively, if the inserted layer has a higher refractive index than the core of the lightguide, then a certain incidence angle requirement will translate into a higher possible incidence angle at the core/upper cladding interface. Similarly, if the inserted layer has an index lower, the angle at the core/upper cladding index will have to be lower than the maximum allowed at the optical filter interface.

As an example, if the first constraint requires the ratio of $n_{clad}$ to $n_{core}$ index to be no more than two-thirds, then the maximum angle allowed to exit the lightguide is $$\frac{n_{clad}}{n_{core}},$$

or approximately 42 degrees. In this particular example, and for the case where the layer of material inserted right before the optical filter has the same refractive index as the core, the more limiting constraint is the core/cladding refractive index ratio. This will limit the maximum collection efficiency of the light coming out of the sensing area into the detector.

As a design guide to maximize the light coming from the sensing area into the detector, it may be desirable to do the following: first, optimize source coupling in different ways so that the ratio of the cladding and core refractive indices is larger and therefore is not the limiting factor; second, maximize the possible allowed by the second constraint above. This can be done by finding a fluorophore with maximum possible separation between source excitation wavelength and emission wavelength from the sensing area, and finding the best possible optical filter to maximize the incidence angle at the optical filter that maintains a high extinction ratio; third; translating this maximum possible angle at the optical filter interface to the maximum possible angle at the core/upper cladding interface through either collimating lenses or insertion of the higher refractive index layer between the cladding and the optical filter to turn the light toward normal incidence at the filter.

Example 7: Detailed Description of an Exemplary Device Utilizing a Waveguide

The following example details the design, structure, and methods of optical design in an exemplary device that utilizes guided light. Guided light is light carried using lightguides or waveguides.

Figure 37:
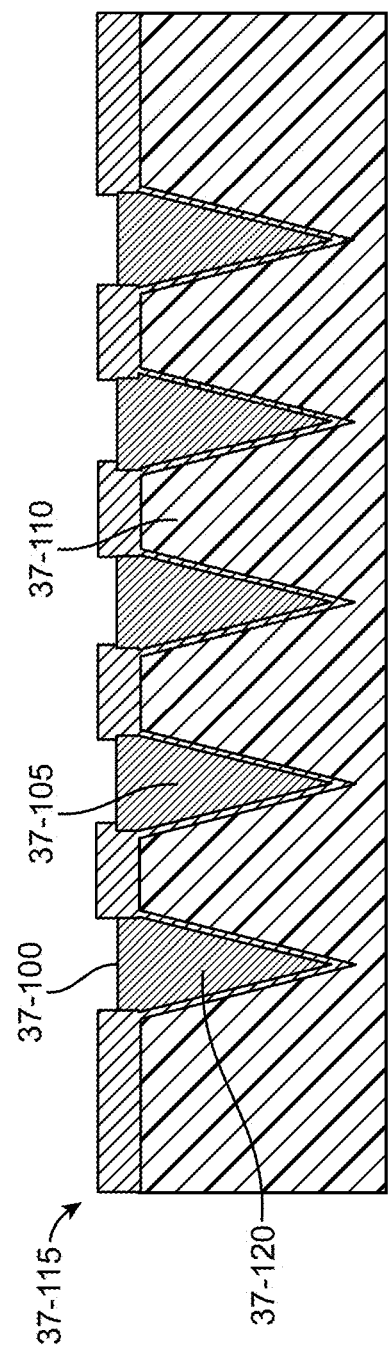
FIG. 37 shows a microneedle array with needles going into human skin. The microneedles are hollow and hold target molecule sensing analyte probes.

FIG. 37 depicts a diagram showing a microneedle array with needles going into human skin. The microneedles are hollow and contain analyte binding probes as described herein. In this figure, 37-100 indicates a microneedle interface, with sidewall angles flexible. 37-105 indicates another microneedle interface that must have open walls. 37-110 indicates that the microneedles are embedded in the dermis and interface with the interstitial fluid. 37-115 indicates the MAP base, with flexible dimensions. 37-120 indicates the microneedle sensing domain, with a hydrogel/fluorophore combination.

The optical system here described has several advantages that make it efficient and conducive to the goal of bringing in the excitation light at a specific wavelength inside the microneedles for the purpose of exciting the fluorophores as well as efficiently transferring the emitted intensity from the fluorophores in the microneedles to the detection system. First, it maximizes the excitation photons getting into the microneedles, depending on the number of light sources that can be efficiently placed around each microneedle and the ability to couple efficiently from those sources into the microneedles. Second, the optical system efficiently couples out the emitted photons from the fluorophores in the microneedles and couples them into the detection system. Third, the optical system makes sure that the source light is very efficiently blocked from getting into the detection system. Fourth, the optical system is relatively low cost. Fifth, the size of the optical system both in the Z direction and in the lateral X-Y direction is small enough to make a portable device.

Figure 38B:
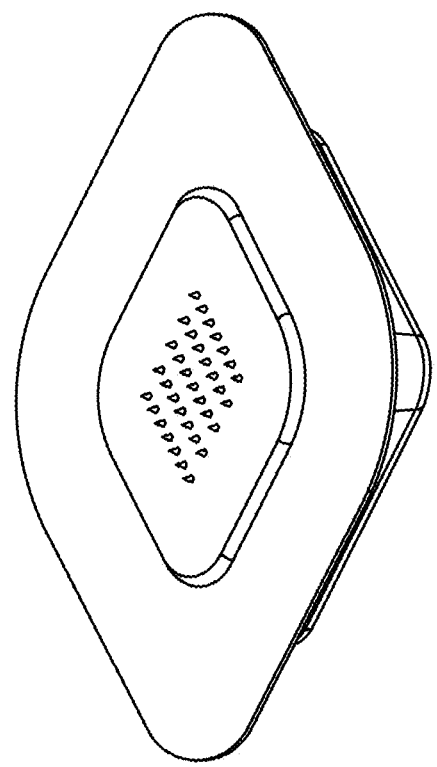
FIGS. 38A-38B show the packaged form of an exemplary sensor that uses guided light.
Figure 38A:
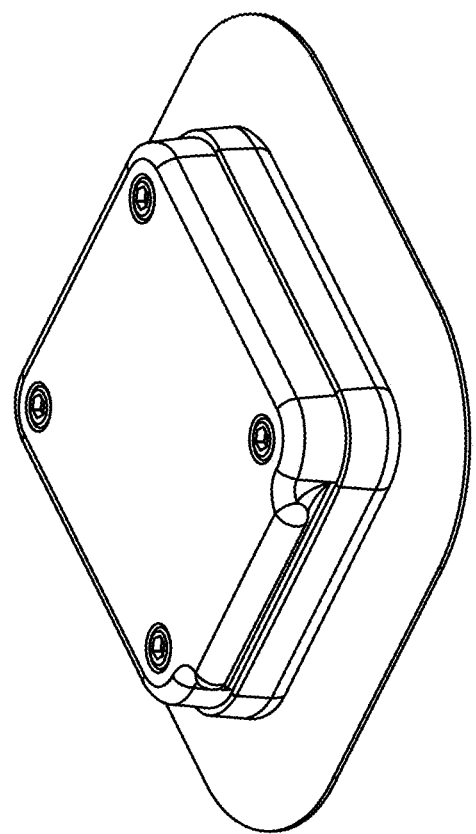

FIG. 38 depicts diagrams showing the packaged view of this exemplary sensor. FIG. 38A shows the front of the sensor and FIG. 38B shows the back of the sensor. FIG. 38B shows the disposable patch and the hollow microneedle array that inserts into the skin and contacts the interstitial fluid below the skin. The adhesive patch in the middle of the two layers attaches to the skin. The hollow microneedle array comprises shallow (between 200 μm and 2 mm) microneedles that penetrate into the skin and are in intimate contact with the interstitial fluid. This microneedle array holds the sensing domain comprising the detection analyte-specific analyte binding probes.

Figure 39A:
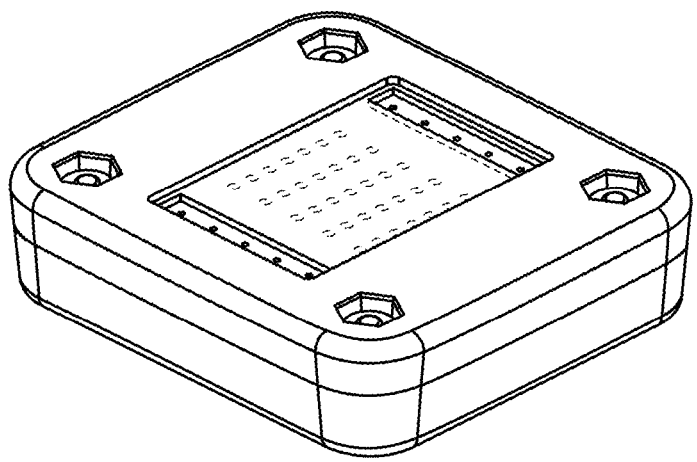
FIGS. 39A-39B show the durable, reusable part of the sensor depicted in FIG. 38.
Figure 39B:
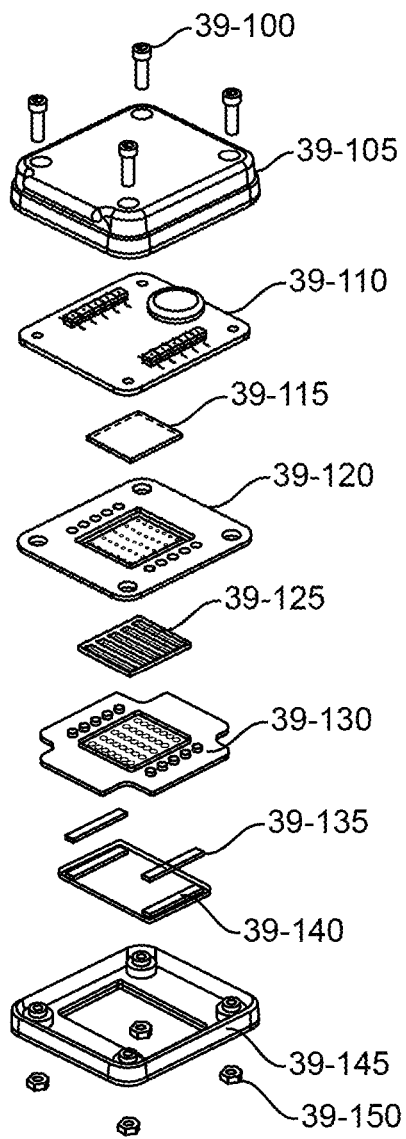

The sensor described in this example comprises two distinct parts. The first part is the durable, reusable sensor. This is the more expensive component, and comprises most of the optics and electronics as well as the lens array. FIG. 39 depicts the reusable part of the sensor. FIG. 39A depicts the packaged reusable part of the sensor from the backside. FIG. 39B shows the exploded view of the main layers and components inside the reusable part of the sensor. The sensor contains an aperture hole array in the center, depicted at the bottom of FIG. 39B. Emitted light from microneedles can enter the aperture holes. Also shown in FIG. 39B are the two rectangular excitation filters that sit in a recessed sensor window. LED light passes through these filters to enter the waveguide in the patch window (not shown). In this figure, 39-100 indicates the screws, 39-105 indicates the cover, 39-110 indicates the sensor board, 39-115 indicates the emission filter, 39-120 indicates the upper aperture plate, 39-125 indicates the lens array, 39-130 indicates the lower aperture plate, 39-135 indicates the excitation filters, 39-140 indicates the sensor window, 39-145 indicates the base, and 39-150 indicates the nuts. FIG. 40 shows a cross sectional views of all of the layers of both the reusable and disposable parts of the exemplary sensor. Excitation light rays trace the excitation path from the LED or LEDs (e.g., the light source) into the microneedles through the aperture hole, excitation filter, mirror, waveguide, and sidewall of the microneedles. Emission light rays trace the path of emission light from the microneedles (e.g., analyte binding probe) through the waveguide, sensor patch window, aperture, lens array, and emission filter to the image sensor.

Figure 41:
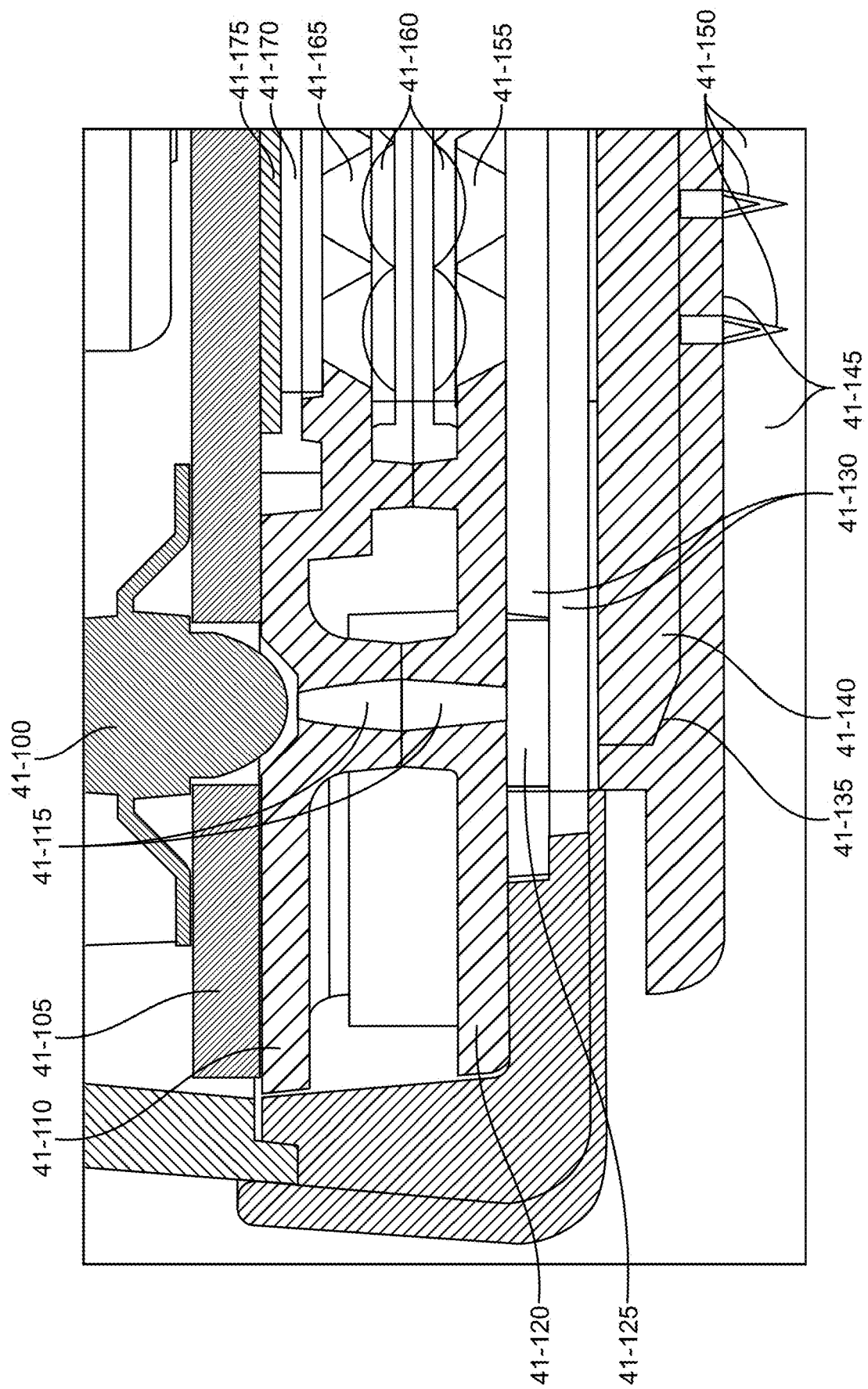

FIG. 41 is a magnified view of FIG. 40 with layers shown in more detail and showing all of the layers that are described in detail in this example. In FIG. 41, 41-100 indicates the LED, 41-105 indicates the sensor board with its electronics, 41-110 indicates the top half of the aperture board, 41-115 indicates the through hole that lets LED light go through and cuts out the larger angles, 41-120 indicates the bottom half of the aperture board, 41-125 indicates the excitation filter recessed in the sensor window, 41-130 indicates the sensor window, 41-135 indicates the turning mirror, 41-140 indicates the lightguide/waveguide in the disposable patch window, 41-145 indicates the base of the microneedle array, 41-150 indicates the microneedle array, 41-155 indicates the bottom aperture board, 41-160 indicates the lens array, 41-165 indicates the top aperture board, 41-170 indicates the emission filter, and 41-175 indicates the image sensor. There is also a lens, which is not shown. In this example, the aperture 41-115 is in a black material that absorbs light. The filter 41-125 only works well if the incidence is substantially normal, within 30 degrees of the angle of the light. This filters out broad angles, only allowing narrow angles. A metallic waveguide, by contrast, can support wide angles, so the filter does not serve that purpose in this embodiment. In this example, there are also free space optics from the light source to the waveguide: there is free space to the waveguide, then from the waveguide to the sample.

Figure 42:
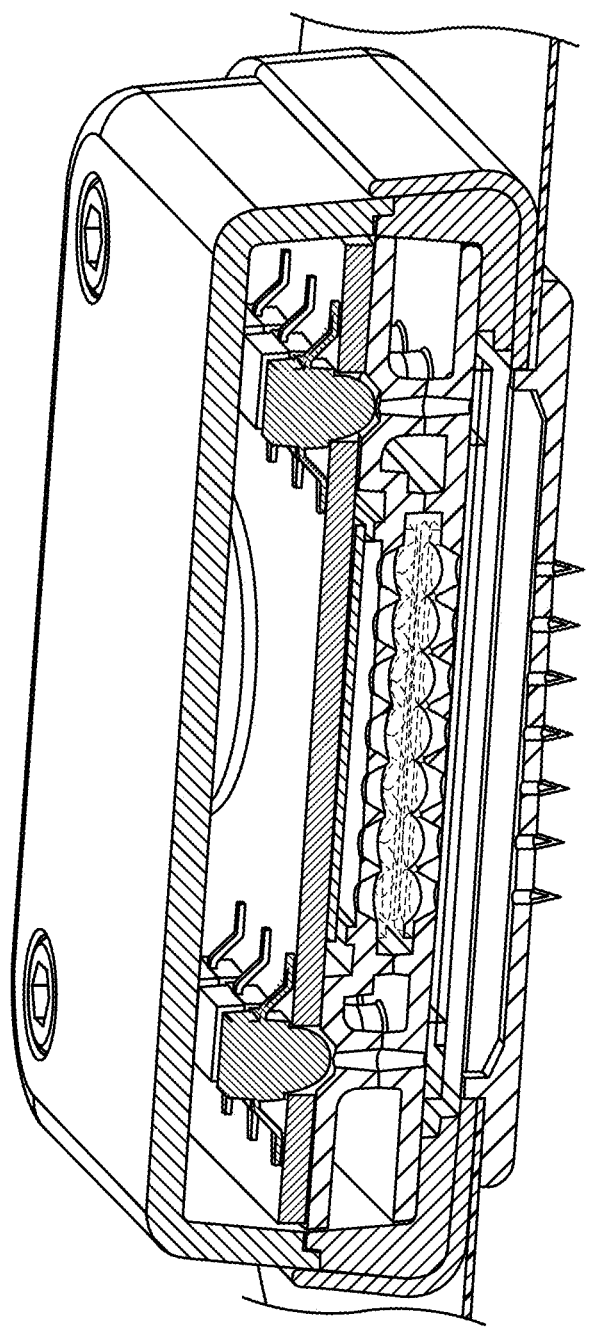

FIG. 42 shows a slightly tilted view of the sensor with the same features as described in FIG. 41. The key components inside the reusable part of the sensor include the MCU, the detector electronics, a Bluetooth radio, and more. There is also an array of LEDs that could be integrated on the same board or could be on a separate board. In this embodiment, the LEDs are down-firing LEDs that have lenses in front of them in order to limit the angular content of the beam coming down. In one embodiment, the constraint of the angular content can be plus or minus 11 degrees of the width of the spread at half of maximum intensity. In this embodiment, the LED array comprises two columns of LEDs on either side of the waveguide that address a row of microneedles. The total number of rows of LEDs is the same as the number of rows of microneedles. An image sensor is below the sensing board and attached to it (not shown in FIG. 39B. This image sensor detects the photons coming out of the microneedles and communicates with the electronics on the sensor board.

Under the CMOS image sensor is the emission filter. This filter may be between 0.4 mm and 1 mm. The purpose of this filter is to only let the long wavelength-emitted light from the microneedle go through to the image sensor, and to reject the lower wavelength source light. The emission filter can either be a long pass filter or a bandpass filter. These filters can be dichroic in nature and may have requirements ranging from OD 3 to OD 9. In addition, the filter should have some tolerance to work reasonably well with non-normal incidence to some extent. In one embodiment, this tolerance can be up to about 30 degrees off-normal.

Below the emission filter is the top half of the aperture board. The aperture board itself is made of a highly absorptive material and/or coated in a highly absorptive material. The light from the LEDs passes through the holes and further eliminates off-angle rays. All angles beyond a certain range of angles cannot be coupled into the waveguide. The purpose of the aperture board is to select for this ideal angle range and absorb the remaining light so that it does not create spurious background signal by accidentally coupling into the detector. The aspect ratio (height to diameter ratio) is optimized for the aperture for the required angular range selection. It comprises one half of the holes for both the excitation path from the LEDs as well as the emission path from the microneedles to the detector. This may constrain the light to narrow angles in both excitation and emission paths. For the emission light, the aperture window may collimate photons such that they are within the angle that the emission filter can reject.

The next layer is a micro lens array. Each lens sits on top of one microneedle in the microneedle array. A micro lens takes the emission light and concentrates it toward an image sensor pixel. The micro lens layer is made of plastic which is transparent and is conducive to being molded in the shape of lenses. This plastic could comprise acrylic, Zeonex, polycarbonate, or some other material. In some embodiments, the micro lens array is made of glass.

The layer below this is the bottom half of the aperture board. Below the bottom aperture board is the plastic sensor patch window. There are recessed trenches in the plastic window which house the excitation filters. The trenches align with the down firing LED arrays on both sides. FIG. 39B also shows the two rectangular excitation filters that sit under the down firing, angularly constrained LED arrays. The purpose of the excitation filter is to filter out any light which is longer wavelength than the excitation wavelength that may interfere with the detection of the emitted light from the microneedles. Since the angles of the light are constrained by the aperture, and its incidence angle is close to normal, the excitation filter can be highly selective and cut off longer wavelengths which may otherwise interfere with the emission signal that occurs at a longer wavelength. In one embodiment, these filters are of the order of 0.5 mm. In some embodiments, these filters can range from 0.3 mm to 1 mm. The filter characteristics can be bandpass in the excitation wavelength range or can also be short-pass. The sensor patch window also protects the reusable sensor from scratches and moisture. The last layer on the down side of the reusable sensor lets the light out and mates it with the disposable part of the sensor. The patch is made of transparent materials, such as but not limited to Zeonex, acrylic, or polycarbonate.

Figure 43:
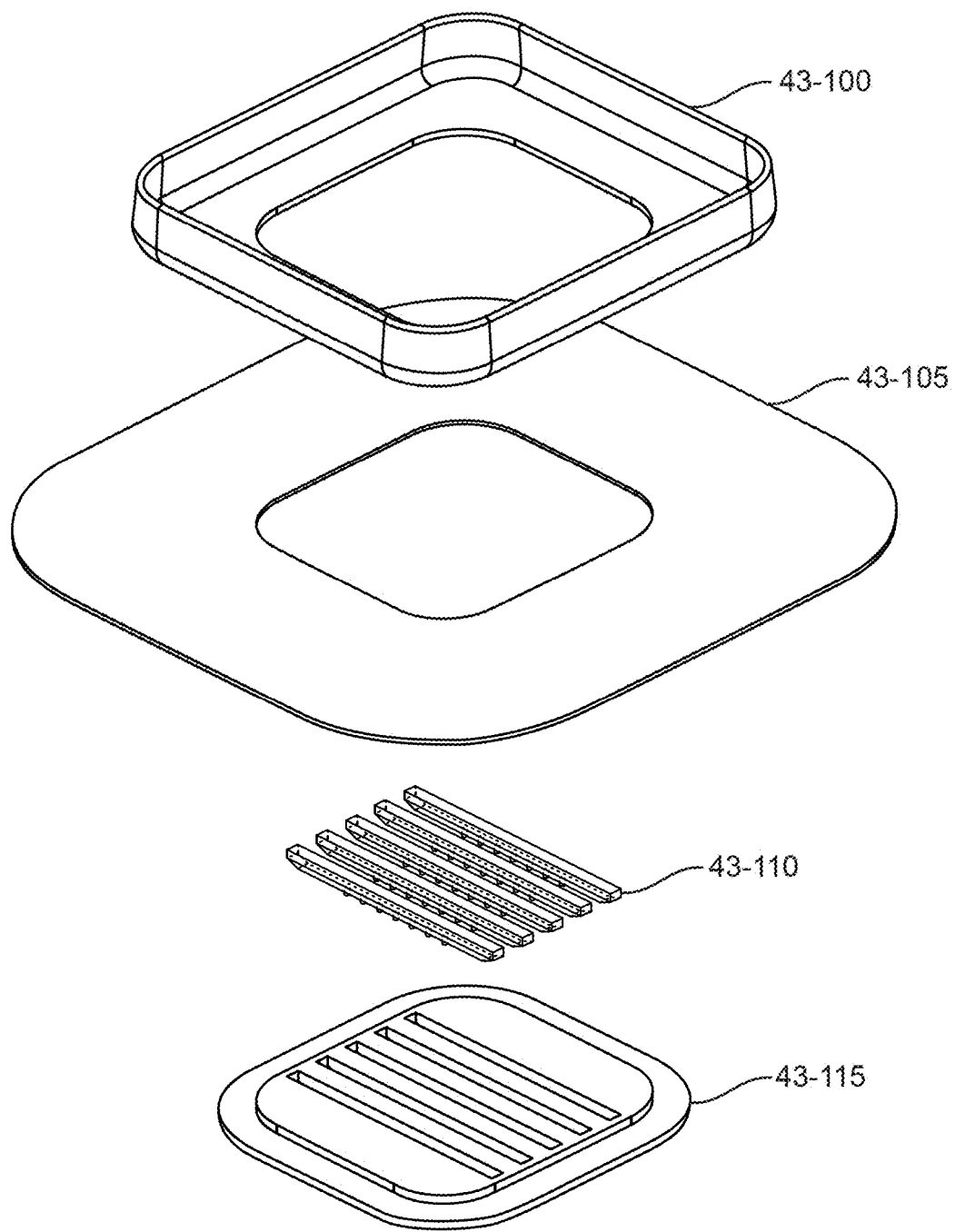
FIG. 43 depicts an exploded view of the disposable portion of the sensor depicted in FIG. 40. It comprises the microneedle array and a plastic waveguide structure with special turning mirrors at both ends of the waveguide.

The second part of the sensor is the disposable part. This part needs to be inserted into the body of the user. It is inexpensive and needs to be disposed of frequently. Upon the end of life of the disposable sensor, which may range from one time use up to a few weeks, the reusable sensor is detached, the disposable sensor is removed from the body, a new disposable patch is inserted, and finally the reusable part is mated with the new disposable patch. FIG. 43 shows an exploded view of the disposable sensor patch shown in FIG. 40. In this figure, 43-100 indicates the patch frame, 43-105 indicates the patch adhesive, 43-110 indicates the patch light guides, and 43-115 indicates the patch base. The disposable portion comprises the microneedle array and a plastic waveguide structure with special turning mirrors at both ends of the waveguide. In one embodiment, these are discrete waveguides which are laterally confined. In this embodiment, there is one waveguide for every pair of LEDs and every row of microneedles. The waveguide also has protrusions sticking out that get inserted into the base of the microneedle structure and facilitate coupling of light into the microneedles. The plastic material that makes up the waveguide must be largely transparent, should have a high refractive index to facilitate coupling from LEDs into the waveguide, should have low autofluorescence, and should generally have some resistance moisture. Filtered light comes out of the sensor patch and enters the waveguide of the disposable patch. Since the disposable patch and the sensor patch are, in some embodiments, similar refractive index materials, the light passes through into the waveguide and the light then encounters an angular mirror. The light is turned by these mirrors and coupled into the waveguides. The angle of the mirror is around 22.5 degrees, so it turns light close to 45 degrees of incidence angle with respect to the upper interface of the waveguide.

The waveguide is designed to have a certain acceptance angle relative to the surface normal of the upper surface of the waveguide. The lower limit of the acceptance angle with respect to the surface normal of the top surface of the waveguide is dictated by the total internal reflectance (TIR) condition. This requires that the incidence angle be greater than the critical angle. For example, in a typical plastic core index (approximately 1.5 index) with an air interface, this angle is approximately $\sin^{-1}(1/1.5)$, or approximately 42 degrees. Different refractive indices can be chosen, leading to slightly different critical cut off angles. All angles lower than this angle will not totally internally reflect and will escape the waveguide.

Figure 45:
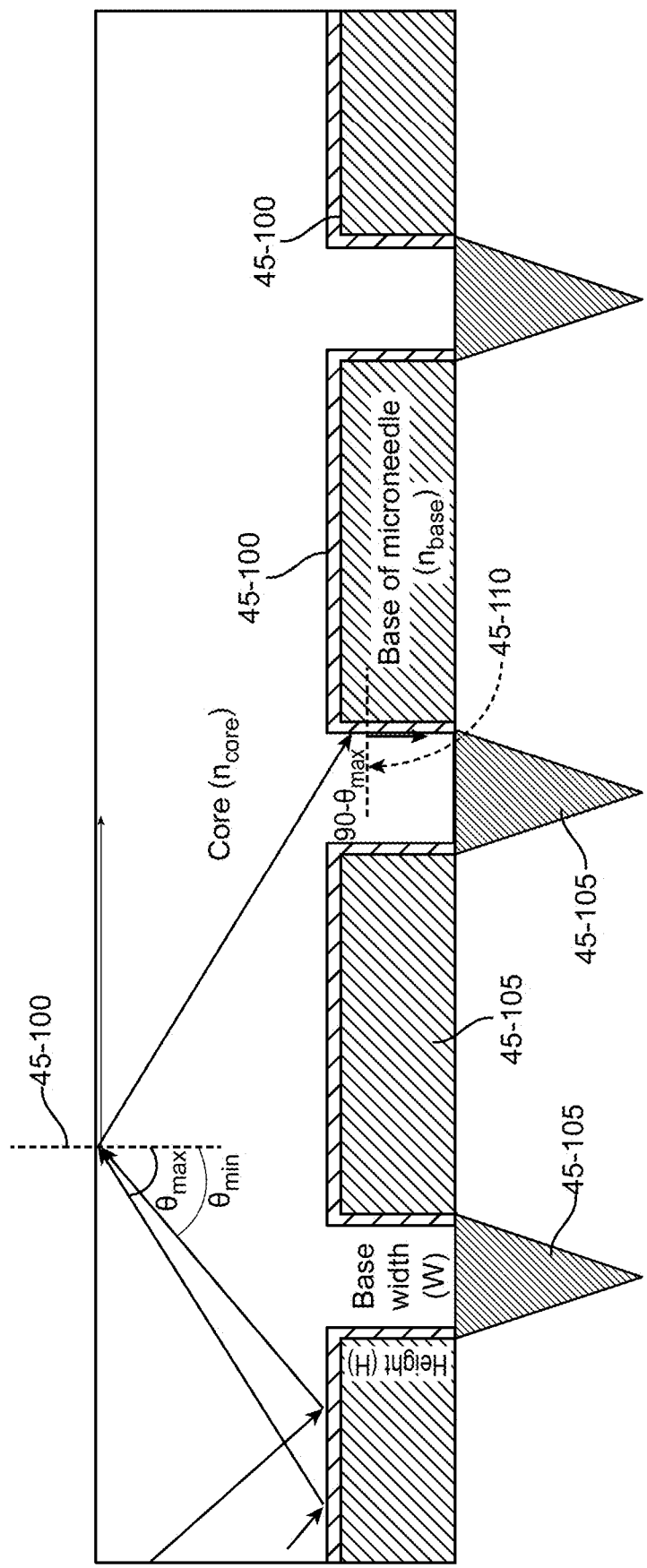
FIG. 45 is a schematic showing the acceptance angle range for an embodiment where the cladding of the light-guide is air everywhere.

The higher angle limit (maximum limit) of the acceptance range into the waveguide is set by the ability of the light to couple from the waveguide into the microneedles (FIG. 45). In this figure, 45-100 indicates the air cladding embodiment, 45-105 indicates the microneedle array, and 45-110 indicates the critical TIR angle at this interface. The angle needs to be larger at this interface to TIR down to the needle. There exists a critical angle with respect to surface normal of the top surface of the waveguide, beyond which the light will not couple into the microneedle (even though it does TIR and gets trapped inside the waveguide). FIG. 45 is a schematic showing the acceptance angle range for an embodiment where the cladding of the lightguide is air everywhere (this would be the case when materials are brought together due to microscopic roughness). FIG. 45 shows that an angle theta incidence on the waveguide upper surface will be incident at an angle (90 minus theta) on the sidewall of the base of the microneedle. In one embodiment, this sidewall also has the core/air interface, hence it requires that the incidence angle at this interface (90 minus theta) is larger than the same critical angle for it to TIR down into the microneedles. Hence, 90 minus theta is greater than the critical angle for TIR. Thus, angle theta has to be less than 90 minus the critical angle. For the above example of a core index of approximately 1.5 with air cladding, the critical angle is approximately 42 degrees. This implies that the maximum incidence angle for this index system is 90-42=48 degrees. Thus, for the above example, the acceptance angle into the waveguide is approximately 42 to 48 degrees.

For straight sidewalls of the base, the acceptance angle is symmetric about 45 degrees. If the refractive index of the core of the waveguide increases, the acceptance angle also increases. In other embodiments, the sidewall of the base of the microneedles may not be straight but at an angle. The angle may be optimized with respect to maximizing both coupling from the LED into the microneedles (the excitation path) as well as the coupling from the microneedles into the detection system (the emission path). The acceptance range of angles into the waveguide will change corresponding to the optimal sidewall angle, and the reflecting mirror has to be adjusted to maximize coupling.

In some embodiments, the aperture may be designed to allow more angular content in the waveguide such that rays can interact with the sidewalls of the base at glancing angles in order to couple more light into the microneedles. In these embodiments, the only constraint is the TIR condition with the top of the waveguide to avoid leaking excitation light toward the detector.

In the above-described optical light path, the aperture aspect ratio under the LED is such that the light beam for the LED is further truncated such that only the acceptance angle range dictated by the waveguide strikes the mirror.

Figure 44B:
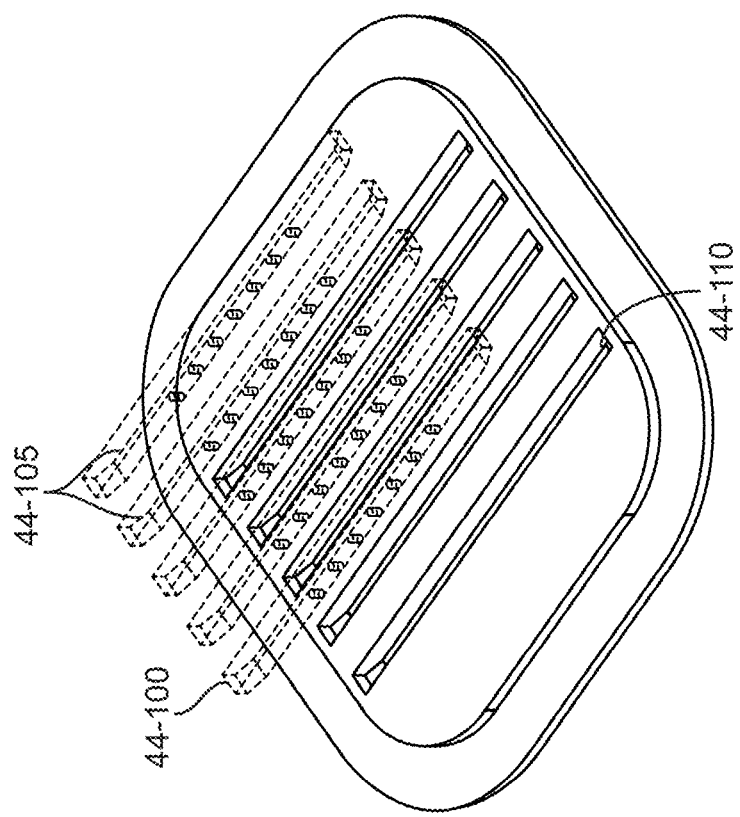
FIGS. 44A and 44B depicts individual pieces of the disposable patch in greater detail. They shows two different views from the top down of the disposable part of the image sensor.
Figure 44A:
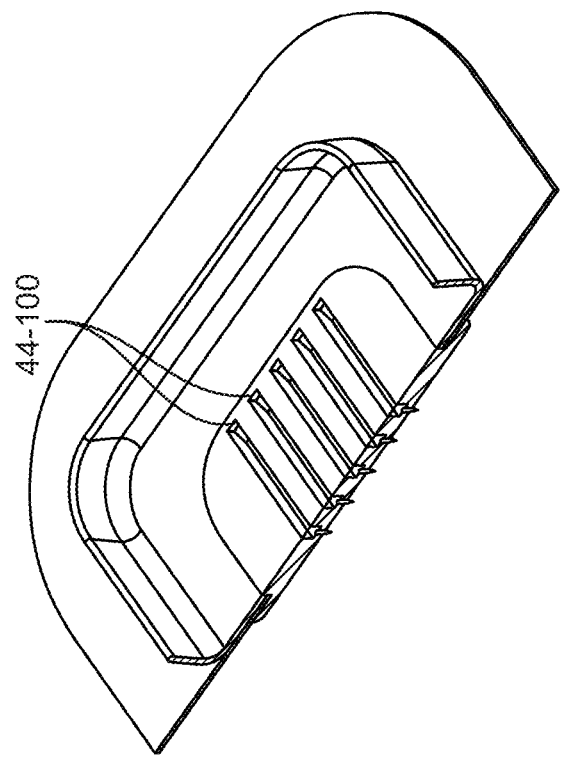

In some embodiments, the waveguides are laterally confined, or there is discretization in rows, as opposed to having a single waveguide which spans many rows of microneedles. In one embodiment, the material in between the discrete lightguides is a highly absorptive material which absorbs any stray light, and the discrete lightguides sit in its trenched pockets. This is shown in FIG. 44. In this figure, 44-100 indicates the turning mirrors, 44-105 indicates the laterally-confined lightguides/waveguides, and 44-110 indicates the lightguide trenches.

Lateral confinement has many benefits, including, but not limited to, increasing the coupling into the microneedles, and preventing cross talk from one row of microneedles into another row. Lateral confinement increases the coupling into the microneedles because even a small angular spread in the beam after it reflects from the mirror spreads the beam in the lateral direction. Having an air/waveguide interface reflects the light from this interface back into the guide and confines it laterally as well, in addition to the vertical confinement. The prevention of cross talk between rows of microneedles is especially critical in a sensor multiplexing scheme for sensing multiple analytes, where each row of microneedles contains only one unique type of analyte binding probe.

In this embodiment, the light path of the emitted light from the analyte binding probes in the microneedle is designed to maximize the collection of photons by the detector. The path from the needles to the detector can be seen in the cross section (e.g., FIGS. 35, 40). The light comes out of each microneedle and is assumed to be emitted in a Lambertian manner from the analyte binding probe in the microneedle. In some embodiments, the system is designed so most of the light gets TIR from the side wall of the base of the microneedle (e.g., FIG. 35). In some embodiments, the system is designed so most of the light gets TIR from a reflective coating about a surface of the microneedle. A substantial amount of the light comes out at angles such that it escapes the waveguide in the patch and enters the sensor window path in the reusable part of the sensor. Subsequently, the light goes through the bottom part of the aperture layer, which is a continuation of the bottom part of the aperture for the incoming LED light as discussed above. There is an aperture above every microneedle to absorb substantially non-normal incidence angles. Above the aperture is a lens array with a lens above each microneedle. In one embodiment, the lenses, or a first lens of a plurality of lenses, is a collimator which aligns the light in one direction. Once aligned, the light can be transmitted with high coupling efficiency to an optical filter, e.g., a dichroic filter, an absorptive filter, or combinations thereof. In some embodiments, the transmission efficiency of filtered light is increased by the collimator which aligns the light in one direction prior to transmission through the optical filter. In one embodiment, for example, as second lens of a plurality of lenses, the lens(es) can be aspherical and designed to focus the light onto a smaller area, and increase the light intensity on the center pixels of the detector. In some embodiments, the second lens of a plurality of lenses are positioned after the optical filter, and before the detector. In some cases, in the emission path, the light passes through the upper part of the aperture and the emission filter. The emission filter can be a long pass or band pass filter designed to let the longer emission wavelength pass through but block the shorter source waveguide. In addition, the aperture-based and lens-based angular discrimination limits the incidence angles on the emission filter substantially close to normal incidence. This in turn makes the filters much more effective. The light then crosses the filter and enters the detection system attached to the sensor board. In one embodiment, the photon detection system comprises a CMOS image sensor.

The disposable patch also comprises an adhesive layer, which attaches to the skin. Finally, the disposable patch has housing that mates with the reusable sensor to create robust optical alignment.

FIG. 44 shows individual pieces of the disposable patch for this embodiment in greater detail. It shows two different views from the top down for the disposable part of the sensor. It also shows waveguides/lightguides with protrusions that insert into the microneedle. FIG. 44 shows turning mirrors and trenches that laterally confined lightguides/waveguides plug into. In FIG. 45, 45-100 indicates the air cladding embodiment, 45-105 indicates the microneedle array, and 45-110 indicates the critical TIR angle at this interface. The angle needs to be larger than the critical angle at this interface in order to TIR down to the needle.

Example 8: Double Lens Based Emission Light Path for Efficient Biosensors

In this example, a novel emission path design that builds upon previous designs mentioned herein is described. This design increases the coupling efficiency from the emission source to the sensor, especially to smaller area image sensor pixels. It also creates a very robust isolation from the excitation path. This isolation is critical because the biosensors under discussion emit light intensity that could be many orders of magnitude lower than photon intensity that is used to excite the image sensor. Hence, they are susceptible to even the smallest amount of light leakage from excitation to emission path, corrupting the signal. The described design also allows for a more efficient excitation coupling efficiency. This is because it decouples the emission coupling optimization from the geometrical parameters that impact the excitation coupling. This allows the excitation coupling to be maximized to the fullest without worrying about adversely impacting the emission coupling. For example, the angle of the posts that bring the excitation light into the area in the microneedles where there are fluorophores can now be made perpendicular to the waveguide. This helps with excitation coupling. The stated double lens emission light path also does not depend on the slope of the sidewall of the posts. The novel design also allows a better light uniformity of the incoming excitation light that is illuminating the fluorophore area. The detailed design also has the potential advantage of reducing the extent of the Z thickness of the sensor, depending on the focal length of the lenses.

Figure 46:
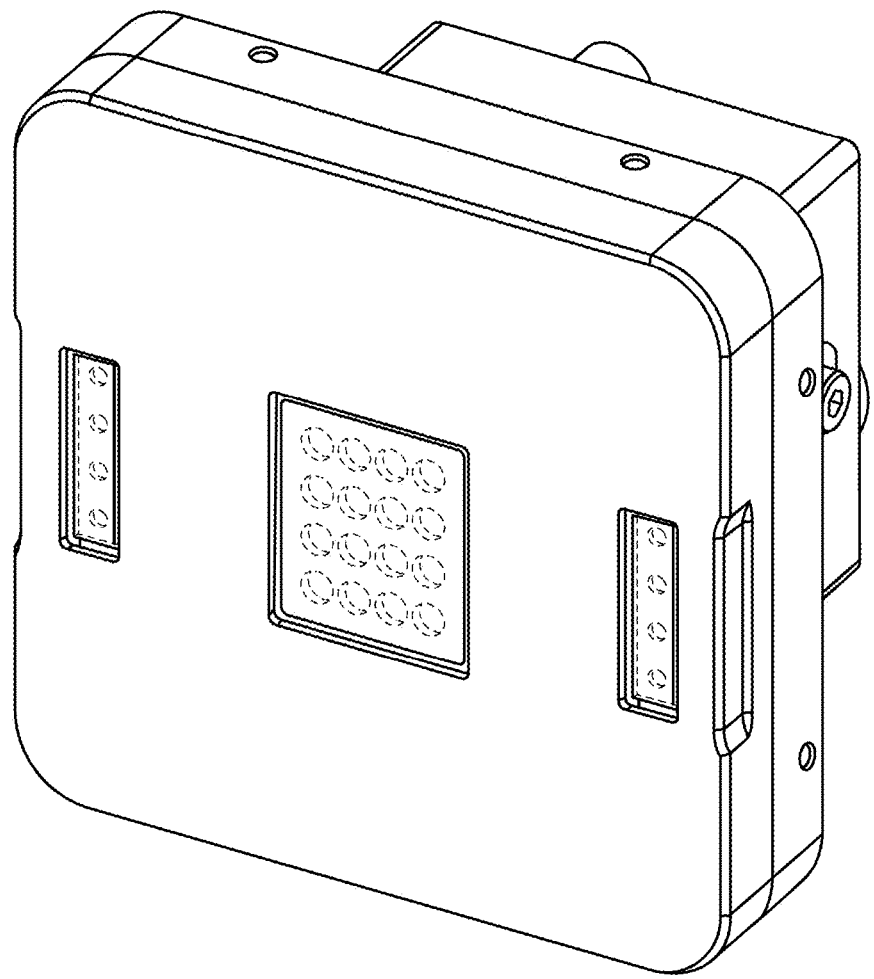
FIG. 46 is a diagram of the reusable fully assembled sensor.

FIG. 46 shows a view of the reusable, fully-assembled sensor.

Figure 47:
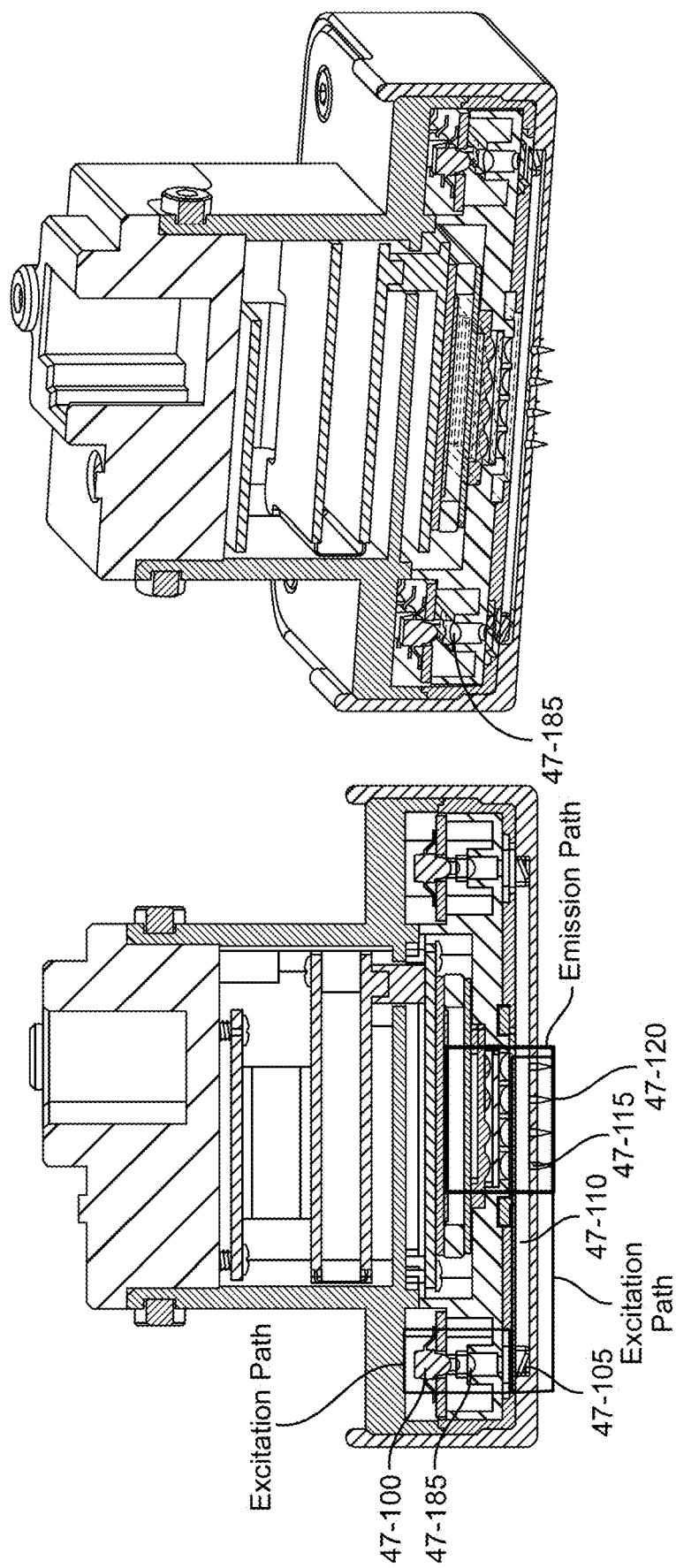
FIG. 47 is an opened-up view of the fully assembled sensor.

FIG. 47 shows an opened-up view of the fully assembled sensor. In this figure, 47-100 indicates the LEDs, which in some embodiments could also be lasers. 47-105 indicates the turning/coupling mirrors into the waveguide. 47-110 indicates the waveguide. 47-115 indicates the light posts that couple the waveguide with the needles. 47-120 indicates the microneedles holding the fluorophore probes.

FIG. 48 shows an exploded view of the various components inside the sensor.

Figure 49:
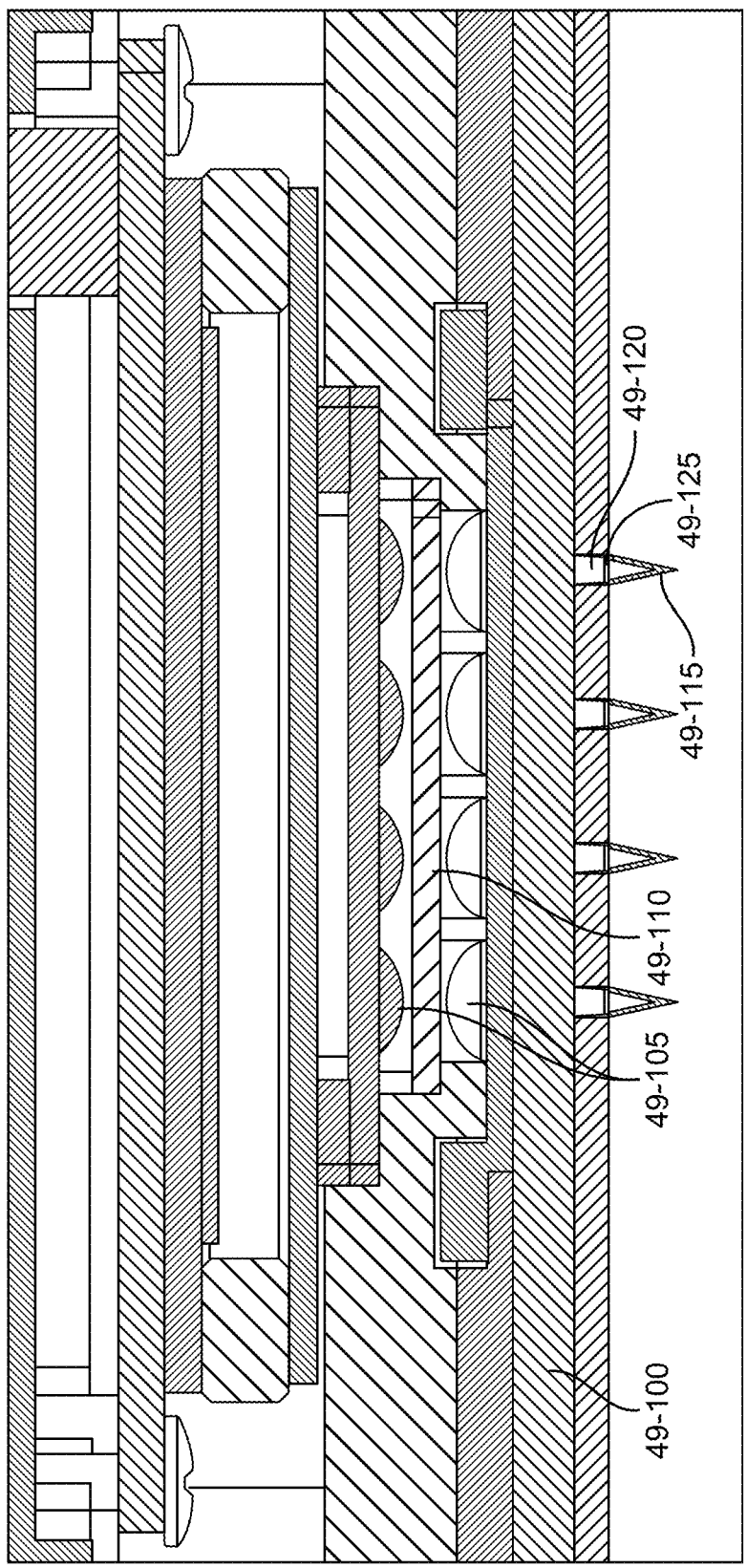
FIG. 49 shows an enlarged cross-sectional view of the emission path.

FIG. 49 shows the cross-sectional view of the emission light path. In this figure, 49-100 indicates the excitation light waveguide, 49-105 indicates the double lens in the emission path, 49-110 indicates the emission filter between the two lenses, 49-115 indicates the microneedles, 49-120 indicates the light-extracting posts, and 49-125 indicates the light-emitting fluorophores. A twin opposing lens system, henceforth also known as the double lens system, used to image fluorescent light in the image sensor/detector is provided. This is largely an imaging system, where light is captured by the first lens according to its numerical aperture. The light is collimated by this lens and is launched toward the second lens. The second lens focuses the light onto the image sensor pixel efficiently, since it is largely receiving collimated incident light. The key to increasing the coupling efficiency in this system is to increase the NA of the lens and to reduce the magnification. The coupling efficiency is given roughly as $$\left(\frac{NA}{M}\right)^2,$$

where NA is the numerical aperture and M is the magnification. Once achieved, this design is efficient at taking small fluorescent areas and transferring that emission into a small detection pixel, as in the case of an image sensor.

In addition, an emission filter, which is either a bandpass around the emission light wavelength or a high pass filter, is placed between the two lenses. The first lens largely collimates the light rays. By placing an emission filter above this, it is ensured that light is largely incident perpendicular to the emission filter. Most filters are very effective in narrow angles near perpendicular incidence and become less effective in filtering out lower wavelengths at wider angles. Hence, this arrangement ensures a good isolation of the excitation light at lower wavelengths by having the emission filter be very effective.

In some embodiments, the detector may be a pixelated detector. The design is highly robust in terms of isolating excitation light from the emission path. Using an image sensor ensures that the design has capability to sample and use only the brightest central pixels. With this design, the only light that gets into the brightest central pixels is the light that is being imaged. All other light, including stray light from excitation scattering, may make it to the adjacent pixels but not the brightest pixels under consideration. Finally, by having the filter between the two lenses, if there is indeed any excitation wavelength in the imaging area moving toward the central pixels, it is effectively filtered out by this arrangement.

FIGS. 50-53 show some other views of the emission path arrangement.

Figure 50:
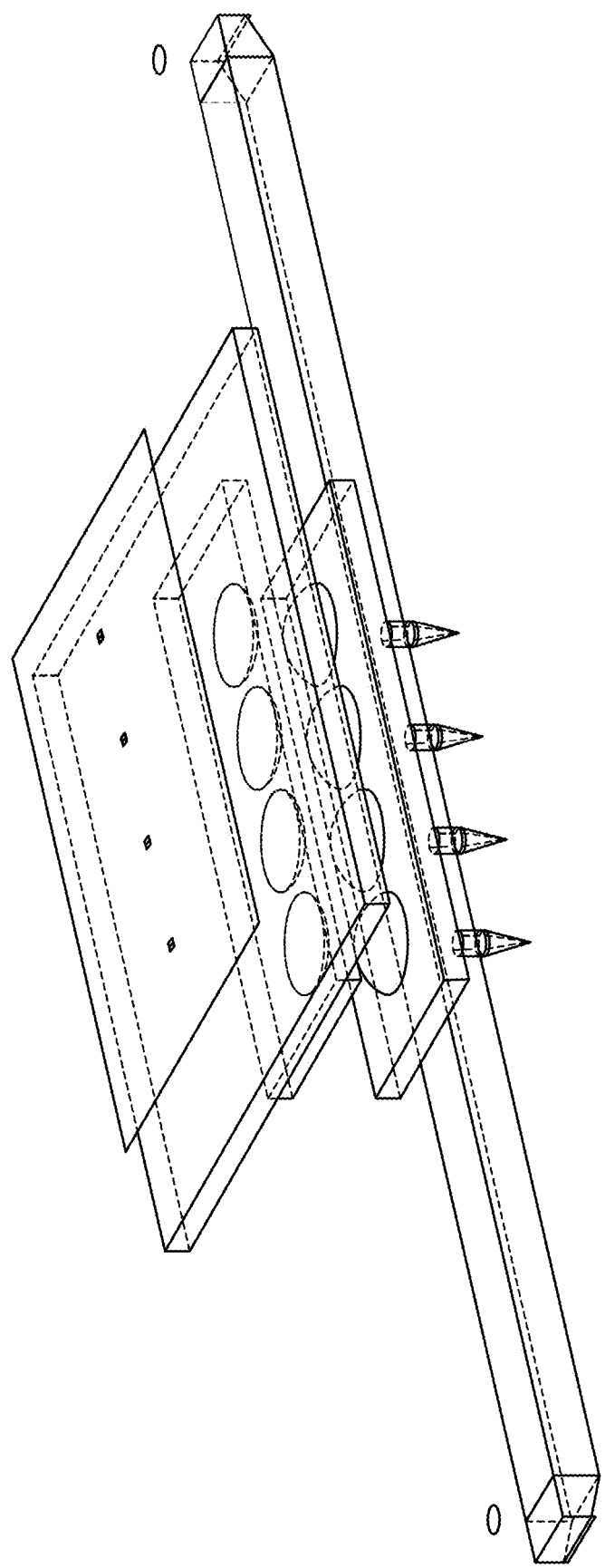
FIG. 50 shows an oblique view of the twin opposing lens design.

FIG. 50 shows an oblique view of the twin opposing lens design.

Figure 51:
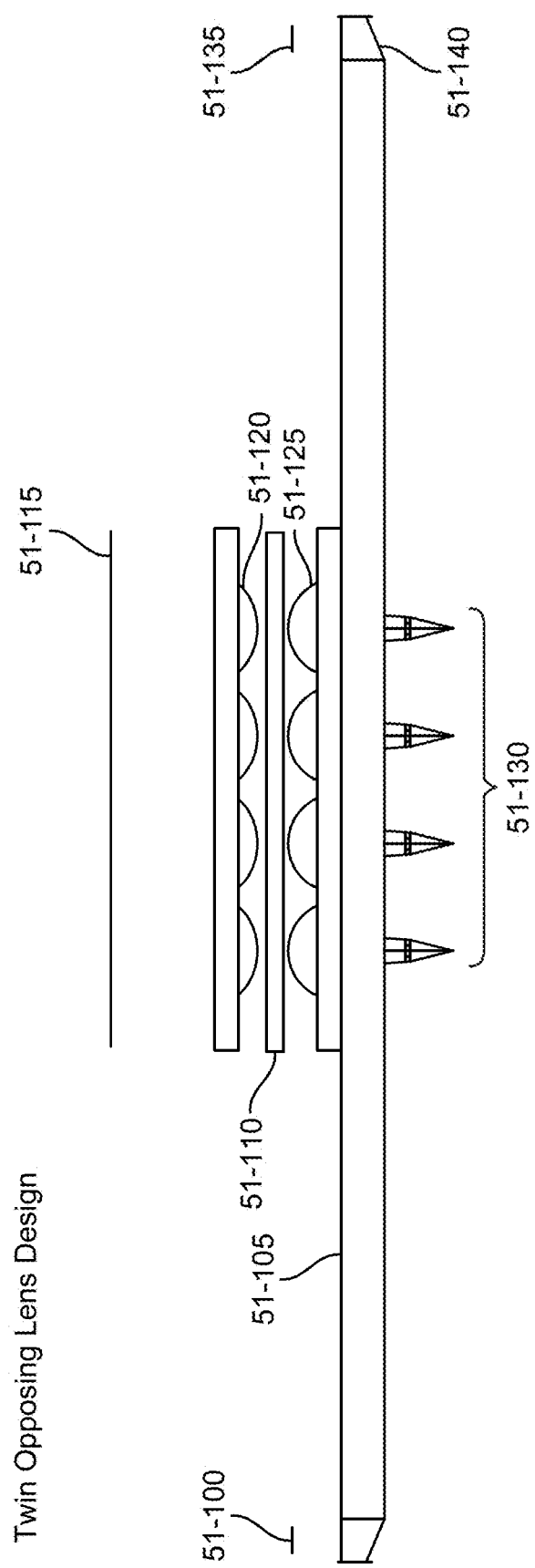
FIG. 51 shows another oblique view of the twin opposing lens design.

FIG. 51 shows the excitation coming from the waveguide into the microneedles. In this figure, 51-100 indicates the ray launch emitters, 51-105 indicates the lightguide, 51-110 indicates the emission filter, 51-115 indicates the sensor plane, 51-120 indicates the upper lens array, 51-125 indicates the lower lens array, 51-130 indicates the pin and needle arrays, 51-135 again indicates the ray launch emitters, and 51-140 indicates the launch mirror.

Figure 52:
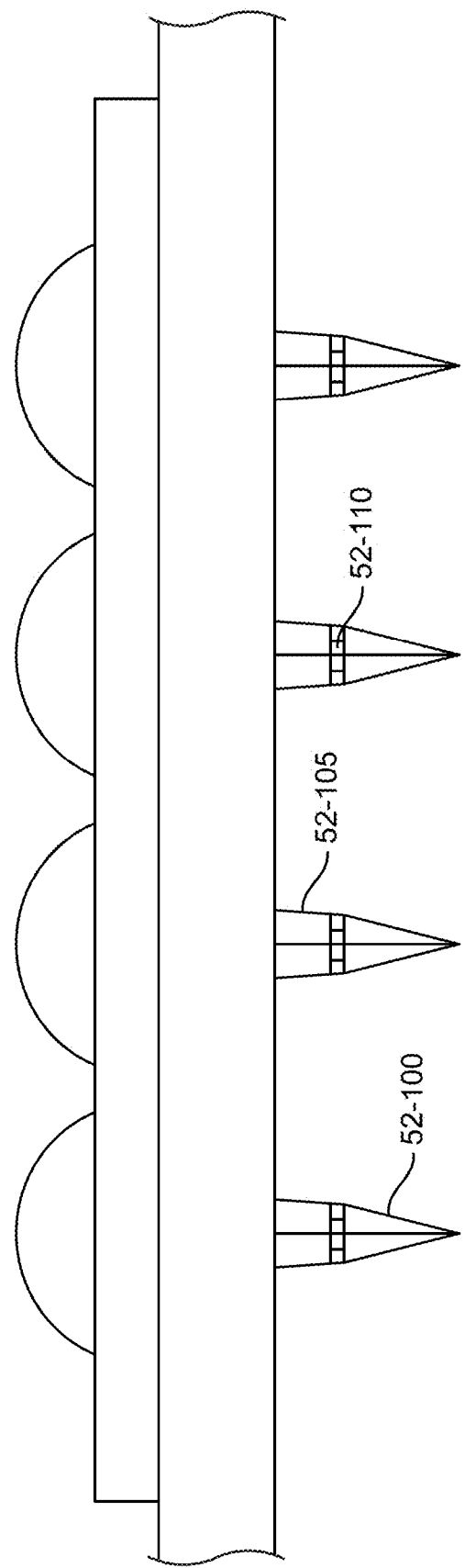
FIG. 52 shows the pin and needle arrays of the twin opposing lens design.

FIG. 52 shows the pin and needle arrays in the twin opposing lens design. In this figure, 52-100 indicates the needle array, 52-105 indicates the metalized lightguide post, and 52-110 indicates the emission reservoir.

Figure 53:
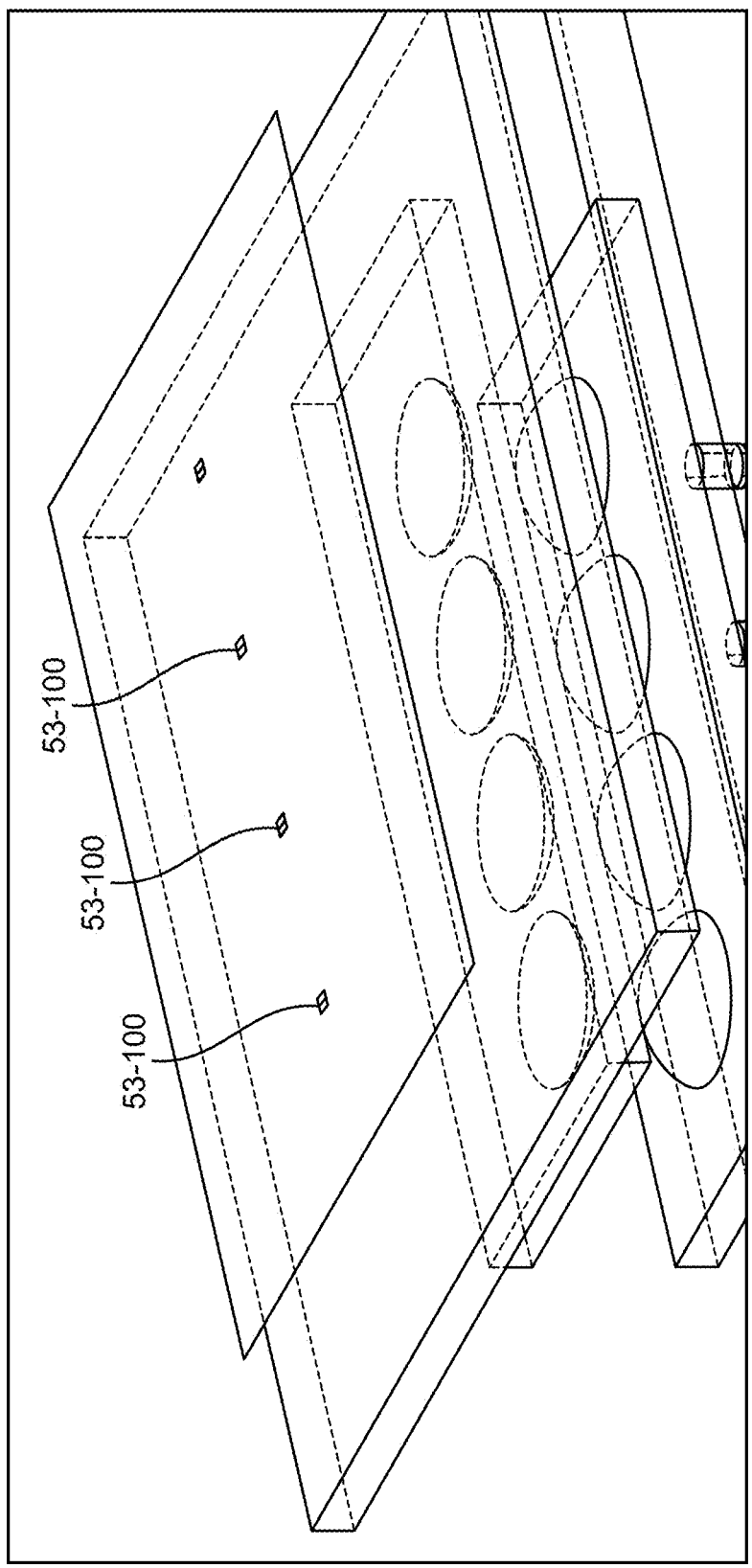
FIG. 53 shows the sensor foci array of the twin opposing lens design.
Figure 54:
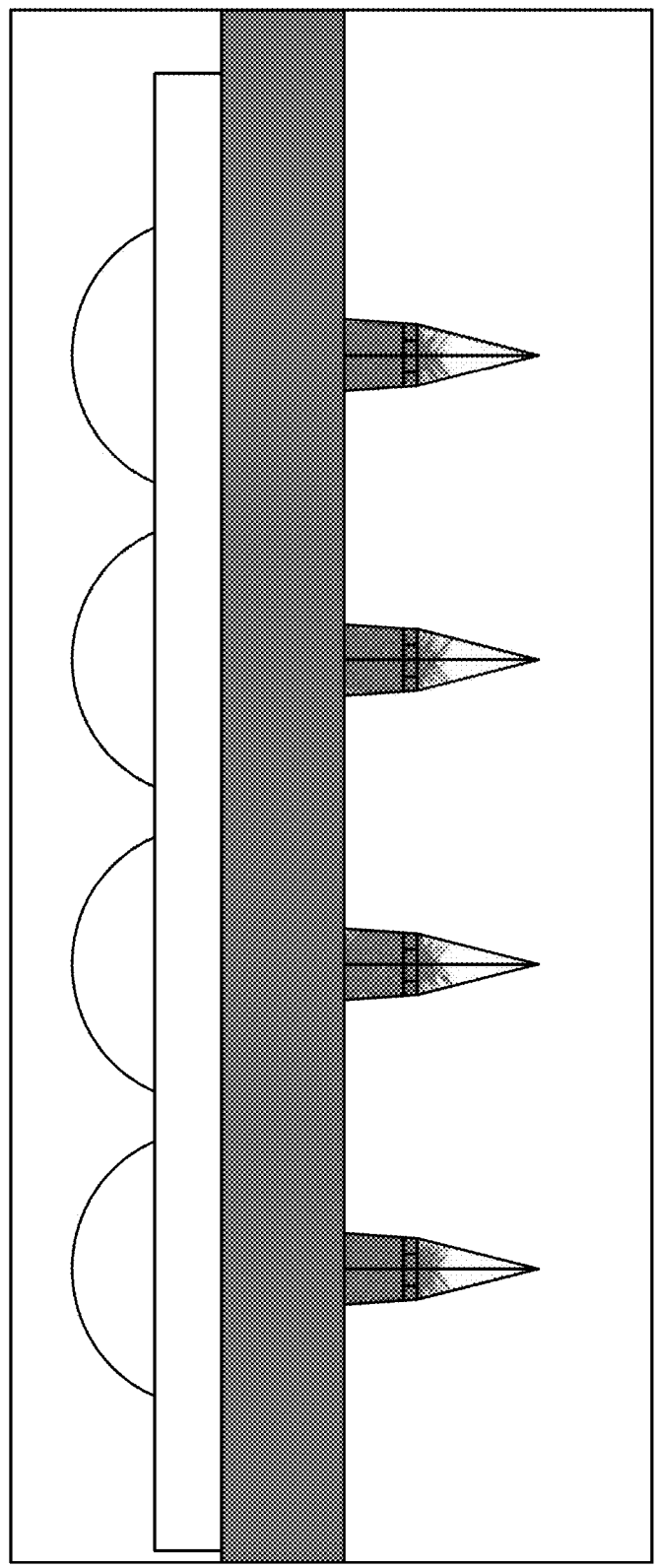
FIG. 54 shows a simulation of the excitation light launched into the waveguide and then coupled into the microneedles.
Figure 55:
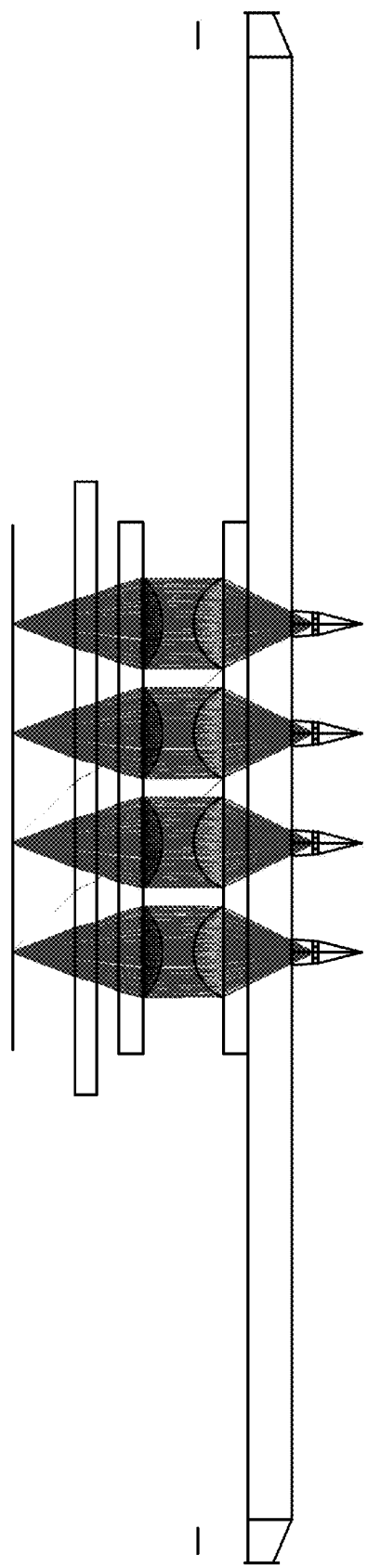
FIG. 55 shows a simulation of emission light launched through the double lens design.
Figure 56:
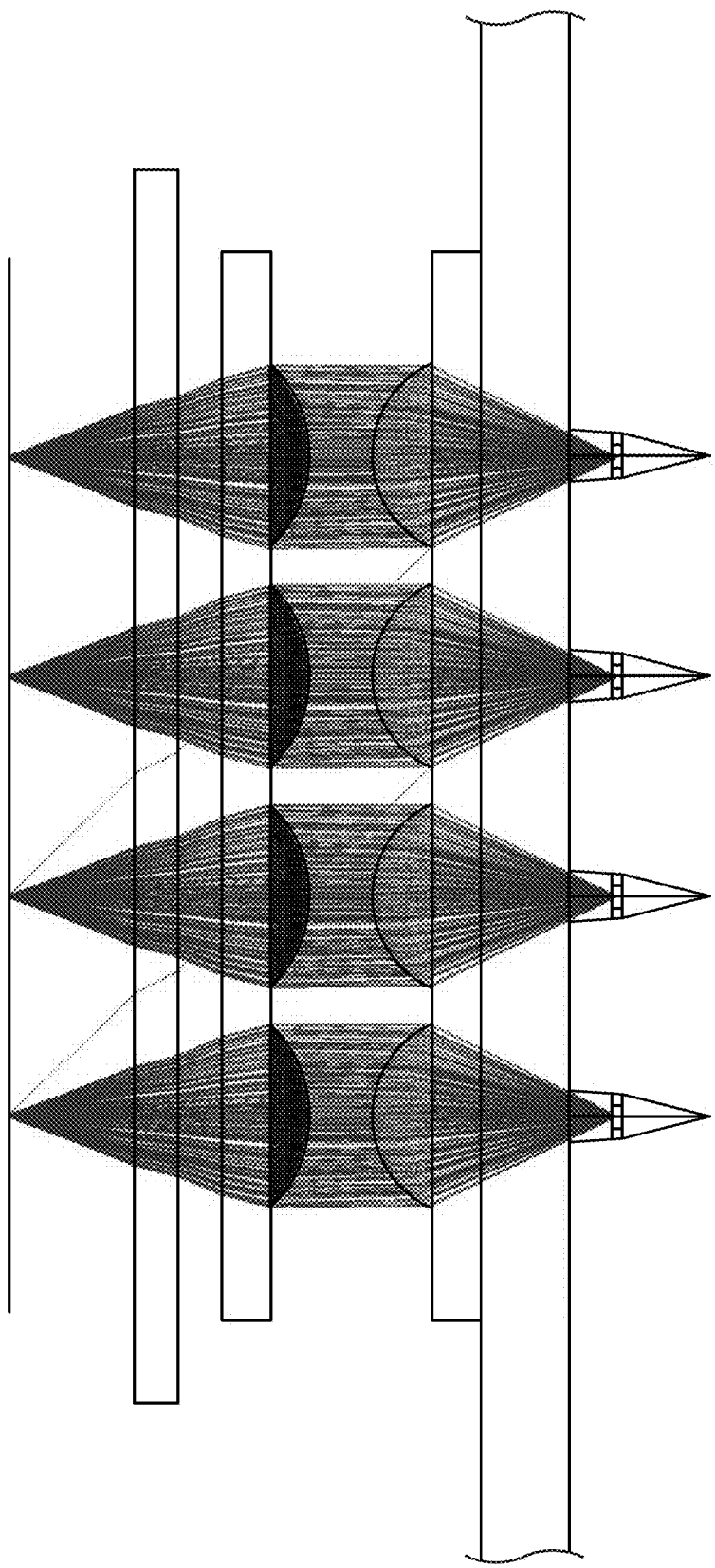
FIG. 56 shows another simulation of emission light launched through the double lens design.
Figure 57:
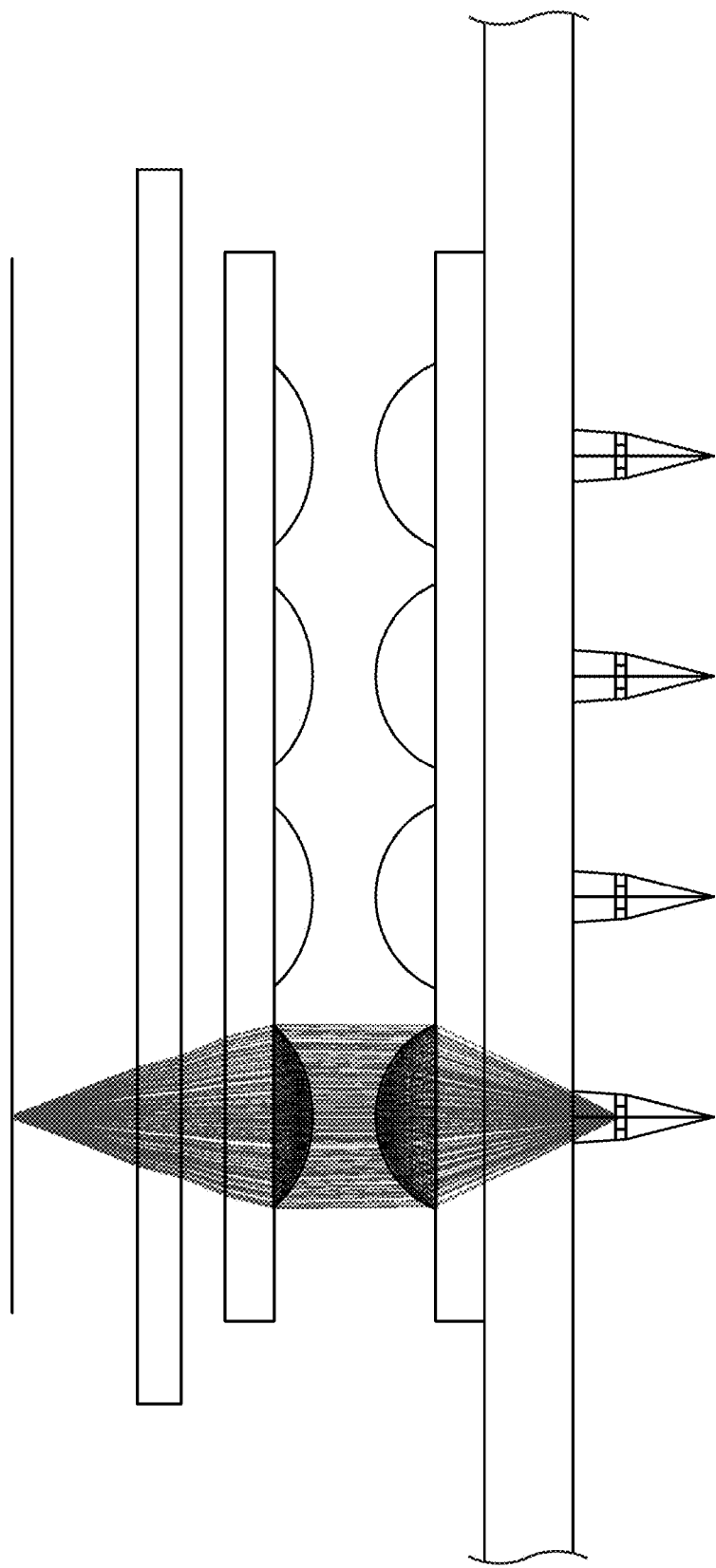
FIG. 57 shows another simulation of emission light launched through the double lens design.
Figure 58:
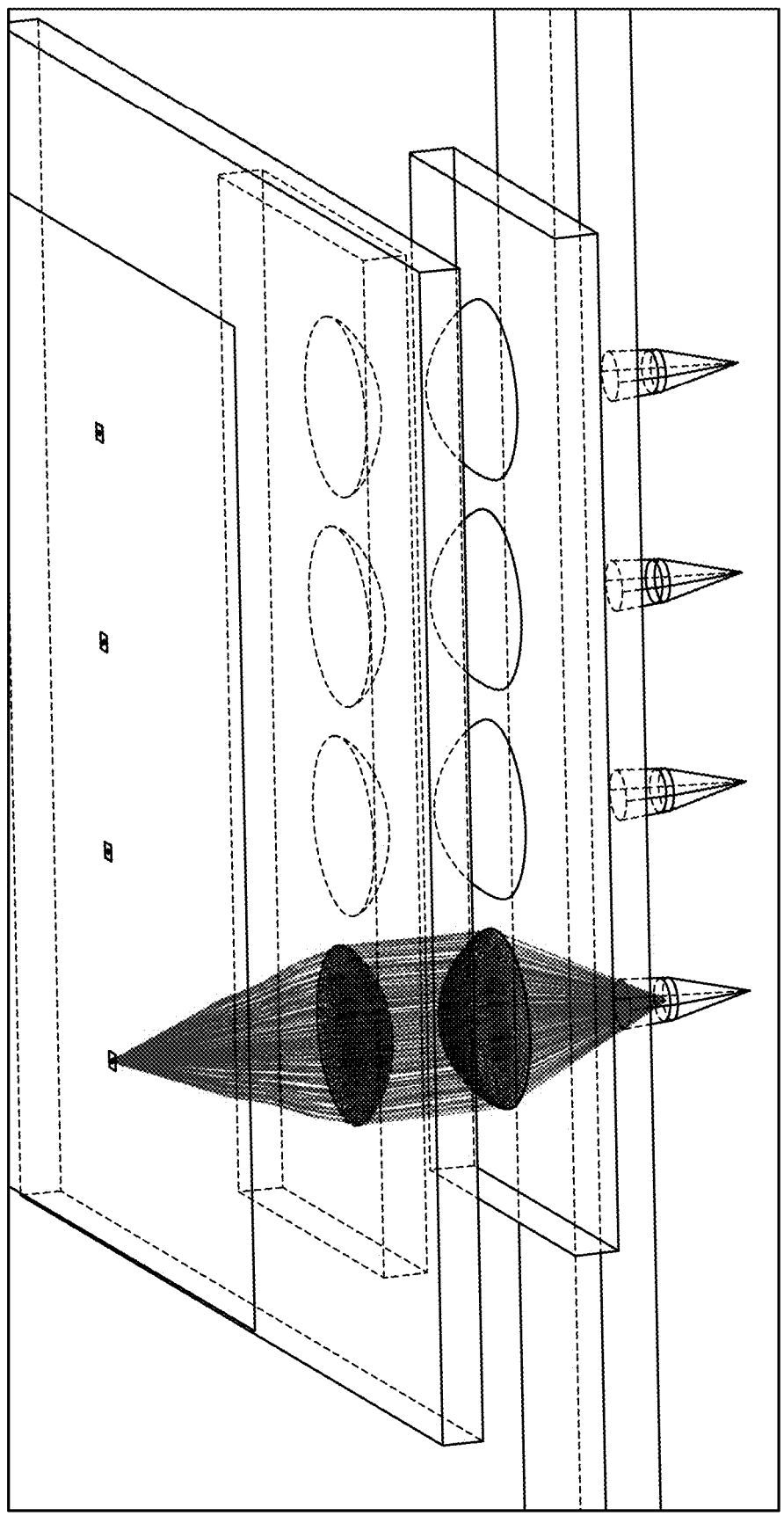
FIG. 58 shows a twin lens focusing light on a small pixel of the image sensor.

FIG. 53 also shows the twin opposing lens design. In this figure, 53-100 indicates the sensor foci array.

FIGS. 54-58 show the launch and imaging of the emission light from where fluorophores are onto a small pixel through the twin opposing lenses. All these figures are shown for 4 different needles; however, this should not be interpreted in a limiting sense and is extendable to any number of needles as required by the design, with each needle having two opposing lenses in the emission path.

In addition to the coupling efficiency and isolation advantages in this configuration, there are also advantages related to the excitation path. As can be seen in FIGS. 54-58, the emission light does not interact with the sidewalls of the posts in this design. In fact, the light captured by the first lens depends on the view angle of the light coming out of the posts that does not interact with the sidewalls of the posts. It can also be seen in FIG. 54 that the excitation light coupling depends on the sidewall of the posts that are extracting light from the waveguide. In fact, straighter (perpendicular) post sidewalls will lead not only to better excitation coupling into the needles area, but will also result in more uniform coupling. An angle at these sidewalls would lead to excitation light coming down at an angle and preferentially illuminating edges of the bottom of the posts preferentially compared to the center. Straightening the sidewall corrects for this problem. If the emission light pathway had relied on a design that depends on light reflecting off the sidewall, it would have an opposing pull on the slope compared to the excitation light. In other words, a more angled sidewall of the posts would have been better for emission. Thus, such a design would require a compromise between excitation and emission coupling efficiencies. However, the proposed design as described here does not require the sidewalls in the emission path, leading to a full optimization of the excitation path efficiency.

Definitions

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "about" or "approximately" generally means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term "about" can mean within an order of magnitude, such as within 5-fold, or within 2-fold, of a value. Where particular values are described in the application and claims, and unless otherwise stated, it should be assumed that the term "about" means within an acceptable error range for the particular value.

The use of the alternative (e.g., "or") should be understood to mean either one, both, or any combination thereof of the alternatives. The term "and/or" should be understood to mean either one, or both of the alternatives.

The term "subject," as used herein, generally refers to an animal, such as a mammal (e.g., human) or avian (e.g., bird), or other organism. The subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a predisposition to the disease, an individual that needs therapy or suspected of needing therapy, or any combination thereof. A subject can be a patient.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to: cortisol; potassium; sodium; bilirubin; bile acids; lactate; 3-hydroxybutyrate; creatinine; serum amyloid A; uric acid; urea; nucleic acids; RNA; DNA; cDNA; proteins; proteins; triglycerides; LDL; HDL; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free 3-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, leptospira, measles/mumps/rubella, *Mycobacterium leprae*, *Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms "foreign body response," "FBR," "foreign body reaction," "foreign body capsule," and "FBC" as used herein are broad terms and used in their ordinary sense, including, without limitation, body's response to the introduction of a foreign object. The foreign body reaction is a process which takes place when a material becomes implanted into the body. The foreign body reaction consists of both acute (predominantly inflammatory) and chronic (fibrotic) stages during which a capsule can form around the foreign object. There are three main layers of a foreign body capsule (FBC): the innermost layer, adjacent to the object, is com-posed generally of macrophages, foreign body giant cells, and occlusive cell layers; the intermediate FBC layer, lying distal to the first layer with respect to the object, is a wide zone (for example, about 30-100 microns) composed primarily of fibroblasts, contractile fibrous tissue fibrous matrix; and the outermost FBC layer is loose connective granular tissue containing new blood vessels. Over time, this FBC tissue becomes muscular in nature and contracts around the foreign object so that the object remains tightly encapsulated.

NUMBERED EMBODIMENTS

1. A device for sensing an analyte in a biological sample of a subject, comprising:
   a support;
   a piercing element coupled to the support, wherein the piercing element is configured to pierce a body surface of the subject when the device is coupled to the body surface, to thereby bring the piercing element in contact with the biological sample;
   an analyte binding probe on or within the piercing element, wherein the analyte binding probe is configured to provide a change in an optical signal when the analyte binding probe comes in contact with the analyte in the biological sample of the subject;
   a detector operatively coupled to the support, wherein the detector is configured to detect the optical signal; and
   at least one of:
   an optical excitation path comprising a waveguide and a light coupler and: i) comprising one or more focusing elements configured to focus light from a light source towards the light coupler, ii) a reflective cladding layer surrounding the waveguide configured to reflect the light back inside the waveguide and guide the light toward the piercing element; or iii) the light coupler being configured to couple light from a light source into the waveguide; or
   an optical emission path comprising: i) apertures in a reflective cladding layer surrounding a waveguide configured to transmit an emission light from the analyte probe towards the detector, or ii) one or more focusing elements configured to focus emission light from the analyte binding probe towards the detector; or
   comprising a waveguide, an optical excitation path comprising the waveguide, and an optical emission path comprising the waveguide, wherein the waveguide transmits light from a light source to the analyte binding probe, and wherein the waveguide is configured to permit light to be transmitted through the waveguide from the analyte binding probe to the detector; or
   wherein the analyte binding probe is comprised in a sensing domain comprising a hydrogel matrix comprising one or more particles comprising the analyte binding probe, or
   wherein the analyte binding probe has a dissociation constant of at least 1 pM with respect to the analyte.

2. The device of embodiment 1, further comprising a light source, wherein the light source emits light at wavelengths of 600 nm to 750 nm.

3. The device of embodiment 1, further comprising a light source, wherein the light source emits light at wavelengths of 350 nm to 1500 nm.

4. The device of embodiment 2, wherein the light source emits light within a 50 nm band within the wavelengths of 600 nm to 750 nm.

5. The device of embodiment 3, wherein the light source emits light within a 50 nm band within the wavelengths of 350 nm to 1500 nm.

6. The device of embodiment 1, wherein the optical waveguide is configured to transmit light at wavelengths of 350 nm to 1500 nm.

7. The device of embodiment 1, wherein the optical emission path is configured to reject light from the optical excitation path.

8. The device of embodiment 7, wherein the optical emission path is configured to reject at least 75% of light from the optical excitation path.

9. The device of embodiment 2, wherein the optical emission path is configured to reject light that is a which is a same wavelength as light emitted by the light source.

10. The device of embodiment 6, wherein the optical emission path is configured to reject light which is a same wavelength through the optical waveguide from the light source 11. The device of embodiment 1, wherein the optical excitation path and the optical emission path are configured to minimize interference with each other.

12. The device of embodiment 11, wherein the optical excitation path and the optical emission path are partially co-located within the optical waveguide.

13. The device of embodiment 1, wherein the excitation path is configured to transmit light in a vertical direction and a horizontal direction.

14. The device of embodiment 1, wherein the emission path is configured to transmit light in a vertical direction.

15. The device of embodiment 1, wherein the emission path is configured to transmit light only in a vertical direction.

16. The device of embodiment 1, wherein the reflective cladding layer comprises an air gap.

17. The device of embodiment 16, wherein at least a portion of the air gap is positioned between a base of the piercing element and the optical waveguide.

18. The device of embodiment 16, wherein the air gap is configured to reflect light towards the piercing element.

19. The device of embodiment 18, wherein the air gap has a lower refractive index than the waveguide.

20. The device of embodiment 16, wherein the waveguide comprises a refractive index of greater than 1.

21. The device of embodiment 1, wherein the waveguide comprises a geometrical core that is made of a dielectric material, wherein the reflective cladding surrounding the dielectric core is a reflective metal or a dielectric material of lower refractive index that the dielectric core optionally, wherein the reflective metal comprises Al or Ag.

22. The device of embodiment 1, wherein the waveguide comprises a geometrical cross section that is a rectangle.

23. The device of embodiment 22, wherein the two dimensions of the rectangle range from 100 microns to 5 mm.

24. The device of embodiment 1, wherein the optical waveguide is configured to only transmit the excitation light to the piercing element, and wherein the optical waveguide is a dielectric waveguide comprising the reflective cladding, wherein light is configured to enter the optical waveguide within a narrow range of angles around the surface normal of the top, light-source facing side of the waveguide.

25. The device of embodiment 24, wherein the range of the angles is 40-50 degrees as measured from the surface normal of the bottom coupling surface of the waveguide.

26. The device of embodiment 1, further comprising a light coupler.

27. The device of embodiment 26, wherein the light coupler is configured to transmit light from the light source to a waveguide.

28. The device of embodiment 1, wherein the waveguide comprises a dielectric core, wherein the reflective cladding surrounds the dielectric core.

29. The device of embodiment 28, wherein the reflective cladding comprises a metal, Al, or Ag.

30. The device of embodiment 26, wherein the reflective cladding comprises an aperture between the light source and the light coupler and the aperture is defined by the absence of the reflective cladding.

31. The device of embodiment 28, wherein the dielectric core surrounded by the reflective cladding is configured to confine light within the waveguide.

32. The device of embodiment 1, wherein the waveguide comprises a protruding portion which extends into a base of the piercing element.

33. The device of embodiment 1, wherein the waveguide comprises a connecting portion which extends into a base of the piercing element.

34. The device of embodiment 1, wherein the excitation path comprises connecting materials between the waveguide and the location of the analyte probe that optically extracts light from the waveguide towards the piercing element and the analyte probe.

35. The device of embodiment 34, wherein the connecting material is an extension of the dielectric core material of the waveguide.

36. The device of embodiment 34, wherein the connecting material is different than the core of the waveguide and comprises a substantially similar refractive index as the core of the wave guide, and, optionally, comprises multiple layers.

37. The device of embodiment 32, wherein the piercing element comprises a reflective material about a base of the piercing element.

38. The device of embodiment 37, wherein the optical excitation path guides light from a light source through the protruding portion of waveguide and to the reflective material about the base of the piercing element, wherein the reflective material about the base of the piercing element reflects the light to the analyte binding probe on or within the piercing element.

39. The device of embodiment 1, wherein the optical excitation path is configured to reject light which does not enter the waveguide at a critical angle.

40. The device of embodiment 39, wherein the critical angle is between ±20 degrees as measured from a vector normal to a base of the piercing element.

41. The device of embodiment 39, wherein the critical angle is an angle which is approximately 0 degrees from the vector normal to the base of the piercing element.

42. The device of embodiment 39, further comprising an opaque layer comprising apertures, wherein light must enter the optical excitation path at the critical angle to pass through the apertures.

43. The device of embodiment 1, wherein the optical emission path comprises a first focusing element configured to focus at least part of the emission light from the analyte binding probe into a first beam.

44. The device of embodiment 43, wherein the first beam comprises light rays that are substantially parallel to each other and substantially perpendicular to the surface of the detector.

45. The device of embodiment 43, wherein the first beam is configured to be incident on one or more pixels of the detector.

46. The device of embodiment 43, further comprising a second focusing element configured to focus the first beam towards the detector.

47. The device of embodiment 46, wherein a diameter of the second beam coming from the second focusing element is configured to be a smaller size diameter than the first beam when the second beam crosses the plane of the detector and is incident on one or more pixels of the detector, thereby improving the signal to noise ratio of the detector.

48. The device of embodiment 43, wherein an optical path of the first beam is isolated from an optical path of the excitation light.

49. The device of embodiment 43, further comprising an optical filter between the first beam and the detector which does not transmit a portion of light that falls on the filter.

50. The device of embodiment 49, wherein the portion of the light blocked from transmission by filter has a wavelength which is a same wavelength as the light source.

51. The device of embodiment 49, wherein the optical filter is a dichroic filter, an absorptive filter, or a combination thereof.

52. The device of embodiment 49, wherein the first focusing element transmits light to the filter at an angle within approximately +/−25 degrees with respect to a surface normal vector of the filter.

53. The device of embodiment 49, wherein the first focusing element transmits light to the filter at an angle of approximately 0 degrees with respect to the surface normal vector of the filter.

54. The device of embodiment 52, wherein the portion of light not transmitted through the filter comprises wavelengths of light less than 700 nm in wavelength.

55. The device of embodiment 49, wherein the optical filter substantially transmits emission light wavelengths coming from the analyte probe, while substantially blocking light which is a similar wavelength as excitation light.

56. The device of embodiment 49, wherein the optical filter is configured to block at least 99, 99.9, 99.99, 99.999, 99.9999, 99.99999, 99.99999% of light having a same wavelength as light from the light source transmitted through the excitation path.

57. The device of embodiment 49, wherein having a same wavelength as light from the light source transmitted through the emission path.

58. The device of embodiment 49, further comprising a second optical filter, wherein the second optical filter is a dichroic filter, an absorptive filter, or a combination thereof.

59. The device of embodiment 58, wherein the first optical filter and the second optical filter in combination transmit emission light while substantially blocking light which is a similar wavelength as excitation light.

60. The device of embodiment 1, further comprising a light source.

61. The device of embodiment 60, wherein the light source is a downward firing light source positioned above the pierceable member.

62. The device of embodiment 61, further comprising an opaque layer comprising apertures, wherein light must enter the optical excitation path at the critical angle to pass through the apertures.

63. The device of embodiment 62, wherein the light source is positioned on a first side of the opaque layer, and wherein the detector is positioned on a opposite side of the opaque layer.

64. The device of embodiment 1, further comprising an opaque material with an aperture in the emission path that is configured to block transmission of excitation light that does not strike the optical filter within approximately +/−25 degrees with respect to a vector normal to the surface of the optical filter.

65. The device of embodiment 26, wherein the optical excitation path further comprises an optical filter between the light source and the light coupler.

66. The device of embodiment 65, wherein the optical filter is a dichroic filter, an absorptive filter, or a combination thereof.

67. The device of embodiment 1, wherein the analyte binding probe is an aptamer switch, or an antibody switch.

68. The device of embodiment 26, wherein the light coupler comprises a faceted mirror.

69. The device of embodiment 68, wherein the faceted mirror is configured to direct light towards the waveguide.

70. The device of embodiment 68, wherein the faceted mirror is configured to direct light from a section of free space optics towards the waveguide.

71. The device of embodiment 70, wherein the faceted mirror is partially metalized.

72. The device of embodiment 70, wherein the faceted mirror is fully metalized.

73. The device of embodiment 70, wherein the faceted mirror is non-metalized.

74. The device of embodiment 1, further comprising an optoelectronics system, the optoelectronics system comprising the detector, wherein the optoelectronics system is operatively coupled to the support, and wherein the optoelectronic system is configured to detect the change in the optical signal using the detector.

75. The device of embodiment 1, further comprising an excitation light source.

76. The device of embodiment 75, wherein the excitation light source comprises a laser, or an LED.

77. The device of embodiment 1, further comprising an electrical system coupled to the detector that processes the change and generates an electrical signal related to the concentration of the analyte.

78. The device of embodiment 1, wherein the optical excitation path comprises a section of free space optics between a light source and a waveguide.

79. The device of embodiment 1, wherein the optical emission path comprises a section of free space optics between where the emission light starts from the analyte probe area and a detector.

80. The device of embodiment 1, wherein the device further comprises a battery.

81. The device of embodiment 80, wherein the light source is configured to increase a single battery cycle life of the device.

82. The device of embodiment 80, wherein the detector is configured to increase a single battery cycle life of the device.

83. The device of embodiment 1, wherein the optical excitation path is configured to increase light coupling efficiency from the excitation light source to the analyte probe, and is configured to increase a single battery cycle life of the device.

84. The device of embodiment 1, wherein the optical emission path is configured to increase light coupling efficiency from the analyte probe to a detector, and is configured to increase a single battery cycle life of the device.

85. The device of embodiment 1, wherein the piercing element comprises a structural domain, a barrier domain, and a sensing domain.

86. The device of embodiment 1, wherein the hydrogel matrix is based on PEG or PVA.

87. The device of embodiment 1, wherein the PEG-based hydrogel is comprised of PEGDMA monomer subunits with a weight of about 750 daltons to 20 kilodaltons at weight percentages of about 5% to about 30%.

88. The device of embodiment 87, wherein the PEGDMA monomer subunits are photo-crosslinked or chemically crosslinked.
89. The device of embodiment 1, wherein the analyte binding probe is comprised in a sensing domain comprising a hydrogel matrix comprising one or more particles comprising the analyte binding probe.
90. The device of embodiment 89, wherein the particles comprise a polymer, optionally, wherein the polymer is polystyrene.
91. The device of embodiment 89, wherein the particles are magnetic.
92. The device of embodiment 89, wherein the particles comprise a diameter of about 100 nm to about 1000 microns.
93. The device of embodiment 89, wherein the particles comprise a diameter of at least 100 nm.
94. The device of embodiment 89, wherein the particles comprise a diameter of up to about 100 microns.
95. The device of embodiment 89, wherein the particles comprise a diameter of about 1 micron to about 50 microns.
96. The device of embodiment 89, wherein the number of particles in a single sensor is about 1 particle to about $10^9$ particles.
97. The device of embodiment 89, wherein the number of particles in a single sensor is at least $10^3$ particles.
98. The device of embodiment 89, wherein the number of particles in a single sensor is at least 10=particles.
99. The device of embodiment 89, wherein the number of particles in a single sensor is about $10^5$ particles to about $10^8$ particles.
100. The device of any one of embodiments 96-99, wherein the single sensor is an individual member of the piercing element.
101. The device of any one of embodiments 96-99, wherein the single sensor is located in a well separate from the piercing element, and is fluidically connected to the piercing element.
102. The device of embodiment 89, wherein a concentration of particles in the sensing domain ranges from $10^3$ particles to $10^9$ particles/mL.
103. The device of embodiment 89, wherein a concentration of particles in the sensing domain ranges from $10^5$ particles to $10^8$ particles/mL.
104. The device of embodiment 89, wherein the concentration of analyte binding probes on a surface of the one or more particles is about $10^6$ to about $5*10^{13}$ analyte binding probes per $cm^2$.
105. The device of embodiment 89, wherein the concentration of analyte binding probes on a surface of the one or more particles is about $10^{10}$ to about $10^{13}$ analyte binding probes per $cm^2$.
106. The device of embodiment 89, wherein the analyte binding probe is an aptamer, wherein the concentration of analyte binding probes on a surface of the one or more particles is about $10^6$ to about $5*10^{13}$ DNA strands per $cm^2$.
107. The device of embodiment 89, wherein the analyte binding probe is an aptamer, wherein the concentration of analyte binding probes on a surface of the one or more particles is about $10^{10}$ DNA strands/$cm^2$ to about $10^{13}$ DNA strands/$cm^2$.
108. The device of embodiment 89, wherein the analyte binding probe is an aptamer, wherein an average spacing of the analyte binding probes ranges from about 1.4 nm to about 10 micrometers between DNA strands.
109. The device of embodiment 89, wherein the analyte binding probe is an aptamer, wherein an average spacing of the analyte binding probes ranges from about 3 nm to about 100 nm between DNA strands.
110. The device of embodiment 1, further comprising a light source.
111. The device of embodiment 1, wherein the device is configured to be placed in optical communication with an external light source.
112. The device of embodiment 1, further comprising two or more analyte binding probes on or within the piercing element, each of the two or more analyte binding probes configured to provide a change in an optical signal when the two or more analyte binding probes contact a second analyte in the biological sample of the subject.
113. The device of embodiment 1, further comprising two or more analyte binding probes on or within the piercing element, each of the two or more analyte binding probes configured to provide a change in an optical signal when the two or more analyte binding probes contact a second analyte in the biological sample of the subject.
114. The device of embodiment 1, wherein the analyte binding probe comprises a fluorophore conjugated to an aptamer configured to bind to the analyte, wherein the analyte binding probe is configured to contact the biological sample of the subject and provide the change in an optical signal when the piercing element is inserted into a skin of a subject.
115. The device of embodiment 1, further comprising a multiplexed array of analyte binding probes on or within the piercing element, each of the multiplexed array of analyte binding probes configured to provide a change in an optical signal when the multiplexed array of analyte binding probe contacts a subsequent analyte in the biological sample of the subject.
116. The device of embodiment 115, wherein the subsequent analyte is a different analyte, the multiplexed array of analyte binding probes is configured to detect a plurality of analytes in the biological sample of the subject.
117. The device of embodiment 1, wherein the piercing element comprises a plurality of piercing elements.
118. The device of embodiment 1, wherein the plurality of piercing elements defines subsets of piercing elements, wherein each subset of piercing elements comprises a different analyte binding probe configured to detect a different analyte in the biological sample of the subject.
119. The device of embodiment 1, wherein the subsets of piercing elements comprising the different analyte binding probes comprises the multiplexed array of analyte binding probes.
120. The device of embodiment 1, wherein the waveguide comprises a polymer glassy matrix comprising dispersed photoluminescent particles.
121. The device of embodiment 120, wherein the polymer comprises silicones, polysiloxanes, silsequioxanes, or combinations thereof.
122. The device of embodiment 1, wherein the polymer comprises: polymethylmethacrylate (PMMA), polystyrene (PS), polycarbonate (PC), polyurethane (PU), epoxy resin, deuterated and halogenated polyacrylates, fluorinated polyimides, perfluorocyclobutyl (PFCB) aryl ether polymers, nonlinear optical polymers, benzocylcobutene (BCB), perfluorovinyl ether cyclopolymer (CYTOP), tetrafluoroethylene and perfluorovinyl ether copolymer (Teflon AF), silicone, fluorinated poly(arylene ether sulfide), poly(pentafluorostyrene), fluorinated dendrimers, fluorinated hyperbranched polymers, or combinations thereof.

123. The device of embodiment 1, wherein the piercing element is coupled to the support using a lock and key attachment.
124. The device of embodiment 1, wherein the piercing element is coupled to the support using a mortise and tenon attachment.
125. The device of embodiment 1, wherein the piercing element is coupled to the support using a dovetail attachment.
126. The device of embodiment 1, wherein the piercing element is coupled to the support using a magnetic attachment.
127. The device of embodiment 1, wherein the piercing element is coupled to the support using an adhesive.
128. The device of embodiment 1, wherein the piercing element is coupled to the support using one or more elastically deformable attachment elements.
129. The device of embodiment 1, wherein the piercing element is coupled to the support using one or more elastically deformable attachment elements configured to rebound once inserted into the support.
130. The device of embodiment 1, wherein the piercing element is removably coupled to the support.
131. The device of embodiment 1, wherein the piercing element comprises a microneedle array which is removably coupled to the support.
132. The device of embodiment 1, wherein the optical light guide is removably coupled to the support.
133. The device of embodiment 1, wherein the analyte binding probe coupled to the optical reporter is an oligonucleotide probe.
134. The device of embodiment 133, wherein the oligonucleotide probe is an aptamer.
135. The device of embodiment 134, wherein the aptamer is coupled to a displacement strand, wherein the displacement strand is partially complementary to the aptamer.
136. The device of embodiment 135, wherein the displacement strand is coupled to a second optical reporter.
137. The device of embodiment 136, wherein the second optical reporter is a fluorophore or a quencher.
138. The device of embodiment 134, wherein the aptamer is coupled to a linker moiety placed between the aptamer and the displacement strand.
139. The device of embodiment 138, wherein the linker moiety is a nucleotide acid moiety, a peptide nucleic acid (PNA) moiety, a peptide moiety, a disulfide bond, a phosphodiester linkage, or a polymer.
140. The device of embodiment 1, wherein one or more sidewalls of the piercing element are reflective.
141. The device of embodiment 131, wherein one or more sidewalls of each microneedle of the microneedle array are reflective.
142. The device of embodiment 1, wherein the piercing element comprises a structural domain, a barrier domain, and a sensing domain.
143. The device of embodiment 142, wherein the structural domain is positioned on a surface of the support and extends outward from the surface to define a needle, and defines an interior space, wherein the sensing domain is contained within the interior space.
144. The device of embodiment 142, wherein the structural domain encapsulates the barrier domain.
145. The device of embodiment 142, wherein the structural domain encloses the sensing domain.
146. The device of embodiment 142, wherein the sensing domain encapsulates the analyte binding probe within a matrix of the sensing domain, wherein the barrier domain comprises a hydrogel, a polymer, or combinations thereof.
147. The device of embodiment 142, wherein the sensing domain comprises the analyte binding probe.
148. The device of embodiment 142, wherein the sensing domain comprises the analyte binding probe in a hydrogel matrix.
149. The device of embodiment 148, wherein the analyte binding probe is bound to one or more beads in the hydrogel matrix.
150. The device of embodiment 142, wherein the barrier domain comprises a hydrogel, a polymer, or combinations thereof.
151. The device of embodiment 142, wherein the structural domain encapsulates the sensing domain, wherein the sensing domain is configured to control transfer of the analyte to the analyte binding probe.
152. The device of embodiment 142, wherein the barrier domain is configured to control transfer of the analyte to sensing domain via diffusion.
153. The device of embodiment 142, wherein the sensing domain and/or the barrier domain comprise a plurality of pores.
154. The device of embodiment 142, wherein the analyte binding probe is contained within the sensing domain at a concentration of about 10 pM to about 1 mM.
155. The device of embodiment 142, wherein the analyte binding probe is contained within the sensing domain at a concentration of about 1 nM to about 1 uM.
156. The device of embodiment 1, wherein the detector comprises a semiconductor material.
157. The device of embodiment 1, wherein the detector comprises a semiconductor photodetector.
158. The device of embodiment 1, wherein the detector comprises a semiconductor photodetector comprising a silicon photomultiplier chip, an avalanche photodiode, a metal-semiconductor-metal photodiode, a CMOS sensor array, a CCD (charge coupled device), a lateral semiconductor photodiode, an array of photodetectors, an ambient light sensor, an array of ambient light sensors, or combinations thereof, or combinations thereof.
159. The device of embodiment 157, wherein the semiconductor material or the semiconductor photodetector comprises a p-n junction.
160. The device of embodiment 157, wherein the semiconductor material or the semiconductor photodetector comprises Si, Ge, InGaAs, GaAs, InP, Ge, SiGe, InGaN, GaN, or combinations thereof.
161. The device of embodiment 1, wherein the detector comprises a silicon photomultiplier (SiPM) detector.
162. The device of embodiment 1, wherein the piercing element is configured to transmit light within the piercing element towards the analyte binding probe.
163. The device of embodiment 1, wherein the piercing element is configured to guide light emitting from the analyte binding probe out of the piercing element.
164. The device of embodiments 162-163, wherein the piercing element is configured to transmit light using a reflective metal coating on a surface within the piercing element, optionally, wherein the reflective metal coating comprises Ag or Au.
165. The device of embodiments 162-163, wherein the piercing element is made of a reflective metal configured to reflect light, optionally, wherein the reflective metal comprises stainless steel, Ti, Au Ag, or combinations thereof.
166. The device of embodiment 1, wherein the piercing element comprise a polymer, a plastic polymer, or polymer coated with reflective metal, or combinations thereof, optionally wherein the reflective metal is optionally Ag, Au, or combinations thereof.

167. The device of embodiment 164, wherein the reflective metal coating is configured to increases an efficiency of light coupling from a top of the piercing element towards the analyte binding probe within the piercing element.

168. The device of embodiment 164, wherein the reflective metal coating is configured to increases an efficiency of light coupling from the analyte binding probe towards the detector.

169. The device of embodiments 162-163, wherein the piercing element is configured to guide light using a dielectric material comprised within the piercing element.

170. The device of embodiment 169, wherein the dielectric material is a dielectric waveguide with a core and cladding.

171. The device of embodiment 170, wherein the dielectric waveguide is an optical fiber.

172. The device of embodiment 170, wherein the second waveguide guides an excitation light towards the analyte binding probe, and an emission light from the analyte binding probe towards the detector.

173. The device of embodiment 1, wherein the analyte binding probe is located above the piercing elements.

174. The device of embodiment 1, wherein the piercing element comprises a plurality of piercing members held together by a base.

175. The device of embodiment 174, wherein the plurality of piercing members is at least partially hollow.

176. The device of embodiment 174, wherein at least one of the plurality of piercing members provides a fluorescence signal of known magnitude to establish a reference signal as to the change in optical signal from the analyte binding probe under a given biological condition.

177. The device of embodiment 176, wherein the given biological conditions comprise a pH value, a temperature, a salt concentration, or combinations thereof.

178. The device of embodiment 174, wherein at least two of the piercing members comprise a same analyte binding probe.

179. The device of embodiment 174, wherein at least two of the piercing members comprise a same analyte binding probe in a same concentration.

180. The device of embodiment 168, wherein at least two of the piercing members comprise two different analyte binding probes that detect two different analytes.

181. The device of embodiment 1, wherein the change in optical signal when the analyte binding probe comes in contact with the analyte is detected using fluorescence resonance energy transfer (FRET) or a time resolved fluorescence (TRY) or change in optical emission intensity.

182. The device of embodiment 1, wherein the change in analyte concentration when the analyte binding probe comes in contact with the analyte is detected using a change in intensity of the fluorescence.

183. The device of embodiment 1, wherein the analyte binding probe comprises a quantum dot.

184. The device of embodiment 1, wherein the analyte binding probe comprises an aptamer conjugated to a quantum dot.

185. The device of embodiment 1, wherein the optical coupler is an optical grating.

186. The device of embodiment 185, wherein the optical grating is a diffraction element configured to guide light from a free space into the waveguide, or from the waveguide into a free space.

187. The device of embodiment 185, wherein the optical grating is configured to direct light from the waveguide toward the piercing element.

188. The device of embodiment 185, wherein the optical grating is configured to direct light from the piercing element towards the waveguide.

189. The device of embodiment 1, wherein the piercing element is separable from the device.

190. The device of embodiment 1, wherein the piercing element is configured to store the biological sample for subsequent analysis.

191. A method for sensing an analyte in a biological sample of a subject, comprising:
   A. piercing a skin of the subject to contact a biological sample, and bringing the biological sample in contact with an analyte binding probe;
   B. inducing a conformational change in the analyte binding probe by binding a target analyte with the analyte binding probe;
   C. applying a light source to the analyte binding probe to produce an optical signal;
   D. measuring a presence, a lack of presence, an increase, or a decrease of the optical signal to determine the presence or concentration of the target analyte in the sample.

192. The method of embodiment 191, further comprising passing light through an optical waveguide from a light source to the analyte binding probe.

193. The method of embodiment 191, further comprising passing light through an optical waveguide from the analyte binding probe to a detector.

194. The method of embodiment 191, wherein applying the light source to the analyte binding probe comprises transmitting light through an optical excitation path comprising a waveguide and a light coupler and: i) transmitting light through one or more focusing elements and focusing light from a light source towards the light coupler, ii) transmitting light through a waveguide and reflecting it within the waveguide using a reflective cladding layer surrounding the waveguide, thereby guiding the light toward the piercing element or iii) transmitting light from a light source, through the light coupler, and into the waveguide.

195. The method of embodiment 191, wherein measuring a presence, a lack of presence, an increase, or a decrease of the optical signal comprises transmitting light through an optical emission path comprising: i) apertures in a reflective cladding layer surrounding a waveguide, transmitting light through the apertures towards the detector, or ii) one or more focusing elements configured to focus emission light from the analyte binding probe towards the detector, transmitting lights through the one or more focusing elements towards the detector.

196. The method of embodiment 191, wherein applying a light source to the analyte binding probe to produce an optical signal comprises transmitting light about an optical excitation path comprising a waveguide, and an optical emission path comprising the waveguide, the waveguide transmitting light from the light source to the analyte binding probe, and the transmitting light through the waveguide from the analyte binding probe to a detector.

197. The method of embodiment 191, wherein applying the light source to the analyte binding probe and/or measuring a presence, a lack of presence, an increase, or a decrease of the optical signal comprises the waveguide transmitting light from a light source to the analyte binding probe, and the waveguide transmitting light from the analyte binding probe to the detector.

198. The method of embodiment 191, wherein the analyte binding probe is comprised in a sensing domain comprising a hydrogel matrix comprising one or more particles comprising the analyte binding probe.

199. The method of embodiment 191, wherein the analyte binding probe has a dissociation constant of at least 1 pM with respect to the analyte.

200. The method of embodiment 191, wherein piercing the skin of the subject comprises piercing the skin of the subject with a piercing element that is removable from a device.

201. The method of embodiment 200, wherein piercing the skin of the subject comprises storing the biological sample in the piercing element for subsequent analysis.

202. The method of embodiment 191, wherein measuring the presence, the lack of presence, the increase, or the decrease of the optical signal to determine the presence or concentration of the target analyte in the sample occurs using a device coupled to a piercing element.

203. The method of embodiment 191, wherein measuring the presence, lack of presence, increase of optical signal, or decrease of optical signal to determine the concentration of the target analyte in the biological sample occurs while the piercing element is attached to the body of a subject.

204. The method of embodiment 191, wherein measuring the presence, lack of presence, increase of optical signal, or decrease of optical signal to determine the concentration of the target analyte in the biological sample occurs while the piercing element is removed from the body of a subject.

205. A device for sensing an analyte in a biological sample of a subject, comprising:
a support; a piercing element coupled to the support, wherein the piercing element is configured to pierce a body surface of the subject when the device is coupled to the body surface, to thereby bring the piercing element in contact with the biological sample;
an analyte binding probe on or within the piercing element, wherein the analyte binding probe is configured to provide a change in an optical signal when the analyte binding probe comes into contact with the analyte in the biological sample of the subject; and
a detector operatively coupled to the support, wherein the detector is configured to detect the optical signal.

206. The device of any of the preceding embodiments, further comprising a light source.

207. The device of any of the preceding embodiments, wherein the device is configured to be placed in optical communication with an external light source.

208. The device of any of the preceding embodiments, further comprising two or more analyte binding probes on or within the piercing element, each of the two or more analyte binding probes configured to provide a change in an optical signal when the two or more analyte binding probes contacts a second analyte in the biological sample of the subject.

209. The device of any of the preceding embodiments, further comprising a multiplexed array of analyte binding probes on or within the piercing element, each of the multiplexed array of analyte binding probes configured to provide a change in an optical signal when the multiplexed array of analyte binding probe contacts a subsequent analyte in the biological sample of the subject.

210. The device of any of the preceding embodiments, wherein the subsequent analyte is a different analyte, the multiplexed array of analyte binding probes is configured to detect a plurality of analytes in the biological sample of the subject.

211. The device of any of the preceding embodiments, wherein the piercing element comprises a plurality of piercing elements.

212. The device of any of the preceding embodiments, wherein the plurality of piercing elements defines subsets of piercing elements, wherein each subset of piercing elements comprises a different analyte binding probe configured to detect a different analyte in the biological sample of the subject.

213. The device of any of the preceding embodiments, wherein the subsets of piercing elements comprising the different analyte binding probe comprises the multiplexed array of analyte binding probes.

214. The device of any of the preceding embodiments, wherein the support comprises an optical light guide, or an optical waveguide.

215. The device of any of the preceding embodiments, wherein the optical light guide comprises a 2-dimensional array of light guides.

216. The device of any of the preceding embodiments, wherein the optical light guide comprises a light guide core.

217. The device of any of the preceding embodiments, wherein the optical light guide comprises a light guide core.

218. The device of any of the preceding embodiments, wherein the optical light guide comprises a coupling region.

219. The device of any of the preceding embodiments, wherein the optical light guide comprises a coupling region where the optical light guide contacts the microneedle.

220. The device of any of the preceding embodiments, wherein the optical light guide comprises a coupling region positioned at a base of the microneedle.

221. The device of any of the preceding embodiments, wherein the coupling region is in contact with the base of the microneedle, or is adjacent to the base of the microneedle.

222. The device of any of the preceding embodiments, wherein light passes through the coupling region to the analyte binding probe.

223. The device of any of the preceding embodiments, wherein the coupling region comprises a higher refractive index than the light guide core.

224. The device of any of the preceding embodiments, wherein the coupling region comprises a higher refractive index than the light guide core, and refracts light toward the aptamer binding probe.

225. The device of any of the preceding embodiments, wherein the coupling region comprises a lower refractive index than the light guide core, and refracts light toward the detector.

226. The device of any of the preceding embodiments, wherein the coupling region comprises a same refractive index as the light guide core.

227. The device of any of the preceding embodiments, wherein the optical light guide comprises one or more reflectors.

228. The device of any of the preceding embodiments, wherein the reflectors are positioned in contact with a base of the piercing element.

229. The device of any of the preceding embodiments, wherein the reflectors surround a base of the piercing element.

230. The device of any of the preceding embodiments, wherein the reflectors form an array about a base of the piercing element.

231. The device of any of the preceding embodiments, wherein the reflectors are adjacent to a base of the piercing element.

232. The device of any of the preceding embodiments, wherein the reflectors are configured to reflect light toward the piercing element.

233. The device of any of the preceding embodiments, wherein the reflectors are configured focus light toward the analyte binding probe.

234. The device of any of the preceding embodiments, wherein the reflectors comprise a reflective material on a sidewall of a structure.

235. The device of any of the preceding embodiments, wherein the 2-dimensional array comprises dichroic mirrors.

236. The device of any of the preceding embodiments, wherein the 2-dimensional array comprises gratings.

237. The device of any of the preceding embodiments, wherein the 2-dimensional array is etched.

238. The device of any of the preceding embodiments, wherein the light guide comprises a glass or a polymer.

239. The device of any of the preceding embodiments, wherein the optical light guide comprises a polymer glassy matrix comprising dispersed photoluminescent particles.

240. The device of any of the preceding embodiments, wherein the polymer comprises silicones, polysiloxanes, silsequioxanes, or combinations thereof.

241. The device of any of the preceding embodiments, wherein the polymer comprises: polymethylmethacrylate (PMMA), polystyrene (PS), polycarbonate (PC), polyurethane (PU), epoxy resin, deuterated and halogenated polyacrylates, fluorinated polyimides, perfluorocyclobutyl (PFCB) aryl ether polymers, nonlinear optical polymers, benzocylcobutene (BCB), perfluorovinyl ether cyclopolymer (CYTOP), tetrafluoroethylene and perfluorovinyl ether copolymer (Teflon AF), silicone, fluorinated poly(arylene ether sulfide), poly(pentafluorostyrene), fluorinated dendrimers, fluorinated hyperbranched polymers, or combinations thereof.

242. The device of any of the preceding embodiments, wherein the optical light guide is configured to: couple to a light source, to guide at least a portion of light from the light source along a length of the optical light guide, and to divert at least a portion of the light from the light guide to the piercing element.

243. The device of any of the preceding embodiments, wherein the support comprises an optical light guide is configured to provide a light transmission efficiency of at least 1, 5, 10, 15, 20, 25, 30, 35, 40, 45, 50, 50, 60, 65, 70, 75, 80, 85, 90, 95, or 99% transmission efficiency.

244. The device of any of the preceding embodiments, wherein the support comprises an optical light guide is configured to provide a light transmission efficiency of at least 1, 5, 10, 15, 20, 25, 30, 35, 40, 45, 50, 50, 60, 65, 70, 75, 80, 85, 90, 95, or 99% transmission efficiency from the light source to the piercing element.

245. The device of any of the preceding embodiments, wherein the optical light guide is configured to collect an emission light of the optical reporter from the analyte binding probe, to guide at least a portion of the emission light to the detector.

246. The device of any of the preceding embodiments, wherein the support comprises an optical light guide is configured to provide an essentially losses light transmission from the piercing element to the detector.

247. The device of any of the preceding embodiments, wherein the support comprises an optical light guide is configured to provide a light transmission efficiency of at least 1, 5, 10, 15, 20, 25, 30, 35, 40, 45, 50, 50, 60, 65, 70, 80, 85, 90, 95, or 99% transmission efficiency from the piercing element to the detector.

248. The device of any of the preceding embodiments, wherein the optical light guide defines a plurality of paths from the light source to the piercing element.

249. The device of any of the preceding embodiments, wherein the light source is configured to provide light in different wavelengths.

250. The device of any of the preceding embodiments, wherein the light source comprises a plurality of light sources each configured to provide a different wavelength of light.

251. The device of any of the preceding embodiments, wherein the device is configured to be coupled to an external light source each configured to provide a different wavelength of light.

252. The device of any of the preceding embodiments, wherein the plurality of paths from the light source to the piercing element comprises one or more distinct paths from the light source to the multiplexed array of analyte binding probes.

253. The device of any of the preceding embodiments, wherein multiplexed array of analyte binding probes is spatially multiplexed across the piercing element.

254. The device of any of the preceding embodiments, wherein at least one of the plurality of paths is configured to guide light from one of the plurality of light sources with a specific wavelength of light to one of the analyte binding probes in the multiplexed array of analyte binding probes which is configured to be responsive to the specific wavelength of light.

255. The device of any of the preceding embodiments, wherein the plurality of paths from the light source to the piercing element comprises one or more distinct paths from the light source to the subsets of piercing elements.

256. The device of any of the preceding embodiments, wherein at least one of the plurality of paths is configured to guide light from one of the plurality of light sources with a specific wavelength of light to one of the analyte binding probes in the subsets of piercing elements.

257. The device of any of the preceding embodiments, wherein the optical light guide comprises one or more switches configured to block one or more of the plurality of paths.

258. The device of any of the preceding embodiments, wherein the piercing element is coupled to the support using one or more holes.

259. The device of any of the preceding embodiments, wherein the piercing element is coupled to the support using one or more insertable elements configured to attach to a corresponding one or more receiving elements.

260. The device of any of the preceding embodiments, wherein the piercing element is coupled to the support using a lock and key attachment.

261. The device of any of the preceding embodiments, wherein the piercing element is coupled to the support using a mortise and tenon attachment.

262. The device of any of the preceding embodiments, wherein the piercing element is coupled to the support using a dovetail attachment.

263. The device of any of the preceding embodiments, wherein the piercing element is coupled to the support using a magnetic attachment.

264. The device of any of the preceding embodiments, wherein the piercing element is coupled to the support using an adhesive.

265. The device of any of the preceding embodiments, wherein the piercing element is coupled to the support using one or more elastically deformable attachment elements.

266. The device of any of the preceding embodiments, wherein the piercing element is coupled to the support using one or more elastically deformable attachment elements configured rebound once inserted into the support.
267. The device of any of the preceding embodiments, wherein the piercing element is removably coupled to the support.
268. The device of any of the preceding embodiments, wherein the piercing element comprises a microneedle array which is removably coupled to the support.
269. The device of any of the preceding embodiments, wherein the optical light guide is removably coupled to the support.
270. The device of any of the preceding embodiments, wherein the optical light guide is removably coupled to the support, and is removable from the support while remaining coupled to the light guide.
271. The device of any of the preceding embodiments, wherein the optical light guide comprises a first portion and a second portion, wherein the first portion is removably coupled to the support, and the second portion is coupled to the piercing element.
272. The device of any of the preceding embodiments, wherein the optical light guide comprises a first portion and a second portion removably coupled to each other.
273. The device of any of the preceding embodiments, wherein the second portion is removably coupled to the support, wherein the second portion is coupled to the piercing element,
274. The device of any of the preceding embodiments, wherein the second portion is removable from the first portion.
275. The device of any of the preceding embodiments, wherein the support does not comprise an optical light guide.
276. The device of any of the preceding embodiments, wherein the device uses direct light.
277. The device of any of the preceding embodiments, wherein the device comprises miniaturized structural layers interrogated using direct light.
278. The device of any of the preceding embodiments, wherein the miniaturized structural layers comprise a light delivery system from the light source to the sensing apparatus, a light carrying apparatus from the sensing apparatus to the detection system, and a detection system.
279. The device of any of the preceding embodiments, wherein the optical delivery apparatus and optical detection apparatus are arranged to perform dual functions while being simultaneously operational.
280. The device of any of the preceding embodiments, wherein the light delivery system in the optical delivery apparatus comprises an array of light emitting sources, arranged in a plane that is substantially above the sensing apparatus so as to provide direct illumination on the sensing apparatus.
281. The device of any of the preceding embodiments, wherein the light emitting sources are LEDs.
282. The device of any of the preceding embodiments, wherein the light emitting sources are lasers.
283. The device of any of the preceding embodiments, wherein the light emitting sources are placed substantially above the sensing area in order to provide direct illumination.
284. The device of any of the preceding embodiments, wherein the light emitting sources are arranged such that there is the same number of light emitting sources as the sensing apparatus so as there is to be substantial light coupling into each sensing apparatus.
285. The device of any of the preceding embodiments, wherein some of the light emitting sources can be independently turned on or off.
286. The device of any of the preceding embodiments, wherein the optical delivery system has wavelength between 300 nanometers and 1000 nanometers and the light emitted from the sensing apparatus is red-shifted.
287. The device of any of the preceding embodiments, wherein the light emitting array is between the sensing apparatus and the detection apparatus.
288. The device of any of the preceding embodiments, wherein the light emitting array is on a board that allows the light coming from the sensing apparatus to pass through itself and go to the detecting apparatus.
289. The device of any of the preceding embodiments, wherein the light coming from the sensing apparatus and passing through itself is accomplished using holes in a board that holds the light emitters.
290. The device of any of the preceding embodiments, wherein the sensing apparatus comprises a hollow microneedle array that is capable of holding the fluorescence-based sensing molecules.
291. The device of any of the preceding embodiments, wherein the sensing apparatus comprises a single microneedle that is capable of holding the fluorescence-based sensing molecules.
292. The device of any of the preceding embodiments, wherein the fluorescence-based sensing molecules are aptamers.
293. The device of any of the preceding embodiments, wherein the microneedles have sharp needles that insert into the sensing area and a second base region which holds a multitude of these needles together.
294. The device of any of the preceding embodiments, wherein there are periodic holes in the base region of the microneedles directly above the sharp needles.
295. The device of any of the preceding embodiments, wherein the lightguide/waveguide has protruding periodic extension structures which insert into the hollow part of the microneedle base, thus providing a continuation of the waveguide/lightguide material down to the microneedles and facilitating coupling into the sensing area.
296. The device of any of the preceding embodiments, wherein the continuing protruding structures of the waveguide are pitch-matched with the microneedle array so as they insert into the base part of the microneedles directly above the sharp needles.
297. The device of any of the preceding embodiments, wherein the guided light carried by the waveguide/lightguide is diverted into the underlying sensing apparatus using protruding structures, where the light continues inside the base of the microneedles and strikes the sidewall and is reflected down toward the sensing region in the sharp needles.
298. The device of any of the preceding embodiments, wherein there is a filter layer between the light emitter layer and the sensor layer.
299. The device of any of the preceding embodiments, wherein the filters in the filter layer are low pass filters.
300. The device of any of the preceding embodiments, wherein there is an optical layer between the light emitting layer and the sensing layer.
301. The device of any of the preceding embodiments, wherein the optical layer performs the function of substantially collimating the light coming from the sensing layer.
302. The device of any of the preceding embodiments, wherein the detection system relies on a CMOS sensor.

303. The device of any of the preceding embodiments, wherein the detection system is a CCD sensor.

304. The device of any of the preceding embodiments, wherein the detection system relies on a photodetector.

305. The device of any of the preceding embodiments, wherein there is a filter between the light emitting layer and the detection layer.

306. The device of any of the preceding embodiments, wherein the filter is a long pass emission filter that allows the red-shifted light from the sensor system to pass through while blocking any light from the source.

307. The device of any of the preceding embodiments, wherein the device comprises structural layers interrogated using guided light.

308. The device of any of the preceding embodiments, wherein the light emitter is spatially removed from the sensing apparatus so as to not have a direct line of sight with the sensing apparatus.

309. The device of any of the preceding embodiments, wherein the light from the light emitter is coupled to the lightguide or waveguide from one or both edges and the lightguide or waveguide carries the coupled light to the region wherein the sensing apparatus resides.

310. The device of any of the preceding embodiments, wherein the sensing apparatus physically resides below the waveguide/lightguide and can be anywhere along the waveguide/lightguide between the two edges of the waveguide/lightguide.

311. The device of any of the preceding embodiments, wherein the detection system physically resides above the waveguide/lightguide.

312. The device of any of the preceding embodiments, wherein there is an optical filter that resides between the waveguide/lightguide and the detection system and physically above the waveguide/lightguide.

313. The device of any of the preceding embodiments, wherein the waveguide or lightguide is laterally confined to make a rectangular waveguide or lightguide with the purpose of enhancing the light intensity above the microneedles and preventing cross talk between different discrete rectangular waveguides or lightguides.

314. The device of any of the preceding embodiments, wherein the light delivery path to the sensing region comprises a light emitter or array of light emitters geometrically placed in a layer above the waveguide layer but to the edge of the waveguide, an aperture layer, a reflecting mirror at an angle, a waveguide or lightguide, and the microneedle array.

315. The device of any of the preceding embodiments, wherein the light emitting source is a downfiring LED which intrinsically has an emission spectrum in a narrow angle range, for example the emission angles can vary from plus or minus 5 degrees to plus or minus 20 degrees.

316. The device of any of the preceding embodiments, wherein the light coming down passes through an aperture, the function of which is to further narrow the range of angles of the light according to what is acceptable in the waveguide, wherein aperture walls are absorptive and absorb wider angles such that only narrower angles make it through the aperture, optionally, wherein the light source is an LED.

317. The device of any of the preceding embodiments, wherein the aspect ratio of the aperture hole controls the range of the angular spread of light that is allowed to pass through the hole.

318. The device of any of the preceding embodiments, wherein one end of the range of the angular spread of light that is allowed to pass through the aperture, which is dictated by the aspect ratio of the aperture, is determined by the refractive index of the core or cladding of the lightguide and the critical angle dictating the total internal reflection inside the waveguide or lightguide.

319. The device of any of the preceding embodiments, wherein the other end of the range of the angular spread of light that is allowed to pass through the aperture, which is dictated by the aspect ratio of the aperture, is determined by coupling considerations from the lightguide into the underlying microneedles. The light hitting the sidewall of the base of the microneedle must also go through total internal reflection.

320. The device of any of the preceding embodiments, wherein the light strikes an angled mirror after passing through the aperture.

321. The device of any of the preceding embodiments, wherein the mirror resides at an angle which is conducive to coupling into the waveguide. This angle is close to 22.5 degrees from the horizontal to facilitate about a 45 degree angle at the core/cladding interface. The acceptance angle is around this angle.

322. The device of any of the preceding embodiments, wherein the light emitting source is a laser.

323. The device of any of the preceding embodiments, wherein the detection system physically resides above the waveguide or lightguide and comprises a lens array layer, an aperture layer, an emission filter, a photodetection system, and a circuit board or a multitude of circuit boards to process the optical signal into electrical signal and communicate to the outside world.

324. The device of any of the preceding embodiments, wherein there is an optical filter that resides between the waveguide or lightguide and the detection system and resides physically above the waveguide or lightguide. This filter is known as the emission filter.

325. The device of any of the preceding embodiments, wherein the optical filter is either a dichroic filter or an absorptive filter that is a bandpass filter letting through the red-shifted light from the sensing region.

326. The device of any of the preceding embodiments, wherein there is an angular rejection layer having high aspect ratio periodic holes situated directly above the microneedles that facilitate in letting through only light striking substantially perpendicular to the detection system and rejecting angles that are not substantially perpendicular.

327. The device of any of the preceding embodiments, wherein the angular rejection layer is above the optical filter and both are between the lightguide/waveguide and the detection system.

328. The device of any of the preceding embodiments, wherein there is a lens array with a lens above every microneedle with the purpose of enhancing the photon density at the specific pixels in the image sensor.

329. The device of any of the preceding embodiments, wherein there is a lensing layer between the waveguide and the detection system which facilitates collimation.

330. The device of any of the preceding embodiments, wherein there is a lensing layer between the waveguide and the detection system which facilitates focusing of light on smaller sizes on the CMOS.

331. The device of any of the preceding embodiments, wherein there is both a collimation and a focusing lens between the waveguide/lightguide and the detection system.

332. The device of any of the preceding embodiments, wherein the optical elements are relatively arranged in a way that is efficient in coupling emitted light from small areas to detectors in small areas.

333. The device of any of the preceding embodiments, wherein the optical elements comprise two opposing lenses separated by a distance.
334. The device of any of the preceding claims, wherein the wavelength filter is a bandpass or a high pass dichroic filter.
335. The device of any of the preceding embodiments, wherein the wavelength filter is a composite dichroic and an absorption filter.
336. The device of any of the preceding embodiments, wherein the filter is designed to pass the emission wavelength and block the lower excitation wavelength.
337. The device of any of the preceding embodiments, wherein the emission wavelength is in the range of 720 nm with some spread, and excitation wavelength is in the 630 nm range with some spread.
338. The device of any of the preceding embodiments, wherein the optical lenses are such that the first lens grabs light and collimates light.
339. The device of any of the preceding embodiments, wherein the second lens takes the collimated light and attempts to focus the light onto a detector that resides above it.
340. The device of any of the preceding embodiments, wherein the assembly includes the two lenses, the filter, and the detection system resides above the excitation system comprising a waveguide with posts.
341. The device of any of the preceding embodiments, wherein the entire assembly is optimized with respect to the distance from the emission source and detection so as to maximize the ratio of $(NA/Mag)^2$, where NA is the numerical aperture and Mag is the magnification of the lens.
342. The device of any of the preceding embodiments, wherein there are additional aperture holes that are added to the light path to further assist with efficiency and isolation.
343. The device of any of the preceding embodiments, wherein the device comprises a free space optical system.
344. The device of any of the preceding embodiments, wherein the device comprises a free space optical system configured to transfer light from the light source to the analyte binding probe.
345. The device of any of the preceding embodiments, wherein the device comprises a free space optical system configured to transfer light from the analyte binding probe to the detector.
346. The device of any of the preceding embodiments, wherein the free space optical system comprises a light source coaxially aligned with the analyte binding probe.
347. The device of any of the preceding embodiments, wherein the free space optical system comprises a light source vertically integrated with the analyte binding probe.
348. The device of any of the preceding embodiments, wherein the free space optical system comprises a light source directly coupled to the piercing element.
349. The device of any of the preceding embodiments, wherein the detector is directly coupled to the piercing element.
350. The device of any of the preceding embodiments, wherein there is a light path between the analyte binding probe and the detector.
351. The device of any of the preceding embodiments, wherein a light source is directly coupled to the analyte binding probe.
352. The device of any of the preceding embodiments, wherein there is a light path between the analyte binding probe and the light source.
353. The device of any of the preceding embodiments, wherein there is an unobstructed light path between the analyte binding probe and the light source.
354. The device of any of the preceding embodiments, wherein the light source is a plurality of light-emitting diodes (LEDs) or lasers.
355. The device of any of the preceding embodiments, wherein the light source is a plurality of light-emitting diodes (LEDs) or lasers, each of the plurality of light-emitting diodes (LEDs) or lasers configured to deliver a different wavelength of light.
356. The device of any of the preceding embodiments, wherein the light source has wavelength of at least about 200 nanometers.
357. The device of any of the preceding embodiments, wherein the light source has wavelength of at most about 2 micrometers.
358. The device of any of the preceding embodiments, wherein the analyte binding probe is coupled to an optical reporter.
359. The device of any of the preceding embodiments, wherein the optical reporter is a fluorophore or a quencher.
360. The device of any of the preceding embodiments, wherein the analyte binding probe coupled to the optical reporter is an oligonucleotide probe.
361. The device of any of the preceding embodiments, wherein the oligonucleotide probe is an aptamer.
362. The device of any of the preceding embodiments, wherein the aptamer is coupled to a displacement strand, wherein the displacement strand is partially complementary to the aptamer.
363. The device of any of the preceding embodiments, wherein the displacement strand is coupled to a second optical reporter.
364. The device of any of the preceding embodiments, wherein the second optical reporter is a fluorophore or a quencher.
365. The device of any of the preceding embodiments, wherein the aptamer is coupled to a linker moiety placed between the aptamer and the displacement strand.
366. The device of any of the preceding embodiments, wherein the linker moiety is a nucleotide acid moiety, a peptide nucleic acid (PNA) moiety, a peptide moiety, a disulfide bond, a phosphodiester linkage, or a polymer.
367. The device of any of the preceding embodiments, wherein the analyte binding probe coupled to the optical reporter is a polynucleotide probe.
368. The device of any of the preceding embodiments, wherein the analyte binding probe comprises an antibody.
369. The device of any of the preceding embodiments, wherein the analyte binding probe is configured to undergo a conformational change when the analyte interacts with the analyte binding probe.
370. The device of any of the preceding embodiments, wherein the conformation is configured to provide the change in the optical signal.
371. The device of any of the preceding embodiments, wherein the change in the optical signal is in a function of a concentration of the analyte.
372. The device of any of the preceding embodiments, wherein the optical signal is the emission light.
373. The device of any of the preceding embodiments, wherein the analyte binding probe is configured to detect one or plurality of analytes.
374. The device of any of the preceding embodiments, wherein the analyte is an antibody.

375. The device of any of the preceding embodiments, wherein the analyte is a oligonucleotide, mRNA, RNA, DNA, cDNA, a lipid, lipid particle, an exosome, a viral particle, or combinations thereof.

376. The device of any of the preceding embodiments, wherein the analyte is a protein.

377. The device of any of the preceding embodiments, wherein the analyte is a small molecule.

378. The device of any of the preceding embodiments, wherein the small molecule is a drug.

379. The device of any of the preceding embodiments, wherein the piercing element is a needle.

380. The device of any of the preceding embodiments, wherein the piercing element is a microneedle.

381. The device of any of the preceding embodiments, wherein the needle is configured to penetrate a stratum corneum of the subject.

382. The device of any of the preceding embodiments, wherein the piercing element is configured to penetrate into a dermis of the subject.

383. The device of any of the preceding embodiments, wherein one or more sidewall of the piercing element are reflective.

384. The device of any of the preceding embodiments, wherein one or more sidewall of the needle are reflective.

385. The device of any of the preceding embodiments, wherein the needle comprises a structural domain, a barrier domain, and a sensing domain.

386. The device of any of the preceding embodiments, wherein the structural domain is positioned on a surface of the support and extends outward from the surface to define a needle, and defines an interior space, wherein the sensing domain is contained within the interior space.

387. The device of any of the preceding embodiments, wherein the needle comprises a well.

388. The device of any of the preceding embodiments, wherein the sensing domain is contained within the well.

389. The device of any of the preceding embodiments, wherein the barrier domain coats an exterior surface of the structural domain.

390. The device of any of the preceding embodiments, wherein the structural domain defines one or more opening on a lateral face of the needle.

391. The device of any of the preceding embodiments, wherein the structural domain defines pyramidal needles.

392. The device of any of the preceding embodiments, wherein the structural domain defines pyramidal needles comprising an opening on each fac pf the pyramidal needles.

393. The device of any of the preceding embodiments, wherein the barrier domain coats the openings.

394. The device of any of the preceding embodiments, wherein the barrier domain contacts a portion of the sensing domain.

395. The device of any of the preceding embodiments, wherein the barrier domain contacts a portion of the sensing domain at the openings.

396. The device of any of the preceding embodiments, wherein the needle comprises a structural domain, and the sensing domain.

397. The device of any of the preceding embodiments, wherein the structural domain encapsulates the barrier domain.

398. The device of any of the preceding embodiments, wherein the structural domain encloses the sensing domain.

399. The device of any of the preceding embodiments, wherein the sensing domain encapsulates the analyte binding probe within a matrix of the sensing domain, wherein the barrier domain comprises a hydrogel, a polymer, or combinations thereof.

400. The device of any of the preceding embodiments, wherein the sensing domain comprises the analyte binding probe.

401. The device of any of the preceding embodiments, wherein the sensing domain comprise the analyte binding probe in a hydrogel matrix.

402. The device of any of the preceding embodiments, wherein the sensing domain encapsulates the analyte binding probe in a hydrogel matrix.

403. The device of any of the preceding embodiments, wherein the analyte binding probe is attached to hydrogel by conjugation methods comprising: DBCO-Azide, BCN-Tetrazine, biotin-streptavidin, EDC, NHS/EDC, thiol maleimide, DBCO-N3, DBCO-DHPA, BCN-N3, or any combination thereof.

404. The device of any of the preceding embodiments, wherein the hydrogel is produced from Cu-click reactions.

405. The device of any of the preceding embodiments, wherein the hydrogel is produced from Cu-free click reaction.

406. The device of any of the preceding embodiments, wherein the sensing domain encapsulates the analyte binding probe within a matrix of the sensing domain.

407. The device of any of the preceding embodiments, wherein the barrier domain comprises a hydrogel, a polymer, or combinations thereof.

408. The device of any of the preceding embodiments, wherein the structural domain encapsulates the sensing domain, wherein the sensing domain is configured to control transfer of the analyte to analyte binding probe.

409. The device of any of the preceding embodiments, wherein the barrier domain coats a portion of the sensing domain, wherein the barrier domain is configured to control transfer of the analyte to sensing domain.

410. The device of any of the preceding embodiments, wherein the barrier domain is configured to control transfer of the analyte to sensing domain via diffusion.

411. The device of any of the preceding embodiments, wherein the sensing domain is configured to control transfer of the analyte to analyte binding probe via diffusion.

412. The device of any of the preceding embodiments, wherein the sensing domain comprises a plurality of pores.

413. The device of any of the preceding embodiments, wherein the barrier domain comprises a plurality of pores.

414. The device of any of the preceding embodiments, wherein the structural domain comprises one or more openings on an exterior surface of the structural domain.

415. The device of any of the preceding embodiments, wherein the one or more openings is configured to allow the analyte to contact the sensing domain.

416. The device of any of the preceding embodiments, wherein the sensing domain defines a passage connecting the one or more openings to the analyte binding probe.

417. The device of any of the preceding embodiments, wherein the needle a plurality of openings.

418. The device of any of the preceding embodiments, wherein the needle comprises a structural domain comprising a hollow region of the needle.

419. The device of any of the preceding embodiments, wherein the hollow region is orientated in a longitudinal direction.

420. The device of any of the preceding embodiments, wherein the plurality of openings are positioned on a lateral face of the needle.

421. The device of any of the preceding embodiments, wherein the plurality of openings are positioned on opposing lateral faces of the needle.
422. The device of any of the preceding embodiments, wherein the sensing domain extends longitudinally into the needle.
423. The device of any of the preceding embodiments, wherein the sensing domain extends longitudinally into the needle and defines a passage connecting the one or more openings to the analyte binding probe.
424. The device of any of the preceding embodiments, wherein there is one opening on a lateral surface of the needle.
425. The device of any of the preceding embodiments, wherein the structural domain is directly in contact with the sensing domain.
426. The device of any of the preceding embodiments, wherein the structural domain and the sensing domain extends longitudinally from the device.
427. The device of any of the preceding embodiments, wherein the sensing domain is positioned orthogonally to a longitudinal axis of the needle.
428. The device of any of the preceding embodiments, wherein the sensing domain is positioned orthogonally to a longitudinal axis of the needle, wherein the sensing domain is positioned parallel to a longitudinal axis of the needle.
429. The device of any of the preceding embodiments, wherein the sensing domain is positioned on the exterior surface of the structural domain.
430. The device of any of the preceding embodiments, wherein the barrier domain is positioned on the exterior surface of the structural domain, and wherein the sensing positioned within an interior space of the structural domain.
431. The device of any of the preceding embodiments, wherein the barrier domain is positioned on the exterior surface of the structural domain, positioned within an interior space of the structural domain, and wherein the sensing domain is positioned within the structural domain an in contact with the barrier domain positioned within an interior space of the structural domain.
432. The device of any of the preceding embodiments, wherein the barrier domain is positioned on the exterior surface of the structural domain and wherein the barrier domain is positioned within an interior space of the structural domain, and wherein the sensing domain is positioned within the structural domain orthogonally to a longitudinal axis of the needle, and is in contact with the barrier domain positioned within an interior space of the structural domain.
433. The device of any of the preceding embodiments, wherein the barrier domain is positioned on the exterior surface of the structural domain and wherein the barrier domain is positioned within an interior space of the structural domain, and wherein the sensing domain is positioned throughout a matrix of the barrier domain.
434. The device of any of the preceding embodiments, wherein the barrier domain is partially within an interior space of the structural domain.
435. The device of any of the preceding embodiments, wherein the sensing domain is within an interior space of the structural domain and is exposed to an exterior surface of the needle through the one or more openings, and wherein the analyte binding probe is positioned throughout a matrix of the sensing domain.
436. The device of any of the preceding embodiments, wherein the barrier domain is positioned on the exterior surface of the structural domain and wherein the sensing domain is positioned within an interior space of the structural domain, and wherein the analyte binding probe is positioned throughout a matrix of the sensing domain, wherein there are at least two opening on opposing lateral faces of the needle.
437. The device of any of the preceding embodiments, wherein the analyte binding probe is contained within the sensing domain at a concentration of about 1 nM to about 1 mM.
438. The device of any of the preceding embodiments, wherein the analyte binding probe is contained within the sensing domain at a concentration of about 1 nM to about 1 uM.
439. The device of any of the preceding embodiments, wherein the analyte binding probe is distributed substantially uniformly dispersed throughout the barrier domain.
440. The device of any of the preceding embodiments, wherein the needle has a length of at least about 3 millimeters.
441. The device of any of the preceding embodiments, wherein the needle has a length of at least about 1 millimeter.
442. The device of any of the preceding embodiments, wherein the needle has a length of at least about 500 micrometers.
443. The device of any of the preceding embodiments, wherein the needle has a length of at least about 100 micrometers.
444. The device of any of the preceding embodiments, wherein the needle is a 3-dimensional printed needle.
445. The device of any of the preceding embodiments, wherein the needle is a hydrogel needle.
446. The device of any of the preceding embodiments, wherein the needle is a polymer.
447. The device of any of the preceding embodiments, wherein the needle comprises a cavity filled with a hydrogel matrix.
448. The device of any of the preceding embodiments, wherein the barrier domain comprises a hydrogel matrix.
449. The device of any of the preceding embodiments, wherein the microneedle is solid.
450. The device of any of the preceding embodiments, wherein the microneedle has a hollow core.
451. The device of any of the preceding embodiments, wherein the microneedle is porous.
452. The device of any of the preceding embodiments, wherein the microneedle is a swellable microneedle.
453. The device of any of the preceding embodiments, wherein the device comprises a plurality of piercing elements, wherein the plurality of piercing elements comprises the piercing element.
454. The device of any of the preceding embodiments, wherein at least one piercing element of the plurality of piercing element is coupled to a control reference probe.
455. The device of any of the preceding embodiments, wherein the device is configured to perform a single time-point measurement of the analyte.
456. The device of any of the preceding embodiments, wherein the device is configured to perform continuous, real-time measurement of the analyte.
457. The device of any of the preceding embodiments, wherein the device is configured to present some information related to the analyte.
458. The device of any of the preceding embodiments, wherein the information includes a presence of the analyte.
459. The device of any of the preceding embodiments, wherein the information includes a concentration of the analyte.

460. The device of any of the preceding embodiments, wherein the detector comprises a semiconductor material.

461. The device of any of the preceding embodiments, wherein the detector comprises a semiconductor photodetector.

462. The device of any of the preceding embodiments, wherein the detector comprises a semiconductor photodetector comprising a silicon photomultiplier chip, an avalanche photodiode, a metal-semiconductor-metal photodiode, a CMOS sensor array, a CCDs (charge coupled device), a lateral semiconductor photodiode, an array of photodetectors, or combinations thereof.

463. The device of any of the preceding embodiments, wherein the semiconductor material or the semiconductor photodetector comprises an p-n junction.

464. The device of any of the preceding embodiments, wherein the semiconductor material or the semiconductor photodetector comprises Si, Ge, InGaAs, GaAs, InP, Ge, SiGe, InGaN, GaN, or combinations thereof.

465. The device of any of the preceding embodiments, wherein the detector comprises a silicon photomultiplier (SiPM) detector.

466. The device of any of the preceding embodiments, wherein the SiPM detector has a dimension up to about 1 cm.

467. The device of any of the preceding embodiments, wherein the SiPM detector has a dimension up to about 3 millimeters.

468. The device of any of the preceding embodiments, wherein the device further comprises a battery.

469. The device of any of the preceding embodiments, wherein the device further comprises a wireless communication configured to communicate with an external device to exchange the information.

470. The device of any of the preceding embodiments, wherein the device is a skin patch.

471. The device of any of the preceding embodiments, wherein the skin patch is removable.

472. The device of any of the preceding embodiments, wherein the device is configured to emit the optical signal when the analyte contacts the analyte binding probe.

473. The device of any of the preceding embodiments, wherein the device is configured to result in a decrease in the optical signal when the analyte binding probe is bound to the analyte.

474. The device of any of the preceding embodiments, wherein the device is configured to emit the optical signal in a default configuration when not in contact with the analyte.

475. The device of any of the preceding embodiments, wherein the analyte binding probe emits the optical signal, and does not emit the optical signal when bound to the analyte.

476. The device of any of the preceding embodiments, wherein the analyte binding probe emits the optical signal, and undergoes the conformational change when bound to the analyte as to not emit the optical signal.

477. The device of any of the preceding embodiments, wherein the analyte binding probe emits an optical signal, and undergoes the conformational change when bound to the analyte as to emit a reduced optical signal.

478. The device of any of the preceding embodiments, wherein the device measures a concentration of the analyte in the biological sample of the subject by measuring a decrease in the optical signal.

479. The device of any of the preceding embodiments, further comprising an LED array.

480. The device of any of the preceding embodiments, further comprising an LED driver.

481. The device of any of the preceding embodiments, further comprising a temperature sensor.

482. The device of any of the preceding embodiments, further comprising an MCU, a Bluetooth low energy model, or a CMOS image sensor, or combinations thereof.

483. A method for sensing an analyte in a biological sample of a subject, comprising:
  a. piercing a skin of the subject to contact a biological sample;
  b. bringing the biological sample in contact with an analyte binding probe;
  c. inducing a conformational change in the analyte binding probe by binding a target analyte with the analyte binding probe;
  d. applying a light source to the analyte binding probe to produce an optical signal;
  e. measuring a presence, a lack of presence, an increase, or a decrease of the optical signal to determine the presence or concentration of the target analyte in the sample.

484. The method of any of the preceding embodiments, further comprising passing light through an optical waveguide from a light source to the analyte binding probe.

485. The method of any of the preceding embodiments, further comprising passing light through an optical waveguide from the analyte binding probe to a detector.

What is claimed is:

1. A device for sensing an analyte in a biological sample of a subject, comprising:
  a support;
  a piercing element coupled to the support, wherein the piercing element is configured to pierce a body surface of the subject when the device is coupled to the body surface to bring the piercing element in contact with the biological sample;
  an analyte binding probe on or within the piercing element, wherein the analyte binding probe is configured to provide a change in an optical signal when the analyte binding probe comes in contact with the analyte in the biological sample of the subject;
  a light source operatively coupled to the support;
  a detector operatively coupled to the support, wherein the detector is configured to detect the optical signal;
  a waveguide comprising an optical excitation path and an optical emission path,
  wherein the waveguide is configured to transmit light from the light source to the analyte binding probe through the optical excitation path, and
  wherein the waveguide is configured to transmit light through the optical emission path from the analyte binding probe towards the detector, and wherein the optical emission path further comprises apertures in a reflective cladding layer surrounding the waveguide configured to transmit an emission light from the analyte binding probe to the detector.

2. The device of claim 1, wherein the reflective cladding layer surrounding the waveguide is configured to reflect light back inside the waveguide and guide the light toward the piercing element.

3. The device of claim 1, further comprising a light coupler and one or more focusing elements, wherein the one or more focusing elements are configured to focus light from the light source towards the light coupler.

4. The device of claim 3, wherein the light coupler is configured to couple light from the light source into the waveguide.

5. The device of claim 3, wherein the waveguide comprises a dielectric core, wherein the reflective cladding layer surrounds the dielectric core.

6. The device of claim 5, wherein the reflective cladding layer comprises an aperture between the light source and the light coupler, and the aperture is defined by the absence of the reflective cladding layer.

7. The device of claim 1, wherein the piercing element comprises a reflective material about a base of the piercing element, wherein the optical excitation path guides light from the light source through a protruding portion of the waveguide and to the reflective material about the base of the piercing element, wherein the reflective material about the base of the piercing element reflects the light to the analyte binding probe.

8. The device of claim 1, wherein the optical emission path further comprises one or more focusing elements configured to focus emission light from the analyte binding probe towards the detector.

9. The device of claim 8, wherein the one or more focusing elements comprises a first focusing element configured to focus at least part of the emission light from the analyte binding probe into a first beam, and a second focusing element configured to focus the first beam towards the detector.

10. The device of claim 9, wherein a diameter of a second beam coming from the second focusing element is configured to be a smaller size diameter than the first beam when the second beam crosses a plane of the detector and is incident on one or more pixels of the detector, thereby improving a signal to noise ratio of the detector.

11. The device of claim 9, further comprising an optical filter between the first beam and the detector which does not transmit a portion of light that falls on the optical filter, wherein the portion of the light blocked from transmission by the optical filter has a wavelength which is a same wavelength as the light source.

12. The device of claim 11, wherein the first focusing element transmits light to the optical filter at an angle within approximately +/−25 degrees with respect to a surface normal vector of the filter.

13. The device of claim 1, wherein the optical emission path is configured to reject emission light from the analyte binding probe which does not enter the waveguide at a critical angle between ±20 degrees as measured from a vector normal to a base of the piercing element.

14. The device of claim 1, wherein the analyte binding probe is disposed in a sensing domain comprising a hydrogel matrix comprising one or more particles comprising the analyte binding probe.

15. The device of claim 1, wherein the analyte binding probe comprises a fluorophore conjugated to an aptamer configured to bind to the analyte, wherein the aptamer is configured to undergo a conformation change resulting in a shift in the optical signal upon contacting the analyte.

16. The device of claim 15, wherein the analyte binding probe is disposed in a sensing domain comprising a hydrogel matrix comprising one or more particles comprising the analyte binding probe.

17. The device of claim 16, wherein the one or more particles comprise a diameter of about 1 micron to about 50 microns.

18. The device of claim 17, wherein the piercing element comprises a plurality of microneedles, wherein a number of particles in a microneedle of the plurality of microneedles is at least 10^3 particles.

19. The device of claim 18, wherein a surface of the one or more particles comprises about at least 10^6 analyte binding probes per cm^2.

* * * * *